US012582720B2

(12) United States Patent
Lu et al.

(10) Patent No.: US 12,582,720 B2
(45) Date of Patent: Mar. 24, 2026

(54) COMPOUND FOR PREVENTING OR TREATING LIPID METABOLISM-RELATED DISEASES

(71) Applicant: Fudan University, Shanghai (CN)

(72) Inventors: Boxun Lu, Shanghai (CN); Yuhua Fu, Shanghai (CN); Yu Ding, Shanghai (CN)

(73) Assignee: Fudan University, Shanghai (CN)

( * ) Notice: Subject to any disclaimer, the term of this patent is extended or adjusted under 35 U.S.C. 154(b) by 702 days.

(21) Appl. No.: 17/996,867

(22) PCT Filed: Apr. 23, 2021

(86) PCT No.: PCT/CN2021/089453

§ 371 (c)(1),
(2) Date: Feb. 16, 2023

(87) PCT Pub. No.: WO2021/213518

PCT Pub. Date: Oct. 28, 2021

(65) Prior Publication Data

US 2023/0181744 A1 Jun. 15, 2023

(30) Foreign Application Priority Data

Apr. 23, 2020 (CN) ......................... 202010328911.2

(51) Int. Cl.

| | |
|---|---|
| ***A61K 47/54*** | (2017.01) |
| ***A61K 41/00*** | (2020.01) |
| ***A61K 47/55*** | (2017.01) |
| ***A61P 3/06*** | (2006.01) |

(52) U.S. Cl.

CPC ............ *A61K 47/545* (2017.08); *A61K 41/00* (2013.01); *A61K 47/55* (2017.08); *A61K 47/554* (2017.08); *A61P 3/06* (2018.01)

(58) Field of Classification Search

CPC .................................................... A61K 47/545

See application file for complete search history.

(56) References Cited

U.S. PATENT DOCUMENTS

| | | | | |
|---|---|---|---|---|
| 2009/0124641 | A1* | 5/2009 | Coleman ................. | A61P 35/00 514/266.3 |
| 2019/0290778 | A1* | 9/2019 | Nomura ............. | A61K 47/6889 |

FOREIGN PATENT DOCUMENTS

| | | | |
|---|---|---|---|
| CN | 101106998 | A | 1/2008 |
| CN | 105503840 | A | 4/2016 |
| CN | 111808078 | A | 10/2020 |
| JP | 2005099419 | A | 4/2005 |
| WO | 2006064044 | A1 | 6/2006 |

OTHER PUBLICATIONS

International Search Report issued Jun. 30, 2021 in PCT/CN2021/089453.

Lang, Wenjie, et al., "Expanding the "Minimalist" Small Molecule Tagging Approach to Different Bioactive Compounds," Organic & Biomolecular Chemistry, vol. 17, No. 11, Feb. 21, 2019.

Li, Zhaoyang, et al., "Allele-Selective Lowering of Mutant HTT Protein by HTT-LC3 Linker Compounds," Nature, vol. 575, No. 7, pp. 203-209, Oct. 30, 2019.

Naumov, Mikael I., et al., "2-(Azidomethyl)arylboronic Acids in the Synthesis of Coumarin-Type Compounds," Synthesis, vol. 2009, No. 10, pp. 1673-1682, Apr. 20, 2009.

Written Opinion issued Jun. 30, 2021 in PCT/CN2021/089453.

Extended European Search Report issued Apr. 15, 2024 in EP 21793702.8.

Andrea Sartori, et al., "Synthesis of Novel c(AmpRDG)-Sunitinib Dual Conjugates as Molecular Tools Targeting the aVβ3 Integrin/VEGFR2 Couple and Impairing Tumor-Associated Angiogenesis", J. Med. Chem. 2017, v. 60, pp. 248-262.

Rika Sakai et al.: "Quantification of azide groups on a material surface and a biomolecule using a clickable and cleavable fluorescent compound", RSC Adv. 2019, v. 9, pp. 4621-4625.

M.R Mahmoud et al,: "Synthesis and spectral study of novel benzopyrone and quinolinone derivatives", J. Chem. Res. 2013, v. 37, pp. 535-541.

J. Chem. Res. 2013, v. 37, pp. 535-541.

* cited by examiner

*Primary Examiner* — Rei Tsang Shiao
(74) *Attorney, Agent, or Firm* — Ice Miller LLP

(57) ABSTRACT

The present invention relates to the field of biomedicine, and specifically relates to an "LC3 binding portion-lipid droplet binding portion-conjugate" formed by means of covalently linking a structure capable of binding LC3 and a structure capable of binding lipid droplets, and a pharmaceutically acceptable salt, stereoisomer, solvate, polymorph, tautomer, isotope compound, metabolite or prodrug thereof, and the use thereof in the preparation of drugs for preventing or treating lipid metabolism-related diseases.

22 Claims, 22 Drawing Sheets

Specification includes a Sequence Listing.

COMPOUND FOR PREVENTING OR TREATING LIPID METABOLISM-RELATED DISEASES

CROSS-REFERENCE TO RELATED APPLICATION

This application is a Section 371 of International Application No. PCT/CN2021/089453 filed Apr. 23, 2021, which was published in the Chinese language Oct. 28, 2021, under International Publication No. WO 2021/213518 A1, which claims priority to Chinese Patent Application No. 202010328911.2 filed Apr. 23, 2020, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "065812-45US1 Sequence Listing" and a creation date of Feb. 10, 2023 and having a size of 5 kb. The sequence listing submitted via EFS-Web is part of the specification and is herein incorporated by reference in its entirety.

TECHNICAL FIELD

The present disclosure relates to the biomedical field, and in particular to a compound of formula (I), or a pharmaceutically acceptable salt, stereoisomer, solvate, polymorph, tautomer, isotopic compound, metabolite, or prodrug thereof, and use for the manufacture of a medicament for preventing or treating of a lipid metabolism related disease.

BACKGROUND

The lipid droplet (LD) (also known as liposome), which is present in all cells, is a conserved organelle for intracellular neutral lipid storage. The compositions of neutral lipids may vary in different tissues but are mainly triglyceride and sterol ester. The lipid droplet is a highly dynamic organelle that not only stores neutral lipids, but also participates in various physiological processes as well as various pathological processes, such as metabolic disturbance, immune response and pathogen infection, the quantity and level of which are relevant with various diseases. Many common metabolic diseases, such as metabolic syndrome, obesity or the like often result in abnormal accumulation of lipid droplets in non-adipose tissue. For example, the abnormal accumulation of lipid droplets in the liver is also known as hepatic steatosis. Recent reports suggest that the deposition of lipid droplets (LDs) in cells is involved in lipotoxicity and prior to neurodegeneration.

Many diseases are caused by overly high levels of lipid droplets in specific cells or tissues. For such diseases, a common treating strategy is to reduce lipid or lipid droplet levels. Some methods are currently used to control lipid or lipid droplet levels but most of them are in the basic research stage and have poor specificity. Therefore, a feasible therapeutic strategy is to use a compound for controlling lipid or lipid droplet levels by reducing the number and size of lipid droplets (compound for abbreviation).

Therefore, it is desirable in the art for a compound that can be used to treat or prevent a lipid droplet related disease.

SUMMARY

In an aspect, provided is a compound of formula (I) or a pharmaceutically acceptable salt, stereoisomer, solvate, polymorph, tautomer, isotopic compound, metabolite, or prodrug thereof,

LCM-L-TM (I)

wherein:

LCM is a LC3 binding moiety;

L is a linker moiety;

TM is a lipid droplet binding moiety.

The LCM moiety is a moiety with affinity to LC3 protein, and the TM moiety is a moiety which can interact non-covalently with the lipid droplet.

In another aspect, provided is use of the compound of formula (I), or a pharmaceutically acceptable salt, stereoisomer, solvate, polymorph, tautomer, isotopic compound, metabolite, or prodrug thereof, or the pharmaceutical composition according to the present disclosure, for the manufacture of a medicament for treating a lipid metabolism related disease. In an embodiment, the lipid metabolism related disease is selected from the group consisting of MADD, obesity, NAFLD, type II diabetes, hepatocellular carcinoma, Alzheimer's disease and atherosclerosis.

In another aspect, provided is a process for preparing the compound according to the present disclosure, comprising: covalently linking a structure moiety capable of binding to LC3 and a structure moiety capable of binding to a lipid droplet, to form a "LC3 binding moiety-lipid droplet binding moiety conjugate" ("conjugated compound").

In yet another aspect, provided is a method for reducing lipid droplets in a cell, comprising contacting a conjugated compound comprising a LC3 binding moiety and a lipid droplet binding moiety with a cell or tissue comprising the lipid droplets, wherein the lipid droplets are contained by the cell under physiological or pathological conditions and/or produced by the cell under induction. In an embodiment, the conjugated compound is the compound of formula (I), or a pharmaceutically acceptable salt, stereoisomer, solvate, polymorph, tautomer, isotopic compound, metabolite, or prodrug thereof.

BRIEF DESCRIPTION OF THE DRAWINGS

In the accompanying drawings, C1 denotes Compound 1A, C2 denotes Compound 2A, C3 denotes Compound 3A, C4 denotes Compound 4A, C5 denotes Compound 5A, C6 denotes Compound 6, C7 denotes Compound 7, C8 denotes Compound 8, C9 denotes Compound 9, C10 denotes Compound 10A, C11 denotes Compound 11A, and OA denotes sodium oleate. SIV or ORBB denotes Sudan IV (Oil Red BB), SIII denotes Sudan III, GW5074 denotes Compound A1, DP or AN2 denotes Compound A5, and Linker denotes 10-bromo-1-decanol.

DETAILED DESCRIPTION

Figure 1:
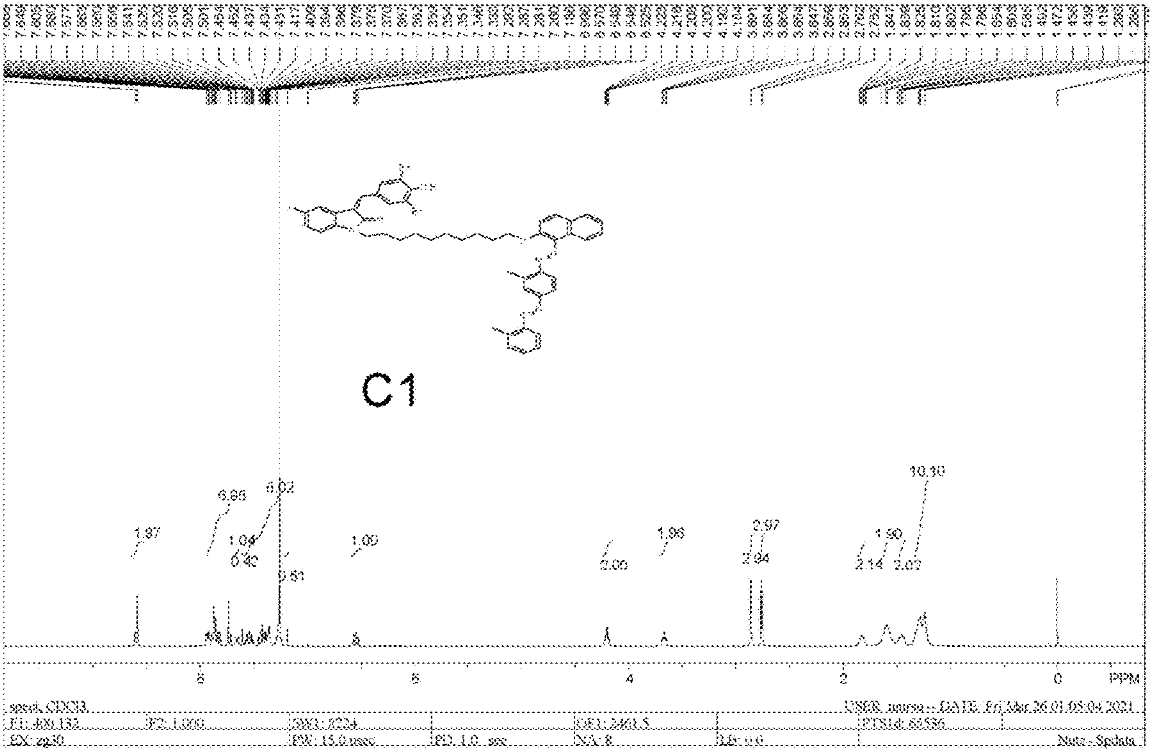
FIG. 1: $^1$H NMR and $^1$H-$^1$H NOESY spectrums of Compound 1A. Among them, two auxiliary lines intersecting at right angles and the auxiliary circle at the intersection in the $^1$H-$^1$H NOESY spectrum show the signals associated with Ha and Hb in the figure.
Figure 1:
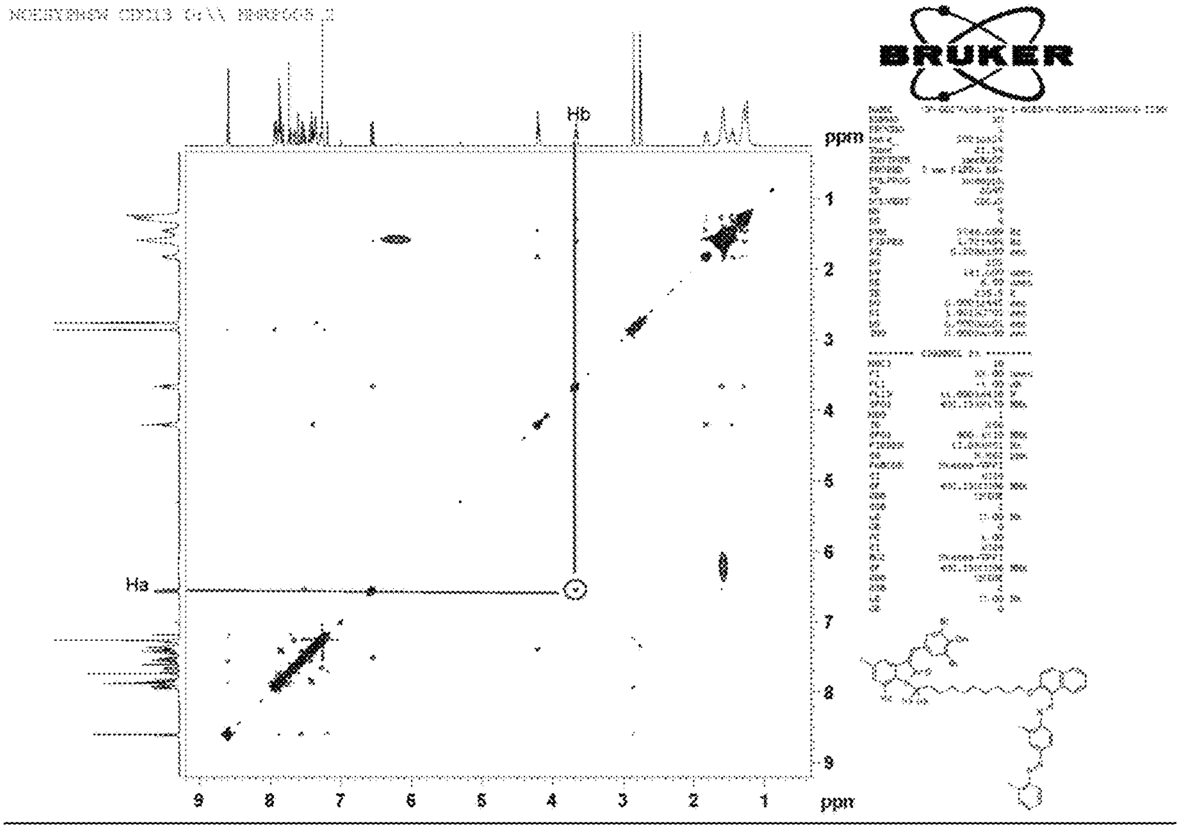

Unless otherwise defined, all technical and scientific terms used herein have the same meaning as commonly understood by one of ordinary skill in the art to which this disclosure belongs. In case of any contradiction, the definition provided in this application shall prevail.

When a trade name appears herein, it is intended to refer to its corresponding commercial product or its active ingredient. All patents, published patent applications, and publications cited herein are incorporated by reference.

General Terms and Definitions

Unless otherwise defined, all technical and scientific terms used herein have the same meaning as commonly understood by one of ordinary skill in the art to which this disclosure belongs. In case of any contradiction, the definition provided in this application shall prevail.

When a trade name appears herein, it is intended to refer to its corresponding commercial product or its active ingredient. All patents, published patent applications, and publications cited herein are incorporated by reference.

The term "include", "comprise", "have", "contain" or "relate to" and other variants used herein are meant to be inclusive or open-ended, which does not exclude other unlisted elements or method steps. It should be understood by one of ordinary skill in the art that the above-mentioned terms like "comprise" encompass the expression "consist of".

The term "one or more" or the similar term "at least one" refers to e.g., 1, 2, 3, 4, 5, 6, 7, 8, 9, 10 or more.

When the lower and upper limits of a numerical range are disclosed, any numerical value and any inclusive range falling within that range is specifically disclosed. In particular, every range of values disclosed herein should be understood to mean every value and range that falls within the broader range.

The expression m-n as used herein refers to the range of m to n and the sub-ranges consisting of each point value therein and each point value. For example, the expression "$C_1$-$C_8$" or "$C_{1-8}$" covers the range of 1-8 carbon atoms and should be understood to also cover any subrange and each point value, such as $C_2$-$C_5$, $C_3$-$C_4$, $C_1$-$C_2$, $C_1$-$C_3$, $C_1$-$C_4$, $C_1$-$C_5$, $C_1$-$C_6$, $C_1$-$C_7$, etc., and $C_1$, $C_2$, $C_3$, $C_4$, $C_5$, $C_6$, $C_7$, $C_8$, ect. For example, the expression "$C_3$-$C_{10}$" or "$C_{3-10}$" should also be understood in a similar manner, for example, it can cover any subrange and point value contained therein, such as $C_3$-$C_9$, $C_6$-$C_9$, $C_6$-$C_8$, $C_6$-$C_7$, $C_7$-$C_{10}$, $C_7$-$C_9$, $C_7$-$C_8$, $C_5$-$C_9$, etc., and $C_3$, $C_4$, $C_5$, $C_6$, $C_7$, $C_8$, $C_9$, $C_{10}$, etc. For another example, the expression "3- to 10-membered" should be understood as covering any subrange and each point value, such as 3- to 5-membered, 3- to 6-membered, 3- to 7-membered, 3- to 8-membered, 4- to 5-membered, 4- to 6-membered, 4- to 7-membered, 4- to 8-membered, 5- to 7-membered, 5- to 8-membered, 6- to 7-membered, 6- to 8-membered, 9- to 10-membered, etc., and 3-, 4-, 5-, 6-, 7-, 8-, 9-, 10-membered, etc. Other similar expressions herein should also be understood in a similar manner.

The terms "optional" or "optionally" mean that the subsequently described event or circumstance may or may not occur, and that the description includes both the occurrence and the non-occurrence of said event or circumstance.

The terms "substitute" and "substituted" mean that one or more (e.g., one, two, three or four) hydrogen on the specified atom is replaced by selection from the indicated group, provided that the normal atomic valence of the specified atom in the current situation is not exceeded and the substitution forms a stable compound. Combinations of substituents and/or variables are permissible only if such combinations form stable compounds. When describing that a substituent is absent, it should be understood that the substituent can be one or more hydrogen atoms, provided that the structure can result in a stable state of the compound.

When each carbon atom in a group is described as can be optionally substituted by a heteroatom, provided that not exceeding the normal valence of all the atoms in the group under the circumstance and forming a stable compound.

If a substituent is described as "optionally substituted," the substituent may be unsubstituted, or it may be substituted. If an atom or group is described as optionally substituted by one or more substituents of the list of the substituents, one or more hydrogen on the atom or group may be replaced by an independently selected, optional substituent. When the substituent is oxo (i.e., =O), it means that two hydrogen atoms are substituted.

Unless indicated, as used herein, the point of attachment of a substituent can be from any suitable position on the substituent. When a bond of a substituent is shown to pass through a bond connecting two atoms in a ring, such substituent can bond to any of the ring-forming atoms in the substitutable ring.

When any variable (such as R), as well as variables with markers (such as $R^{X1}$, $R^{X2}$, $R^{X3}$, $R^2$, $R^7$, $R^8$, $R^{a1}$, $R^{b1}$, $R^{c1}$, $R^{a2}$, $R^{b2}$, $R^{c2}$, $R^{19}$, $R^E$, $R^F$, $R^G$, $R^{a1}$, $R^b$, $R^c$, $R^d$, etc.) appear more than once in the composition or structure of the compound, its definition in each case is independent at each occurrence. For example, if a group is substituted with 0, 1, 2, 3, or 4R substituents, the group may optionally be substituted with up to four R substituents, and all the options of R substituent are all independent of each other.

The term "halo" or "halogen" or "halogenated" should be understood to mean a fluorine (F), chlorine (Cl), bromine (Br) or iodine (I) atom, preferably a fluorine, chlorine, bromine atom.

The term "alkyl" refers to a straight or branched saturated aliphatic hydrocarbon group composed of carbon atoms and hydrogen atoms, which is connected to the rest of the molecule by a single bond. "Alkyl" may have 1-8 atoms, referring to "$C_1$-$C_8$ alkyl", for example, $C_{1-4}$ alkyl, $C_{1-3}$ alkyl, $C_{1-2}$ alkyl, $C_3$ alkyl, $C_4$ alkyl, $C_{1-6}$ alkyl, $C_{3-6}$ alkyl. Non-limiting examples of alkyl groups include, but are not limited to methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or their isomers. "-ylene" or "-ylidene" refers to a group having two linkage sites to the rest of the molecule, which is obtained by removal of one hydrogen atom from the carbon atom with the free valence. For example, "alkylene" or "alkylidene" refers to a saturated linear or branched divalent hydrocarbon group. When the described groups are interconnected, it should be understood that each interconnected groups thereby have increased linkage sites. For example, when an alkyl is further linked to other groups, such that the alkyl has two linkage sites, the alkyl can be considered to be formed as an alkylene.

The term "alkylene", when used alone or in combination with other groups herein, refers to a straight or branched saturated divalent hydrocarbon group. For example, the term "$C_{1-8}$ alkylene" refers to an alkylene having 1-8 carbon atoms, for example, methylene, ethylene, propylene, butylene, pentylene, hexylidene, 1-methylethylene, 2-methylethylene, methylpropylene or ethylpropylene, etc. The term "cycloalkylene" refers to a saturated circular divalent hydrocarbon group. For example, term "$C_{3-6}$ cycloalkylene" refers to a cycloalkylidene having 3-6 carbon atoms, for example, cyclopropylene, cyclobutylene, cyclopentylene, cyclohexylene, etc. The term "alkoxylene" refers to "—O-alkylene" or "alkylene-O—". Examples of "$C_{1-8}$alkoxylene" include but not limited to —O-methylene, —O-ethylene, —O-propylene, —O— butylene, methylene-O—, ethylene-O—, propylene-O—, butylene-O—, etc.

The term "alkenyl" refers to a straight or branched unsaturated aliphatic hydrocarbon group consisting of carbon atoms and hydrogen atoms with at least one double bond. The alkenyl group may have 2-8 carbon atoms, referring to, "$C_{2-8}$ alkenyl", for example, $C_{2-4}$ alkenyl, $C_{3-4}$ alkenyl. Non-limiting examples of alkenyl groups include, but are not limited to ethenyl, allyl, (E)-2-methylethenyl, (Z)-2-methylethenyl, (E)-but-2-enyl, (Z)-but-2-enyl, (E)-but-1-enyl, (Z)-but-1-enyl, etc. When an alkenyl is further linked to other groups such that the alkenyl has two linkage sites, the alkenyl can be considered to be formed as an alkenylene.

The term "alkynyl" refers to a straight or branched unsaturated aliphatic hydrocarbon group consisting of carbon atoms and hydrogen atoms with at least one triple bond. The alkynyl group may have 2-8 carbon atoms, referring to "$C_{2-8}$ alkynyl", for example, $C_{2-4}$ alkynyl, $C_{3-4}$ alkynyl. Non-limiting examples of alkynyl groups include, but are not limited to ethynyl, prop-1-ynyl, prop-2-ynyl, but-1-ynyl, but-2-ynyl, but-3-ynyl, etc. When an alkynyl is further linked to other groups such that the alkynyl has two linkage sites, the alkynyl can be considered to be formed as an alkynylene.

The term "cyclohydrocarbyl" refers to a saturated or unsaturated non-aromatic cyclic hydrocarbon group consisting of carbon atoms and hydrogen atoms, preferably containing 1 or 2 rings. The cycloalkyl may be a monocyclic, fused polycyclic, bridge ring or spirocyclic structure. The cyclohydrocarbyl group may have 3-10 carbon atoms, i.e., "$C_{3-10}$cyclohydrocarbyl", for example, $C_{3-8}$ cyclohydrocarbyl, $C_{3-6}$ cyclohydrocarbyl, $C_5$ cyclohydrocarbyl, $C_6$ cyclohydrocarbyl, $C_7$ cyclohydrocarbyl. Non-limiting examples of cycloalkyl groups include, but are not limited to, cyclopropyl, cyclobutyl, cyclopentyl, cyclohexyl, cycloheptyl, bicyclo[2.2.1]heptyl, spiro[3.3]heptyl, etc. The term also covers situations where the C atom can be substituted by oxo (═O). When a cyclohydrocarbyl is further linked to other groups such that the cyclohydrocarbyl has two linkage sites, the cyclohydrocarbyl can be considered to be formed as a cyclohydrocarbylene.

The term "cycloalkyl" refers to a saturated cyclohydrocarbyl. "Cycloalkyl" may have 3-carbon atoms, i.e., "$C_{3-10}$ cycloalkyl", for example $C_{3-8}$ cycloalkyl, $C_{3-6}$ cycloalkyl, $C_5$ cycloalkyl, $C_6$ cycloalkyl, $C_7$ cycloalkyl. When a cycloalkyl is further linked to other groups such that the cycloalkyl has two linkage sites, the cycloalkyl can be considered to be formed as a cycloalkylene.

The term "heterocyclyl" or "heterocyclic hydrocarbon group" refers to a monocyclic or bicyclic ring system having, for example, 3-10 (suitably 3-8, more suitably 3-7, especially 4-6) ring atoms (3- to 10-membered, 3- to 8-membered, 3- to 7-membered, 4- to 6-membered), in which at least one of ring atoms (for example, 1, 2 or 3) is a heteroatom selected from the group consisting of N, O, S and P, and the remaining ring atoms are C. The ring system may be saturated (also understood as the corresponding "heterocycloalkyl") or unsaturated (i.e., having one or more double and/or triple bonds within the ring). "Heterocyclyl" or "heterocyclic hydrocarbon group" does not possess aromaticity. The term also covers situations where the C atom can be substituted with oxo (═O) and/or the S atom on the ring can be substituted with 1 or 2 oxo (═O) and/or the P atom on the ring can be substituted with 1 or 2 oxo (═O). When a heterocyclyl is further linked to other groups such that the heterocyclyl has two linkage sites, the heterocyclyl can be considered to be formed as a heterocyclylene.

The heterocyclyl may be, for example, a 4-membered ring, such as azetidinyl, oxetanyl, or a 5-membered ring, such as tetrahydrofuranyl, dioxolinyl, pyrrolidinyl, imidazolidinyl, pyrazolidinyl, pyrrolinyl, oxopyrrolidinyl, 2-oxo-imidazolidin-1-yl; or 6-membered ring, such as tetrahydropyranyl, piperidinyl, morpholinyl, dithianyl, thiomorpholinyl, piperazinyl, 1,1-dioxo-1,2-thiazinan-2-yl or trithianyl; or a 7-membered ring, such as a diazepine ring. Optionally, the heterocyclyl may be benzo-fused.

The heterocyclyl may be bicyclic without limitation, for example, a 5-membered fused 5-membered ring, such as hexahydrocyclopentane[c]pyrrole-2(1H)-yl ring; or a 5-membered fused 6-membered bicyclic ring, such as hexahydropyrrolo[1,2-a]pyrazine-2(1H)-yl ring.

As mentioned above, the heterocycle may be unsaturated; that is to say, it may contain one or more double bonds without limitation. For example, an unsaturated heterocycle containing a nitrogen atom may be 1,6-dihydropyrimidine, 1,2-dihydropyrimidine, 1,4-dihydropyrimidine, 1,6-dihydropyridine, 1,2-dihydropyridine, 1,4-dihydropyridine, 2,3-dihydro-1H-pyrrole, 3,4-dihydro-1H-pyrrole, 2,5-dihydro-1H-pyrrolyl, 4H-[1,3,4]thiadiazinyl, 4,5-dihydrooxazolyl or 4H-[1,4] thiazinyl ring. An unsaturated heterocycle containing an oxygen atom may be 2H-pyran, 4H-pyran, or 2,3-dihydrofuran, and the unsaturated heterocycle containing a sulfur atom may be 2H-thiopyran or 4H-thiopyran. The heterocycle can be benzo-fused, but not limited thereto, such as dihydroisoquinolinyl ring.

The term "aryl" refers to an all-carbon monocyclic or fused polycyclic (such as bicyclic) aromatic ring group with a conjugated 2-electron system. For example, aryl may have 6-14 carbon atoms, suitably 6-10, more suitably 6 or 10. Examples of aryl include, but are not limited to, phenyl, naphthyl, anthracenyl, etc. When an aryl is further linked to other groups such that the aryl has two linkage sites, the aryl can be considered to be formed as an arylene.

The term "heteroaryl" should be understood to preferably mean a monovalent monocyclic, bicyclic, or tricyclic aromatic ring system having 5, 6, 7, 8, 9 or 10 ring atoms ("5- to 10-membered heteroaryl"), especially 5 or 6 or 9 or 10 ring atoms, and at least one (suitably 1-4, more suitably 1, 2 or 3) of the ring atoms are heteroatoms, which may be the same with or different form each other, for example, oxygen, nitrogen, or sulfur. In addition, the heteroaryl can be benzo-fused in each case. In particular, the heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl, etc., and their benzo derivatives, such as benzofuranyl, benzothienyl, benzoxazolyl, benzisoxazolyl, benzimidazolyl, benzotriazolyl, indazole, indolyl, isoindolyl, etc.; or pyridyl, pyridazinyl, pyrimidinyl, pyrazinyl, triazinyl, etc., and their benzo-fused derivatives, such as quinolinyl, quinazolinyl, isoquinolinyl, etc., or azocinyl, indolizinyl, purinyl, etc., and their benzo derivatives; or cinnolinyl, phthalazinyl, quinazolinyl, quinoxalinyl, naphthyridinyl, carbazolyl, acridinyl, etc. when a heteroaryl is further linked to other groups such that the heteroaryl has two linkage sites, the heteroaryl can be considered to be formed as an heteroarylene.

The term "hydrocarbon chain" refers to a chain-like group composed of carbon atoms and hydrogen atoms, which may be straight or branched. The hydrocarbon chain can be saturated (i.e., alkylene) or unsaturated; that is to say, it may contain one or more (preferably one) carbon-carbon double bond or triple bond. Non-limiting examples of alkylene include but are not limited to methylene ($—CH_2—$), 1,1-ethylene ($—CH(CH_3)—$), 1,2-ethylene ($—CH_2CH_2—$), 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$), 1,7-heptylene ($—CH_2CH_2CH_2CH_2CH_2CH_2CH_2—$) etc.

When a chemical bond herein is depicted to be linked to a certain molecule or a certain moiety of a certain molecule, if the specific atom that linked by the chemical bond is not depicted, it means any atom of the molecule or the moiety to which the chemical bond can be linked, provided that a stable structure can be formed. For example, a certain moiety of a molecule can be depicted, and it can be deposed in a bracket, such as parenthesis or square brackets; when other moieties of the molecule are depicted to be linked to the moiety in bracket through chemical bond, if the specific atom in the bracket to which the chemical bond is linked is not depicted, it means that the chemical bond can link any atom of the moiety in the bracket, provided that a stable structure can be formed.

The term "pharmaceutically acceptable" refers to that when contacted with the patient's tissue within the scope of normal medical judgment without undue toxicity, irritation, allergic reactions, etc., having reasonable advantage-disadvantage ratios and effective for the intended use.

The pharmaceutically acceptable salts of the compound of the present invention include acid addition salts and base addition salts thereof. Suitable acid addition salts are formed from acids that form pharmaceutically acceptable salts. Examples include hydrochloride, acetate, aspartate, benzoate, bicarbonate/carbonate, glucoheptonate, gluconate, nitrate, orotate, palmitic acid salt and other similar salt. Suitable base addition salts are formed from bases that form pharmaceutically acceptable salts. Examples include aluminum salts, arginine salts, choline salts, magnesium salts, and other similar salts. The method for preparing the pharmaceutically acceptable salt of the compound of the present disclosure is known to those skilled in the art.

The compound of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and their racemic mixtures and other mixtures, for example, mixtures enriched in enantiomers or diastereomers, all of which are within the scope of the present disclosure. There may be other asymmetric carbon atoms in substituents such as alkyl. All these isomers and their mixtures are included in the scope of the present disclosure. In some embodiments, the preferred compounds are those isomeric compounds that show better biological activity. Purified or partially purified isomers and stereoisomers, or racemic mixtures or diastereomeric mixtures of the compound of the present disclosure are also included in the scope of the present disclosure. The purification and separation of such substances can be achieved by standard techniques known in the art.

Optically pure enantiomers can be obtained by resolving racemic mixtures according to conventional methods, for example, by using optically active acids or bases to form diastereomeric salts, or by forming covalent diastereomers. A mixture of diastereomers can be separated into single diastereomer based on their physical and/or chemical differences by methods known in the art (for example, by chromatography or fractional crystallization). Then, the optically active enantiomeric base or acid are released from the separated diastereomeric salt. Another method for separating racemic enantiomers can use chiral chromatography (such as a chiral HPLC column). The separated chiral isomers can be subjected to conventional derivatization or non-derivatization before separation, depending on what method can achieve more effective separation of chiral isomers. Enzymatic methods can also be used to separate derivatized or underivatized chiral isomers. Similarly, optically active raw materials can be used to obtain the optically pure compound of the present disclosure through chiral synthesis.

In addition, the compound of the present disclosure may exist in the form of tautomers. The present disclosure includes all possible tautomers of the compound of the present disclosure, and also includes single tautomers or the form of any mixtures of said tautomers in any ratio.

The compound of the present disclosure may exist in the form of solvates (preferably hydrates), wherein the compound of the present disclosure contains a polar solvent as a structural element of the compound crystal lattice, especially for example water, methanol, or ethanol. Amount of polar solvents, especially water, can be present in stoichiometric or non-stoichiometric ratios.

The present disclosure also covers all possible crystalline forms or polymorphs of the compound of the present disclosure, which can be a single polymorph or a mixture of more than one polymorph in any ratio.

The present disclosure also contemplates all pharmaceutically acceptable isotopically labeled compounds, which are identical to the compounds of the invention except that one or more atoms are replaced by the atom(s) of the same atomic number but having atomic mass or mass number different from the atomic mass or mass number prevailing in nature.

The metabolites of the compound of the present disclosure are also included within the scope of the present disclosure, namely the substances formed in the body when the compound of the present disclosure is administered. The metabolites of compounds can be identified by techniques known in the art, and their activity can be characterized by experimental methods. Such products can be produced, for example, by oxidation, reduction, hydrolysis, amidation, deamidation, esterification, enzymatic hydrolysis, etc. of the administered compound. Therefore, the present disclosure includes metabolites of the compound of the present disclosure, including compounds prepared by contacting the compound of the present disclosure with a mammal for a time sufficient to produce its metabolites.

The present disclosure further includes within its scope the prodrugs of the compound of the present disclosure, which are certain derivatives of the compound of the present disclosure that have less or no pharmacological activity themselves but when administered to or on the body, can be converted into the compound of the present disclosure with the desired activity by, for example, hydrolytic cleavage. Usually, such prodrugs will be functional group derivatives of the compound, which are easily converted into the desired therapeutically active compound in vivo. For a review of prodrugs and their preparation methods, see, for example, J. Rautio et al. Nature Reviews Drug Discovery (2008) 7, 255-270 and Prodrugs: Challenges and Rewards (V. Stella et al. ed. Springer, 2007). The prodrugs of the present disclosure can be prepared, for example, by replacing an appropriate functional group in the compound of the present disclosure with a certain moiety known to those skilled in the art as “pro-moiety”.

The term “polymorphism” or “polymorph” refers to a single polymorph or a mixture of more than one polymorph in any ratio.

The term “crystal form” or “crystal” refers to any solid substance exhibiting a three-dimensional order, as opposed to amorphous solid substance, which produces a characteristic X-ray powder diffraction pattern with well-defined peaks.

The term “amorphous” refers to any solid substance which lacks order in three dimensions.

The term “hydrate” describes a solvate containing a drug and a stoichiometric or non-stoichiometric amount of water.

The term “pharmaceutically acceptable carrier” refers to those substances that have no obvious stimulating effect on the organism and will not damage the biological activity and performance of the active compound. “Pharmaceutically acceptable carriers” include, but are not limited to, glidants, sweeteners, diluents, preservatives, dyes/colorants, flavoring agents, surfactants, wetting agents, dispersing agents, disintegrating agents, stabilizers, solvents or emulsifiers. Non-limiting examples of the carrier include calcium carbonate, calcium phosphate, various sugars and various starches, cellulose derivatives, gelatin, vegetable oils and polyethylene glycols, etc.

The terms “administration” or “administrate” and the like refer to methods by which a compound or composition can be delivered to the desired site of biological action. Such methods comprise but not limited to oral or parenteral (including intracerebroventricular, intravenous, subcutaneous, intraperitoneal, intramuscular, intravascular injection or infusion), local, rectal administration, etc. Especially injection or oral.

As used herein, the terms “treat” includes alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, promoting the remission of the disease or condition, or stopping the symptoms of the disease or condition, and are intended to include prophylaxis. “Treat” further include achieving a therapeutic benefit and/or a prophylactic benefit. Therapeutic benefit is meant eradication or amelioration of the condition being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. Prophylactic benefit is meant the compositions may be administered to a patient for the prevention of certain disease risk, or to a patient reporting one or more of the physiological symptoms of a disease, even though a diagnosis of this disease may not have been made.

The terms “active ingredient”, “therapeutic agent”, “active substance” or “active agent” refer to a chemical entity that can effectively treat or prevent the target disorder, disease, or symptom.

For drugs, drug units or active ingredients, the terms “effective amount”, “therapeutically effective amount” or “prophylactically effective amount” refer to an amount of a drug or agent that has acceptable side effects but is sufficient to achieve the desired effect. The effective amount may be determined individually and depends on the age and general condition of the receptor as well as specific active substance. The effective amount in specific case can be determined by a person skilled in the art through conventional test.

As used herein, the term “subject” includes a human or non-human animal. An exemplary human subject includes a human subject having a disease (such as one described herein) (referred as a patient), or a normal subject. The term “non-human animal” as used herein includes all vertebrates, such as non-mammals (e.g., birds, amphibians, reptiles) and mammals, such as non-human primates, livestock and/or domesticated animals (such as sheep, dog, cat, cow, pig and the like).

Lipid droplet (LD) is a conservative organelle that stores neutral lipids in a cell. The lipid droplet has a monolayer phospholipid membrane on its surface, and a lipid droplet protein is embedded on the monolayer phospholipid membrane. In different tissues, the neutral lipid stored in a lipid droplet may have a different composition, however, it mainly comprises triglyceride and sterol ester. According to the cell types, some other endogenous neutral lipid (for example retinyl ester, ether lipid and free cholesterol) may also stored in LD. The main proteins on the surface of a lipid droplet are, for example Perilipin family proteins (PAT family proteins), and their members include, for example Perilipin1, Perilipin2 (PLIN2, also referred as Adipophilin or ADRP), Perilipin3 (PLIN3, also referred as TIP47), Perilipin4 (PLIN4, also referred as S3-12), Perilipin5 (PLIN5, or OXPAT/LSDP5).

The term “lipid” refers to an organic compound with lipophilicity or amphipathicity. The term “lipid” herein specifically refers to lipophilic organic compound that present in vivo. Wherein, the lipid molecule with acidic groups, such as carboxyl group, phosphoric acid/phosphate ester group, sulfonic acid group, is an acidic lipid, and examples of acidic lipid include but not limited to fatty acid and phospholipid. The lipid molecule without acidic groups is neutral lipid, and examples of neutral lipid include but no limited to triglyceride, steroid (for example sterol), steroid ester (for example sterol ester), ether lipid, neutral glycolipid. Examples of sterol include but not limited to cholesterol. Examples of ether lipid include but not limited to alkyl glycerol (AKG), alkyl-phospholipid. The neutral lipid herein specifically refers to those stored in lipid droplet.

The term “steroid”, also known as steroid, refers to cyclopentane polyhydrophenanthrene derivatives. The term “sterol” refers to a steroid having alcoholic hydroxyl group, also known as sterols. The sterol is preferably a sterol comprising 3-OH, for example cholesterol. (Also known as cholesterin).

The term “steroid ester” or “sterol ester” refers to an ester that formed by steroid (sterol) comprising alcoholic hydroxyl group with acid, especially the ester formed with fatty acid. Examples of steroid ester include but not limited to cholesterol ester, for example cholesterol oleate, cholesterol linoleate, etc.

The term “lipid droplet probe” refers to a known small molecule for use in indicating lipid droplet. Some lipid droplet probes can be detected by light signal under suitable conditions. The light signal can be fluorescent, and its wavelength can be within visible light region, or it can be invisible to naked eyes, such as infrared, near infrared, etc. Preferably, “lipid droplet probe” tends to be distributed in lipid, rather than in an aqueous phase. It should be understood that with respect to some environmentally sensitive probes, although they can emit a stronger signal in a lipophilic environment, it does not mean that they tend to be distributed in lipid.

The term "lipid droplet binding structure", "lipid droplet binding compound", "lipid droplet binding moiety" refer to a structure, compound or molecule moiety that is capable of binding to a lipid droplet, and it preferably binds lipid droplet selectively in cells. The lipid droplet binding compound herein includes a known lipid droplet probe, a compound that is capable of binding to lipid droplet marker protein, or a compound that is capable of binding to neutral lipid in lipid droplet. Wherein, lipid droplet marker protein includes but not limited to Perilipin2 (PLIN2, also referred as Adipophilin or ADRP, PMID: 30351430), Perilipin3 (PLIN3, also referred as TIP47, PMID: 25961502). Compound that is capable of binding to a neutral lipid in lipid droplet includes but not limited to steroid and steroid ester. Lipid droplet probe includes but not limited to lipid droplet specific probe and probe that preferably points to lipid droplet in cells, preferably is lipid droplet specific probe. Examples of lipid droplet specific probe include but not limited to lipophilic dye molecule that has affinity with lipid droplet, for example the following molecules reported by Fam, et al. ("Recent Advances in Fluorescent Probes for Lipid Droplets." *Materials* (2018), 11, 1768): azo dye that has affinity with lipid droplet (for example Sudan I, Sudan II, Sudan III, Oil Red BB (also referred as Sudan IV)), Oil Red O (also referred as Sudan 5B), Sudan Red G, Sudan Black B (also referred as Solvent Black 3), Nile Red, BODIPY® 493/503, monodansylpentane(compatible in multicolor, MDH), PyrPy 10d, PyrPy 11c, PITE (pyroindole-tetraphenylethylene hybrid), TPE-AmAl, TPA-BI, LipidGreen, LipidGreen2, LD540, AF8, AF10, AFN, NAP AIEgen dye (for example, NAP-Ph, NAP-Br, NAP-CF3, NAP-Py), LD-BTD1, LipiDye, Phos 2a, Phos 2b, Phos 3a, Phos 3b, SF44, SF58, FAS, DPAS, BTD-Coumarin Hybrid (for example, BTD-Lip), IND-TPA, photoactivatable AIE probe (for example, BZT 3a, BZT 4a), LD-TPZn, LQD, photoactivatable AIEgen probe (for example, PhotoAFN 2a-c), TPE-AC, TPMN, TTMN, MeTTMN, MeOTTMN, DCMa, DCI, DCFu, NLV-1, StatoMerocynaine dye (SMCy dye, for example, SMCy 3, SMCy 5.5).

LC3 protein refers to the microtubule-associated protein 1 light chain 3 (MAP1LC3, LC3) family in the Atg8 protein family. LC3 protein preferably refers to the following members of human LC3 family: human microtubule-associated protein 1 light chain 3α (MAP1LC3A, LC3A, for instance see Uniprot Accession: Q9H492-1 and Q9H492-2), human microtubule-associated protein 1 light chain 3β (MAP1LC3B, LC3B, for instance see Uniprot Accession: Q9GZQ8) or human microtubule protein 1 light chain 3γ (MAP1LC3C, LC3C, for instance see Uniprot Accession: Q9BXW4), specifically LC3A and LC3B, especially LC3B.

LC3 protein, for example, LC3A, LC3B and LC3C can be located on the membrane of preautophagosome and autophagosome and are essential proteins during autophagy process.

Forms of LC3 that can be used include LC3-I and LC3-II, but not limited thereto. Specifically, the LC3 protein that can be used includes but not limited to LC3A-I, LC3A-II, LC3B-I, LC3B-II, LC3C-I or LC3C-II, preferably LC3A-II, LC3B-I, LC3B-II, LC3C-I or LC3C-II, particularly LC3A-II, LC3B-I or LC3B-II, especially LC3B-I or LC3B-II.

Homologues of LC3 protein can be used herein, provided that it can be used in method of the present disclosure, for example the interaction with lipid droplet.

Homologues of LC3 protein as used herein may be derived from a eukaryote, for example yeast or other non-human animal, e.g., insect (such as drosophila), fish, rodent, even-toed ungulate, primate and the like. Homologue of LC3 protein may as well derived from other proteins with similar structure function, for example GABARAP and GABARAPL1, but not limited thereto. For instance, see GABARAP (Uniprot Accession: 095166) and GABARAPL1 (Uniprot Accession: Q9HOR8-1 and Q9HOR8-2), but not limited thereto.

Fragments of LC3 protein or a homologue thereof can be used herein, provided that it can be used in method of the present disclosure, for example the interaction with lipid droplet. Such fragments, for example, may have 25% or more, 30% or more, 35% or more, 40% or more, 50% or more, 60% or more, 70% or more, 80% or more, 90% or more, 95% or more or 100% identity with LC3 protein or the homologue thereof.

Proteins or fragments thereof that have identity or homology with LC3 protein, or a homologue thereof can be used to achieve the purpose of present disclosure, provided that it can be used in method of the present disclosure. For example, such interaction with lipid droplet. For example, such homology may be 25% or more, 30% or more, 35% or more, 40% or more, 50% or more, 60% or more, 70% or more, 80% or more, 90% or more, 95% or more or 100%.

In an exemplary embodiment, LC3 protein or a homologue thereof or fragments thereof has 25% or more, 30% or more, 35% or more, 40% or more, 50% or more, 60% or more, 70% or more, 80% or more, 90% or more, 95% or more, or 100% sequence identity with any one amino acid sequence in SEQ ID NO: 1 to SEQ ID NO: 4. Those skilled in the art shall understand that this may as well mean that the used LC3 protein or a homologue thereof or fragments thereof may comprise such sequences.

Those skilled in the art shall understand that modified or mature forms of LC3 protein or a homologue thereof or fragments thereof can be used. For example, in some cases, amino acid 121-125 at C-terminal of LC3 protein, such as LC3A (e.g., SEQ ID NO: 1 or SEQ ID NO: 2) or LC3B (e.g., SEQ ID NO: 3) or LC3C (e.g., SEQ ID NO: 4) are cleaved. For example, in some cases, when amino acids at C-terminal are cleaved, LC3 protein is lipidated to form the modified form of Phosphatidylethanolamine (PE). Such embodiment is also within the scope of LC3 protein described in present disclosure.

Those skilled in the art shall understand that according to actual requirement, the used LC3 protein or a homologue thereof or fragments thereof are modified or engineered to be used in present disclosure. Such solutions are as well covered within the scope of present disclosure. Such modification or engineering may include but not limited to adding tags (for example, GST or HIS) or labeling and the like, alternatively substitution, deletion, addition or replacement for some amino acids. For example, for convenience of cleaving tag, the terminal of sequence SEQ ID NO: 3 may be slightly modified or engineered, for example M of the N terminal of sequence SEQ ID NO: 3 may be replaced as GG, and then the engineered or unengineered sequence can optionally be added with a tag such as GST, there by to be used in present disclosure. Such modified or engineered sequence or a sequence that have of 25% or more, 30% or more, 35% or more, 40% or more, 50% or more, 60% or more, 70% or more, 80% or more, 90% or more, 95% or more, or 100% sequence identity with the modified or engineered sequence are as well within the scope of present disclosure.

The term "affinity activity screening" refers to the process of detecting the affinity binding process between a sample and a target. Detecting method used in affinity activity screening can be, for example, absorptiometry, radiometry (for example scintillation proximity assay), fluorometry (for example fluorescence resonance energy transfer, fluorescence polarization detection, especially for example time-resolved fluoroimmunoassay), chemiluminescence (for example amplified luminescent proximity homogeneous assay, ALPHAScreen), surface plasmon resonance (SPR, which can be conducted, for example, by using Biacore series of GE company), isothermal titration calorimetry (ITC), microscale thermophoresis (MST) or oblique-incidence reflectivity difference.

As used herein, "sequence identity" between two amino acid sequences represents the percentage of identical amino acids between the sequences. "Sequence homology" means the percentage of amino acids that are identical or represent the substitution of conservative amino acids. For sequence comparison, usually a sequence is used as the reference sequence, and the test sequence is compared with it. When using the sequence comparison algorithm, the test and reference sequences were input into the computer. If necessary, the sub sequence coordinates and sequence algorithm program parameters are specified. Based on the specified program parameters, the sequence comparison algorithm calculates the sequence identity percentage of the test sequence relative to the reference sequence. Examples of algorithms suitable for determining sequence identity and sequence similarity percentages include, but are not limited to, BLAST and BLAST 2.0 algorithms. Software for BLAST analysis is available from the National Center of Biotechnology Information (NCBI).

The term "small molecule compound", "organic small molecule", or "low molecular compound" refers to the molecule that has a comparable size with that of an organic molecule used as a medicament. The term excludes biological macromolecules (for example protein, nucleic acid and the like), but covers small molecular weight protein or derivative, for example dipeptide, tripeptide, tetrapeptide, pentapeptide, and the like.

The term "binding" as used herein refers to covalent binding or non-covalently interaction. Examples of covalent binding includes but not limited to the covalent binding via orthogonal organic chemistry action, for example Click reaction. Preferably, "LC3 binding" refers to affinity for LC3 protein (also referred as binding affinity), "lipid droplet binding" refers to non-covalent interaction with lipid droplet or component that constituting lipid droplet. Examples of non-covalent interaction includes affinity effect, ion-pair interaction, electrostatic interaction associated with dipole, hydrogen bond, 21 effect, induced dipole interaction, hydrophobic effect.

Affinity can be detected by any known method. For example, determining parameters of the binding intensity between the molecule to be tested and LC3 protein or a homologue thereof or fragments thereof. Depending on the performed binding test, the above mentioned "parameters" may be various, but particularly may be, for example, absorbance value, radioactive signal and/or radioactive signal distribution in the sample, fluorescence signal intensity and/or fluorescence signal distribution in the sample, heat change, reflected light intensity, reflected light phase change, etc.

Non-covalently interaction can be detected by any known method. For example, determining parameters of binding intensity between the molecule to be tested and neutral lipid, for example determining the distribution in the sample. Some methods can be used to predict or infer the distribution of molecules in a sample containing neutral lipids, for example, determining the solubility of molecules in neutral lipid under suitable conditions, or determining the distribution of molecules between an aqueous phase and an oil phase formed by neutral lipid under suitable conditions.

The term "LC3 binding structure", "LC3 binding compound", "LC3 binding moiety" refers to the structure, compound or molecular moiety capable of binding to LC3 protein or a homologue thereof or fragments thereof.

The term "conjugating" or "conjugated", or "attaching" an LC3 binding moiety to a lipid droplet binding moiety refers that moieties with specific functions are attached together through covalent attachment. For example, the expression "coupling LC3 binding moiety and lipid droplet binding moiety" refers that structure capable of binding to LC3 is attached with structure capable of binding to lipid droplet through covalent attachment, thereby forming "LC3 binding moiety-lipid droplet binding moiety conjugate", which is also referred as "conjugated compound" herein. "Unconjugated" refers that LC3 binding compound is not attached with lipid droplet binding moiety through covalent attachment, or lipid droplet binding compound is not attached with LC3 binding moiety through covalent attachment.

The term "lipid metabolism associated disease" refers to the disease that is caused by lipid metabolism disorder and/or disorder caused by vigorous lipid metabolism, particularly disease caused by metabolism disorder (for example neutral lipid metabolism disorder). Lipid metabolism associated disease includes but not limited to lipid droplet abnormal accumulation associated disease.

The term "lipid droplet abnormal accumulation associated disease" refers to disease caused by abnormal accumulation of lipid droplet in somatic cells or disease with abnormal enrichment of lipid droplet during disease pathogenesis. By detecting the contents of triglyceride and sterol in tissue, subjects suffering from lipid droplet abnormal accumulation associated disease or at risk for lipid droplet abnormal accumulation associated disease can be identified. Triglyceride and sterol are stored in lipid droplet of present discussion. Tissue or tissue separation based cell can be detect by histochemistry method, for example by Oil red O staining/BODIPY (for example BODIPY® 493/503) staining, or detected by triglyceride or sterol kit (for example commercially available kits). In a mouse model of non-alcoholic fatty liver disease (NAFLD), DAG and ceramide level in hepatocyte, heart and muscle LD increases. Examples of lipid droplet abnormal accumulation associated disease include but not limited to neutral lipid storage disease (NLSD), multiple acyl-CoA dehydrogenase deficiency (MADD) in mutated lymphoblast, obesity, intrahepatic lipid deposition (also referred as hepatic steatosis, for example NAFLD), particularly non-alcoholic steatohepatitis (NASH), type II diabetes, hepatocellular carcinoma, Alzheimer's disease, atherosclerosis and the like. Examples of NLSD includes but not limited to NLSD I (Chanarin-Dorfman syndrome), neutral lipid storage disease with myopathy (NLSDM).

Examples of lipid droplet abnormal accumulation associated disease further include, for example Cholesteryl ester storage disease (CESD), familial hypercholesterolemia, metabolic syndrome, stroke. "Condition of lipid droplet abnormal accumulation associated disease" includes symptoms of lipid droplet abnormal accumulation associated disease, and other pathological conditions or symptoms caused by lipid abnormal accumulation. Secondary hyperlipemia or dyslipidemia caused by various disease will generate "lipotoxicity", and such situation is as well included in the lipid droplet abnormal accumulation associated conditions.

The basic mechanisms of autophagy are divided into three different types: macroautophagy, chaperone mediated autophagy (CMA) and microautophagy. As used herein, "autophagy" is not specifically limited to macroautophagy, CMA, or microautophagy. Preferably, "autophagy" refers to macroautophagy. Wherein macroautophagy is not specifically limited to selective macroautophagy or non-selective macroautophagy. Some literatures refer macroautophagy form of lipid as lipid autophagy, which abbreviated as lipophagy. Some literatures consider that lipophagy can selectively identify lipid. Lipophagy is covered within the scope of "autophagy" as described herein.

The following detailed description of the disclosure is intended to illustrate non-limiting embodiments, so that other skilled in the art can more fully understand the technical solutions, principles and practical applications of the present disclosure, so that other skilled in the art can modify and implement the present disclosure in many forms to make it best suit the requirements of a particular use.

The Compound According to the Present Disclosure

In an aspect, provided is a compound of formula (I) or a pharmaceutically acceptable salt, stereoisomer, solvate, polymorph, tautomer, isotopic compound, metabolite, or prodrug thereof,

LCM-L-TM (I)

wherein:

LCM is a LC3 binding moiety;

L is a linker moiety;

TM is a lipid droplet binding moiety.

In an embodiment, the LCM moiety and the TM moiety are each independently selected from the group consisting of small molecule compounds. In a specific embodiment, LCM moiety and the TM moiety each independently have a molecular weight of about 100- about 2000 Da, preferably about 200- about 1000 Da, for example about 200- about 900 Da, about 200- about 800 Da, about 200- about 700 Da, about 200- about 600 Da, about 200- about 500 Da.

In an alternative embodiment, the TM moiety binds to a target related to a lipid droplet. The target related to a lipid droplet is a component of the lipid droplet and is preferably selected from the group consisting of a neutral lipid and a lipid droplet marker protein. In an embodiment, the neutral lipid is selected from the group consisting of triglyceride and cholesteryl ester. In an embodiment, the lipid droplet marker protein is selected from the group consisting of proteins of Perilipin family (e.g., Perilipin 1, Perilipin 2 and Perilipin 3). In another embodiment, the lipid droplet marker protein is a protein which can be detected with a commercial antibody against the lipid droplet marker protein.

In another alternative embodiment, in the compound of formula (I), the LCM moiety can be linked to one or more TM moieties, and vice versa. In the presence of multiple TM moieties, the TM moieties each can be selected independently, the TM moieties can be identical or different. In an embodiment, more than one TM moieties are present against the same target. It should be understood that multiple identical or different TM moieties can be used in a conjugated compound as desired, even for the same target. When multiple TM moieties are present, the linker L used each can also be selected independently. Among them, the target by TM moiety is a lipid droplet related target.

In an embodiment, the LCM moiety interacts with the LC3 protein, and TM moiety interacts with the lipid droplet, by increasing the recognition of the lipid droplet by an autophagosome, the lipid droplet is localized near the autophagosome and lipid droplet degradation is promoted.

In another embodiment, the TM moiety per se has no affinity for autophagosome or lysosome in cells.

LCM Moiety

In an embodiment, the LC3 binding moiety refers to a moiety that has affinity for the LC3 protein. In an embodiment, the LCM moiety has a structure of formula (1), or a pharmaceutically acceptable salt thereof:

(1)

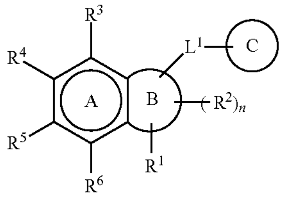

wherein:

ring A is benzene ring;

ring B is saturated or unsaturated 5- or 6-membered heterocyclic ring, the heterocyclic ring comprises 1, 2 or 3 heteroatoms each independently selected from the group consisting of N, O and S;

ring C is selected from the group consisting of $C_{6-10}$ aryl and 5- to 10-membered heteroaryl, the aryl or heteroaryl is optionally substituted with one or more groups each independently selected from the group consisting of $R^{X1}$;

$L^1$ is bond, or is $C_1$-$C_6$ hydrocarbyl chain;

or, ring C is absent and, L1 is absent;

$R^1$ is =Y, wherein Y is O or S, or is $OR^7$;

$R^2$, on each occurrence, is each independently selected from the group consisting of H, halogen, —$NO_2$, —CN, $C_{1-8}$alkyl, $C_{2-8}$alkenyl, $C_{2-8}$alkynyl, $C_{3-10}$cyclohydrocarbyl, $C_{3-10}$ cyclohydrocarbyl-$C_{1-4}$alkyl, 3- to 10-membered heterocyclyl, 3- to 10-membered heterocyclyl-$C_{1-4}$alkyl, $C_{6-10}$ aryl-$C_{1-4}$alkyl, 5- to 10-membered heteroaryl-$C_{1-4}$alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O, —NCS, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$ alkyl, $C_{2-8}$alkenyl, $C_{2-8}$alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;

$R^3$, $R^4$, $R^5$, $R^6$ are each independently selected from the group consisting of H and $R^{X2}$;

$R^{X1}$ and $R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$, —S(=O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$ alkylene-$C_{3-6}$ cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH ($C_{3-6}$cyclohydrocarbyl), —N($C_{3-6}$ cyclohydrocarbyl)$_2$, —NH($C_{1-4}$alkylene-$C_{3-6}$cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, =O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$ aryl-$C_{1-4}$alkyl, wherein the alkyl, alkenyl, alkynyl, cyclohydrocarbyl, heterocyclyl or aryl is optionally substituted with one or more substituents selected from the group consisting of halogen, —$NO_2$, —CN, $C_{1-6}$alkyl, —OH, —O($C_{1-6}$alkyl), —$NH_2$, —NH ($C_{1-6}$alkyl), —N($C_{1-6}$alkyl)$_2$, —COOH, —C(=O)O ($C_{1-6}$alkyl), —C(=O)NH($C_{1-6}$alkyl), —C(=O)N ($C_{1-6}$alkyl)$_2$, —OC(=O)($C_{1-6}$alkyl), —NHC(=O) ($C_{1-6}$alkyl), —C(=O)($C_{1-6}$alkyl);

$R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$, —S(=O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, =O and —COOH;

n is 1 or 2.

In an embodiment, $R^1$ is =O. In another embodiment, $R^1$ is =S. In another embodiment, $R^1$ is $OR^7$.

In an embodiment, ring B is saturated or unsaturated 5- or 6-membered heterocyclic ring, the heterocyclic ring comprises 1, 2 or 3 heteroatoms each independently selected from the group consisting of N, O and S. In an embodiment, ring B is saturated or unsaturated 5-membered heterocyclic ring, the heterocyclic ring comprises 1 or 2 heteroatoms each independently selected from the group consisting of N and O. In another embodiment, ring B is dihydropyrrole. In another embodiment, ring B is selected from the group consisting of 2,3-dihydro-1H-pyrrole and 3,4-dihydro-1H-pyrrole, preferably 2,3-dihydro-1H-pyrrole. In another embodiment, ring B is pyrrolidine.

In a more preferable embodiment, ring A-B system is

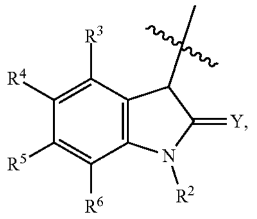

wherein Y is O or S; and ring C is 5- to 7-membered heteroaryl, preferably 5- to 6-membered heteroaryl, particularly 5-membered heteroaryl, the heteroaryl is optionally substituted with 1, 2, 3, 4 or 5 groups each independently selected from the group consisting of $R^{X1}$. In a particular embodiment, ring A-B system is ring A-B system is

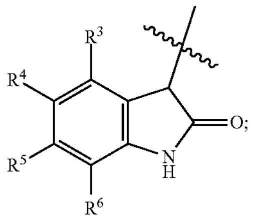

and ring C is 5- to 7-membered heteroaryl, preferably 5- to 6-membered heteroaryl, particularly 5-membered heteroaryl, the heteroaryl is optionally substituted with 1, 2, 3, 4 or 5 groups each independently selected from the group consisting of $R^{X1}$. In another embodiment, ring C comprises 1, 2, 3 or 4 heteroatoms each independently selected from the group consisting of N, O and S, preferably selected from the group consisting of N and O. In another embodiment, ring C comprises at least one N atom. In an embodiment, ring C is 5-membered heteroaryl comprising 1 or 2 N atoms, which is optionally substituted with 1, 2, 3, 4 or 5 groups each independently selected from the group consisting of $R^{X1}$. In another embodiment, ring C is selected from the group consisting of pyrrole and imidazole.

In an embodiment, ring B is saturated or unsaturated 6-membered heterocyclic ring, the heterocyclic ring comprises 1 or 2 heteroatoms each independently selected from the group consisting of N and O. In another embodiment, ring B is dihydropyrimidine. In a preferable embodiment, ring B is selected from the group consisting of 1,6-dihydropyrimidine, 1,2-dihydropyrimidine, 1,4-dihydropyrimidine.

In a more preferable embodiment, ring A-B system is

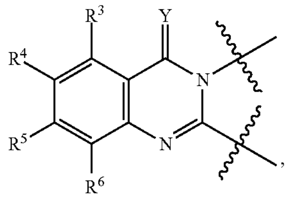
, wherein Y is O or S. In a particular embodiment, ring A-B system is

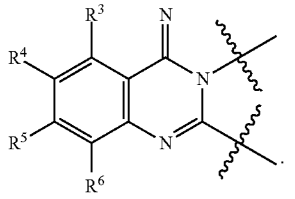
.

In another embodiment, ring B is 2H-pyran or 4H-pyran. In a preferable embodiment, ring A-B system is

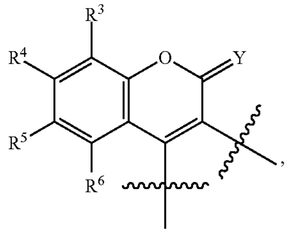
, wherein Y is O or S. In a particular embodiment, ring A-B system is

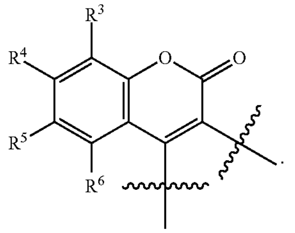
.

In another embodiment, ring C is phenyl, which is optionally substituted with 1, 2, 3, 4 or 5 groups each independently selected from the group consisting of $R^{X1}$.

In an embodiment, $L^1$ is bond. In another embodiment, $L^1$ is $C_1$-$C_6$ hydrocarbyl chain. In a preferable embodiment, $L^1$ is $C_1$-$C_2$ hydrocarbyl chain.

In an embodiment, ring A-B system is

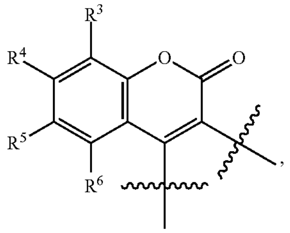
, ring C is absent, and $L^1$ is absent.

In another embodiment:

ring A is benzene ring;

ring B is saturated or unsaturated 5- or 6-membered heterocyclic ring, the heterocyclic ring comprises 1, 2 or 3 heteroatoms each independently selected from the group consisting of N, O and S;

ring C is selected from the group consisting of $C_{6-10}$ aryl and 5- to 10-membered heteroaryl, the aryl or heteroaryl is optionally substituted with one or more groups each independently selected from the group consisting of $R^{X1}$;

$L^1$ is bond, or is $C_1$-$C_6$ hydrocarbyl chain;

$R^1$ is =Y, wherein Y is O or S, or is $OR^7$;

$R^2$, on each occurrence, is each independently selected from the group consisting of H, halogen, —$NO_2$, —CN, $C_{1-8}$alkyl, $C_{2-8}$alkenyl, $C_{2-8}$alkynyl, $C_{3-10}$cyclohydrocarbyl, $C_{3-10}$ cyclohydrocarbyl-$C_{1-4}$alkyl, 3- to 10-membered heterocyclyl, 3- to 10-membered heterocyclyl-$C_{1-4}$alkyl, $C_{6-10}$ aryl-$C_{1-4}$alkyl, 5- to 10-membered heteroaryl-$C_{1-4}$alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O, —NCS, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$ alkyl, $C_{2-8}$alkenyl, $C_{2-8}$alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;

$R^3$, $R^4$, $R^5$, $R^6$ are each independently selected from the group consisting of H and $R^{X2}$;

$R^{X1}$ and $R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$, —S(=O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$ alkylene-$C_{3-6}$ cyclohydrocarbyl), —O(3- to 7-membered heterocyclyl), —O($C_{1-4}$alkylene)-(3- to 7-membered heterocyclyl), —SH, —S($C_{1-6}$alkyl), —S ($C_{3-6}$cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$ cyclohydrocarbyl)$_2$, —NH($C_{1-4}$alkylene-$C_{3-6}$cyclohydrocarbyl), —N($C_{1-4}$alkylene-$C_{3-6}$ cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, ═O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$ aryl-$C_{1-4}$alkyl, wherein the alkyl, alkenyl, alkynyl, cyclohydrocarbyl, heterocyclyl or aryl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$ alkyl)$_2$, —OC(═O)($C_{1-6}$alkyl), —NHC(═O)($C_{1-6}$alkyl), —C(═O)($C_{1-6}$alkyl);

$R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, —S(═O)$_2OR^{Y1}$, —S(═O)$_2R^{Y1}$, —S(═O)$_2NR^{Y1}R^{Y2}$, —S(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, ═O, ═S, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, ═O and —COOH;

n is 1.

Accordingly, in an embodiment, formula (I) has a structure of formula (i), wherein the LCM moiety has a structure of above formula (1) (see above formula (1) and embodiments thereof) or a pharmaceutically acceptable salt thereof (i)

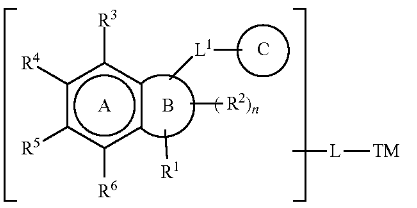

In an embodiment, L can covalently bind to any suitable site in formula (1).

The structure of following formula (2) falls within the scope of the structure of formula (1). In an embodiment, the LCM moiety has a structure of formula (2):

(2)

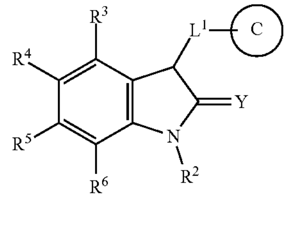

wherein:

Y is O or S;

ring C is selected from the group consisting of $C_{6-10}$ aryl and 5- to 7-membered heteroaryl, the aryl or heteroaryl is optionally substituted with one or more groups each independently selected from the group consisting of $R^{X1}$;

$R^2$ is selected from the group consisting of H, $C_{1-8}$alkyl;

$L^1$ is bond, or is $C_1$-$C_6$ hydrocarbyl chain;

$R^3$, $R^4$, $R^5$, $R^6$ are each independently selected from the group consisting of H and $R^{X2}$;

wherein $R^{X1}$, $R^{X2}$ are as defined in formula (1).

In an embodiment, Y is O. When Y is O, formula (2) is

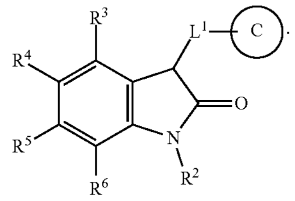

In an embodiment, ring C is 5- to 6-membered heteroaryl, the heteroaryl is optionally substituted with 1, 2, 3, 4 or 5 groups each independently selected from the group consisting of $R^{X1}$. In a preferable embodiment, ring C is 5-membered heteroaryl, the heteroaryl is optionally substituted with 1, 2, 3, 4 or 5 groups each independently selected from the group consisting of $R^{X1}$. In another embodiment, ring C comprises 1, 2, 3 or 4 heteroatoms each independently selected from the group consisting of N, O and S, preferably selected from the group consisting of N and O. In another embodiment, ring C comprises at least one N atom. In an embodiment, ring C is 5-membered heteroaryl comprising 1 or 2 N atoms, which is optionally substituted with 1, 2, 3, 4 or 5 groups each independently selected from the group consisting of $R^{X1}$. In another embodiment, ring C is selected from the group consisting of pyrrole and imidazole.

In an embodiment, $L^1$ is bond. In another embodiment, $L^1$ is $C_1$-$C_6$ hydrocarbyl chain. In a preferable embodiment, $L^1$ is $C_1$-$C_2$ hydrocarbyl chain. In an embodiment, $L^1$ is methylene or methyne. In a particular embodiment, $L^1$ is methyne. In another particular embodiment, $L^1$ is

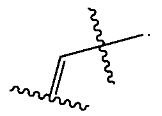 [SMILES: *C=*]

In another particular embodiment, formula (2) has a structure selected from the group consisting of Compound A1, A2 and A3:

A1

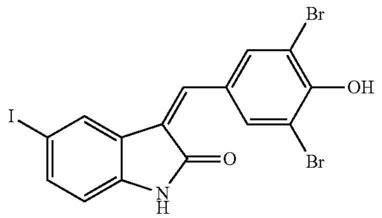

A2

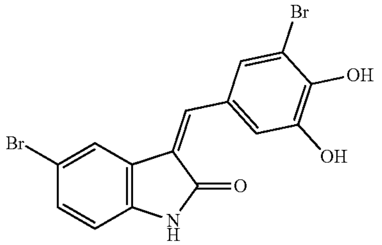

and

A3

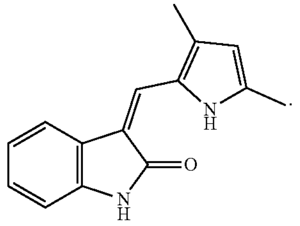

Accordingly, in an embodiment, formula (I) has a structure of formula (ii), wherein the LCM moiety has a structure of above formula (2) (see above formula (2) and embodiments thereof) or a pharmaceutically acceptable salt thereof (ii)

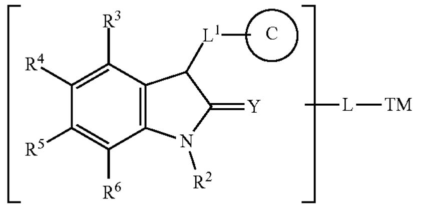

In an embodiment, L can covalently bind to any suitable site in formula (2). The suitable site comprises for example, —OH, suitable N atom at heterocyclic ring or the like.

In another particular embodiment, formula (2) has a structure selected from the group consisting of Compound A1, A2 and A3:

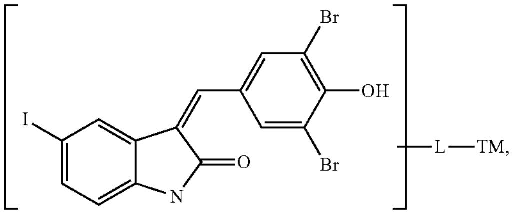

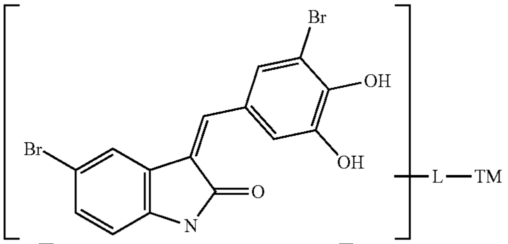

and

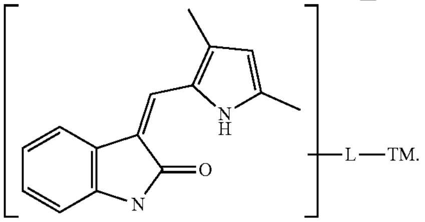

The structure of following formula (3) falls within the scope of the structure of formula (1). In an embodiment, the LCM moiety has a structure of formula (3):

(3)

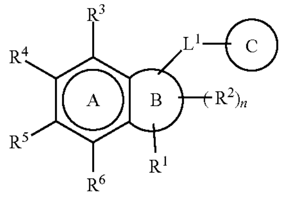

wherein:

ring B is saturated or unsaturated 6-membered heterocyclic ring, the heterocyclic ring comprises 1, 2 or 3 heteroatoms each independently selected from the group consisting of N, O and S;

ring C is $C_{6-10}$ aryl, which is optionally substituted with one or more groups each independently selected from the group consisting of $R^{X1}$;

or, ring C is absent and, L1 is absent;

ring A, $L^1$, $R^1$, $R^2$, $R^3$, $R^4$, $R^5$, $R^6$, $R^{X1}$, n are as defined in formula (1).

In an embodiment, ring B is saturated or unsaturated 6-membered heterocyclic ring, the heterocyclic ring comprises 1, 2 or 3 heteroatoms each independently selected from the group consisting of N, O and S. In an embodiment, ring B is saturated or unsaturated 6-membered heterocyclic ring, the heterocyclic ring comprises 1 or 2 heteroatoms each independently selected from the group consisting of N and O. In another embodiment, ring B is dihydropyrimidine. In a preferable embodiment, ring B is selected from the group consisting of 1,6-dihydropyrimidine, 1,2-dihydropyrimidine, 1,4-dihydropyrimidine.

In a more preferable embodiment, ring A-B system is

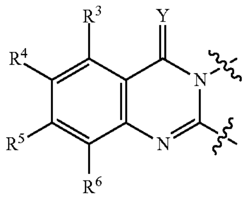

, wherein Y is O or S. In a particular embodiment, ring A-B system is

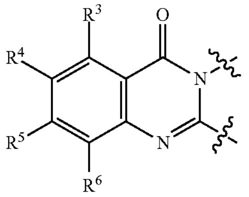

.

In another embodiment, ring B is 2H-pyran or 4H-pyran. In a preferable embodiment, ring A-B system is

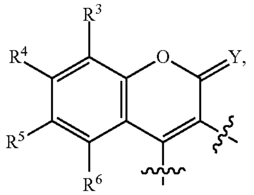

wherein Y is O or S. In a particular embodiment, ring A-B system is

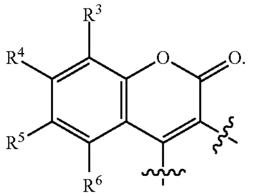

In another embodiment, ring C is phenyl, which is optionally substituted with 1, 2, 3, 4 or 5 groups each independently selected from the group consisting of $R^{X1}$.

In an embodiment, $L^1$ is bond. In another embodiment, $L^1$ is $C_1$-$C_6$ hydrocarbyl chain. In a preferable embodiment, $L^1$ is $C_1$-$C_2$ hydrocarbyl chain.

In an embodiment, ring A-B system is

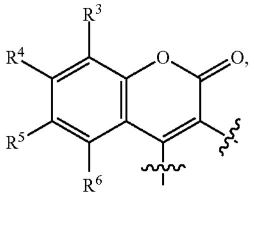

ring C is absent, and $L^1$ is absent.

Accordingly, in an embodiment, formula (I) has a structure of formula (iii), wherein the LCM moiety has a structure of above formula (3) (see above formula (3) and embodiments thereof) or a pharmaceutically acceptable salt thereof (iii)

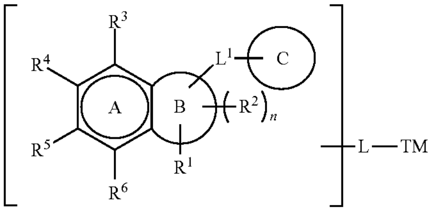

In an embodiment, L can covalently bind to any suitable site in formula (3).

In an alternative embodiment, ring B and ring C in formula (3) are further linked via $L^2$, so as to give a variant of the compound of formula (3) having a structure of formula (3')

(3')

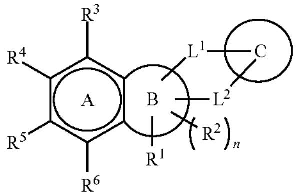

wherein:

ring C is $C_{6-10}$ aryl, which is optionally substituted with one or more groups each independently selected from the group consisting of $R^{X1}$;

$R^1$ is H, =O, or is $OR^7$;

$L^1$ is bond, or is $C_1$-$C_2$ hydrocarbyl chain;

$L^2$ is bond, or is $C_1$-$C_2$ hydrocarbyl chain;

Provided that $L^1$ and $L^2$ are not bond at the same time;

$R^3$, $R^4$, $R^5$, $R^6$ are each independently selected from the group consisting of H and $R^{X2}$;

ring A, ring B, $R^2$, n, $R^{X1}$ are as defined in formula (3).

In an embodiment, $R^1$ is H.

In another embodiment, $R^2$ is —OH.

In an embodiment, $R^{X2}$, on each occurrence, is each independently selected from the group consisting of halogen, —$NO_2$, —CN, $C_{1-6}$alkyl, —OH, —O($C_{1-6}$alkyl).

Accordingly, in an embodiment, formula (I) has a structure of formula (iii'), wherein the LCM moiety has a structure of above formula (3') (see above formula (3') and embodiments thereof) or a pharmaceutically acceptable salt thereof (iii')

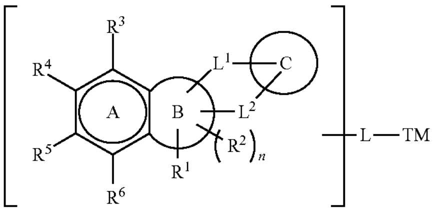

In an embodiment, L can covalently bind to any suitable site in formula (3').

The structure of following formula (4) falls within the scope of the structures of formula (1) and formula (3). In an embodiment, the LCM moiety has a structure of formula (4):

(4)

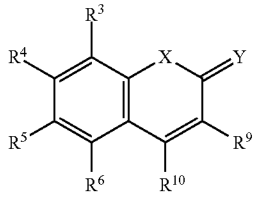

wherein:

Y is O or S;

X is O;

$R^9$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$, —S(═O)$_2OR^{a2}$, —S(═O)$_2R^{a2}$, —S(═O)$_2NR^{a2}R^{b2}$ and —S(═O)$R^{a2}$; wherein $R^{a1}$, $R^{b1}$, $R^{a2}$, $R^{b2}$ are as defined in formula (3);

$R^{10}$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl;

$R^3$ is selected from the group consisting of H, halogen, $C_{1-6}$alkyl, —OH, —$NH_2$, —NH($C_{1-6}$alkyl), —N($C_{1-6}$ alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$;

$R^4$ is selected from the group consisting of H, halogen, —$NO_2$, —CN, $C_{1-6}$alkyl, —$OR^7$, —$SR^7$, —$NR^7R^8$; $R^7$, $R^8$, on each occurrence, are each independently selected from the group consisting of H, $C_{1-6}$alkyl, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl);

$R^5$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl), wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl);

$R^6$ is selected from the group consisting of H, halogen, —$NO_2$, —CN, $C_{1-6}$alkyl, —OH, —O($C_{1-6}$alkyl), —O(benzyl), —SH, —S($C_{1-6}$alkyl), —S(benzyl), —$NH_2$, —NH($C_{1-6}$alkyl), —N($C_{1-6}$alkyl)$_2$, —NH (benzyl), wherein the alkyl or benzyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$.

In an embodiment, Y is O. When Y is O, formula (4) is

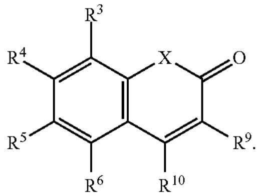

In an embodiment, $R^9$ is selected from the group consisting of H, halogen, $C_{1-6}$alkyl, —$OR^{a1}$, —$NR^{a1}R^{b1}$, —C(═O)$OR^{a1}$, —C(═O)$NR^{a1}R^{b1}$, —S(═O)$_2NR^{a1}R^{b1}$, wherein the alkyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$. In an embodiment, $R^9$ is selected from the group consisting of H, halogen, —$OR^1$, —$NR^{a1}R^{b1}$, —C(═O)$OR^{a1}$, —C(═O)$NR^{a1}R^{b1}$. In an embodiment, $R^9$ is —$OR^{a1}$ or —$NR^{a1}R^{b1}$. In another embodiment, $R^9$ is —C(═O)$OR^{a2}$ or —C(═O)$NR^{a2}R^{b2}$. In a particular embodiment, $R^9$ is —C(═O)O($C_{1-6}$alkyl). In a particular embodiment, $R^9$ is —COOH.

In an embodiment, $R^{10}$ is selected from the group consisting of H, halogen or methyl. In another embodiment, $R^{10}$ is H.

In an embodiment, $R^{a1}$, $R^{b1}$, on each occurrence, are each independently selected from the group consisting of H, $C_{1-6}$alkyl, —C(═O)$R^{Y1}$, wherein the alkyl is optionally substituted with one or more substituents selected from the group consisting of halogen, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$. Wherein $R^{Y1}$, $R^{Y3}$, $R^{Y4}$ are as defined in formula (3). In an embodiment, $R^{a1}$, $R^{b1}$, on each occurrence, are each independently selected from the group consisting of H, $C_{1-6}$alkyl, —C(═O)($C_{1-6}$alkyl), wherein the alkyl is optionally substituted with one or more substituents selected from the group consisting of halogen, —OH, —O($C_{1-6}$alkyl), —O($C_{3-6}$cyclohydrocarbyl), —$NH_2$, —NH($C_{1-6}$alkyl), —N($C_{1-6}$alkyl)$_2$, —NH($C_{3-6}$ cyclohydrocarbyl), —N($C_{3-6}$ cyclohydrocarbyl)$_2$, —C(═O)($C_{1-6}$alkyl), —C(═O)O($C_{1-6}$ alkyl), —C(═O)O($C_{3-6}$cyclohydrocarbyl), —C(═O)NH ($C_{1-6}$alkyl), —C(═O)N($C_{1-6}$alkyl)$_2$. In an embodiment, $R^{a1}$, $R^{b1}$, on each occurrence, are each independently selected from the group consisting of H and $C_{1-6}$alkyl.

In an embodiment, $R^{a2}$, $R^{b2}$, on each occurrence, are each independently selected from the group consisting of H and $C_{1-6}$alkyl.

In an embodiment, $R^3$ is selected from the group consisting of H, —OH, $C_{1-6}$alkyl, wherein the alkyl is optionally substituted with one or more substituents selected from the group consisting of halogen, —$NO_2$, —CN, —OH, —SH, —$NH_2$, —NH($C_{1-6}$alkyl), —N($C_{1-6}$alkyl)$_2$, —NH($C_{3-6}$ cyclohydrocarbyl), —N($C_{3-6}$cyclohydrocarbyl)$_2$, —NH ($C_{1-4}$alkylene-$C_{3-6}$cyclohydrocarbyl), —N($C_{1-4}$alkylene- $C_{3-6}$cyclohydrocarbyl$)_2$, —NH(3- to 7-membered heterocyclyl), —N(3- to 7-membered heterocyclyl$)_2$, —NH($C_{1-4}$alkylene-3- to 7-membered heterocyclyl), —N($C_{1-4}$alkylene-3- to 7-membered heterocyclyl$)_2$ and —COOH. In an embodiment, $R^3$ is selected from the group consisting of H, halogen, methyl, —OH, —$NH_2$, —$NHCH_3$, wherein the methyl is optionally substituted with one or more substituents selected from the group consisting of halogen, —OH, —$NH_2$, —NH($C_{1-2}$alkyl). In an embodiment, $R^3$ is selected from the group consisting of H, halogen, methyl, —OH —$NH_2$, —$NHCH_3$, wherein the methyl is optionally substituted with one or more substituents selected from the group consisting of halogen, —OH, —$OCH_3$, —$NH_2$, —$NHCH_3$. In an embodiment, $R^3$ is selected from the group consisting of H, halogen, methyl, —OH, —$NH_2$. In an embodiment, $R^3$ is selected from the group consisting of H, F, $C_1$, methyl, —OH, —$NH_2$. In an embodiment, $R^3$ is selected from the group consisting of H, F, methyl, —OH, —$NH_2$. In a particular embodiment, $R^3$ is H, methyl, —OH. In another particular embodiment, $R^3$ is H. In yet another particular embodiment, $R^3$ is —OH. In another embodiment, $R^3$ is dimethylaminomethyl.

In an embodiment, $R^4$ is selected from the group consisting of H, —$OR^7$, —$SR^7$, —$NR^7R^8$; $R^7$, $R^8$, on each occurrence, are each independently selected from the group consisting of H, $C_{1-6}$alkyl, wherein the alkyl is optionally substituted with one or more substituents selected from the group consisting of halogen, $C_{1-6}$alkyl, —OH, —O($C_{1-6}$ alkyl), —$NH_2$, —NH($C_{1-6}$alkyl), —N($C_{1-6}$alkyl$)_2$, —COOH, —C(═O)O($C_{1-6}$alkyl), —C(═O)NH($C_{1-6}$alkyl), —C(═O)N($C_{1-6}$alkyl$)_2$. In an embodiment, $R^4$ is $C_{1-6}$alkyl, wherein the alkyl is optionally substituted with one or more substituents selected from the group consisting of halogen, —COOH, —C(═O)O($C_{1-6}$alkyl), —C(═O)NH($C_{1-6}$alkyl), —C(═O)N($C_{1-6}$alkyl$)_2$. In a particular embodiment, $R^4$ is —$CH_2$COOH. In another embodiment, $R^4$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl$)_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl$)_2$. In an embodiment, $R^4$ is selected from the group consisting of H, halogen, $C_{1-3}$alkyl, —OH, —O($C_{1-3}$alkyl), —$NH_2$, —NH($C_{1-3}$alkyl), —N($C_{1-3}$ alkyl$)_2$ and —COOH, wherein the alkyl is optionally substituted with one or more substituents selected from the group consisting of halogen, —OH, —O($C_{1-2}$alkyl), —$NH_2$, —NH($C_{1-2}$alkyl), —N($C_{1-2}$alkyl$)_2$ and —COOH. In another particular embodiment, $R^4$ is —OH.

In an embodiment, $R^5$ is selected from the group consisting of H, $C_{1-6}$alkyl, wherein the alkyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$ cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl$)_2$, —NH ($C_{3-6}$cyclohydrocarbyl), —N($C_{3-6}$ cyclohydrocarbyl$)_2$, —NH($C_{1-4}$alkylene-$C_{3-6}$cyclohydrocarbyl), —N($C_{1-4}$alkylene-$C_{3-6}$ cyclohydrocarbyl$)_2$, —NH(3- to 7-membered heterocyclyl), —N(3- to 7-membered heterocyclyl$)_2$, —NH ($C_{1-4}$alkylene-3- to 7-membered heterocyclyl), —N($C_{1-4}$alkylene-3- to 7-membered heterocyclyl$)_2$ and —COOH. In another embodiment, $R^5$ is selected from the group consisting of H, halogen, $C_{1-3}$alkyl, —OH, —O($C_{1-3}$alkyl), —$NH_2$, —NH($C_{1-3}$alkyl), —N($C_{1-3}$alkyl$)_2$ and —COOH, wherein the alkyl is optionally substituted with one or more substituents selected from the group consisting of halogen, —OH, —O($C_{1-2}$alkyl), —$NH_2$, —NH($C_{1-2}$alkyl), —N($C_{1-2}$alkyl$)_2$ and —COOH.

In an embodiment, $R^5$ is selected from the group consisting of H, halogen, $C_{1-3}$alkyl, —OH, —O($C_{1-3}$alkyl), —$NH_2$, —NH($C_{1-3}$alkyl), —N($C_{1-3}$alkyl$)_2$, wherein the alkyl is optionally substituted with one or more substituents selected from the group consisting of halogen, —OH, —O($C_{1-2}$ alkyl), —$NH_2$, —NH($C_{1-2}$alkyl), —N($C_{1-2}$alkyl$)_2$. In an embodiment, $R^5$ is dimethylaminomethyl. In an embodiment, $R^5$ is —OH.

In an embodiment, $R^6$ is selected from the group consisting of H, halogen, $C_{1-6}$alkyl, —OH, —$NH_2$, wherein the alkyl is optionally substituted with one or more substituents selected from the group consisting of halogen, —OH, —$NH_2$. In an embodiment, $R^6$ is selected from the group consisting of H, F, Cl, Br, $C_{1-6}$alkyl, —OH, —$NH_2$, wherein the alkyl is optionally substituted with one or more substituents selected from the group consisting of halogen, —OH, —$NH_2$. In an embodiment, $R^6$ is selected from the group consisting of H, F, Cl, Br, methyl, —OH, —$NH_2$. In an embodiment, $R^6$ is H or —OH.

In an embodiment, $R^3$ is methyl, and $R^4$ is selected from the group consisting of $C_{1-3}$alkyl substituted with —OH, —$NH_2$, —NH($C_{1-3}$alkyl), —N($C_{1-3}$alkyl$)_2$, —COOH, wherein the substituted $C_{1-3}$alkyl is substituted with one or more substituents selected from the group consisting of —OH, —$NH_2$, —NH($C_{1-2}$alkyl), —N($C_{1-2}$alkyl$)_2$ and —COOH. In an embodiment, $R^3$ is methyl, and $R^4$ is selected from the group consisting of $C_{1-3}$alkyl substituted with —$NH_2$, —NH($C_{1-3}$alkyl), —N($C_{1-3}$alkyl$)_2$, —COOH, wherein the substituted $C_{1-3}$alkyl is substituted with one or more substituents selected from the group consisting of —OH, —$NH_2$, —NH($C_{1-2}$alkyl), —N($C_{1-2}$alkyl$)_2$ and —COOH.

In another embodiment, $R^3$ is methyl, and $R^5$ is selected from the group consisting of $C_{1-3}$ alkyl substituted with —OH, —$NH_2$, —NH($C_{1-3}$alkyl), —N($C_{1-3}$alkyl$)_2$, —COOH, wherein the substituted $C_{1-3}$alkyl is substituted with one or more substituents selected from the group consisting of —OH, —$NH_2$, —NH($C_{1-2}$alkyl), —N($C_{1-2}$ alkyl$)_2$ and —COOH. In another embodiment, $R^3$ is methyl, and $R^5$ is selected from the group consisting of $C_{1-3}$alkyl substituted with —$NH_2$, —NH($C_{1-3}$alkyl), —N($C_{1-3}$alkyl$)_2$, —COOH, wherein the substituted $C_{1-3}$alkyl is substituted with one or more substituents selected from the group consisting of —OH, —$NH_2$, —NH($C_{1-2}$alkyl), —N($C_{1-2}$ alkyl$)_2$ and —COOH.

Accordingly, in an embodiment, formula (I) has a structure of formula (iv), wherein the LCM moiety has a structure of above formula (4) (see above formula (4) and embodiments thereof) or a pharmaceutically acceptable salt thereof (iv)

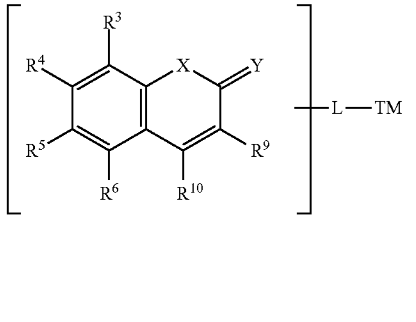

In an embodiment, L can covalently bind to any suitable site in formula (4).

The structure of following formula (5) falls within the scope of the structures of formula (1), formula (3) and formula (4). In an embodiment, the LCM moiety has a structure of formula (5):

(5)

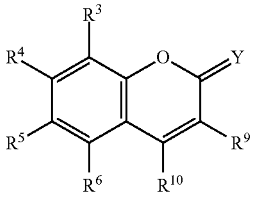

wherein:

Y, $R^9$, $R^{10}$, $R^3$, $R^4$, $R^5$, $R^6$ are as defined in formula (4);

In an embodiment, Y is O. When Y is O, formula (5) is

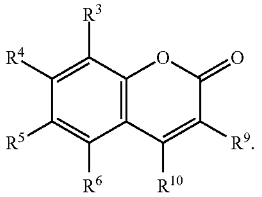

In a particular embodiment, formula (5) has a structure of Compound A4

A4

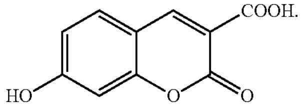

Accordingly, in an embodiment, formula (I) has a structure of formula (v), wherein the LCM moiety has a structure of above formula (5) (see above formula (5) and embodiments thereof) or a pharmaceutically acceptable salt thereof (v)

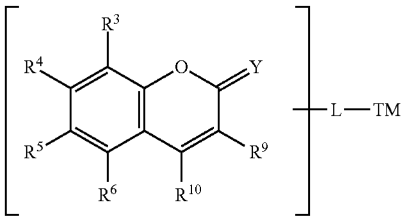

In an embodiment, L can covalently bind to any suitable site in formula (5). The suitable site comprises for example, —OH, —COOH or the like.

In a particular embodiment, formula (v) has a structure of

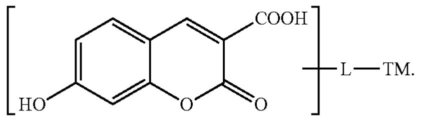

The structure of following formula (6) falls within the scope of the structures of formula (1) and formula (3). In an embodiment, the LCM moiety has a structure of formula (6):

(6)

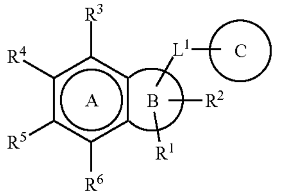

wherein:

ring B is saturated or unsaturated 6-membered heterocyclic ring, the heterocyclic ring comprises 1, 2 or 3 heteroatoms each independently selected from the group consisting of N, O and S;

ring C is $C_{6-10}$ aryl, which is optionally substituted with one or more groups each independently selected from the group consisting of $R^{X1}$;

$L^1$ is bond, or is $C_1$-$C_6$ hydrocarbyl chain;

$R^2$ is selected from the group consisting of H, halogen, —$NO_2$, —CN, $C_{1-8}$alkyl, $C_{2-8}$alkenyl, $C_{2-8}$alkynyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$ aryl-$C_{1-4}$alkyl, 5- to 10-membered heteroaryl-$C_{1-4}$alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O, —NCS, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2$ $NR^{a2}R^{b2}$—S(=O)$R^{a2}$ and —C(=$NR^{a2}$)$NR^{b2}R^{c2}$;

$R^3$, $R^4$, $R^5$, $R^6$ are each independently selected from the group consisting of H and $R^{X2}$;

$R^{X1}$ and $R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$, —S(=O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$ alkylene-$C_{3-6}$ cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$ cyclohydrocarbyl)$_2$, —NH($C_{1-4}$alkylene-$C_{3-6}$cyclohydrocarbyl), —N($C_{1-4}$alkylene-$C_{3-6}$ cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, =O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, wherein the alkyl, alkenyl, alkynyl, cyclohydrocarbyl or heterocyclyl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), —C(=O)($C_{1-6}$alkyl);

$R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$, —S(=O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, =O and —COOH;

ring A, $R^1$ are as defined in formula (3).

In an embodiment, ring B is saturated or unsaturated 6-membered heterocyclic ring, the heterocyclic ring comprises 1 or 2 heteroatoms each independently selected from the group consisting of N and O. In another embodiment, ring B is dihydropyrimidine. In a preferable embodiment, ring B is selected from the group consisting of 1,6-dihydropyrimidine, 1,2-dihydropyrimidine, 1,4-dihydropyrimidine.

In a more preferable embodiment, ring A-B system is

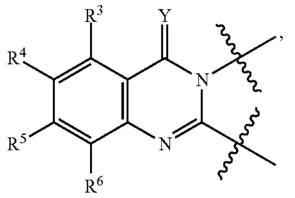

wherein Y is O or S. In a particular embodiment, ring A-B system is

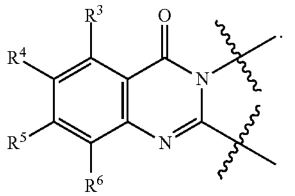

In another embodiment, ring B is 2H-pyran or 4H-pyran. In a preferable embodiment, ring A-B system is

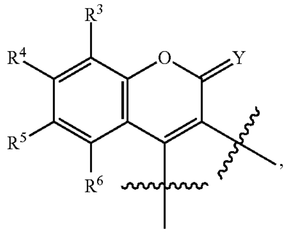

wherein Y is O or S. In a particular embodiment, ring A-B system is

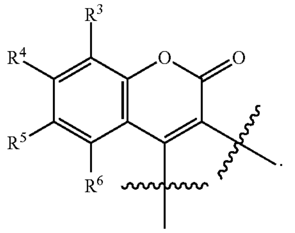

In another embodiment, ring C is phenyl, which is optionally substituted with 1, 2, 3, 4 or groups each independently selected from the group consisting of $R^{X1}$.

In an embodiment, $L^1$ is bond. In another embodiment, $L^1$ is $C_1$-$C_6$ hydrocarbyl chain. In a preferable embodiment, $L^1$ is $C_1$-$C_2$ hydrocarbyl chain.

In another embodiment, $R^2$ is selected from the group consisting of H, halogen, —$NO_2$, —CN, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, =O, =S, —$OR^{a1}$, —$SR^{a1}$, —$NR^{a1}R^{b1}$, —C(=O)$OR^{a1}$, —C(=O)$NR^{a1}R^{b}1$, —C(=O)$R^{a1}$, —S(=O)$_2OR^{a1}$, —S(=O)$_2R^{a1}$, —S(=O)$_2$ $NR^{a1}R^{b1}$, —S(=O)$R^{a1}$, wherein the alkyl, alkenyl, alkynyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$, —S(═O)$_2OR^{a2}$, —S(═O)$_2R^{a2}$, —S(═O)$_2$ $NR^{a2}R^{b2}$ and —S(═O)$R^{a2}$. In another embodiment, $R^2$ is selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH ($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$cyclohydrocarbyl), —NH(C═O)(3- to 7-membered heterocyclyl), —C(═O)($C_{1-6}$alkyl), —COOH, —C(═O)O($C_{1-6}$alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH ($C_{1-6}$alkyl), —C(═O)N($C_{1-6}$alkyl)$_2$, —C(═O)NH($C_{1-4}$alkylene-$C_{3-6}$ cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —SH, —$NH_2$ and —COOH. In yet another embodiment, $R^2$ is selected from the group consisting of H, halogen, —$NO_2$, —CN, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$; In a preferable embodiment, $R^2$ is selected from the group consisting of H, halogen, —$NO_2$, —CN, $C_{1-6}$alkyl, —OH, wherein the alkyl is optionally substituted with one or more substituents selected from the group consisting of halogen, —$NO_2$, —CN, $C_{1-6}$alkyl, —$NR^{a2}R^{b2}$. In a more preferable embodiment, $R^2$ is selected from the group consisting of H, halogen, $C_{1-6}$alkyl, —OH, wherein the alkyl is optionally substituted with one or more groups selected from the group consisting of halogen, $C_{1-6}$alkyl and —$NR^{a2}R^{b2}$. In a further embodiment, $R^2$ is selected from the group consisting of H, $C_{1-4}$alkyl, —OH, wherein the alkyl is optionally substituted with one or more groups selected from the group consisting of —$NR^{a2}R^{b2}$. In a particular embodiment, $R^2$ is selected from the group consisting of H, $C_{1-4}$alkyl, —OH, wherein the alkyl is —$CH_2$[CH($CH_3$)$_2$], and is optionally substituted with one or more groups selected from the group consisting of —$NR^{a2}R^{b2}$. In another embodiment, $R^2$ is alkyl substituted with —$NR^{a1}R^{b1}$. In a particular embodiment, $R^2$ is

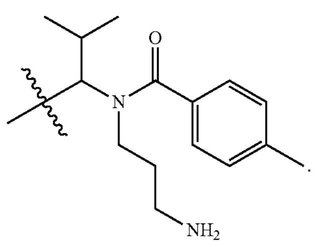 [SMILES: *C(C(C)C)N(CCCN)C(=O)c1ccc(C)cc1]

In an embodiment, $R^{X1}$ and $R^{X2}$, on each occurrence, are each independently selected from the group consisting of halogen, —$NO_2$, —CN, $C_{1-6}$alkyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2$ $R^7$, —S(═O)$_2NR^7R^8$, —OS(═O)$_2R^7$, —NS(═O)$_2R^7R^8$, —S(═O)$R^7$, wherein the alkyl is optionally substituted with one or more substituents selected from the group consisting of halogen, —$NO_2$, —CN, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$ alkyl), —S($C_{3-6}$ cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$ alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, ═O, —COOH. In a preferable embodiment, $R^{X1}$ and $R^{X2}$, on each occurrence, are each independently selected from the group consisting of halogen, —$NO_2$, —CN, $C_{1-6}$alkyl, —$OR^7$, —$SR^7$, —$NR^7R^8$, —OC(═O)$R^7$, —NC(═O)$R^7R^8$, —OS(═O)$_2R^7$, —NS (═O)$_2R^7R^8$, wherein the alkyl is optionally substituted with one or more substituents selected from the group consisting of halogen, —$NO_2$, —CN, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —$NH_2$, —NH ($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$. In a preferable embodiment, $R^{X1}$ and $R^{X2}$, on each occurrence, are each independently selected from the group consisting of halogen, $C_{1-6}$alkyl, —$OR^7$, —$NR^7R^8$, more preferably each independently selected from the group consisting of halogen, —$OR^7$, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$. In a more preferable embodiment, $R^{X1}$ and $R^{X2}$, on each occurrence, are each independently selected from the group consisting of F, Cl, Br, —OH, —O($C_{1-6}$alkyl), —$NH_2$, —NH($C_{1-6}$alkyl), —N($C_{1-6}$alkyl)$_2$, optionally substituted $C_{1-6}$alkyl, wherein the optionally substituted $C_{1-6}$alkyl is optionally substituted with one or more substituents selected from the group consisting of halogen, —$NO_2$, —CN, —OH, —O($C_{1-6}$alkyl), —$NH_2$, —NH($C_{1-6}$ alkyl), —N($C_{1-6}$alkyl)$_2$. In a particular embodiment, $R^{X1}$ and $R^{X2}$, on each occurrence, are each independently selected from the group consisting of F, Cl, Br, methyl, —OH, dimethylaminomethyl.

$R^7$, $R^8$, on each occurrence, are each independently selected from the group consisting of H, $C_{1-6}$alkyl, $C_{2-6}$alkenyl, $C_{2-6}$alkynyl, wherein the alkyl, alkenyl, alkynyl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl). In a preferable embodiment, $R^7$, $R^8$, on each occurrence, are each independently selected from the group consisting of H, $C_{1-6}$alkyl, wherein the alkyl is optionally substituted with one or more substituents selected from the group consisting of halogen, $C_{1-6}$alkyl, —OH, —O($C_{1-6}$ alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl). In a particular embodiment, $R^7$, $R^8$, on each occurrence, are each independently selected from the group consisting of H, $C_{1-6}$alkyl, wherein the alkyl is optionally substituted with one or more substituents selected from the group consisting of halogen, —N($C_{1-6}$alkyl)$_2$, —COOH. In another particular embodiment, $R^7$, $R^8$, on each occurrence, are each independently selected from the group consisting of H, $C_{1-6}$alkyl, wherein the alkyl is optionally substituted with one or more substituents selected from the group consisting of halogen, —N($C_{1-6}$ alkyl)$_2$.

In an embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$ aryl-$C_{1-4}$alkyl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$. In a preferable embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{6-10}$ aryl-$C_{1-4}$alkyl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, wherein the alkyl, aryl or heteroaryl is optionally substituted with one or more substituents selected from the group consisting of halogen, —$OR^{Y3}$ and —$NR^{Y3}R^{Y4}$.

In another preferable embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$OR^{Y1}$, —C(═O)$NR^{Y1}R^{Y2}$, —C(═O)$R^{Y1}$, wherein the alkyl is optionally substituted with one or more groups selected from the group consisting of halogen, —$OR^{Y3}$ and —$NR^{Y3}R^{Y4}$. In a more preferable embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$R^{Y1}$, wherein the alkyl is optionally substituted with one or more groups selected from the group consisting of halogen, —$OR^{Y3}$ and —$NR^{Y3}R^{Y4}$. In a further embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$R^{Y1}$, wherein the alkyl is optionally substituted with one or more groups selected from the group consisting of halogen, —$NR^{Y3}R^{Y4}$. In a particular embodiment, $R^{a1}$, $R^{b1}$, $R^{c1}$, $R^{a2}$, $R^{b2}$, $R^{c2}$, on each occurrence, are each independently selected from the group consisting of H, $C_{1-3}$alkyl, —OH, p-methylbenzoyl; wherein the alkyl is optionally substituted with one or more groups selected from the group consisting of halogen, —$NH_2$.

In another embodiment, $R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$ cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, —OH, —SH, —$NH_2$, —COOH and $C_{1-6}$alkyl. In a preferable embodiment, $R^{Y1}$, $R^{Y2}$, $R^{Y3}$, $R^{Y4}$, on each occurrence, are each independently selected from the group consisting of H, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, phenyl, phenyl-$C_{1-4}$alkyl, 5- to 6-membered heteroaryl, 5- to 6-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, —OH, —SH, —$NH_2$, —COOH and $C_{1-6}$alkyl. In a more preferable embodiment, $R^{Y1}$, $R^{Y2}$, $R^{Y3}$, $R^{Y4}$, on each occurrence, are each independently selected from the group consisting of H, $C_{1-6}$alkyl, phenyl, phenyl-$C_{1-4}$alkyl, 5- to 6-membered heteroaryl, 5- to 6-membered heteroaryl-$C_{1-4}$alkyl, wherein the alkyl or phenyl is optionally substituted with one or more substituents selected from the group consisting of halogen, —$NO_2$, —CN, —OH, —SH, —$NH_2$, —COOH and $C_{1-6}$alkyl. In a more preferable embodiment, $R^{Y1}$, $R^{Y2}$, $R^{Y3}$, $R^{Y4}$, on each occurrence, are each independently selected from the group consisting of H, $C_{1-6}$alkyl, phenyl, phenyl-$C_{1-4}$ alkyl, wherein the alkyl or phenyl is optionally substituted with one or more groups selected from the group consisting of halogen, $C_{1-6}$alkyl. In a particular embodiment, $R^{Y1}$, $R^{Y2}$, $R^{Y3}$, $R^{Y4}$, on each occurrence, are each independently selected from the group consisting of H and p-methylphenyl.

In another embodiment, $R^2$ is selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$ cyclohydrocarbyl), —O(C═O)($C_{1-4}$alkylene-$C_{3-6}$ cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$ cyclohydrocarbyl)$_2$, —NH($C_{1-4}$alkylene-$C_{3-6}$cyclohydrocarbyl), —N($C_{1-4}$alkylene-$C_{3-6}$-cyclohydrocarbyl)$_2$, —NH (3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$ cyclohydrocarbyl), —NH(C═O)(3- to 7-membered heterocyclyl), —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$ cyclohydrocarbyl), —C(═O)O(3- to 7-membered heterocyclyl), —C(═O)O($C_{1-4}$alkylene)-(3- to 7-membered heterocyclyl), —C(═O)NH($C_{1-6}$alkyl), —C(═O)N($C_{1-6}$alkyl)$_2$, —C(═O)NH($C_{1-4}$alkylene-$C_{3-6}$ cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH ($C_{1-4}$alkylene-3- to 7-membered heterocyclyl), —C(═O)N ($C_{1-4}$alkylene-3- to 7-membered heterocyclyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —SH, —$NH_2$. In another yet embodiment, $R^2$ is selected from the group consisting of H, halogen, —$NO_2$, —CN, $C_{1-6}$alkyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$; In a preferable embodiment, $R^2$ is selected from the group consisting of H, halogen, —$NO_2$, —CN, $C_{1-6}$alkyl, —OH, wherein the alkyl is optionally substituted with one or more substituents selected from the group consisting of halogen, —$NO_2$, —CN, $C_{1-6}$alkyl, —$NR^{a2}R^{b2}$. In a more preferable embodiment, $R^2$ is selected from the group consisting of H, halogen, $C_{1-6}$alkyl, —OH, wherein the alkyl is optionally substituted with one or more groups selected from the group consisting of halogen, $C_{1-6}$alkyl and —$NR^{a2}R^{b2}$. In a further embodiment, $R^2$ is selected from the group consisting of H, $C_{1-4}$alkyl, —OH, wherein the alkyl is optionally substituted with one or more groups selected from the group consisting of —$NR^{a2}R^{b2}$. In a particular embodiment, $R^2$ is selected from the group consisting of H, $C_{1-4}$alkyl, —OH, wherein the alkyl is —$CH_2$[CH($CH_3$)$_2$], and is optionally substituted with one or more groups selected from the group consisting of —$NR^{a2}R^{b2}$. In another embodiment, $R^2$ is alkyl substituted with—$NR^{a1}R^{b1}$. In a particular embodiment, $R^2$ is

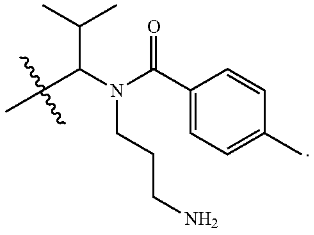 [SMILES: *C(C(C)C)N(CCCN)C(=O)c1ccc(C)cc1]

In an embodiment, $R^{X1}$ and $R^{X2}$, on each occurrence, are each independently selected from the group consisting of halogen, —$NO_2$, —CN, $C_{1-6}$alkyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl is optionally substituted with one or more substituents selected from the group consisting of halogen, —$NO_2$, —CN, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$ alkyl), —S($C_{3-6}$ cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$ alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, ═O. In a preferable embodiment, $R^{X1}$ and $R^{X2}$, on each occurrence, are each independently selected from the group consisting of halogen, —$NO_2$, —CN, $C_{1-6}$alkyl, —$OR^7$, —$SR^7$, —$NR^7R^8$, —OC (═O)$R^7$, —NC(═O)$R^7R^8$, —OS(═O)$_2R^7$, —NS(═O)$_2$ $R^7R^8$, wherein the alkyl is optionally substituted with one or more substituents selected from the group consisting of halogen, —$NO_2$, —CN, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —$NH_2$, —NH ($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$. In a preferable embodiment, $R^{X1}$ and $R^{X2}$, on each occurrence, are each independently selected from the group consisting of halogen, $C_{1-6}$alkyl, —$OR^7$, —$NR^7R^8$, more preferably each independently selected from the group consisting of halogen, —$OR^7$, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$. In a more preferable embodiment, $R^{X1}$ and $R^{X2}$, on each occurrence, are each independently selected from the group consisting of F, Cl, Br, —OH, —O($C_{1-6}$ alkyl), —$NH_2$, —NH($C_{1-6}$alkyl), —N($C_{1-6}$alkyl)$_2$, optionally substituted $C_{1-6}$alkyl, wherein the optionally substituted $C_{1-6}$alkyl is optionally substituted with one or more substituents selected from the group consisting of halogen, —$NO_2$, —CN, —OH, —O($C_{1-6}$alkyl), —$NH_2$, —NH($C_{1-6}$ alkyl), —N($C_{1-6}$alkyl)$_2$. In a particular embodiment, $R^{X1}$ and $R^{X2}$, on each occurrence, are each independently selected from the group consisting of F, Cl, Br, methyl, —OH, dimethylaminomethyl.

$R^7$, $R^8$, on each occurrence, are each independently selected from the group consisting of H, $C_{1-6}$alkyl, $C_{2-6}$alkenyl, $C_{2-6}$alkynyl, wherein the alkyl, alkenyl, alkynyl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH ($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl). In a preferable embodiment, $R^7$, $R^8$, on each occurrence, are each independently selected from the group consisting of H, $C_{1-6}$alkyl, wherein the alkyl is optionally substituted with one or more substituents selected from the group consisting of halogen, $C_{1-6}$ alkyl, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl). In a particular embodiment, $R^7$, $R^8$, on each occurrence, are each independently selected from the group consisting of H, $C_{1-6}$alkyl, wherein the alkyl is optionally substituted with one or more substituents selected from the group consisting of halogen, —N($C_{1-6}$alkyl)$_2$. In another particular embodiment, $R^7$, $R^8$, on each occurrence, are each independently selected from the group consisting of H, $C_{1-6}$alkyl, wherein the alkyl is optionally substituted with one or more substituents selected from the group consisting of halogen, —N($C_{1-6}$alkyl)$_2$.

In an embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$ aryl-$C_{1-4}$ alkyl, 5- to 10-membered heteroaryl-$C_{1-4}$alkyl, —$OR^{Y1}$, —$SR^{y1}$, —$NR^{Y1}R^{Y2}$, —C(═O)$OR^{Y1}$, —C(═O)$NR^{Y1}R^{Y2}$, —C(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$. In a preferable embodiment, $R^{a1}$, $R^{b1}$, $R^{c1}$, $R^2$, $R^{b2}$, $R^{c2}$, on each occurrence, are each independently selected from the group consisting of H, $C_{1-6}$alkyl, $C_{6-10}$ aryl-$C_{1-4}$alkyl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, wherein the alkyl, aryl or heteroaryl is optionally substituted with one or more substituents selected from the group consisting of halogen, —$OR^{Y3}$ and —$NR^{Y3}R^{Y4}$. In another preferable embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$OR^{Y1}$, —C(═O)$NR^{Y1}R^{Y2}$, —C(═O)$R^{Y1}$, wherein the alkyl is optionally substituted with one or more groups selected from the group consisting of halogen, —$OR^{Y3}$ and —$NR^{Y3}R^{Y4}$. In a more preferable embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$R^{Y1}$, wherein the alkyl is optionally substituted with one or more groups selected from the group consisting of halogen, —$OR^{Y3}$ and —$NR^{Y3}R^{Y4}$. In a further embodiment, $R^{a1}$, $R^{b1}$, $R^{c1}$, $R^{a2}$, $R^{b2}$, $R^{c2}$, on each occurrence, are each independently selected from the group consisting of H, $C_{1-6}$alkyl, —$OR^{Y1}$, —$NR^{Y1}R^{Y2}$, —C(═O)$R^{Y1}$, wherein the alkyl is optionally substituted with one or more groups selected from the group consisting of halogen, —$NR^{Y3}R^{Y4}$. In a particular embodiment, $R^{a1}$, $R^{b1}$, $R^c$, $R^{a2}$, $R^{b2}$, $R^{c2}$, on each occurrence, are each independently selected from the group consisting of H, $C_{1-3}$alkyl, —OH, p-methylbenzoyl; wherein the alkyl is optionally substituted with one or more groups selected from the group consisting of halogen, —$NH_2$.

In another embodiment, $R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$ cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, —OH, —SH, —$NH_2$ and $C_{1-6}$alkyl. In a preferable embodiment, $R^{Y1}$, $R^{Y2}$, $R^{Y3}$, $R^{Y4}$, on each occurrence, are each independently selected from the group consisting of H, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, phenyl, phenyl-$C_{1-4}$alkyl, 5- to 6-membered heteroaryl, 5- to 6-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, —OH, —SH, —$NH_2$ and $C_{1-6}$alkyl. In a more preferable embodiment, $R^{Y1}$, $R^{Y2}$, $R^{Y3}$, $R^{Y4}$, on each occurrence, are each independently selected from the group consisting of H, $C_{1-6}$alkyl, phenyl, phenyl-$C_{1-4}$alkyl, 5- to 6-membered heteroaryl, 5- to 6-membered heteroaryl-$C_{1-4}$alkyl, wherein the alkyl or phenyl is optionally substituted with one or more substituents selected from the group consisting of halogen, —$NO_2$, —CN, —OH, —SH, —$NH_2$ and $C_{1-6}$alkyl. In a more preferable embodiment, $R^{Y1}$, $R^{Y2}$, $R^{Y3}$, $R^{Y4}$, on each occurrence, are each independently selected from the group consisting of H, $C_{1-6}$alkyl, phenyl, phenyl-$C_{1-4}$alkyl, wherein the alkyl or phenyl is optionally substituted with one or more groups selected from the group consisting of halogen, $C_{1-6}$alkyl. In a particular embodiment, $R^{Y1}$, $R^{Y2}$, $R^{Y3}$, $R^{Y4}$, on each occurrence, are each independently selected from the group consisting of H and p-methylphenyl.

In an embodiment, $R^3$, $R^6$ each independently selected from the group consisting of H, halogen, —$NO_2$, —CN, $C_{1-6}$alkyl, —OH, —O($C_{1-6}$alkyl), wherein the alkyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl). In a preferable embodiment, $R^3$, $R^6$ each independently selected from the group consisting of H, halogen, —OH, more preferably H or —OH.

In an embodiment, $R^4$, $R^5$ each independently selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$ cyclohydrocarbyl), —O(3- to 7-membered heterocyclyl), —O($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —NH($C_{1-4}$alkylene-$C_{3-6}$cyclohydrocarbyl), —NH(3- to 7-membered heterocyclyl), —NH($C_{1-4}$alkylene-3- to 7-membered heterocyclyl), —COOH, —C(═O)O($C_{1-6}$alkyl), —C(═O)$NH_2$, —C(═O)NH($C_{1-6}$ alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl), ═O. In another embodiment, $R^4$, $R^5$ each independently selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)$NH_2$, —C(═O)NH($C_{1-6}$ alkyl), —C(═O)N($C_{1-6}$ alkyl)$_2$, —OC(═O)($C_{1-6}$alkyl), —NHC(═O)($C_{1-6}$alkyl), —C(═O)($C_{1-6}$alkyl), ═O. In another embodiment, $R^4$, $R^5$ are each independently selected from the group consisting of H, halogen, —$NO_2$, —CN, $C_{1-6}$alkyl, —OH, —O($C_{1-6}$alkyl), wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)$NH_2$, —C(═O)NH($C_{1-6}$ alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl), ═O. In another embodiment, $R^4$, $R^5$ are each independently selected from the group consisting of H, halogen, —$NO_2$, —CN, $C_{1-6}$alkyl, —$NH_2$, —NH($C_{1-6}$alkyl), —N($C_{1-6}$alkyl)$_2$, wherein the alkyl is optionally substituted with one or more substituents selected from the group consisting of halogen, —$NO_2$, —CN, —OH, —O($C_{1-6}$alkyl), —$NH_2$, —NH($C_{1-6}$ alkyl), —N($C_{1-6}$alkyl)$_2$, —C(═O)O($C_{1-6}$alkyl), —C(═O)$NH_2$, —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl), ═O.

Accordingly, in an embodiment, formula (I) has a structure of formula (vi), wherein the LCM moiety has a structure of above formula (6) (see above formula (6) and embodiments thereof) or a pharmaceutically acceptable salt thereof (vi)

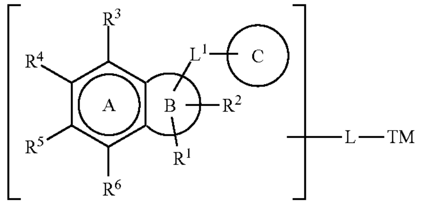

In an embodiment, L can covalently bind to any suitable site in formula (6).

The structure of following formula (7) falls within the scope of the structures of formula (1), formula (3) and formula (6). In an embodiment, the LCM moiety has a structure of formula (7):

(7)

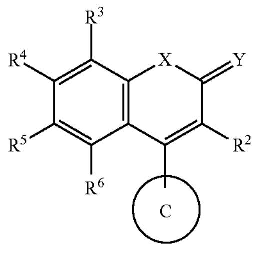

wherein:

X is O;

Y is O or S;

$R^3$, $R^4$, $R^5$, $R^6$ are as defined in formula (6);

ring C is

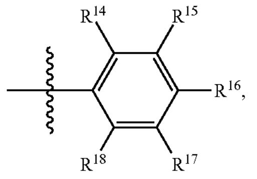

wherein $R^{14}$, $R^{15}$, $R^{16}$, $R^{17}$, $R^{18}$ are each independently selected from the group consisting of H, halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$; wherein $R^7$, $R^8$ are as defined in formula (6);

$R^2$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$, —S(═O)$_2OR^{a2}$, —S(═O)$_2R^{a2}$, —S(═O)$_2NR^{a2}R^{b2}$ and —S(═O)$R^{a2}$; wherein $R^{a2}$, $R^{b2}$ are as defined in formula (6).

In an embodiment, Y is O. When Y is O, formula (7) is

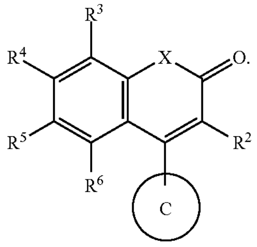

In an embodiment, $R^2$ is selected from the group consisting of H, halogen, $C_{1-6}$alkyl, wherein the alkyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$, —S(═O)$_2OR^{a2}$, —S(═O)$_2R^{a2}$, —S(═O)$_2NR^{a2}R^{b2}$ and —S(═O)$R^{a2}$. In an embodiment, $R^2$ is selected from the group consisting of —$OR^{a1}$, —$NR^{a1}R^{b1}$, —C(═O)$OR^{a1}$, —C(═O)$NR^{a1}R^{b}$i. In another embodiment, $R^2$ is selected from the group consisting of H, halogen, $C_{1-6}$alkyl, wherein the alkyl is optionally substituted with one or more substituents selected from the group consisting of halogen, —$NO_2$, —CN, —OH, —$NH_2$ and —COOH.

In an embodiment, $R^{a2}$, $R^{b2}$, on each occurrence, are each independently selected from the group consisting of H, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, wherein the alkyl, alkenyl, alkynyl, cyclohydrocarbyl or heterocyclyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$. In a preferable embodiment, $R^{a2}$, $R^{b2}$, on each occurrence, are each independently selected from the group consisting of H, $C_{1-6}$alkyl, wherein the alkyl is optionally substituted with one or more substituents selected from the group consisting of halogen, —OH, —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$.

In an embodiment, $R^3$ is selected from the group consisting of H, halogen, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —OH, —O($C_{1-6}$ alkyl), —$NH_2$, —NH($C_{1-6}$alkyl), —N($C_{1-6}$alkyl)$_2$. In an embodiment, $R^3$ is selected from the group consisting of H, halogen, $C_{1-3}$alkyl, —OH, —O($C_{1-3}$alkyl), —$NH_2$, —NH ($C_{1-3}$alkyl), —N($C_{1-3}$alkyl)$_2$, wherein the alkyl is optionally substituted with one or more substituents selected from the group consisting of halogen, —OH, —O($C_{1-2}$alkyl), —$NH_2$, —NH($C_{1-2}$alkyl), —N($C_{1-2}$alkyl)$_2$. In an embodiment, $R^3$ is selected from the group consisting of H, halogen, methyl, —OH, —$OCH_3$, —$NH_2$, —$NHCH_3$, —N($CH_3$)$_2$, wherein the methyl is optionally substituted with a substituent selected from the group consisting of halogen, —OH, —O($C_{1-2}$alkyl), —$NH_2$, —NH($C_{1-2}$alkyl), —N($C_{1-2}$alkyl)$_2$. In an embodiment, $R^3$ is selected from the group consisting of H, halogen, methyl, —OH, —$OCH_3$, —$NH_2$, —$NHCH_3$, —N($CH_3$)$_2$, wherein the methyl is optionally substituted with a substituent selected from the group consisting of halogen, —OH, —$OCH_3$, —$NH_2$, —$NHCH_3$, —N($CH_3$)$_2$. In an embodiment, $R^3$ is selected from the group consisting of H, halogen, methyl, —OH, —$NH_2$, —N($CH_3$)$_2$. In another embodiment, $R^3$ is selected from the group consisting of H, halogen, $C_{1-4}$alkyl, —OH, —O($C_{1-4}$alkyl), —$NH_2$, —NH($C_{1-4}$alkyl), wherein the alkyl is optionally substituted with one or more substituents selected from the group consisting of halogen, —OH, —O($C_{1-4}$alkyl), —$NH_2$, —NH($C_{1-4}$alkyl). In an embodiment, $R^3$ is selected from the group consisting of H, halogen, methyl, —OH, —$OCH_3$, —$NH_2$, —$NHCH_3$, wherein the methyl is optionally substituted with a substituent selected from the group consisting of halogen, —OH, —O($C_{1-2}$alkyl), —$NH_2$, —NH($C_{1-2}$alkyl). In an embodiment, $R^3$ is selected from the group consisting of H, halogen, methyl, —OH, —$OCH_3$, —$NH_2$, —$NHCH_3$, wherein the methyl is optionally substituted with a substituent selected from the group consisting of halogen, —OH, —$OCH_3$, —$NH_2$, —$NHCH_3$. In another embodiment, $R^3$ is selected from the group consisting of H, halogen, $C_{1-4}$alkyl, —OH, —O($C_{1-4}$alkyl), —$NH_2$, wherein the alkyl is optionally substituted with one or more substituents selected from the group consisting of halogen, —OH, —O($C_{1-4}$alkyl), —$NH_2$. In an embodiment, $R^3$ is selected from the group consisting of H, halogen, methyl, —OH, —$OCH_3$, —$NH_2$, wherein the methyl is optionally substituted with a substituent selected from the group consisting of halogen, —OH, —O($C_{1-2}$alkyl), —$NH_2$. In an embodiment, $R^3$ is selected from the group consisting of H, halogen, methyl, —OH, —$OCH_3$, —$NH_2$, wherein the methyl is optionally substituted with a substituent selected from the group consisting of halogen, —OH, —$OCH_3$, —$NH_2$. In an embodiment, $R^3$ is selected from the group consisting of H, halogen, methyl, —OH, —$NH_2$. In another embodiment, $R^3$ is selected from the group consisting of H, halogen, $C_{1-4}$alkyl, —OH, —O($C_{1-4}$alkyl), wherein the alkyl is optionally substituted with one or more substituents selected from the group consisting of halogen, —OH, —O($C_{1-4}$alkyl). In an embodiment, $R^3$ is selected from the group consisting of H, halogen, methyl, —OH, —$OCH_3$, wherein the methyl is optionally substituted with a substituent selected from the group consisting of halogen, —OH, —O($C_{1-2}$alkyl). In an embodiment, $R^3$ is selected from the group consisting of H, halogen, methyl, —OH, —$OCH_3$, wherein the methyl is optionally substituted with a substituent selected from the group consisting of halogen, —OH, —$OCH_3$. In an embodiment, $R^3$ is selected from the group consisting of H, halogen, methyl, —OH. In yet another embodiment, $R^3$ is selected from the group consisting of H, halogen, —OH, —O($C_{1-4}$ alkyl), —$NH_2$, —NH($C_{1-4}$alkyl), —N($C_{1-4}$alkyl)$_2$, substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^3$ is selected from the group consisting of H, halogen, —OH, —$OCH_3$, —$NH_2$, —$NHCH_3$, —N($CH_3$)$_2$, substituted methyl, wherein the substituted methyl is substituted with a substituent selected from the group consisting of halogen, —OH, —O($C_{1-2}$alkyl), —NH($C_{1-2}$alkyl), —N($C_{1-2}$alkyl)$_2$. In an embodiment, $R^3$ is selected from the group consisting of H, halogen, —OH, —$OCH_3$, —$NH_2$, —$NHCH_3$, —N($CH_3$)$_2$, substituted methyl, wherein the substituted methyl is substituted with a substituent selected from the group consisting of halogen, —OH, —$OCH_3$, —$NHCH_3$, —N($CH_3$)$_2$. In an embodiment, $R^3$ is selected from the group consisting of H, halogen, —OH, —$NH_2$, methyl, wherein the methyl is substituted with —N($CH_3$)$_2$. In another embodiment, $R^3$ is selected from the group consisting of H, halogen, —OH, —O($C_{1-4}$alkyl), substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^3$ is selected from the group consisting of H, halogen, —OH, —$OCH_3$, substituted methyl, wherein the substituted methyl is substituted with a substituent selected from the group consisting of halogen, —OH, —O($C_{1-2}$alkyl), —NH($C_{1-2}$ alkyl), —N($C_{1-2}$alkyl)$_2$. In an embodiment, $R^3$ is selected from the group consisting of H, halogen, —OH, —$OCH_3$, substituted methyl, wherein the substituted methyl is substituted with a substituent selected from the group consisting of halogen, —OH, —$OCH_3$, —$NHCH_3$, —N($CH_3$)$_2$. In an embodiment, $R^3$ is selected from the group consisting of H, halogen, —OH, methyl, wherein the methyl is substituted with —N($CH_3$)$_2$. In another embodiment, $R^3$ is selected from the group consisting of H, halogen, —OH, —O($C_{1-4}$ alkyl), substituted $C_{1-4}$alkyl, wherein the substituted $C_{1-4}$alkyl is substituted with one or more substituents selected from the group consisting of halogen, —$NH_2$, —NH($C_{1-4}$ alkyl), —N($C_{1-4}$alkyl)$_2$. In an embodiment, $R^3$ is selected from the group consisting of H, halogen, —OH, $C_{1-2}$alkyl, wherein the alkyl is substituted with one or more substituents selected from the group consisting of halogen, —NH ($C_{1-2}$alkyl), —N($C_{1-2}$alkyl)$_2$. In an embodiment, $R^3$ is selected from the group consisting of H, halogen, —OH, methyl, wherein the methyl is substituted with a substituent selected from the group consisting of halogen, —NH($C_{1-2}$ alkyl), —N($C_{1-2}$alkyl)$_2$. In an embodiment, $R^3$ is selected from the group consisting of H, halogen, —OH, methyl, wherein the methyl is substituted with a substituent selected from the group consisting of halogen, —$NHCH_3$, —N ($CH_3$)$_2$. In an embodiment, $R^3$ is selected from the group consisting of H, halogen, —OH, methyl, wherein the methyl is substituted with —N($CH_3$)$_2$. In another embodiment, $R^3$ is selected from the group consisting of H, halogen, —OH, —O($C_{1-4}$alkyl), —$NH_2$, —NH($C_{1-4}$alkyl), substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl). In an embodiment, $R^3$ is selected from the group consisting of H, halogen, —OH, —$OCH_3$, —$NH_2$, —$NHCH_3$, substituted methyl, wherein the substituted methyl is substituted with a substituent selected from the group consisting of halogen, —OH, —O($C_{1-2}$alkyl), —NH ($C_{1-2}$alkyl). In an embodiment, $R^3$ is selected from the group consisting of H, halogen, —OH, —$OCH_3$, —$NH_2$, —$NHCH_3$, substituted methyl, wherein the substituted methyl is substituted with a substituent selected from the group consisting of halogen, —OH, —$OCH_3$, —$NHCH_3$. In an embodiment, $R^3$ is selected from the group consisting of H, halogen, —OH, —$NH_2$, methyl, wherein the methyl is substituted with —$N(CH_3)_2$. In another embodiment, $R^3$ is selected from the group consisting of H, halogen, —OH, —O($C_{1-4}$alkyl), substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl). In an embodiment, $R^3$ is selected from the group consisting of H, halogen, —OH, —$OCH_3$, substituted methyl, wherein the substituted methyl is substituted with a substituent selected from the group consisting of halogen, —OH, —O($C_{1-2}$alkyl), —NH ($C_{1-2}$alkyl). In an embodiment, $R^3$ is selected from the group consisting of H, halogen, —OH, —$OCH_3$, substituted methyl, wherein the substituted methyl is substituted with a substituent selected from the group consisting of halogen, —OH, —$OCH_3$, —$NHCH_3$. In an embodiment, $R^3$ is selected from the group consisting of H, halogen, —OH, methyl, wherein the methyl is substituted with —$N(CH_3)_2$. In another embodiment, $R^3$ is selected from the group consisting of H, halogen, —OH, —O($C_{1-4}$alkyl), substituted $C_{1-4}$alkyl, wherein the substituted $C_{1-4}$alkyl is substituted with one or more substituents selected from the group consisting of halogen, —$NH_2$, —NH($C_{1-4}$alkyl). In an embodiment, $R^3$ is selected from the group consisting of H, halogen, —OH, $C_{1-2}$alkyl, wherein the alkyl is substituted with one or more substituents selected from the group consisting of halogen, —NH($C_{1-2}$alkyl). In an embodiment, $R^3$ is selected from the group consisting of H, halogen, —OH, methyl, wherein the methyl is substituted with a substituent selected from the group consisting of halogen, —NH($C_{1-2}$alkyl). In an embodiment, $R^3$ is selected from the group consisting of H, halogen, —OH, methyl, wherein the methyl is substituted with a substituent selected from the group consisting of halogen, —$NHCH_3$. In an embodiment, $R^3$ is selected from the group consisting of H, F, $C_1$, methyl, —OH, —$NH_2$. In an embodiment, $R^3$ is selected from the group consisting of H, F, methyl, —OH, —$NH_2$. In an embodiment, $R^3$ is H. In an embodiment, $R^3$ is —OH. In an embodiment, $R^3$ is $CH^3$.

In an embodiment, $R^4$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$. In an embodiment, $R^4$ is selected from the group consisting of H, halogen, —OH, —O($C_{1-4}$alkyl), —$NH_2$, —NH($C_{1-4}$alkyl), —N($C_{1-4}$alkyl)$_2$, substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^4$ is selected from the group consisting of H, halogen, —OH, —O($C_{1-3}$alkyl), —$NH_2$, —NH($C_{1-3}$alkyl), —N($C_{1-3}$alkyl)$_2$, substituted $C_{1-3}$alkyl, wherein the substituted $C_{1-3}$alkyl is optionally substituted with one or more substituents selected from the group consisting of halogen, —OH, —O($C_{1-2}$alkyl), —$NH_2$, —NH($C_{1-2}$alkyl), —N($C_{1-2}$alkyl)$_2$. In an embodiment, $R^4$ is selected from the group consisting of H, halogen, —OH, —$NH_2$, —NH($C_{1-4}$alkyl), substituted $C_{1-4}$alkyl, substituted —O($C_{1-4}$alkyl), substituted —N($C_{1-4}$alkyl)$_2$, wherein the substituted $C_{1-4}$alkyl, substituted —O($C_{1-4}$alkyl) and substituted —N($C_{1-4}$alkyl)$_2$ are substituted with one or more substituents selected from the group consisting of halogen, —OH, —O($C_{1-2}$alkyl), —$NH_2$, —NH($C_{1-4}$alkyl). In an embodiment, $R^4$ is selected from the group consisting of H, halogen, —OH, —O($C_{1-2}$alkyl), —$NH_2$, —NH($C_{1-2}$alkyl), substituted $C_{1-2}$alkyl, substituted —O($C_{1-2}$alkyl), wherein the substituted $C_{1-2}$alkyl and substituted —O($C_{1-2}$alkyl) are substituted with one or more substituents selected from the group consisting of halogen, —OH, —O($C_{1-2}$alkyl), —$NH_2$, —NH($C_{1-2}$alkyl). In an embodiment, $R^4$ is selected from the group consisting of H, halogen, —OH, —$OCH_3$, —$NH_2$, —$NHCH_3$, substituted $C_{1-2}$alkyl, wherein the substituted $C_{1-2}$alkyl is substituted with one or more substituents selected from the group consisting of halogen, —OH, —$OCH_3$, —$NH_2$, —$NHCH_3$. In an embodiment, $R^4$ is selected from the group consisting of H, halogen, —OH, —$NH_2$, —NH($C_{1-4}$alkyl), substituted $C_{1-4}$alkyl, wherein the substituted $C_{1-4}$alkyl is substituted with one or more substituents selected from the group consisting of halogen, —OH, —$OCH_3$, —$NH_2$, —NH($C_{1-4}$alkyl). In an embodiment, $R^4$ is selected from the group consisting of H, halogen, —OH, —$NH_2$, —NH($C_{1-2}$alkyl), —N($C_{1-2}$alkyl)$_2$, substituted $C_{1-2}$alkyl, wherein the substituted $C_{1-2}$alkyl is substituted with one or more substituents selected from the group consisting of halogen, —OH, —O($C_{1-2}$alkyl), —$NH_2$, —NH($C_{1-2}$alkyl). In an embodiment, $R^4$ is selected from the group consisting of H, halogen, —OH, —$NH_2$, —$NHCH_3$, substituted $C_{1-2}$alkyl, wherein the substituted $C_{1-2}$alkyl is substituted with one or more substituents selected from the group consisting of halogen, —OH, —$OCH_3$, —$NH_2$, —$NHCH_3$. In an embodiment, $R^4$ is selected from the group consisting of H, halogen, $C_{1-4}$alkyl, —OH, —O($C_{1-4}$alkyl), wherein the alkyl is optionally substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^4$ is selected from the group consisting of H, halogen, $C_{1-2}$alkyl, —OH, —$OCH_3$, wherein the alkyl halogen, —OH, —$OCH_3$, —$NH_2$, —$NHCH_3$, —$N(CH_3)_2$. In an embodiment, $R^4$ is selected from the group consisting of H, halogen, $C_{1-4}$alkyl, —OH, —O($C_{1-4}$alkyl), —$NH_2$, —NH($C_{1-4}$alkyl), —N($C_{1-4}$alkyl)$_2$, wherein the alkyl is optionally substituted with one or more substituents selected from the group consisting of halogen, —OH, —O($C_{1-4}$alkyl). In an embodiment, $R^4$ is selected from the group consisting of H, halogen, $C_{1-2}$alkyl, —OH, —$OCH_3$, —$NH_2$, —$NHCH_3$, —$N(CH_3)_2$, wherein the alkyl is optionally substituted with one or more substituents selected from the group consisting of halogen, —OH, —$OCH_3$. In an embodiment, $R^4$ is selected from the group consisting of H, halogen, $C_{1-4}$alkyl, —OH, —O($C_{1-4}$alkyl), wherein the alkyl is optionally substituted with one or more substituents selected from the group consisting of halogen, —OH, —O($C_{1-4}$alkyl). In an embodiment, $R^4$ is selected from the group consisting of H, halogen, $C_{1-2}$alkyl, —OH, —$OCH_3$, wherein the alkyl is optionally substituted with one or more substituents selected from the group consisting of halogen, —OH, —$OCH_3$. In an embodiment, $R^4$ is selected from the group consisting of H, —OH, —$OCH_3$. In an embodiment, $R^4$ is H. In an embodiment, $R^4$ is —OH.

In an embodiment, $R^5$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$ alkyl), —C(═O)($C_{1-6}$alkyl), wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$ alkyl), —NHC(═O)($C_{1-6}$alkyl), —C(═O)($C_{1-6}$ alkyl). In an embodiment, $R^5$ is selected from the group consisting of H, halogen, $C_{1-4}$alkyl, —OH, —O($C_{1-4}$alkyl), —$NH_2$, —NH($C_{1-4}$alkyl), —N($C_{1-4}$alkyl)$_2$, wherein the alkyl is optionally substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^5$ is selected from the group consisting of H, halogen, —OH, —O($C_{1-4}$alkyl), —$NH_2$, —NH($C_{1-4}$ alkyl), —N($C_{1-4}$alkyl)$_2$, —C(═O)O($C_{1-4}$alkyl), —C(═O)$NH_2$, —C(═O)NH($C_{1-4}$alkyl), —C(═O)N($C_{1-4}$alkyl)$_2$, —OC(═O)($C_{1-4}$alkyl), —NC(═O)($C_{1-4}$alkyl)$_2$, —C(═O)($C_{1-4}$alkyl), substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl), —N($C_{1-4}$alkyl)$_2$, —C(═O)O($C_{1-4}$alkyl), —C(═O)$NH_2$, —C(═O)NH($C_{1-4}$ alkyl), —C(═O)N($C_{1-4}$alkyl)$_2$, —OC(═O)($C_{1-4}$ alkyl), —NC(═O)($C_{1-4}$alkyl)$_2$, —C(═O)($C_{1-4}$alkyl). In an embodiment, $R^5$ is selected from the group consisting of H, halogen, —OH, —O($C_{1-4}$alkyl), —$NH_2$, —NH($C_{1-4}$alkyl), —N($C_{1-4}$alkyl)$_2$, substituted $C_{1-4}$alkyl, wherein the substituted $C_{1-4}$alkyl is substituted with one or more substituents selected from the group consisting of halogen, —OH, —O($C_{1-4}$alkyl), —$NH_2$, —NH($C_{1-4}$alkyl), —N($C_{1-4}$alkyl)$_2$. In an embodiment, $R^5$ is selected from the group consisting of H, halogen, —O($C_{1-4}$alkyl), —NH($C_{1-4}$alkyl), —N($C_{1-4}$ alkyl)$_2$, substituted $C_{1-2}$alkyl, wherein the substituted $C_{1-2}$alkyl is substituted with one or more substituents selected from the group consisting of halogen, —O($C_{1-4}$alkyl), —NH($C_{1-4}$alkyl), —N($C_{1-4}$alkyl)$_2$. In an embodiment, $R^5$ is selected from the group consisting of H, halogen, —O($C_{1-4}$ alkyl), —NH($C_{1-4}$alkyl), —N($C_{1-4}$alkyl)$_2$, substituted $C_{1-2}$alkyl, wherein the substituted $C_{1-2}$alkyl is substituted with one or more substituents selected from the group consisting of halogen, —$OCH_3$, —$NHCH_3$, —N($CH_3$)$_2$. In an embodiment, $R^5$ is selected from the group consisting of H, halogen, —O($C_{1-2}$alkyl), —NH($C_{1-2}$alkyl), —N($C_{1-2}$alkyl)$_2$, substituted $C_{1-2}$alkyl, wherein the substituted $C_{1-2}$alkyl is substituted with one or more substituents selected from the group consisting of halogen, —$OCH_3$, —$NHCH_3$, —N($CH_3$)$_2$.

In an embodiment, $R^6$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$. In another embodiment, $R^6$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —OH, —$NH_2$. In an embodiment, $R^6$ is selected from the group consisting of H, halogen, —$NO_2$, —CN, $C_{1-2}$alkyl, —OH, —O($C_{1-2}$alkyl), —$NH_2$, —NH($C_{1-2}$alkyl), —N($C_{1-2}$ alkyl)$_2$, wherein the alkyl is optionally substituted with one or more substituents selected from the group consisting of halogen, —OH, —$NH_2$. In another embodiment, $R^6$ is selected from the group consisting of H, halogen, —$NO_2$, —CN, $C_{1-4}$alkyl, —OH, —O($C_{1-4}$alkyl), —$NH_2$, —NH($C_{1-4}$alkyl), —N($C_{1-4}$alkyl)$_2$, wherein the alkyl is optionally substituted with one or more halogens. In another embodiment, $R^6$ is selected from the group consisting of H, halogen, —$NO_2$, —CN, $C_{1-2}$alkyl, —OH, —O($C_{1-2}$alkyl), —$NH_2$, —NH($C_{1-4}$alkyl), —N($C_{1-4}$alkyl)$_2$. In an embodiment, $R^6$ is selected from the group consisting of H, F, Cl, Br, $C_{1-6}$alkyl, —OH, —$NH_2$, wherein the alkyl is optionally substituted with one or more substituents selected from the group consisting of halogen, —OH, —$NH_2$. In another embodiment, $R^6$ is selected from the group consisting of H, F, Cl, Br, methyl, —OH, —$NH_2$. In a particular embodiment, $R^6$ is H or —OH, particularly H.

In an embodiment, $R^3$ is methyl, and $R^4$ is selected from the group consisting of $C_{1-3}$alkyl substituted with —OH, —$NH_2$, —NH($C_{1-3}$alkyl), —N($C_{1-3}$alkyl)$_2$, —COOH, wherein the substituted $C_{1-3}$alkyl is substituted with one or more substituents selected from the group consisting of —OH, —$NH_2$, —NH($C_{1-2}$alkyl), —N($C_{1-2}$alkyl)$_2$ and —COOH. In an embodiment, $R^3$ is methyl, and $R^4$ is selected from the group consisting of $C_{1-3}$alkyl substituted with —$NH_2$, —NH($C_{1-3}$alkyl), —N($C_{1-3}$alkyl)$_2$, —COOH, wherein the substituted $C_{1-3}$alkyl is substituted with one or more substituents selected from the group consisting of —OH, —$NH_2$, —NH($C_{1-2}$alkyl), —N($C_{1-2}$alkyl)$_2$ and —COOH.

In another embodiment, $R^3$ is methyl, and $R^5$ is selected from the group consisting of $C_{1-3}$ alkyl substituted with —OH, —$NH_2$, —NH($C_{1-3}$alkyl), —N($C_{1-3}$alkyl)$_2$, —COOH, wherein the substituted $C_{1-3}$alkyl is substituted with one or more substituents selected from the group consisting of —OH, —$NH_2$, —NH($C_{1-2}$alkyl), —N($C_{1-2}$ alkyl)$_2$ and —COOH. In another embodiment, $R^3$ is methyl, and $R^5$ is selected from the group consisting of $C_{1-3}$alkyl substituted with —$NH_2$, —NH($C_{1-3}$alkyl), —N($C_{1-3}$alkyl)$_2$, —COOH, wherein the substituted $C_{1-3}$alkyl is substituted with one or more substituents selected from the group consisting of —OH, —$NH_2$, —NH($C_{1-2}$alkyl), —N($C_{1-2}$ alkyl)$_2$ and —COOH.

In an embodiment, $R^{14}$, $R^5$, $R^{16}$, $R^{17}$, $R^{18}$ each independently selected from the group consisting of H, halogen, —$NO_2$, —CN, $C_{1-6}$alkyl, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$cyclohydrocarbyl), —NH(C═O)(3- to 7-membered heterocyclyl), —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$ cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, wherein the alkyl, alkylene, alkenyl, alkynyl, cyclohydrocarbyl or heterocyclyl is optionally substituted with one or more substituents selected from the group consisting of H, halogen, nitro, cyano, —OH, —SH, —$NH_2$, ═O and —COOH. In an embodiment, $R^{14}$, $R^{15}$, $R^{16}$, $R^{17}$, $R^{18}$ are each independently selected from the group consisting of H, halogen, —$NO_2$, —CN, $C_{1-6}$alkyl, —$OR^7$, —$NR^7R^8$, —C(═O)$OR^7$, —C(═O)$NR^7R^8$, —OC(═O)$R^7$, —NC(═O)$R^7R^8$, —C(═O)$R^7$. In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —O($C_{1-6}$alkyl), —O($C_{3-6}$cyclohydrocarbyl), —O($C_{1-4}$ alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$cyclohydrocarbyl), —NH(C═O)(3- to 7-membered heterocyclyl). In an embodiment, $R^{14}$, $R^{15}$, $R^{17}$, $R^{18}$ each independently selected from the group consisting of H, halogen, —$NO_2$, —CN, $C_{1-6}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$ alkyl), —O(C═O)($C_{3-6}$ cyclohydrocarbyl), —O(C═O)($C_{1-4}$alkylene-$C_{3-6}$ cyclohydrocarbyl), —O(C═O)(3- to 7-membered heterocyclyl), —O(C═O)($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$ cyclohydrocarbyl)$_2$, —NH($C_{1-4}$alkylene-$C_{3-6}$cyclohydrocarbyl), —N($C_{1-4}$alkylene-$C_{3-6}$ cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$ alkylene-$C_{3-6}$cyclohydrocarbyl), —NH(C═O)(3- to 7-membered heterocyclyl). In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —O($C_{1-6}$alkyl), —O($C_{3-6}$cyclohydrocarbyl), —O($C_{1-4}$ alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl). In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$ alkyl), —O(C═O)($C_{3-6}$ cyclohydrocarbyl), —O(C═O)($C_{1-4}$alkylene-$C_{3-6}$ cyclohydrocarbyl), —O(C═O)(3- to 7-membered heterocyclyl), —O(C═O)($C_{1-4}$alkylene)-(3- to 7-membered heterocyclyl). In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$cyclohydrocarbyl), —NH(C═O)(3- to 7-membered heterocyclyl). In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$ alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cyclohydrocarbyl), —NH(C═O)($C_{1-4}$alkylene-$C_{3-6}$cyclohydrocarbyl), —NH(C═O)(3- to 7-membered heterocyclyl). In an embodiment, $R^{14}$, $R^{15}$, $R^{16}$, $R^{17}$, $R^{18}$ each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH(C═O)($C_{1-6}$alkyl). In an embodiment, $R^{14}$, $R^{15}$, $R^{17}$, $R^{18}$ each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH(C═O)($C_{1-6}$alkyl). In an embodiment, $R^{16}$ is H. In an embodiment, $R^{16}$ is —$OCH_3$.

Accordingly, in an embodiment, formula (I) has a structure of formula (vii), wherein the LCM moiety has a structure of above formula (7) (see above formula (7) and embodiments thereof) or a pharmaceutically acceptable salt thereof (vii)

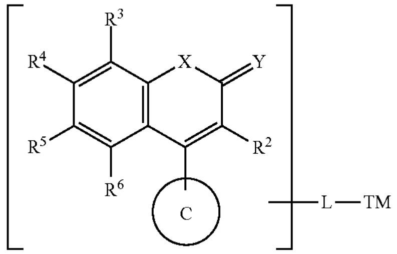

In an embodiment, L can covalently bind to any suitable site in formula (7).

The structure of following formula (8) falls within the scope of the structures of formula (1), formula (3), formula (6) and formula (7). In an embodiment, the LCM moiety has a structure of formula (8):

(8)

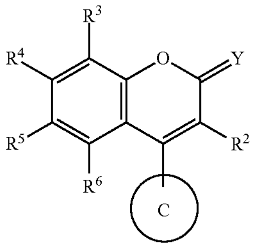

wherein:

Y is O or S;

ring C, $R^2$, $R^3$, $R^4$, $R^5$, $R^6$ are as defined in formula (7);

In an embodiment, Y is O. When Y is O, formula (8) is

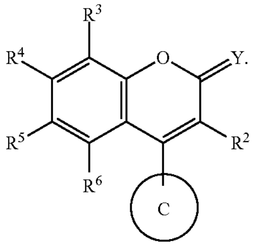

In a particular embodiment, formula (8) has a structure selected from the group consisting of Compound A5, A6 and A7:

A5

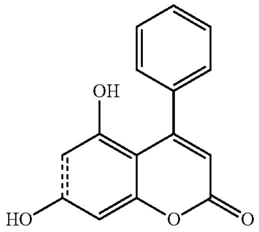

A6

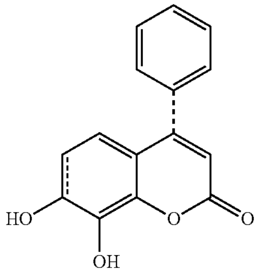

and

-continued

A7

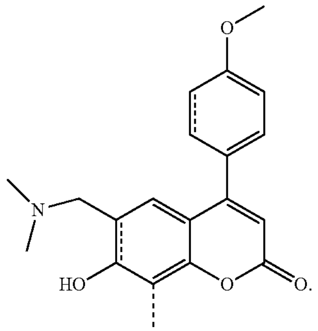

Accordingly, in an embodiment, formula (I) has a structure of formula (viii), wherein the LCM moiety has a structure of above formula (8) (see above formula (8) and embodiments thereof) or a pharmaceutically acceptable salt thereof (viii)

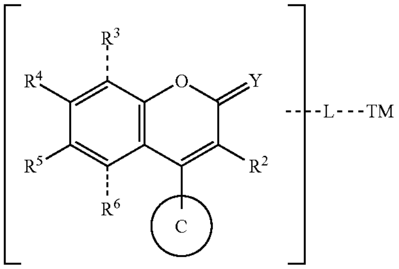

In an embodiment, L can covalently bind to any suitable site in formula (8). The suitable site comprises for example, —OH, or the like.

In an embodiment, formula (viii) is

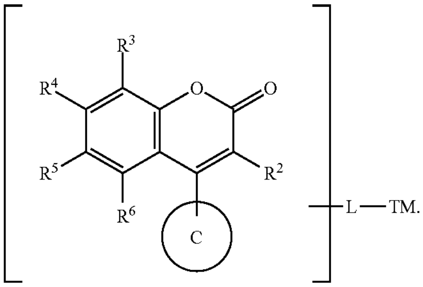

In a particular embodiment, formula (viii) has a structure selected from the group consisting of:

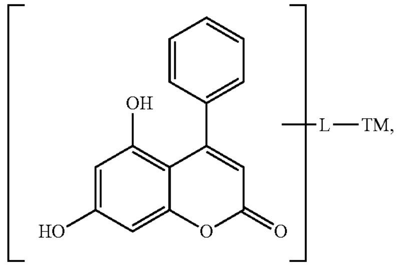

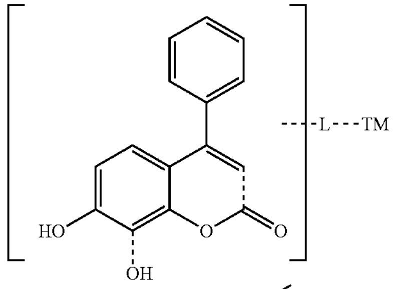

and

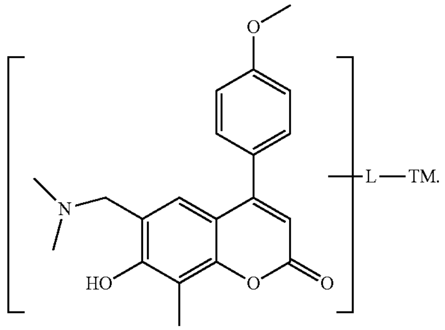

The structure of following formula (9) falls within the scope of the structures of formula (1), formula (3) and formula (6). In an embodiment, the LCM moiety has a structure of formula (9):

(9)

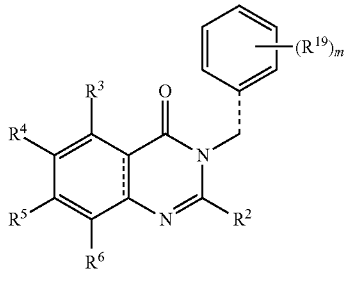

wherein:

$R^{19}$, on each occurrence, is each independently selected from the group consisting of halogen, —$NO_2$, —CN, $C_{1-6}$alkyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl is optionally substituted with one or more substituents selected from the group consisting of halogen, —$NO_2$, —CN, —OH, —O($C_{1-6}$ alkyl), —$NH_2$, —NH($C_{1-6}$alkyl), —N($C_{1-6}$alkyl)$_2$, —COOH;

m is 0, 1, 2, 3, 4 or 5;

$R^2$, $R^3$, $R^4$, $R^5$, $R^6$ are as defined in formula (6);

In an embodiment, $R^2$ is selected from the group consisting of H, halogen, —$NO_2$, —CN, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$ alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$. In a preferable embodiment, $R^2$ is selected from the group consisting of H, halogen, —$NO_2$, —CN, $C_{1-6}$alkyl, —OH, wherein the alkyl is optionally substituted with one or more substituents selected from the group consisting of halogen, —$NO_2$, —CN, $C_{1-6}$alkyl, —$NR^{a2}R^{b2}$. In a more preferable embodiment, $R^2$ is selected from the group consisting of H, halogen, $C_{1-6}$alkyl, —OH, wherein the alkyl is optionally substituted with one or more groups selected from the group consisting of halogen, $C_{1-6}$alkyl and —$NR^{a2}R^{b2}$. In a further embodiment, $R^2$ is selected from the group consisting of H, $C_{1-4}$alkyl, —OH, wherein the alkyl is optionally substituted with one or more groups selected from the group consisting of —$NR^{a2}R^{b2}$. In a particular embodiment, $R^2$ is selected from the group consisting of H, $C_{1-4}$alkyl, —OH, wherein the alkyl is —$CH_2[CH(CH_3)_2]$, and is optionally substituted with one or more groups selected from the group consisting of —$NR^{a2}R^{b2}$. In another embodiment, $R^2$ is alkyl substituted with —$NR^{a1}R^{b1}$. $R^{a1}$, $R^{1b}$, $R^{a2}$, $R^{b2}$ are as defined in formula (6). In a particular embodiment, $R^2$ is

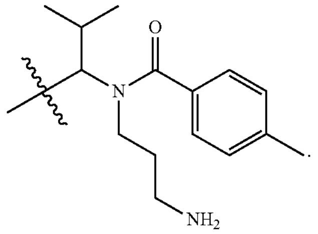 [SMILES: *C(C(C)C)N(CCCN)C(=O)c1ccc(C)cc1]

In an embodiment, $R^{19}$, on each occurrence, is selected from the group consisting of halogen, $C_{1-6}$alkyl, —OH, —O($C_{1-6}$alkyl), —$NH_2$, —NH($C_{1-6}$alkyl), —N($C_{1-6}$alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$ alkyl)$_2$.

In a particular embodiment, formula (9) has a structure of Compound A8:

A8

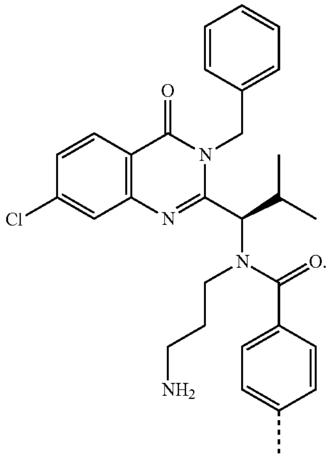

Accordingly, in an embodiment, formula (I) has a structure of formula (ix), wherein the LCM moiety has a structure of above formula (9) (see above formula (9) and embodiments thereof) or a pharmaceutically acceptable salt thereof (ix)

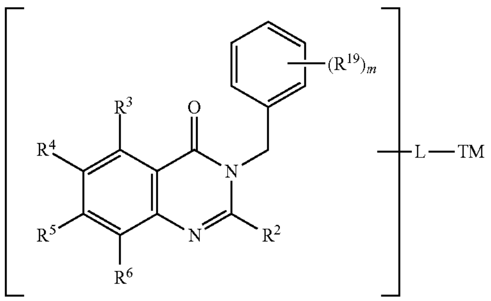

In an embodiment, L can covalently bind to any suitable site in formula (9). The suitable site comprises for example, —$NH_2$, or the like.

In a particular embodiment, formula (ix) has a structure of:

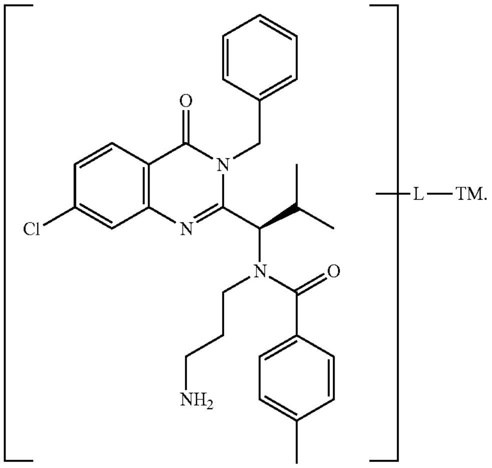

In an embodiment, LCM moiety has a structure of formula (10), or a pharmaceutically acceptable salt thereof:

(10)

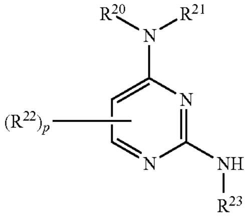

wherein, $R^{20}$ is selected from the group consisting of bicyclic heteroaryl, having 9-10 ring atoms, the ring atoms comprising 1-3 heteroatoms each independently selected from the group consisting of O, S, N, the remaining atoms being C; the heteroaryl is unsubstituted or substituted with at least one group selected from the group consisting of $R^{X3}$;

$R^{21}$ is selected from the group consisting of $C_{1-8}$alkyl;

$R^{22}$ is selected from the group consisting of $R^{X3}$;

$R^{23}$ is phenyl, which is unsubstituted or substituted with at least one group selected from the group consisting of $R^{X3}$;

$R^{X3}$, on each occurrence, is each independently selected from the group consisting of $C_{1-8}$ alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$ alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$ alkyl), —C(═O)N($C_{1-8}$alkyl)$_2$, —S(═O)$_2$OH, —S(═O)$_2$(O$C_{1-8}$alkyl), —S(═O)$_2NH_2$, —S(═O)$_2$NH($C_{1-8}$alkyl), —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

p is 0, 1 or 2.

In an embodiment, $R^{20}$ is selected from the group consisting of the following bicyclic heteroaryl: benzofuranyl, benzothienyl, benzoxazolyl, benzisoxazolyl, benzimidazolyl, benzotriazolyl, indazolyl, indolyl and isoindolyl; and the heteroaryl unsubstituted or substituted with at least one group selected from the group consisting of $C_{1-8}$alkyl.

In an embodiment, $R^{22}$ is selected from the group consisting of $C_{1-8}$alkyl, halogen and —CN.

In an embodiment, p is 0.

In a particular embodiment formula (10) has a structure of Compound A9 or A9':

A9

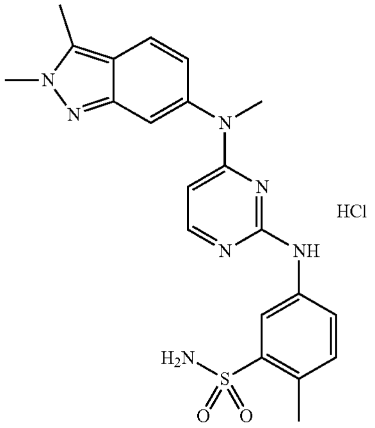

A9'

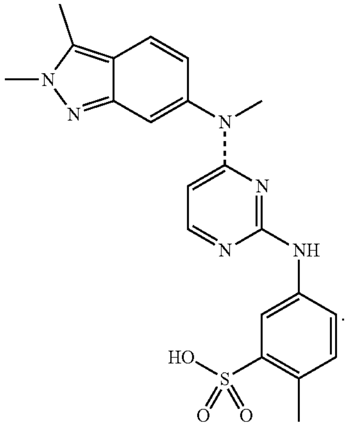

Accordingly, in an embodiment, formula (I) has a structure of formula (x), wherein the LCM moiety has a structure of above formula (10) (see above formula (10) and embodiments thereof) or a pharmaceutically acceptable salt thereof (x)

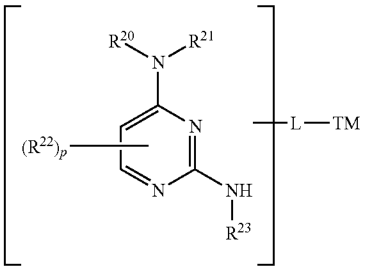

In an embodiment, L can covalently bind to any suitable site in formula (10). The suitable site comprises for example, $—S(O)_2OH$, or the like.

In a particular embodiment, formula (x) has a structure of:

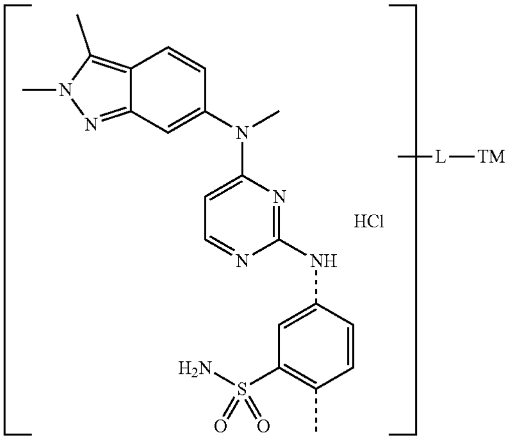

or

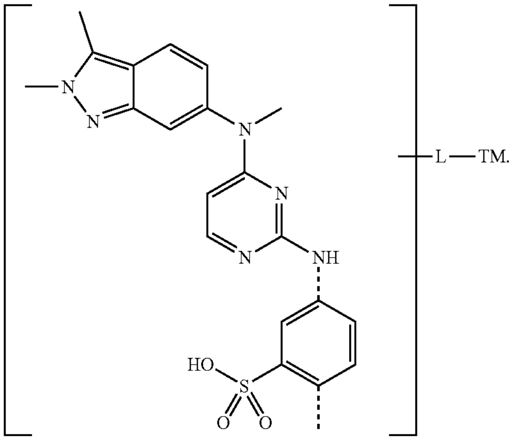

In an embodiment, LCM moiety has a structure of formula (11), or a pharmaceutically acceptable salt thereof:

(11)

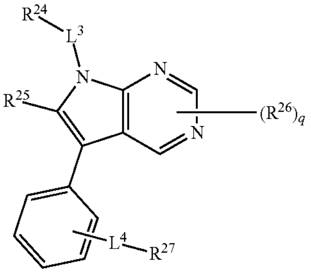

wherein, $R^{24}$ is selected from the group consisting of 3- to 7-membered heterocyclyl; the heterocyclyl is unsubstituted or substituted with at least one group selected from the group consisting of $R^{X3}$;

$L^3$ is selected from a combination consisting of a $C_{1-8}$alkylene and a $C_{3-6}$cycloalkylene;

$R^{25}$ is selected from the group consisting of H, $C_{1-8}$alkyl;

$R^{26}$ is selected from the group consisting of halogen, $—NO_2$, —CN, $C_{1-8}$alkyl, —OH, $—O(C_{1-8}alkyl)$, —SH, $—S(C_{1-8}alkyl)$, $—NH_2$, $—NH(C_{1-8}alkyl)$, $—N(C_{1-8}alkyl)_2$;

$L^4$ is selected from the group consisting of $C_{1-8}$alkylene and $C_{1-8}$alkoxylene;

$R^{27}$ is phenyl, which is unsubstituted or substituted with at least one group selected from the group consisting of $R^{X3}$;

q is 0, 1 or 2;

$R^{X3}$ is as defined in formula (10).

In an embodiment, $R^{24}$ is selected from the group consisting of 5- to 6-membered heterocyclyl, preferably pyrrolidinyl; and the heterocyclyl is unsubstituted or substituted with at least one group selected from the group consisting of $C_{1-8}$alkyl.

In an embodiment, L3 is

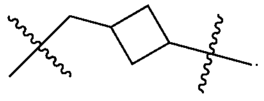 [SMILES: *CC1CC(*)C1]

In an embodiment, q is 1.

In a particular embodiment, formula (11) has a structure of Compound A10:

A10

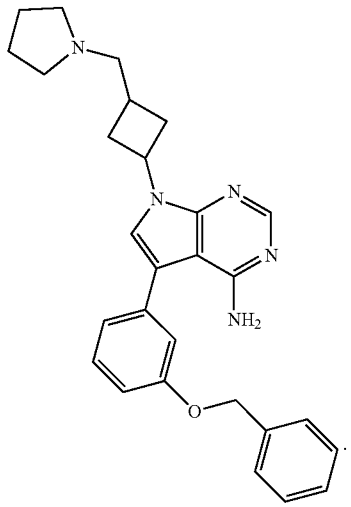

Accordingly, in an embodiment, formula (I) has a structure of formula (xi), wherein the LCM moiety has a structure of above formula (11) (see above formula (11) and embodiments thereof) or a pharmaceutically acceptable salt thereof (xi)

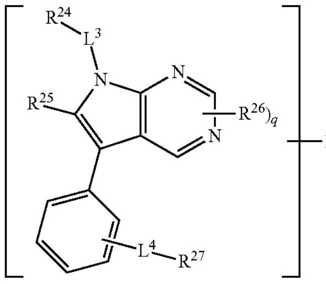

In an embodiment, L can covalently bind to any suitable site in formula (11). The suitable site comprises for example, $—NH_2$, or the like.

In a particular embodiment, formula (xi) has a structure of:

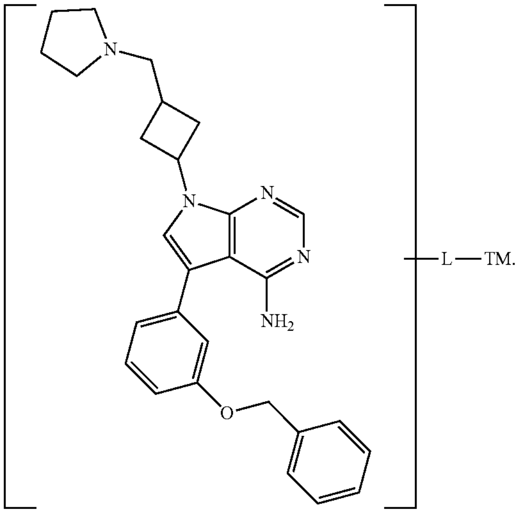

In an embodiment, LCM moiety has a structure of formula (12), or a pharmaceutically acceptable salt thereof:

(12)

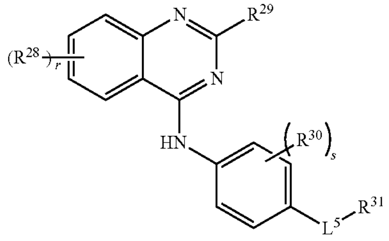

wherein, $R^{28}$ is $C_{1-8}$alkenyl; the alkenyl is substituted with at least one $C_{1-8}$alkyl, the alkyl is optionally substituted with one or more substituents selected from the group consisting of $R^{X4}$;

$R^{29}$ is selected from the group consisting of H, $C_{1-8}$alkyl;

$R^{30}$ is selected from the group consisting of halogen, $—NO_2$, —CN, $C_{1-8}$alkyl, —OH, $—O(C_{1-8}alkyl)$, —SH, $—S(C_{1-8}alkyl)$, $—NH_2$, $—NH(C_{1-8}alkyl)$, $—N(C_{1-8}alkyl)_2$;

$L^5$ is selected from the group consisting of —O—, $C_{1-8}$alkylene and $C_{1-8}$alkoxylene;

$R^{31}$ is selected from the group consisting of 6-membered heteroaryl, having 6 ring atoms, the ring atoms comprising 1-2 heteroatoms each independently selected from the group consisting of O, S, N, the remaining atoms being C, the heteroaryl is unsubstituted or substituted with at least one group selected from the group consisting of $R^{X3}$;

r is 0,1,2,3 or 4;

s is 0, 1, 2, 3 or 4;

$R^{X4}$, on each occurrence, is each independently selected from the group consisting of $C_{1-8}$ alkyl, $C_{1-8}$alkenyl, halogen, —CN, $—CF_3$, $—CHF_2$, $—CH_2F$, $—NO_2$, $—O(C_{1-8}alkyl)$, $—S(C_{1-8}alkyl)$, $—NH(C_{1-8}alkyl)$, $—N(C_{1-8}alkyl)_2$, $—OC(═O)(C_{1-8}alkyl)$, $—NHC(═O)(C_{1-8}alkyl)$, $—NC(═O)(C_{1-8}alkyl)_2$, —OS (═O)$_2$(C$_{1-6}$alkyl), —NHS(═O)$_2$(C$_{1-8}$alkyl), —N(C$_{1-8}$ alkyl)S(═O)$_2$(C$_{1-8}$alkyl); wherein the alkyl is optionally substituted with one or more substituents selected from the group consisting of halogen, —NO$_2$, —CN, C$_{1-8}$alkyl, —OH, —O(C$_{1-8}$alkyl), —SH, —S(C$_{1-8}$alkyl), —NH$_2$, —NH(C$_{1-8}$alkyl), —N(C$_{1-8}$alkyl)$_2$, ═O and —COOH;

$R^{X3}$ is as defined in formula (10).

In an embodiment, $R^{29}$ is H.

In an embodiment, $R^{31}$ is pyridinyl, preferably pyridin-3-yl, the pyridinyl is unsubstituted or substituted with at least one group selected from the group consisting of C$_{1-8}$alkyl.

In an embodiment, $R^{X4}$ is selected from the group consisting of —O(C$_{1-8}$alkyl), preferably —O(C$_{1-3}$alkyl), particularly methoxy.

(xii)

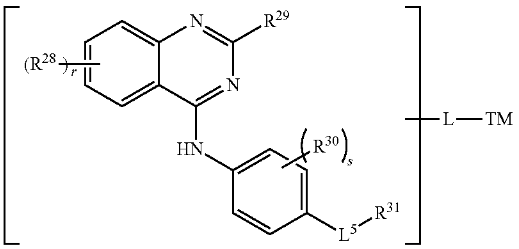

In an embodiment, L can covalently bind to any suitable site in formula (12).

In a particular embodiment, formula (xii) has a structure of:

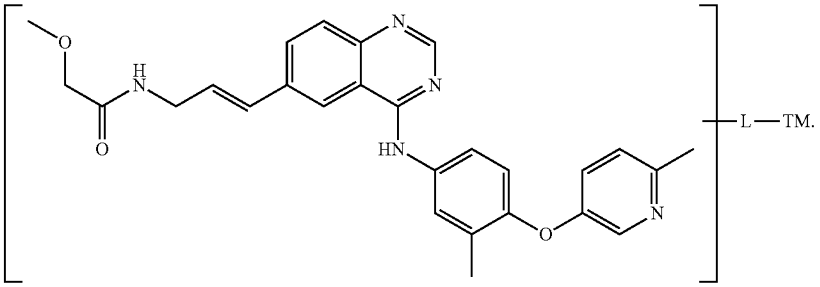

In an embodiment, $R^{28}$ is

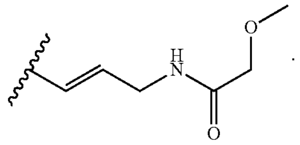 [SMILES: */C=C/CNC(=O)COC]

In an embodiment, r is 1.

In a particular embodiment, formula (12) has a structure of Compound A11:

A11

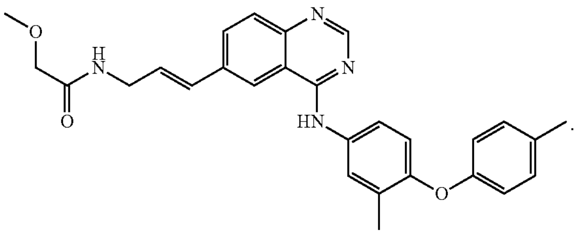

Accordingly, in an embodiment, formula (I) has a structure of formula (xii), wherein the LCM moiety has a structure of above formula (12) (see above formula (12) and embodiments thereof) or a pharmaceutically acceptable salt thereof In an embodiment, LCM moiety has a structure of formula (13), or a pharmaceutically acceptable salt thereof:

(13)

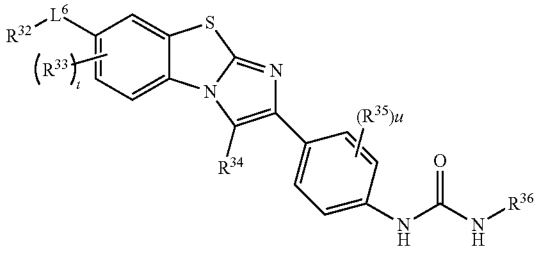

wherein, $R^{32}$ is selected from the group consisting of 3- to 7-membered heterocyclyl; the heterocyclyl is unsubstituted or substituted with at least one group selected from the group consisting of $R^{X3}$;

$L^6$ is selected from the group consisting of —O—, C$_{1-8}$alkylene and C$_{1-8}$alkoxylene;

$R^{33}$, $R^{34}$ are selected from the group consisting of halogen, C$_{1-8}$alkyl;

$R^{35}$ is selected from the group consisting of halogen, —NO$_2$, —CN, C$_{1-8}$alkyl, —OH, —O(C$_{1-8}$ alkyl), —SH, —S(C$_{1-8}$alkyl), —NH$_2$, —NH(C$_{1-8}$alkyl), —N(C$_{1-8}$alkyl)$_2$;

$R^{36}$ is selected from the group consisting of 5-membered heteroaryl, having 5 ring atoms, the ring atoms comprising 1-3 heteroatoms each independently selected from the group consisting of O, S, N, the remaining atoms being C, the heteroaryl is unsubstituted or substituted with at least one group selected from the group consisting of $R^{X3}$;

t is 0, 1, 2 or 3;

u is 0, 1, 2, 3 or 4;

$R^{X3}$ is as defined in formula (10).

In an embodiment, $R^{32}$ is selected from the group consisting of 5- to 6-membered heterocyclyl, the heterocyclyl is preferably pyrrolidinyl, imidazolidinyl, pyrazolidinyl, tetrahydropyranyl, piperidinyl, morpholinyl, thiomorpholinyl or piperazinyl, and the heterocyclyl is unsubstituted or substituted with at least one group selected from the group consisting of halogen, $C_{1-8}$alkyl.

In an embodiment, $R^{36}$ is selected from the group consisting of following 5-membered heteroaryl groups: pyrrolyl, oxazolyl, thiazolyl, imidazolyl, pyrazolyl, isoxazolyl and isothiazolyl, the heteroaryl unsubstituted or substituted with at least one group selected from the group consisting of $C_{1-8}$alkyl.

In an embodiment, t is 0. In another embodiment, u is 0.

In a particular embodiment, formula (13) has a structure of Compound A12:

A12

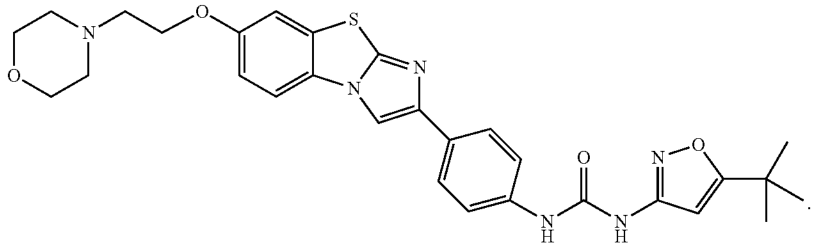

Accordingly, in an embodiment, formula (I) has a structure of formula (xiii), wherein the LCM moiety has a structure of above formula (13) (see above formula (13) and embodiments thereof) or a pharmaceutically acceptable salt thereof (xiii)

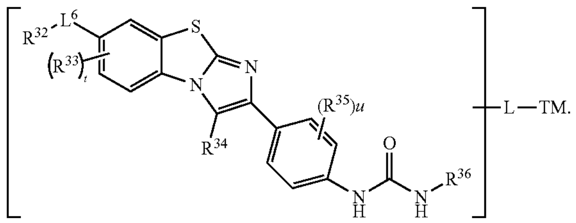

In an embodiment, L can covalently bind to any suitable site in formula (13).

In a particular embodiment, formula (xiii) has a structure of:

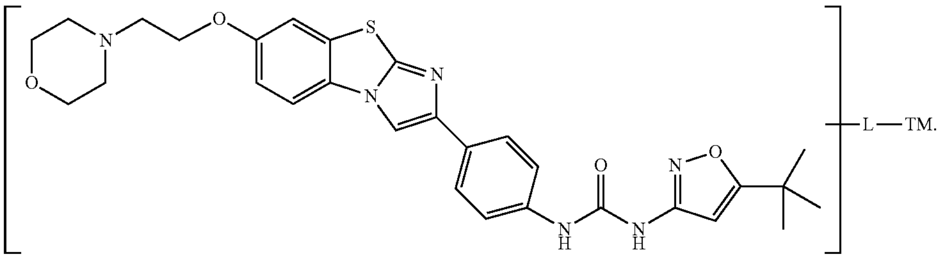

In an embodiment, LCM moiety has a structure of formula (14), or a pharmaceutically acceptable salt thereof:

(14)

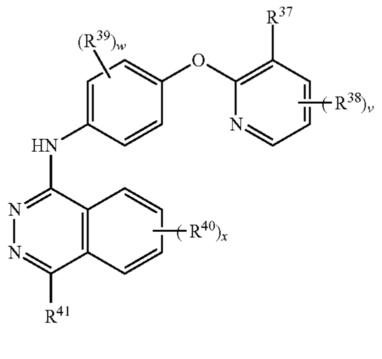

wherein, $R^{37}$ is selected from the group consisting of 6-membered heteroaryl, having 6 ring atoms, the ring atoms comprising 1-2 heteroatoms each independently selected from the group consisting of O, S, N, the remaining atoms being C, the heteroaryl is unsubstituted or substituted with at least one group selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$;

$R^{38}$, $R^{39}$, $R^{40}$ are each independently selected from the group consisting of $R^{X3}$;

$R^{41}$ is selected from the group consisting of 5-membered heteroaryl, having 5 ring atoms, the ring atoms comprising 1-3 heteroatoms each independently selected from the group consisting of O, S, N, the remaining atoms being C, the heteroaryl is unsubstituted or substituted with at least one group selected from the group consisting of $R^{X3}$;

v is 0, 1, 2 or 3;

w is 0, 1, 2, 3 or 4;

x is 0, 1, 2, 3 or 4;

$R^{X3}$ is as defined in formula (10).

In an embodiment, $R^{37}$ is selected from the group consisting of following 6-membered heteroaryl: pyridinyl, pyrimidinyl, pyridazinyl, preferably pyrimidinyl, more preferably pyrimidin-4-yl; and the 6-membered heteroaryl is unsubstituted or substituted with at least one group selected from the group consisting of halogen, —CN, $C_{1-8}$alkyl, —OH, —O($C_{1-8}$alkyl), —$NH_2$, —NH($C_{1-8}$alkyl), —N($C_{1-8}$alkyl)$_2$.

In an embodiment, $R^{41}$ is selected from the group consisting of following 5-membered heteroaryl: thienyl, furyl, pyrrolyl, oxazolyl, thiazolyl, imidazolyl, pyrazolyl, isoxazolyl, isothiazolyl, preferably thienyl or furyl, more preferably thienyl, particularly thien-2-yl; and the 5-membered heteroaryl is unsubstituted or substituted with at least one group selected from the group consisting of halogen, —CN and $C_{1-8}$alkyl.

In an embodiment, v is 0. In another embodiment, w is 0. In an embodiment, x is 0.

In a particular embodiment, formula (14) has a structure of Compound A13:

A13

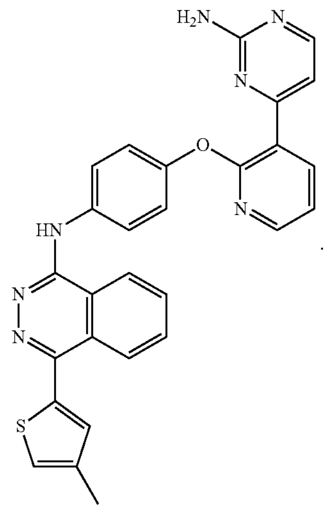

Accordingly, in an embodiment, formula (I) has a structure of formula (xiv), wherein the LCM moiety has a structure of above formula (14) (see above formula (14) and embodiments thereof) or a pharmaceutically acceptable salt thereof (xiv)

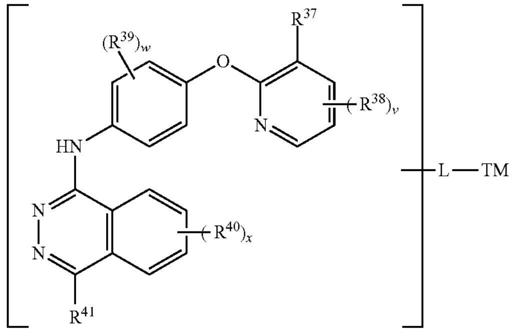

In an embodiment, L can covalently bind to any suitable site in formula (14). The suitable site comprises for example, —$NH_2$, or the like.

In a particular embodiment, formula (xiv) has a structure of:

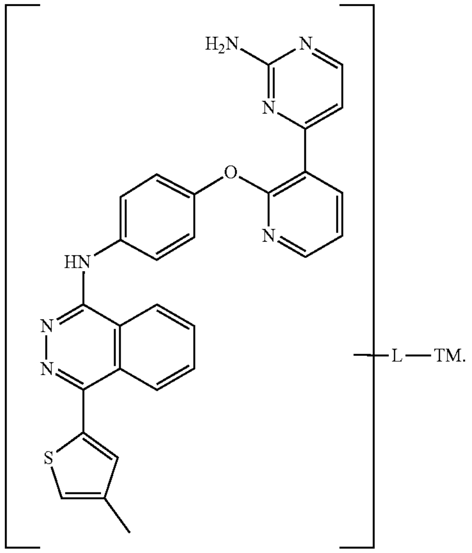

L Linker

L is a chemical bond or group linking the LCM moiety and the TM moiety. In an embodiment, L is rigid or flexible. In a preferable embodiment, L is flexible. In an embodiment, L is chemical bond. In another embodiment, L is linear or branched hydrocarbyl chain comprising 1-60, preferably 1-30, more preferably 2-16 (e.g., 2, 3, 4, 5, 6, 7, 8, 9, 10, 11, 12, 13, 14, 15 or 16) carbon atoms, wherein the carbon atoms are each optionally replaced with one or more heteroatoms, for example 1-3, preferably 1-2, particularly 1; wherein the heteroatoms are selected from the group consisting of O, S, N, P, preferably O, S, or N, more preferably 0, or N, particularly O; wherein the carbon atoms or heteroatoms are optionally substituted with one or more groups selected from the group consisting of $R^{L1}$, $R^{L2}$, $R^{L3}$, $R^{L4}$ and $R^{L5}$; wherein $R^{L1}$, $R^{L2}$, $R^{L3}$, $R^{L4}$ and $R^{L5}$ are each independently selected from the group consisting of: H, halo, $C_{1-6}$alkyl, —O($C_{1-6}$alkyl), —S($C_{1-6}$alkyl), —NH($C_{1-6}$alkyl), —N($C_{1-6}$alkyl)$_2$, $C_{3-6}$cycloalkyl, $C_{6-10}$ aryl, 5- to 7-membered heteroaryl, 3- to 7-membered heterocyclyl, —O($C_{3-6}$cycloalkyl), —S($C_{3-6}$cycloalkyl), —NH($C_{3-6}$cycloalkyl), —N($C_{3-6}$cycloalkyl)$_2$, —N($C_{3-6}$cycloalkyl)($C_{1-6}$alkyl), —OH, —$NH_2$, —SH, —S(═O)$_2$($C_{1-6}$alkyl), —P(═O)(O$C_{1-6}$alkyl)($C_{1-6}$alkyl), —P(═O)(O$C_{1-6}$alkyl)$_2$, —C≡C—$C_{1-6}$alkyl, —C≡CH, —CH═CH($C_{1-6}$alkyl), —C($C_{1-6}$alkyl)═CH($C_{1-6}$alkyl), —C($C_{1-6}$alkyl)═C($C_{1-6}$alkyl)$_2$, —Si(OH)$_3$, —Si($C_{1-6}$alkyl)$_3$, —Si(OH)($C_{1-6}$alkyl)$_2$, —C(═O)($C_{1-6}$alkyl), —COOH, halogen, —CN, —$CF_3$, —$CHF_2$, —$CH_2F$, —$NO_2$, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, —C(═O)NH($C_{1-6}$alkyl), —C(═O)N($C_{1-6}$alkyl)$_2$, —N($C_{1-6}$alkyl)C(═O)NH($C_{1-6}$alkyl), —N($C_{1-6}$alkyl)C(═O)N($C_{1-6}$alkyl)$_2$, —NHC(═O)NH($C_{1-6}$alkyl), —NHC(═O)N($C_{1-6}$alkyl)$_2$, —NHC(═O)$NH_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —NHS(═O)$_2$NH($C_{1-6}$alkyl), —NHS(═O)$_2$N($C_{1-6}$alkyl)$_2$ and NHS(═O)$_2$$NH_2$. The heteroatom can be located in the middle of the chain, or at one or both ends of the chain. When the heteroatom is located at the end, it means that the linker is linked to the LCM moiety and/or the TM moiety through the heteroatom. In an embodiment, L is linear group.

In another embodiment, L has a structure of formula (a), or a pharmaceutically acceptable salt thereof:

$$—Dy— \quad (a)$$

wherein y is an integer greater than 1; and each D is independently selected from the group consisting of: bond, —$CR^{L1}R^{L2}$—, —O—, —S—, —S(═O)—, S(═O)$_2$—, —$NR^{L3}$—, —S(═O)$_2$$NR^{L3}$—, —S(═O)$NR^{L3}$—, —C(═O)$NR^{L3}$—, —$NR^{L3}$C(═O)$NR^{L4}$—, —$NR^{L3}$S(═O)$_2$$NR^{L4}$—, —C(═O)—, —$CR^{L1}$═$CR^{L2}$—, C≡C—, —Si$R^{L1}R^{L2}$—, P(═O)O$R^{L1}$—, —P(═O)O$R^{L1}$—, $C_{3-6}$ cycloalkyl optionally substituted with 0-6 $R^{L1}$ and/or $R^{L2}$ groups, 3- to 7-membered heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups; wherein when y is greater than 1, $R^{L1}$ or $R^{L2}$ is each independently linked to another D group to form cycloalkyl and/or heterocyclyl moiety which may be further substituted with 0-4 $R^{L5}$ groups. Y is an integer less than or equal to 30. In an embodiment, y is an integer less than or equal to 20, preferably less than or equal to 16, e.g., 2, 3, 4, 5, 6, 7, 8, 9, 10, 11, 12, 13, 14, 15 or 16. In an embodiment, y is an integer less than or equal to 12.

In an embodiment, D each independently selected from the group consisting of —$CR^{L1}R^{L2}$—, —O— and —$NR^{L3}$—. In an embodiment, $R^{L1}$, $R^{L2}$ and $R^{L3}$ are H. In a particular embodiment, L has a structure of

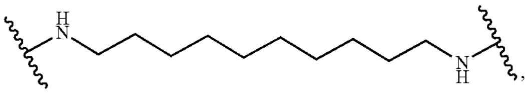

,

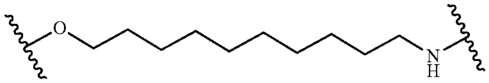

or

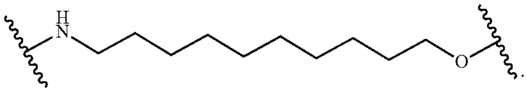

.

In an embodiment, D each independently selected from the group consisting of —$CR^{L1}R^{L2}$—. In a particular embodiment, L has a structure of

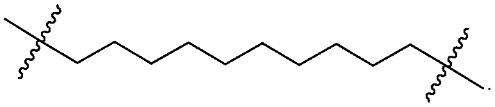 [SMILES: *CCCCCCCCCC*]

.

In a particular embodiment, y is 12, D is selected from the group consisting of —$CR^{L1}R^{L2}$— and —O—. In an embodiment, $R^{L1}$ and $R^{L2}$ are H. In another particular embodiment, L has a structure of

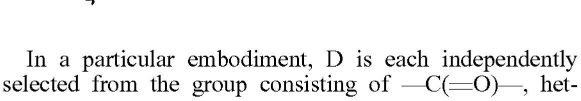

.

In a particular embodiment, D is each independently selected from the group consisting of —C(═O)—, heteroaryl optionally substituted with 0-6 $R^{L1}$ and/or $R^{L2}$ group, —O—, —$CR^{L1}R^{L2}$—, 3— to 7-membered heterocyclyl optionally substituted with 0-6 $R^{L1}$ and/or $R^{L2}$ group, and —$NR^{L3}$. In an embodiment, each $R^{L1}$, $R^{L2}$ and $R^{L3}$ are H. In a particular embodiment, L has a structure of

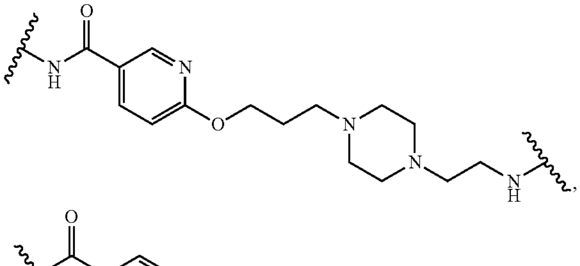
,
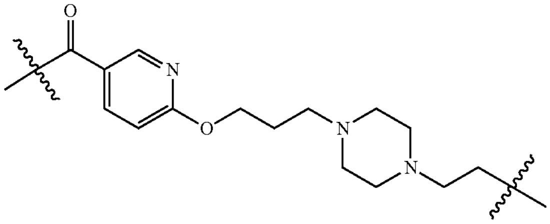
or
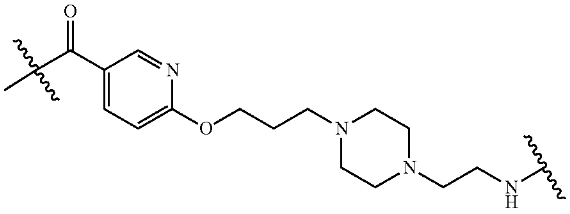
.

TM Moiety

In an embodiment, the lipid droplet binding moiety is a moiety capable of non-covalently interacting with the lipid droplet.

In an embodiment, the lipid droplet binding moiety is a neutral lipid which binds to the lipid droplet. In a specific embodiment, the neutral lipid which binds to the lipid droplet is selected from the group consisting of steroid and steroid ester. It should be understood that the neutral lipid which binds to the lipid droplet can also be an analog of the neutral lipid stored by the lipid droplet. In another embodiment, the neutral lipid which binds to the lipid droplet is an analog of the neutral lipid stored by the lipid droplet. In a specific embodiment, the analog of the neutral lipid is selected from the group consisting of an analog of the cholesteryl ester stored by the lipid droplet.

In an embodiment, the TM moiety is a known lipid droplet probe, a compound capable of binding to lipid droplet marker protein, or a compound capable of binding to neutral lipid in lipid droplet. In an embodiment, the lipid droplet probe is selected from the group consisting of a lipid droplet specific probe and a probe directed to lipid droplet with preference in the cells, preferably lipid droplet specific probe. In another embodiment, the lipid droplet probe is selected from the group consisting of dye molecule with affinity to lipid droplet. In an embodiment, the lipid droplet probe is lipophilic or amphipathic. In another embodiment, the lipid droplet probe is selected from the group consisting of a lipophilic dye molecule with affinity to neutral lipid. In a specific embodiment, the TM moiety is an azo dye with affinity to lipid droplet. In a particular embodiment, the azo dye with affinity to lipid droplet is selected from the group consisting of Sudan I, Sudan II, Sudan III, Oil Red BB, Oil Red O, Sudan Red G, Sudan Black B, preferably selected from the group consisting of Sudan III, Oil Red O and Oil Red BB. In another particular embodiment, the azo dye with affinity to lipid droplet is Oil Red BB. In a specific embodiment, the lipid droplet probe is selected from the group consisting of Sudan I, Sudan II, Sudan III, Oil Red BB, Oil Red O, Sudan Red G, Sudan Black B, Nile Red, BODIPY® 493/503, monodansylpentane, PyrPy 10d, PyrPy 11c, PITE, TPE-AmAl, TPA-BI, LipidGreen, LipidGreen2, LD540, AF8, AF10, AFN, NAPAIEgen dye, LD-BTD1, LipiDye, Phos 2a, Phos 2b, Phos 3a, Phos 3b, SF44, SF58, FAS, DPAS, BTD-Coumarin Hybrid, IND-TPA, photoactivatable AIE probe, LD-TPZn, LQD, photoactivatable AIEgen probe (e.g., PhotoAFN 2a-c), TPE-AC, TPMN, TTMN, MeTTMN, MeOTTMN, DCMa, DCI, DCFu, NLV-1, StatoMerocynaine dye (SMCy dye). In a particular embodiment, the NAP AIEgen dye is selected from the group consisting of NAP-Ph, NAP-Br, NAP-CF3, NAP-Py. In a particular embodiment, the BTD-Coumarin Hybrid is BTD-Lip. In a particular embodiment, the photoactivatable AIE probe is BZT 3a. In a particular embodiment, the photoactivatable AIE probe is BZT 4a. In a particular embodiment, the photoactivatable AIEgen probe is PhotoAFN 2a-c. In a particular embodiment, the SMCy dye is selected from the group consisting of SMCy 3 and SMCy 5.5. In a preferable embodiment, the lipid droplet probe has affinity to the lipid droplet with selectivity. In another preferable embodiment, the lipid droplet probe has affinity to the neutral lipid stored by the lipid droplet with selectivity.

Some exemplary lipid droplet probes have structures as follows:

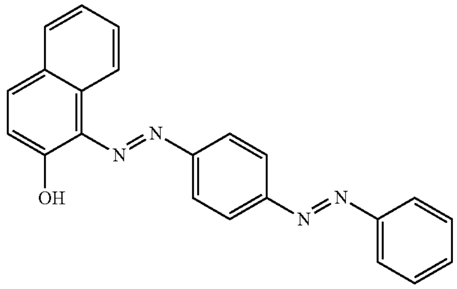

Sudan III

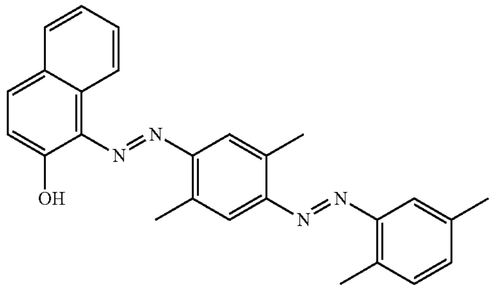

Oil Red O

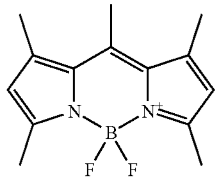

BODIPY 493/503

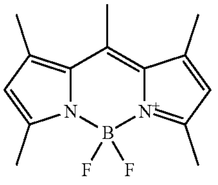

BODIPY 505/515

-continued
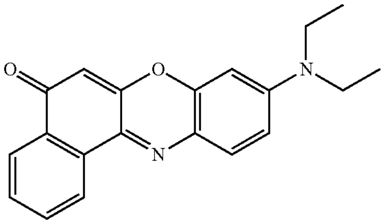
Nile Red
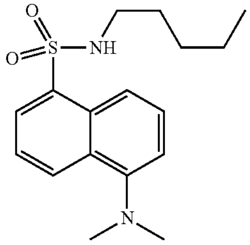
MDH
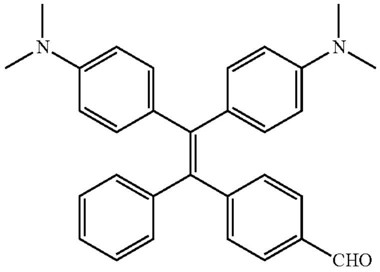
TPE-AmAI
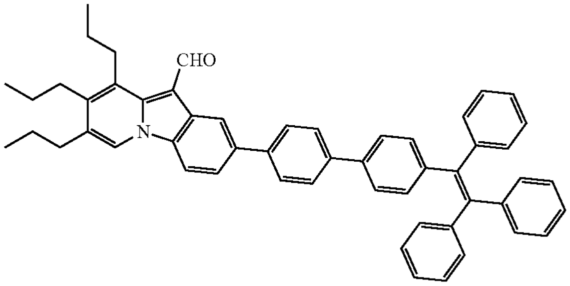
PITE
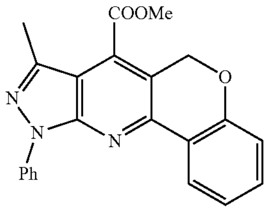
PyrPy 10d
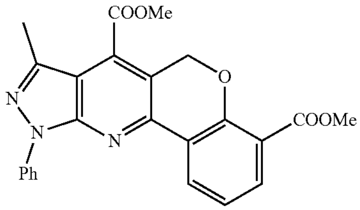
PyrPy 11c
-continued
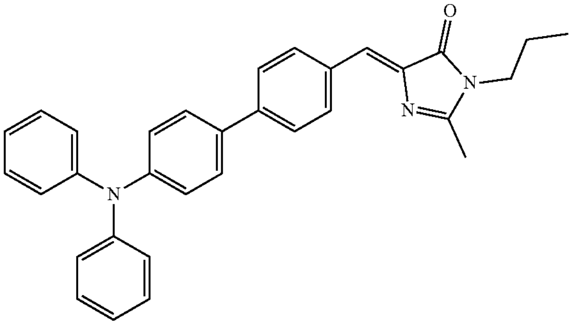
TPA-BI
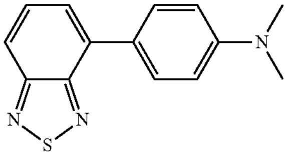
LD-BTD1
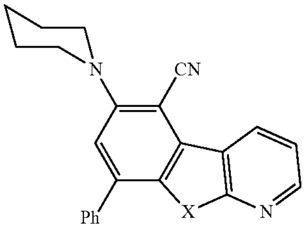
AF8= R=$CH_2$
AFN: R=CO
AF10:R=CHOH
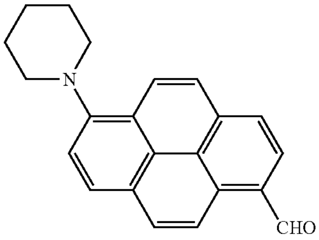
PA
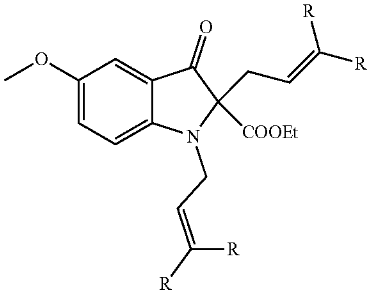
LipidGreen: R=H
LipidGreen2: R=Me
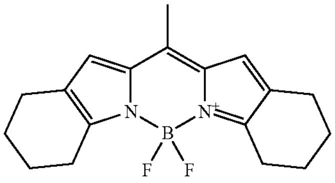
LD540

-continued
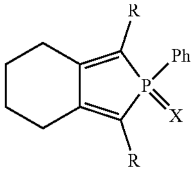
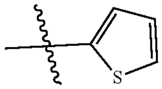
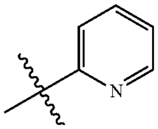
Phos 2a:R= Phos 2b:R=
Phos 3a:X=S; R= Phos 3b:X=S; R=
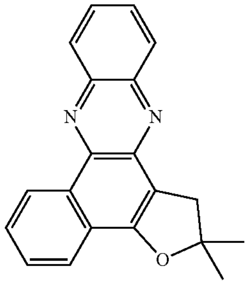
P1
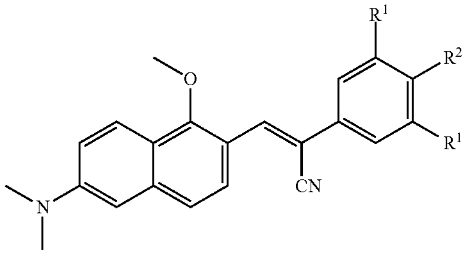
NAP-Ph: $R^1$=H, $R^2$=Ph
NAP-Br: $R^1$=H, $R^2$=Br
NAP-$CF_3$: $R^1$=$CF_3$, $R^2$=H
NAP-Py: $R^1$=H, $R^2$=4-Py
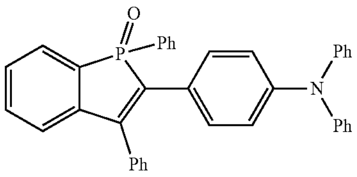
LipiDye
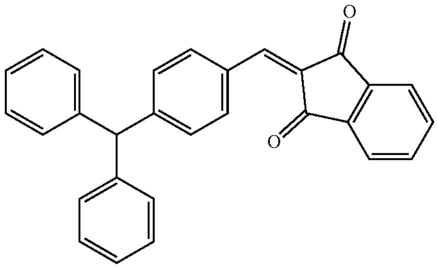
IND-TPA
-continued
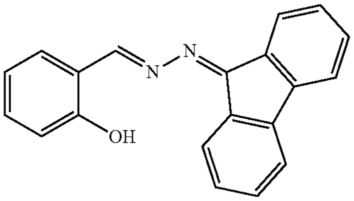
DPAS, FAS
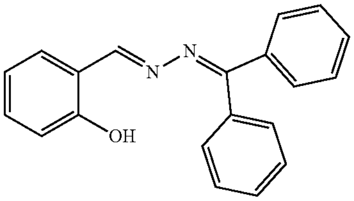
DPAS
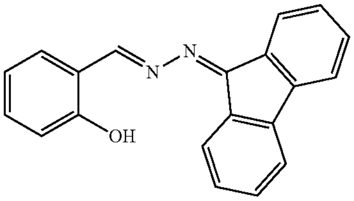
FAS
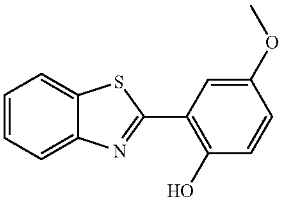
BZT 3a, 4a
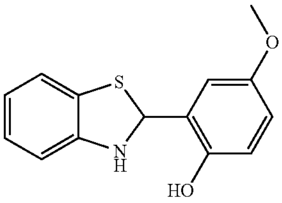
BZT 3a
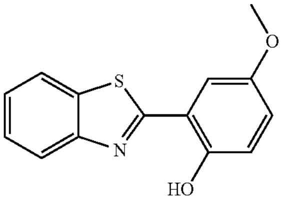
BZT 4a -continued
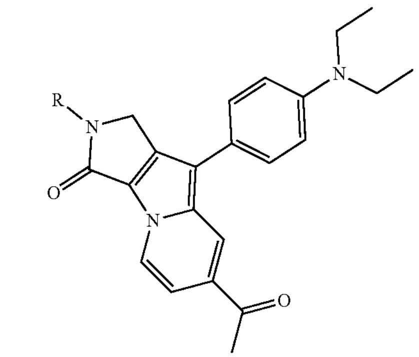
SF44: R=$(CH_2)_2$-NHBoc
SF58: R=$(CH_2)_3$-NHCBz
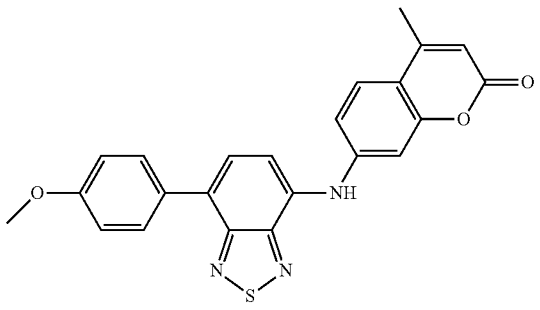
BTD-Lip
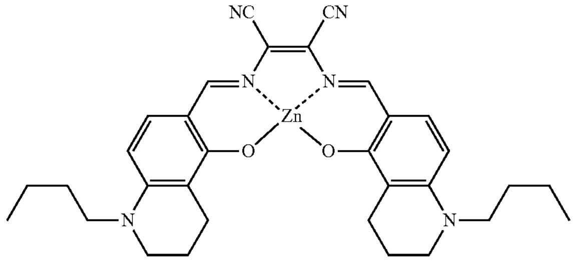
LD-TPZn
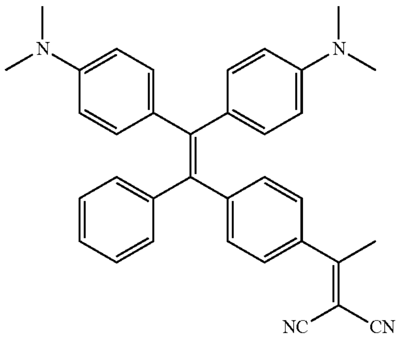
TPE-AC
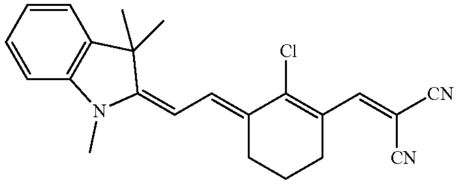
NLV-1
-continued
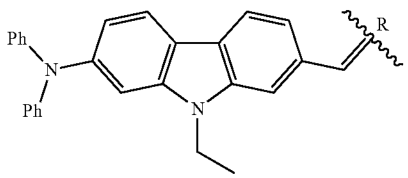
R=
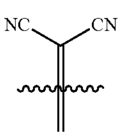
DCMa
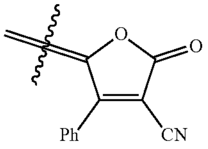
DCFu
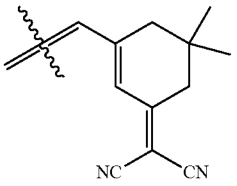
DCis
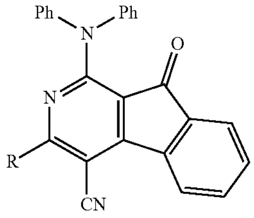
PhotoAFN 2a-c
R= $NH_2$, $NEt_2$, Morpholine
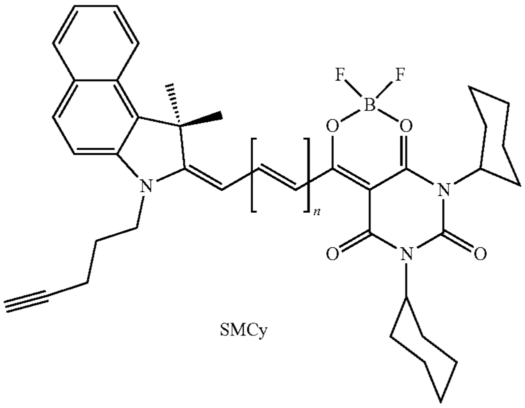
SMCy
n=1, indolenine SMCy3
n=1, benzoindolenine SMCy3.5
n=2, indolenine SMCy5
n=2, benzoindolenine SMCy5.5
n=3,indolenine SMCy7
n=3, benzoindolenine SMCy7.5

-continued

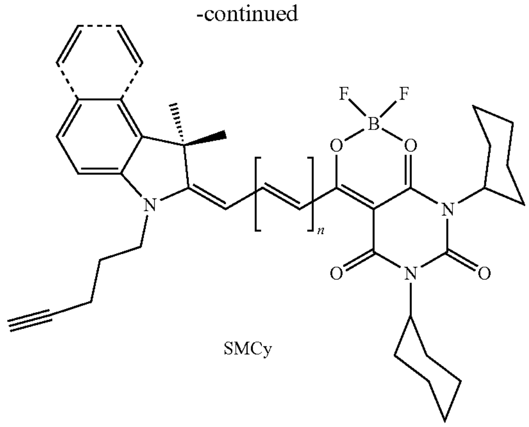

SMCy n=1, indolenine SMCy3
n=1, benzoindolenine SMCy3.5
n=2, indolenine SMCy5
n=2, benzoindolenine SMCy5.5
n=3,indolenine SMCy7
n=3, benzoindolenine SMCy7.5

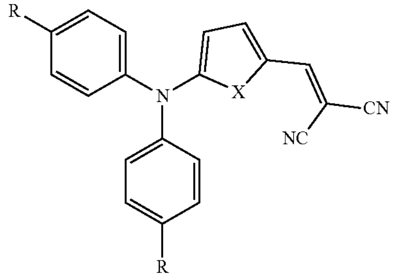

• LQD

LQD • TPMN: R= H, X= CH=CH
LQD • TTMN: R= H, X= S
LQD • MeTTMN: R= Me, X= S
LQD • MeOTTMN: R= OMe, X= S.

wherein LQD refers to the lipophilic quantum dot reported by Mandal et. al., ("Quantum Dot-Based Designed Nanoprobe for Imaging Lipid Droplet", J. Phys. Chem. C 2017, 121, 42, 23727-23735). LQD TPMN, LQD TTMN, LQD MeTTMN and LQD MeOTTMN refer to quantum dot-based fluorescent probes.

In a specific embodiment, the lipid droplet probe is

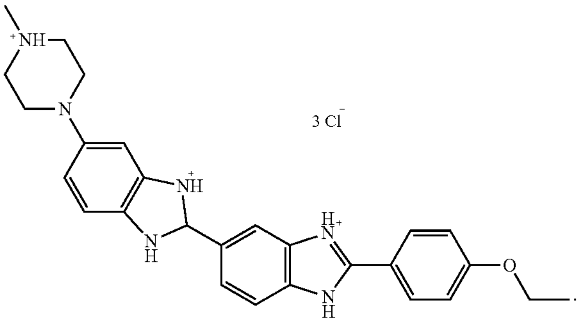

H34158

In a specific embodiment, lipid droplet probe is selected from the group consisting of cholesterol with a visualizable group, cholesteryl ester with a visualizable group and triglyceride with a visualizable group. The visualizable group can be a fluorophore. In a specific embodiment, the lipid droplet probe is selected from the group consisting of cholesterol with a luminous group, cholesteryl ester with a luminous group and triglyceride with a luminous group. The luminous group can be a fluorophore.

In another specific embodiment, the lipid droplet probe is selected from the group consisting of the following molecules (commercially available from Invitrogen)

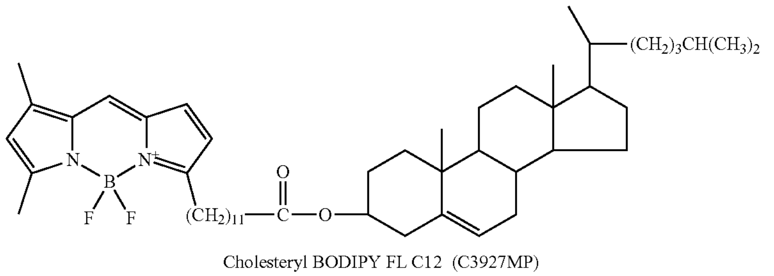

Cholesteryl BODIPY FL C12 (C3927MP)

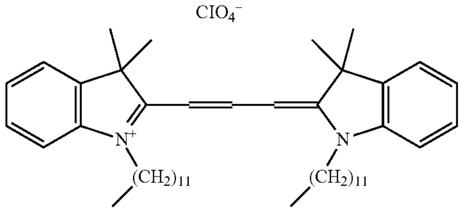

DiIC$_{12}$(3) (D383)

-continued
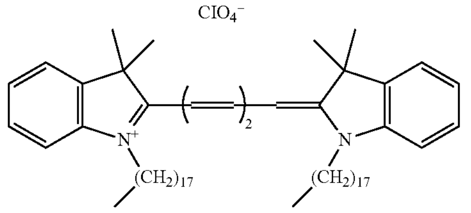
$DiIC_{18}(5)$ (DiD, D307)
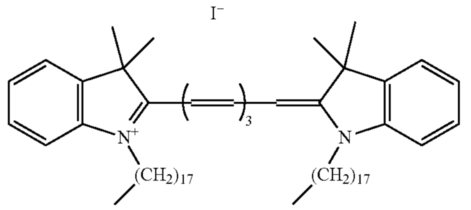
$DiIC_{18}(7)$ (DiR, D12731)
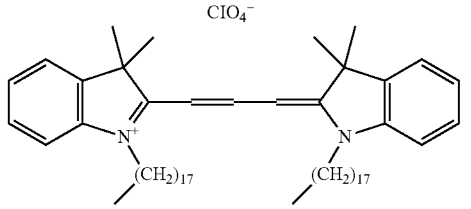
$DiIC_{18}(3)$ (DiI, D282)
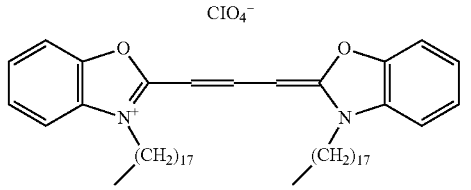
$DiOC_{18}(3)$ (DiO, D275)
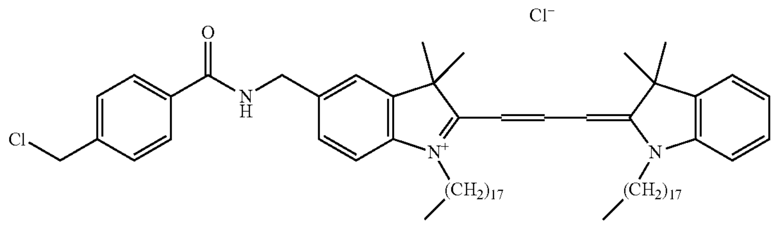
CellTracker CM-DiI (C7000)
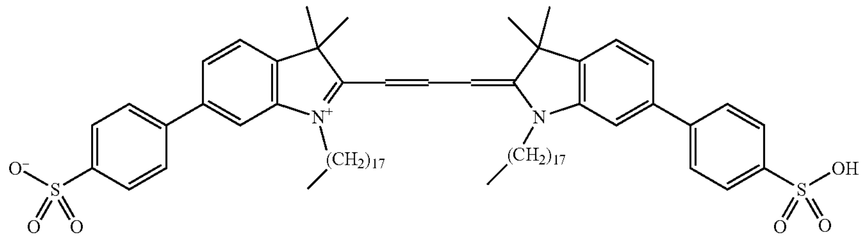
SP-$DiIC_{18}(3)$ (D7777)

-continued
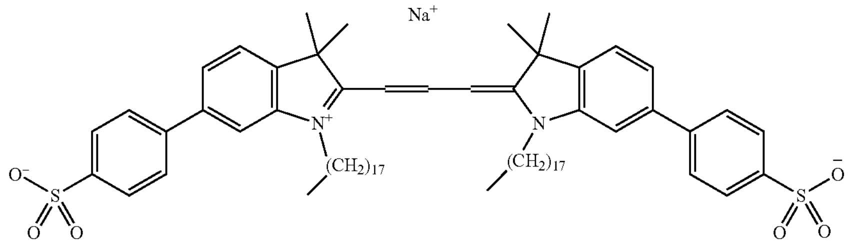
SP-DiOC$_{18}$(3) (D7778)
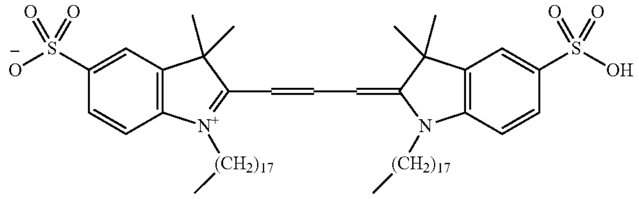
DiIC$_{18}$(3)-DS (D7776)
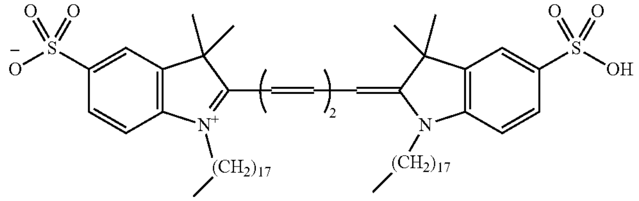
DiIC$_{18}$(5)-DS (D12730)
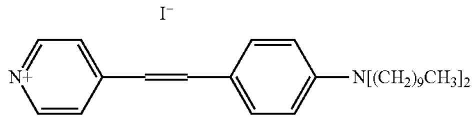
4-Di-10-ASP (D291)
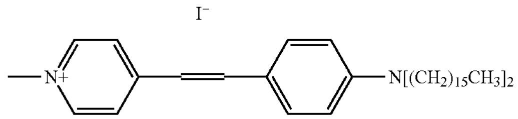
DiA; 4-Di-16-ASP (D3883)
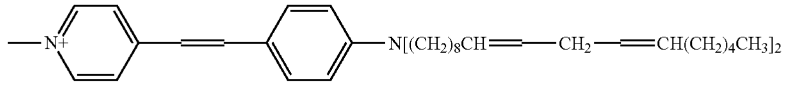
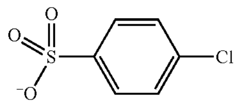
FAST DiA solid; DiΔ$^{9,12}$-C$_{18}$ASP (CBS, D7758)
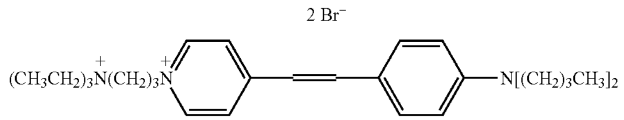
FM 1-43, T3163

-continued
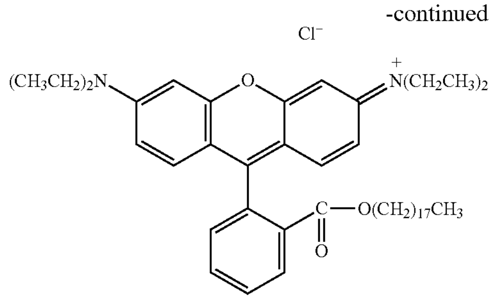
Octadecyl rhodamine B chloride (O246)
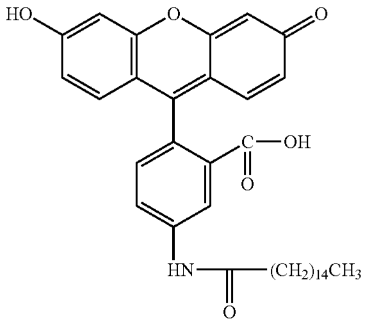
5-Hexadecanoylaminofluorescein (H110)
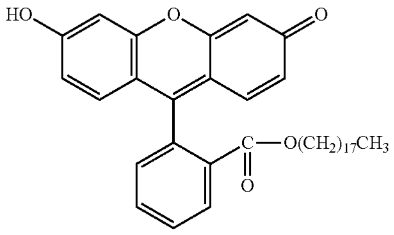
Fluorescein octadecyl ester (F3857)
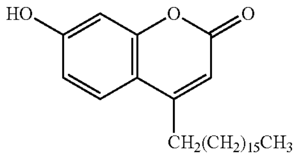
4-Heptadecyl-7-hydroxycoumarin (H22730).
In another specific embodiment, the lipid droplet probe is selected from the group consisting of the following molecules (commercially available from Invitrogen)
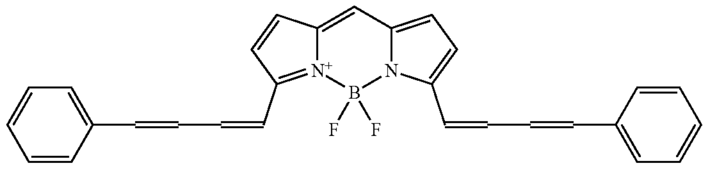
BODIPY 665/676 (B3932)

-continued
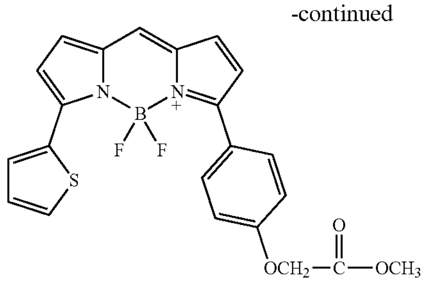
CellTrace BODIPY TR methyl ester (C34556)
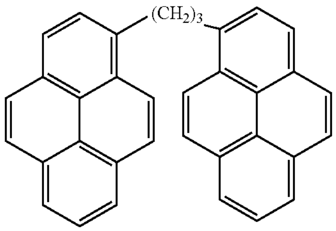
1,3-Bis-(1-pyrenyl)propane (B311).
In a preferable embodiment, the lipid droplet probe is selected from the group consisting of:
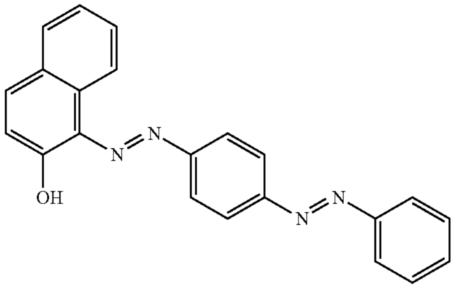
Sudan III
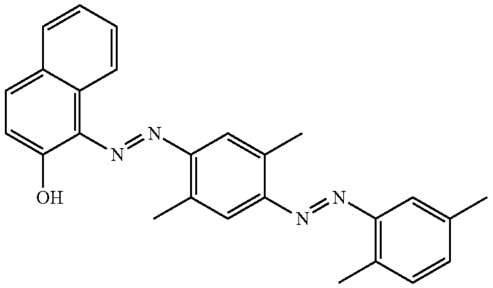
Oil Red O
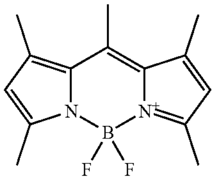
BODIPY 493/503
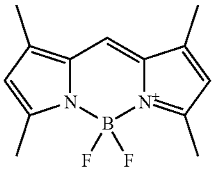
BODIPY 505/515
-continued
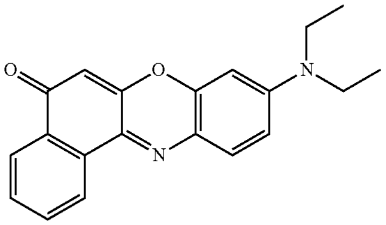
Nile Red
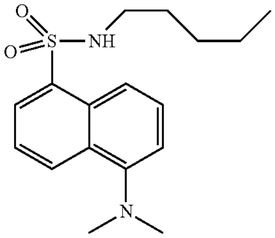
MDH
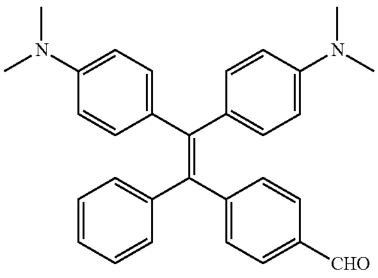
TPE-AmAI -continued
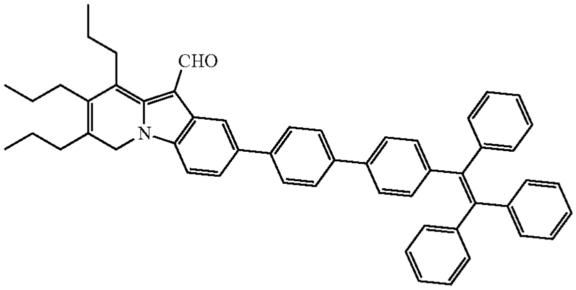
PITE
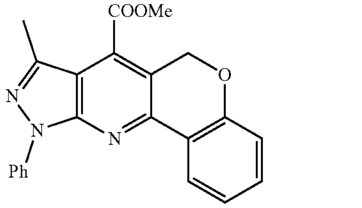
PyrPy 10d
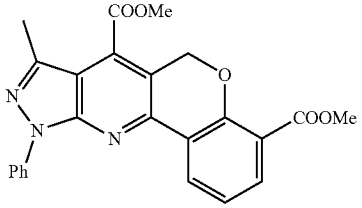
PyrPy 11c
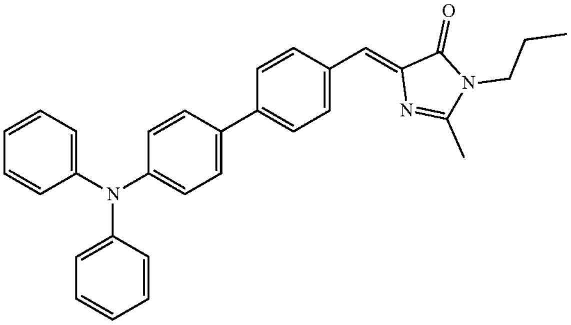
TPA-BI
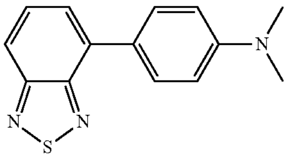
LD-BTD1
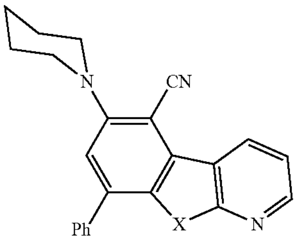
AF8= R=$CH_2$
AFN: R=CO
AF10:R=CHOH
-continued
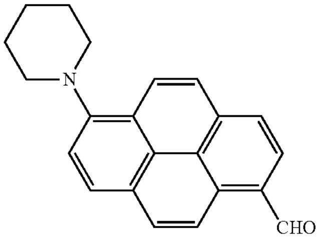
PA
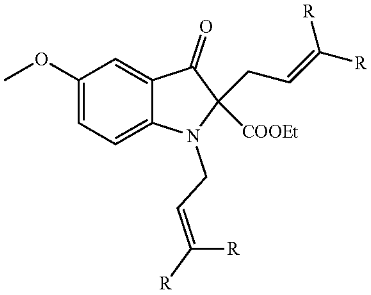
LipidGreen: R=H
LipidGreen2: R=Me
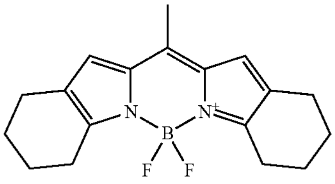
LD540
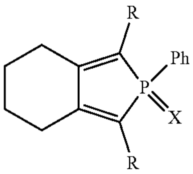
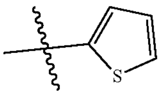
Phos 2a:R=
Phos 3a:X=S; R=
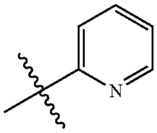
Phos 2b:R=
Phos 3b:X=S; R=
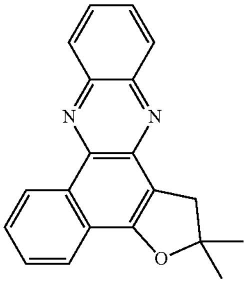
P1
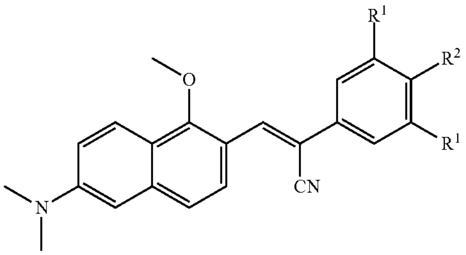
NAP-Ph: $R^1$=H, $R^2$=Ph
NAP-Br: $R^1$=H, $R^2$=Br
NAP-$CF_3$: $R^1$=$CF_3$, $R^2$=H
NAP-Py: $R^1$=H, $R^2$= 4-Py -continued
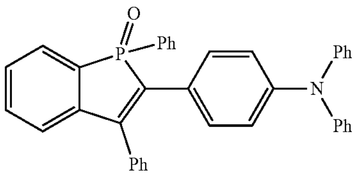
LipiDye
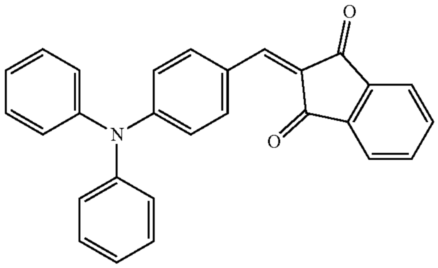
IND-TPA
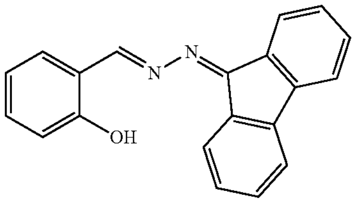
DPAS, FAS
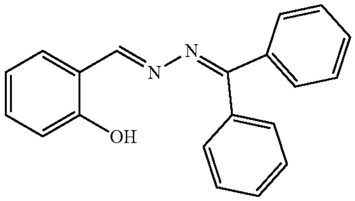
DPAS
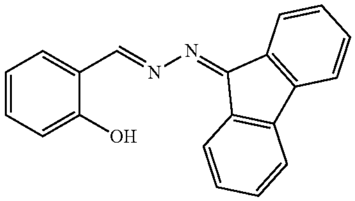
FAS
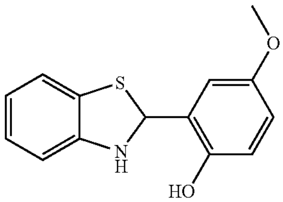
BZT 3a
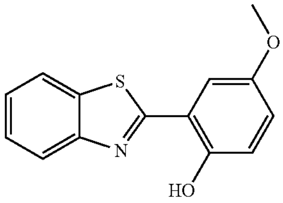
BZT 4a
-continued
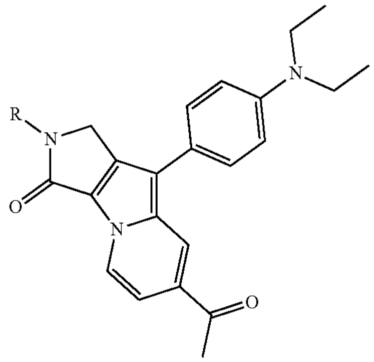
SF44: R=$(CH_2)_2$-NHBoc
SF58: R=$(CH_2)_3$-NHCBz
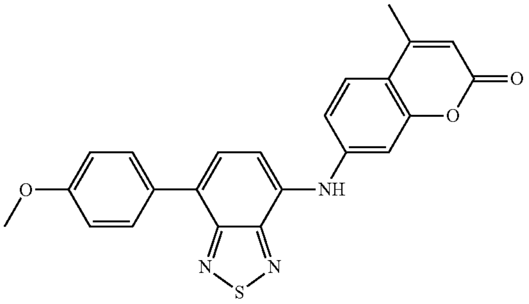
BTD-Lip
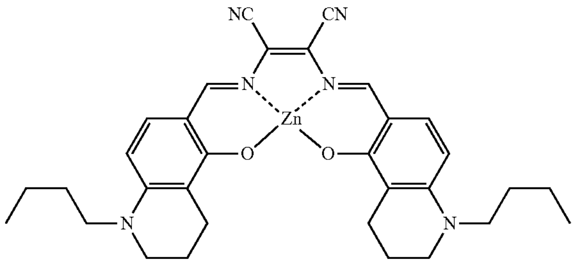
LD-TPZn
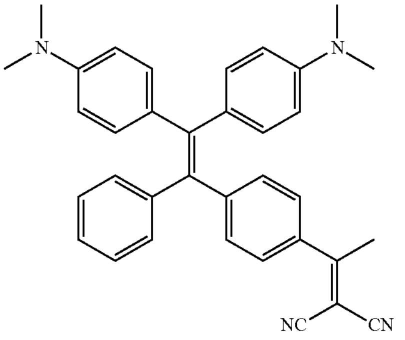
TPE-AC
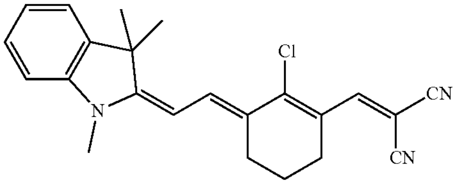
NLV-1

-continued

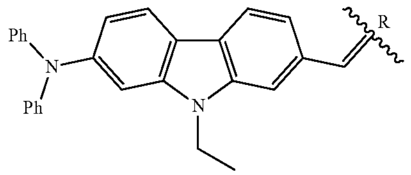

R=

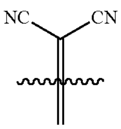

DCMa

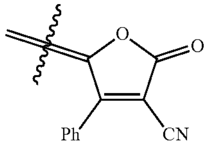

DCFu

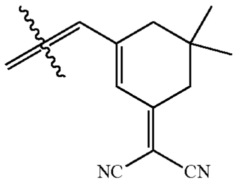

DCis

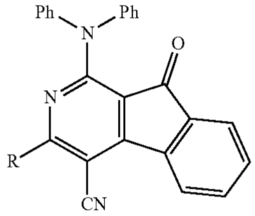

PhotoAFN 2a-c
R= $NH_2$, $NEt_2$, Morpholine

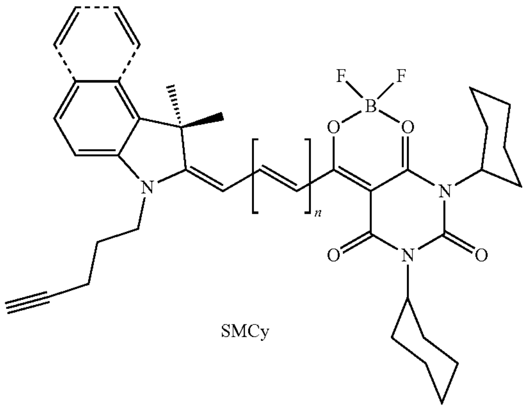

SMCy n=1, indolenine SMCy3
n=1, benzoindolenine SMCy3.5
n=2, indolenine SMCy5
n=2, benzoindolenine SMCy5.5
n=3, indolenine SMCy7
n=3, benzoindolenine SMCy7.5

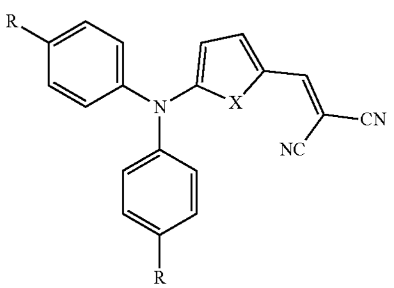

• LQD

LQD • TPMN: R= H, X= CH=CH
LQD • TTMN: R= H, X= S
LQD • MeTTMN: R= Me, X= S
LQD • MeOTTMN: R= OMe, X= S.

-continued

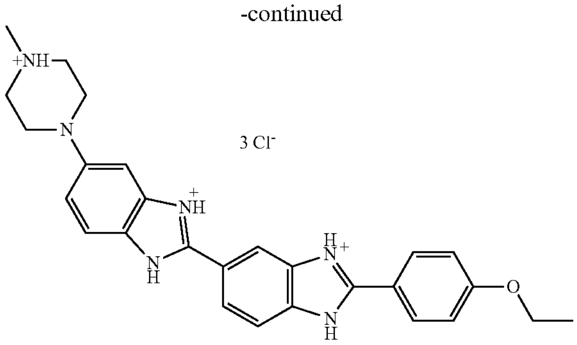

H34158

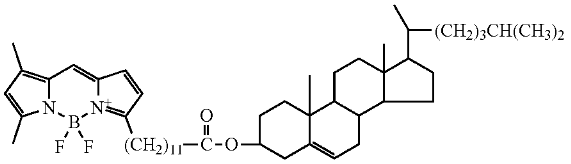

Cholesteryl BODIPY FL C12 (C3927MP)

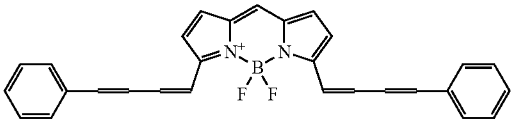

and

BODIPY 665/676 (B3932)

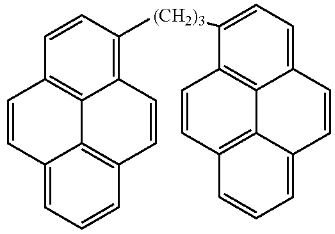

1,3-Bis-(1-pyrenyl)propane (B311) .

In an embodiment, the TM moiety has a structure of formula (II)

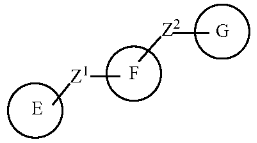

(II)

wherein:

ring E and ring F are each independently selected from the group consisting of benzene ring and naphthalene ring; wherein the ring E is optionally substituted with one or more groups selected from the group consisting of $R^E$, the ring F is optionally substituted with one or more groups selected from the group consisting of $R^F$, the ring G is optionally substituted with one or more groups selected from the group consisting of $R^G$;

ring G is absent, or is selected from the group consisting of benzene ring and naphthalene ring;

$Z^1$ is azo group;

$Z^2$ is absent, or is azo group;

$R^E$, $R^F$ and $R^G$, on each occurrence, are each independently selected from the group consisting of H, halogen, $-NO_2$, $-CN$, $=O$, $=S$, $C_{1-6}$alkyl, $C_{2-6}$alkenyl, $C_{2-6}$alkynyl, $C_{3-6}$ cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$alkyl)-(C═O)($C_{1-6}$alkyl), —NH(C═O)($C_{3-6}$ cyclohydrocarbyl), —N($C_{1-6}$alkyl)-(C═O)($C_{3-6}$ cyclohydrocarbyl), —NH(C═O)($C_{1-4}$alkylene-$C_{3-6}$ cyclohydrocarbyl), —N($C_{1-6}$alkyl)-(C═O)($C_{1-4}$alkylene-$C_{3-6}$cyclohydrocarbyl), —NH(C═O)(3- to 7-membered heterocyclyl), —N($C_{1-6}$alkyl)-(C═O)(3- to 7-membered heterocyclyl), —COOH, —C(═O)($C_{1-6}$alkyl), —C(═O)O($C_{1-6}$alkyl), —C(═O)O($C_{3-6}$ cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$ cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two $R^E$, two $R^F$ or two $R^G$ are bonded each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$. When $Z^2$ is absent, ring G and ring F are linked via a bond.

Accordingly, in an embodiment, formula (I) has a structure of formula (xv), wherein the TM moiety has a structure of above formula (II) (see above formula (II) and embodiments thereof) or a pharmaceutically acceptable salt thereof (xv)

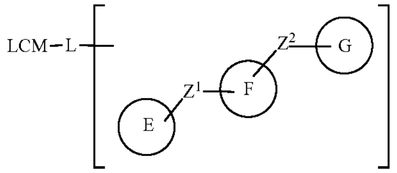

In an embodiment, L can covalently bind to any suitable site in formula (II)).

The structure of following formula (III) falls within the scope of the structure of formula (II). In an embodiment, the TM moiety has a structure of formula (III)

(III)

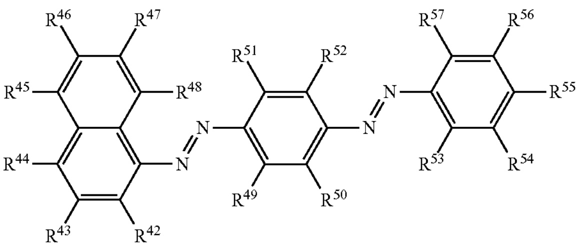

wherein $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$ cyclohydrocarbyl), —O(C═O)($C_{1-4}$alkylene-$C_{3-6}$ cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$ alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$ alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$alkyl)-(C═O)($C_{1-6}$alkyl), —NH(C═O)($C_{3-6}$cyclohydrocarbyl), —N($C_{1-6}$alkyl)-(C═O)($C_{3-6}$cyclohydrocarbyl), —NH(C═O)($C_{1-4}$alkylene-$C_{3-6}$cyclohydrocarbyl), —N($C_{1-6}$alkyl)-(C═O)($C_{1-4}$alkylene-$C_{3-6}$cyclohydrocarbyl), —NH(C═O)(3- to 7-membered heterocyclyl), —N($C_{1-6}$alkyl)-(C═O)(3- to 7-membered heterocyclyl), —COOH, —C(═O)($C_{1-6}$alkyl), —C(═O)O($C_{1-6}$ alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$ alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$ alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$ alkyl)$_2$, —COOH, —C(═O)($C_{1-6}$alkyl), —C(═O)$NH_2$, —C(═O)NH($C_{1-6}$alkyl), —C(═O)N($C_{1-6}$ alkyl)$_2$, —S(═O)$_2$OH, —S(═O)$_2$NH($C_{1-6}$alkyl), —S(═O)$_2$N($C_{1-6}$alkyl)$_2$.

In an embodiment, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ each independently selected from the group consisting of H, halogen, $C_{1-6}$alkyl, $C_{3-6}$ cycloalkyl, $C_{3-6}$cycloalkyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cycloalkyl), —O($C_{1-4}$alkylene-$C_{3-6}$cycloalkyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cycloalkyl), —O(C═O)($C_{1-4}$alkylene-$C_{3-6}$cycloalkyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cycloalkyl), —S($C_{1-4}$alkylene-$C_{3-6}$cycloalkyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cycloalkyl), —N($C_{3-6}$cycloalkyl)$_2$, —NH($C_{1-4}$alkylene-$C_{3-6}$ cycloalkyl), —N($C_{1-4}$alkylene-$C_{3-6}$cycloalkyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cycloalkyl), —NH(C═O)($C_{1-4}$alkylene-$C_{3-6}$cycloalkyl), —NH(C═O)(3- to 7-membered heterocyclyl), wherein the alkyl, alkylene, cycloalkyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$ alkyl)$_2$, —COOH, —C(═O)($C_{1-6}$alkyl), —C(═O)$NH_2$, —C(═O)NH($C_{1-6}$alkyl), —C(═O)N($C_{1-6}$ alkyl)$_2$, —S(═O)$_2$OH, —S(═O)$_2$NH($C_{1-6}$alkyl), —S(═O)$_2$N($C_{1-6}$alkyl)$_2$.

In another embodiment, $R^{42}$, $R^{43}$, $R^{44}$, $R^{45}$, $R^{46}$, $R^{47}$ and $R^{48}$ each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$alkyl)-(C═O)($C_{1-6}$alkyl), —NH(C═O)($C_{3-6}$cyclohydrocarbyl), —NH(C═O)($C_{1-4}$alkylene-$C_{3-6}$ cyclohydrocarbyl), —NH(C═O)(3- to 7-membered heterocyclyl), —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$ cyclohydrocarbyl), —C(═O)O(3- to 7-membered heterocyclyl), —C(═O)O($C_{1-4}$alkylene)-(3- to 7-membered heterocyclyl), —C(═O)NH($C_{1-6}$alkyl), —C(═O)N($C_{1-6}$alkyl)$_2$, —C(═O)NH($C_{1-4}$alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$ and $R^{48}$, preferably selected from the group consisting of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$.

In yet another embodiment, $R^{42}$, $R^{43}$, $R^{44}$, $R^{45}$, $R^{46}$, $R^{47}$ and $R^{48}$ each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cycloalkyl), —O($C_{1-4}$alkylene-$C_{3-6}$cycloalkyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cycloalkyl), —O(C═O)($C_{1-4}$alkylene-$C_{3-6}$cycloalkyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cycloalkyl), —S($C_{1-4}$alkylene-$C_{3-6}$cycloalkyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cycloalkyl), —N($C_{3-6}$ cycloalkyl)$_2$, —NH($C_{1-4}$alkylene-$C_{3-6}$cycloalkyl), —N($C_{1-4}$alkylene-$C_{3-6}$cycloalkyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —NH(C═O)($C_{3-6}$cycloalkyl), —NH(C═O)($C_{1-4}$alkylene-$C_{3-6}$cycloalkyl), —NH(C═O)(3- to 7-membered heterocyclyl), wherein the alkyl, alkylene, cycloalkyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$ and $R^{48}$, preferably selected from the group consisting of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$.

In an embodiment, $R^{49}$, $R^{50}$, $R^{51}$, $R^{52}$, $R^{53}$, $R^{54}$, $R^{55}$, $R^{56}$ and $R^{57}$ each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, wherein the alkyl cycloalkyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$.

In a specific embodiment, $R^{42}$, $R^{43}$, $R^{44}$, $R^{45}$, $R^{46}$, $R^{47}$ and $R^{48}$ each independently selected from the group consisting of H, halogen, —$NO_2$, —CN, ═O, ═S, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$; or, two adjacent groups selected from the group consisting of $R^{42}$, $R^{43}$, $R^{44}$, $R^{45}$, $R^{46}$, $R^{47}$ and $R^{48}$, preferably selected from the group consisting of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; and, $R^{49}$, $R^{50}$, $R^{51}$, $R^{52}$, $R^{53}$, $R^{54}$, R, $R^{56}$ and $R^{57}$ are each independently selected from the group consisting of H, halogen, $C_{1-6}$alkyl, $C_{3-6}$cycloalkyl, $C_{3-6}$ cycloalkyl —$C_{1-4}$alkyl, 3- to 7-membered heterocyclyl, 3- to 7-membered heterocyclyl-$C_{1-4}$alkyl, wherein the alkyl, cycloalkyl or heterocyclyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH.

In yet another embodiment, at least one of $R^{42}$, $R^{43}$, $R^{44}$, $R^{45}$, $R^{46}$, $R^{47}$ and $R^{48}$ is —Cl, —Br, —I, —$NO_2$, —CN, ═O, ═S, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl) or —S(═O)N($C_{1-6}$alkyl)$_2$, rest of the groups are each independently selected from the group consisting of H, halogen, —$NO_2$, —CN, ═O, ═S, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$-S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; or, two adjacent groups selected from the group consisting of $R^{42}$, $R^{43}$, $R^{44}$, $R^{45}$, $R^{46}$, $R^{47}$ and $R^{48}$, preferably selected from the group consisting of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH.

In a particular embodiment, at least one of $R^{42}R^{43}R^{44}$, $R^{45}$, $R^{46}R^{47}$ and $R^{48}$ is —Cl, —Br, —I, —OH, —O($C_{1-6}$ alkyl), —SH, —S($C_{1-6}$alkyl), —$NH_2$, —NH($C_{1-6}$alkyl) or —N($C_{1-6}$alkyl)$_2$, preferably —OH, —SH or —$NH_2$, more preferably —OH or —$NH_2$, particularly preferably —OH, rest of the groups are each independently selected from the group consisting of H, halogen, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; or, two adjacent groups selected from the group consisting of $R^{42}$, $R^{43}$, $R^{44}$, $R^{45}$, $R^{46}$, $R^{47}$ and $R^{48}$, preferably selected from the group consisting of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH.

In another specific embodiment, at least one of $R^{49}$, $R^{50}$, $R^{51}$, $R^{52}$, $R^{53}$, $R^{54}$, $R^{55}$, $R^{56}$ and $R^{57}$ is H, or at least one of $R^{49}$, $R^{50}$, $R^{51}$, $R^{52}$, $R^{53}$, $R^{54}$, $R^{55}$, $R^{56}$ and $R^{57}$, preferably 1-6, more preferably 1-4, particularly preferably 1, 2 or 4, is $C_{1-6}$alkyl or —O($C_{1-6}$alkyl), preferably $C_{1-3}$ alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$.

In yet another specific embodiment, at least one of $R^{42}$, $R^{43}$, $R^{44}$, $R^{45}$, $R^{46}$, $R^{47}$ and $R^{48}$ is —Cl, —Br, —I, —$NO_2$, —CN, ═O, ═S, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl) or —S(═O)N($C_{1-6}$alkyl)$_2$, rest of the groups are each independently selected from the group consisting of H, halogen, —$NO_2$, —CN, ═O, ═S, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$-S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; or, selected from the group consisting of $R^{42}$, $R^{43}$, $R^{44}$, $R^{45}$, $R^{46}$, $R^{47}$ and $R^{48}$, preferably selected from the group consisting of two adjacent groups of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; and, $R^{49}$, $R^{50}$, $R^{51}$, $R^{52}$, $R^{53}$, $R^{54}$, $R^{55}$, $R^{56}$ and $R^{57}$ are H, or at least one, preferably 1-6, more preferably 1-4, particularly 1, 2 or 4 of $R^{49}$, $R^{50}$, $R^{51}$, $R^{52}$, $R^{53}$, $R^{54}$, $R^{55}$, $R^{56}$ and $R^{57}$ are $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$;

In yet another specific embodiment, at least one of $R^{49}$ and $R^{52}$ is $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, and/or at least one of $R^{50}$ and $R^{51}$ is $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, and/or at least one of $R^{53}$ and $R^{56}$ $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, and/or at least one of $R^{54}$ and $R^{57}$ is $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, preferably selected from the group consisting of H and halogen, particularly H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$.

In a particular embodiment, one of $R^{42}$, $R^{43}$, $R^{44}$, $R^{45}$, $R^{46}$, $R^{47}$ and $R^{48}$ is —OH, —SH or —$NH_2$, more preferably —OH or —$NH_2$, particularly preferably —OH, rest of the groups are H; $R^{49}$, $R^{50}$, $R^{51}$, R, $R^{53}$, $R^{54}$, $R^{55}$, $R^{56}$ and $R^{57}$ are H, or at least one of $R^{49}$, $R^{50}$, $R^{51}$, R, $R^{53}$, $R^{54}$, $R^{55}$, $R^{56}$ and $R^{57}$, preferably 1-6, more preferably 2-4, particularly preferably 2 or 4, is $C_{1-3}$alkyl, preferably $C_{1-3}$alkyl, more preferably methyl, rest of the groups are each independently selected from the group consisting of H, or at least one of $R^{49}$, $R^{50}$, $R^{51}$, $R^{52}$, $R^{53}$, $R^{54}$, $R^{55}$, $R^{56}$ and $R^{57}$ preferably 1-6, more preferably 1-4, particularly preferably 1 or 3, is —O($C_{1-6}$alkyl), preferably —O($C_{1-3}$alkyl), more preferably methoxy, rest of the groups are each independently selected from the group consisting of H.

In another particular embodiment, $R^{42}$ is —OH, —SH or —$NH_2$, more preferably —OH or —$NH_2$, particularly preferably —OH, $R^{43}$, $R^{44}$, $R^{45}$, $R^{46}$, $R^{47}$ and $R^{48}$ are each independently selected from the group consisting of H, —OH, —SH or —$NH_2$, more preferably H, —OH or —$NH_2$, particularly preferably H or —OH, particularly H; $R^{49}$, $R^{50}$, $R^{51}$, $R^{52}$, $R^{53}$, $R^{54}$, $R^{55}$, $R^{56}$ and $R^{57}$ are H, or at least one of $R^{49}$, $R^{50}$, $R^{51}$, $R^{52}$, $R^{53}$, $R^{54}$, $R^{55}$, $R^{56}$ and $R^{57}$, preferably 1-6, more preferably 2-4, particularly preferably 2 or 4, is $C_{1-3}$alkyl, preferably $C_{1-3}$alkyl, more preferably methyl, rest of the groups are each independently selected from the group consisting of H, or at least one of $R^{49}$, $R^{50}$, $R^{51}$, $R^{52}$, $R^{53}$, $R^{54}$, $R^{55}$, $R^{56}$ and $R^{57}$, preferably 1-6, more preferably 1-4, particularly preferably 1 or 2, is —O($C_{1-6}$ alkyl), preferably —O($C_{1-3}$alkyl), more preferably methoxy, rest of the groups are each independently selected from the group consisting of H.

In yet another particular embodiment, formula (III) has a structure selected from the group consisting of.

Oil Red BB

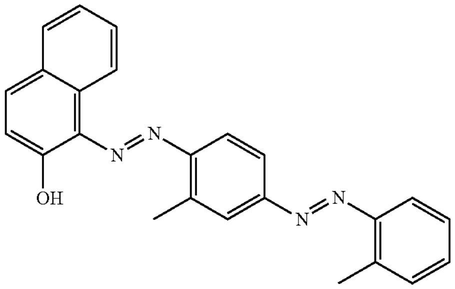

Oil Red O

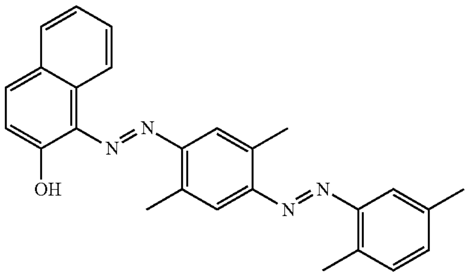

and

Sudan III

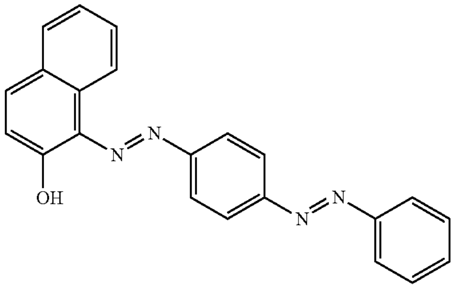

;

particularly, is selected from the group consisting of

Oil Red BB

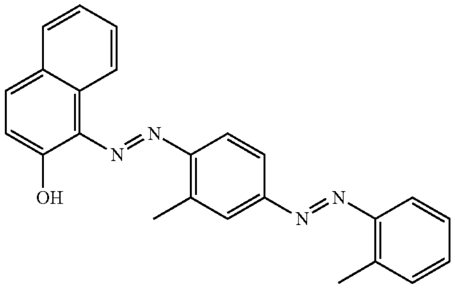

and

-continued

Oil Red O

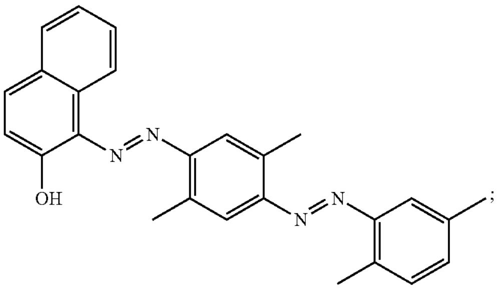

;

particularly

Oil Red BB

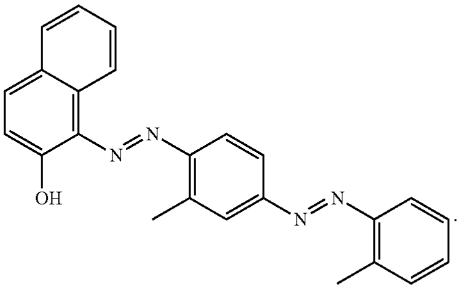

.

Accordingly, in an embodiment, formula (I) has a structure of formula (xvi), wherein the TM moiety has a structure of above formula (III) (see above formula (III) and embodiments thereof) or a pharmaceutically acceptable salt thereof (xvi)

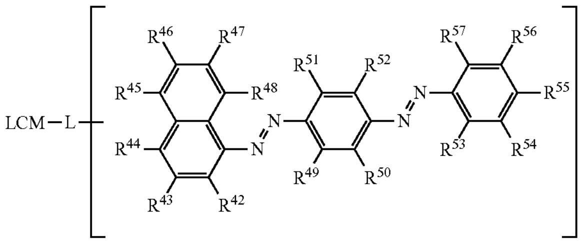

In an embodiment, L can covalently bind to any suitable site in formula (III).

In a particular embodiment, formula (xvi) has a structure selected from the group consisting of

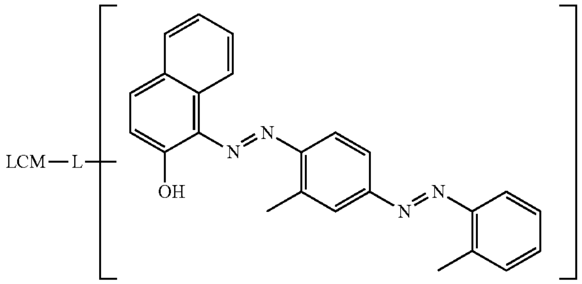

-continued

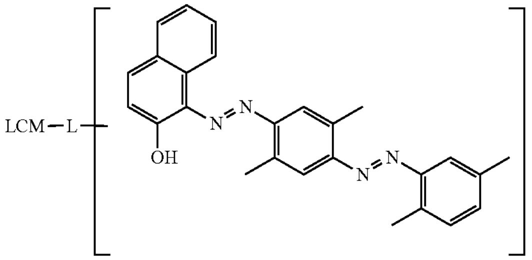

and

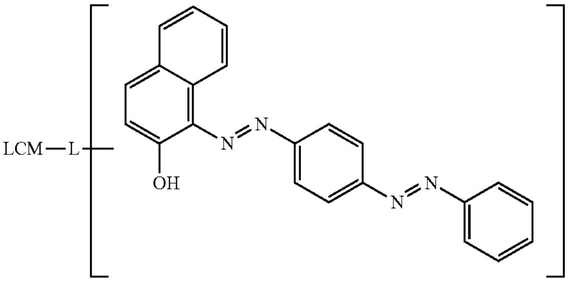

;

particularly, is selected from the group consisting of

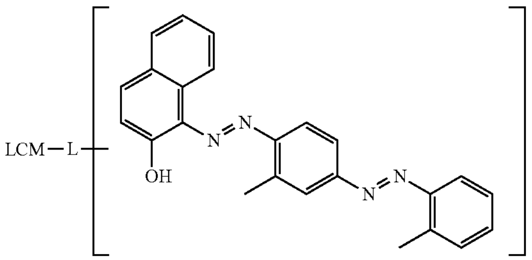

and

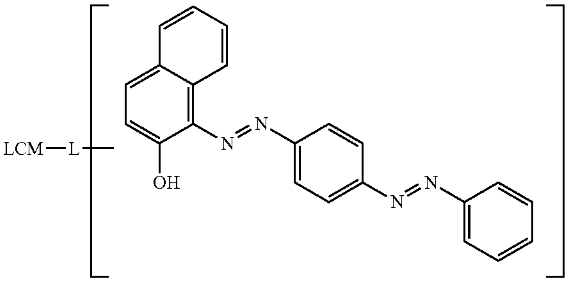

;

particularly

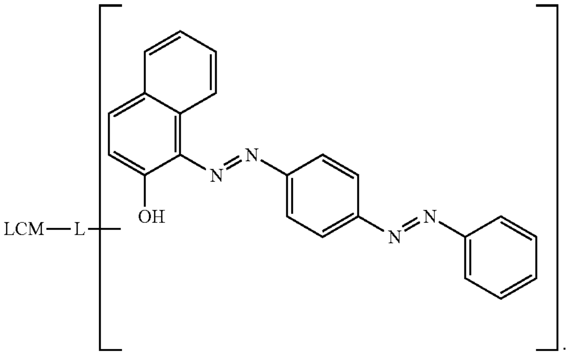

.

The structure of following formula (IV) falls within the scope of the structure of formula (II). In an embodiment, the TM moiety has a structure of formula (IV)

(IV)

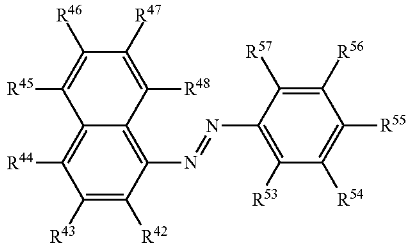

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are as defined in formula (III).

In a particular embodiment, formula (IV) has a structure selected from the group consisting of:

Sudan I

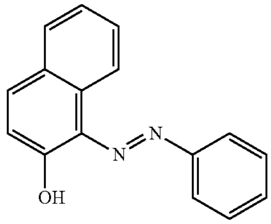

Sudan II

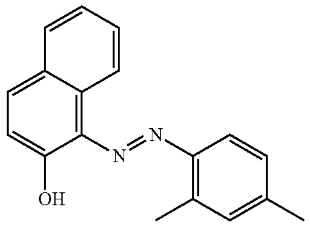

and

Sudan Red G

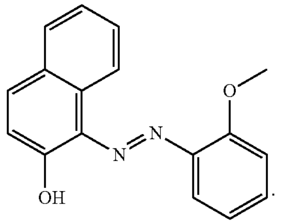

.

Accordingly, in an embodiment, formula (I) has a structure of formula (xvii), wherein the TM moiety has a structure of above formula (IV) (see above formula (IV) and embodiments thereof) or a pharmaceutically acceptable salt thereof (xvii)

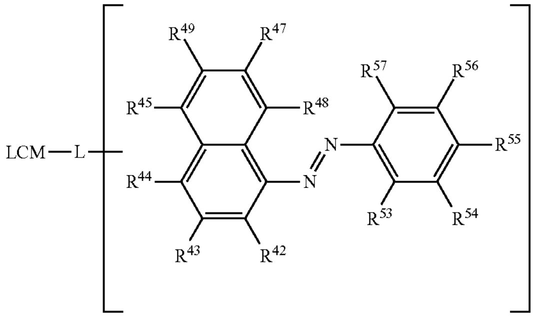

In an embodiment, L can covalently bind to any suitable site in formula (IV).

In a particular embodiment, formula (xvii) has a structure selected from the group consisting of:

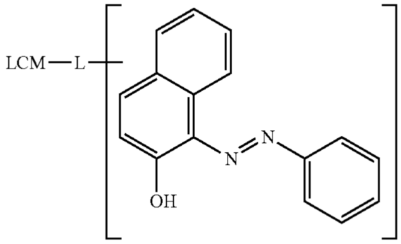

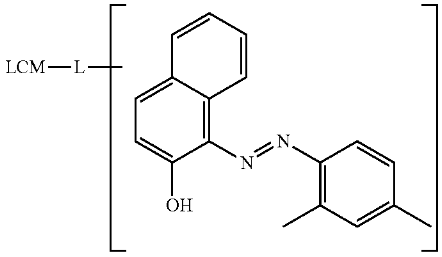

and

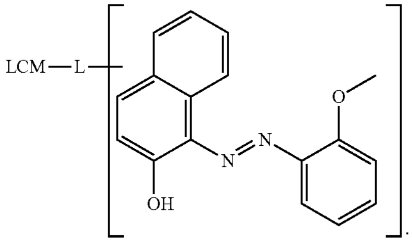

The structure of following formula (V) falls within the scope of the structure of formula (II). In an embodiment, the TM moiety has a structure of formula (V)

(v)

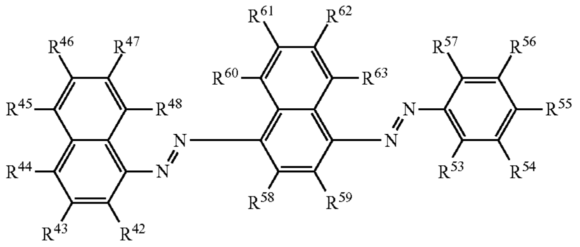

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are as defined in formula (III).

Wherein $R^{58}$, $R^{59}$, $R^{60}$, $R^{61}$, $R^{62}$ and $R^{63}$ are each independently selected from the group consisting of H, halogen, —$NO_2$, —CN, =O, =S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C=O)($C_{1-6}$alkyl), —O(C=O)($C_{3-6}$cyclohydrocarbyl), —O(C=O)($C_{1-4}$alkylene-$C_{3-6}$cyclohydrocarbyl), —O(C=O)(3- to 7-membered heterocyclyl), —O(C=O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C=O)($C_{1-6}$alkyl), —N($C_{1-6}$alkyl)—(C=O)($C_{1-6}$alkyl), —NH(C=O)($C_{3-6}$cyclohydrocarbyl), —N($C_{1-6}$alkyl)—(C=O)($C_{3-6}$ cyclohydrocarbyl), —NH(C=O)($C_{1-4}$alkylene-$C_{3-6}$cyclohydrocarbyl), —N($C_{1-6}$alkyl)—(C=O)($C_{1-4}$alkylene-$C_{3-6}$cyclohydrocarbyl), —NH(C=O)(3- to 7-membered heterocyclyl), —N($C_{1-6}$alkyl)—(C=O)(3- to 7-membered heterocyclyl), —COOH, —C(=O)($C_{1-6}$alkyl), —C(=O)O($C_{1-6}$alkyl), —C(=O)O($C_{3-6}$cyclohydrocarbyl), —C(=O)O($C_{1-4}$alkylene-$C_{3-6}$cyclohydrocarbyl), —C(=O)O(3- to 7-membered heterocyclyl), —C(=O)O($C_{1-4}$alkylene)-(3- to 7-membered heterocyclyl), —C(=O)$NH_2$, —C(=O)NH($C_{1-6}$alkyl), —C(=O)N($C_{1-6}$alkyl)$_2$, —C(=O)NH($C_{1-4}$alkylene-$C_{3-6}$ cyclohydrocarbyl), —C(=O)N($C_{1-4}$alkylene-$C_{3-6}$cyclohydrocarbyl)$_2$, —C(=O)NH(3- to 7-membered heterocyclyl), —C(=O)N(3- to 7-membered heterocyclyl)$_2$, —C(=O)NH($C_{1-4}$alkylene-3- to 7-membered heterocyclyl), —C(=O)N($C_{1-4}$alkylene-3- to 7-membered heterocyclyl)$_2$, —S(=O)$_2$OH, —S(=O)$_2$NH($C_{1-6}$alkyl), —S(=O)$_2$N($C_{1-6}$alkyl)$_2$, —S(=O)NH($C_{1-6}$alkyl), —S(=O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), —C(=O)N($C_{1-6}$alkyl)$_2$, —S(=O)$_2$OH, —S(=O)$_2$NH($C_{1-6}$alkyl), —S(=O)$_2$N($C_{1-6}$alkyl)$_2$.

In a specific embodiment, $R^{58}$, $R^{59}$, $R^{60}$, $R^{61}$, $R^{62}$ and $R^{63}$ are H, or at least one, preferably 1-6, more preferably 1-4, particularly 1, 2 or 4 of $R^{58}$, $R^{59}$, $R^{60}$, $R^{61}$, $R^{62}$ and $R^{63}$ are $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$cycloalkyl—$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$. In a particular embodiment, $R^{58}$, $R^{59}$, $R^{60}$, $R^{61}$, $R^{62}$ and $R^{63}$ are H.

In a particular embodiment, formula (V) has a structure of:

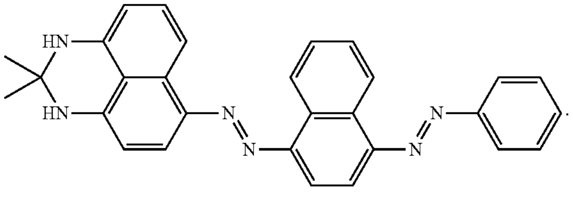

Solvent Black 3

Accordingly, in an embodiment, formula (I) has a structure of formula (xviii), wherein the TM moiety has a structure of above formula (V) (see above formula (V) and embodiments thereof) or a pharmaceutically acceptable salt thereof (xviii)

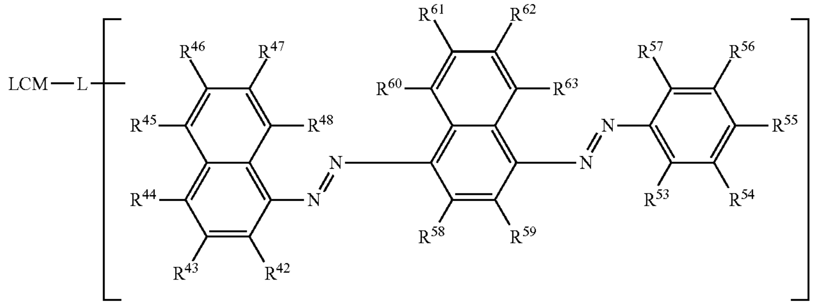

In an embodiment, L can covalently bind to any suitable site in formula (V).

In a particular embodiment, formula (xviii) has a structure of:

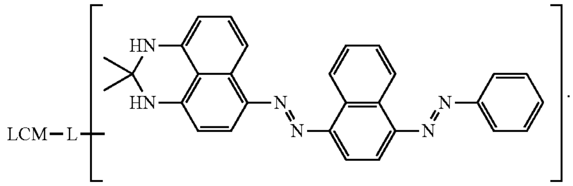

The structure of following formula (VI) falls within the scope of the structure of formula (II). In an embodiment, the TM moiety has a structure of formula (VI)

(VI)

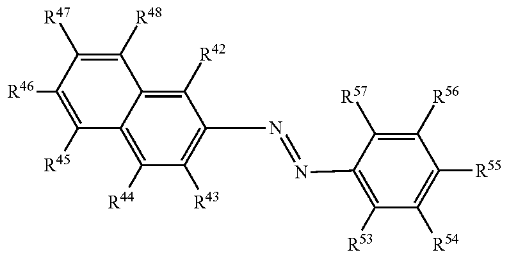

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are as defined in formula (III).

In another particular embodiment, formula (VI) has a structure of:

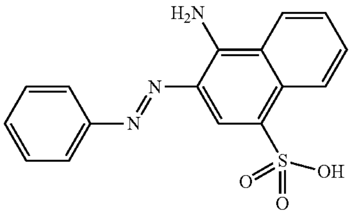 [SMILES: Nc1c(/N=N/c2ccccc2)cc(S(=O)(=O)O)c2ccccc12]

Accordingly, in an embodiment, formula (I) has a structure of formula (xix), wherein the TM moiety has a structure of above formula (VI) (see above formula (VI) and embodiments thereof) or a pharmaceutically acceptable salt thereof (xix)

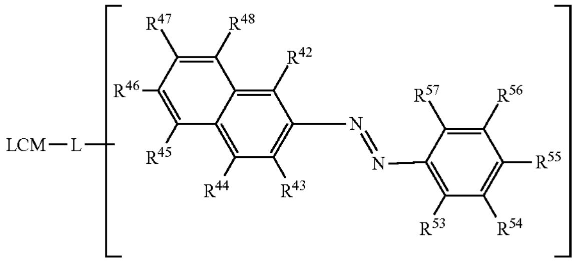

In an embodiment, L can covalently bind to any suitable site in formula (VI).

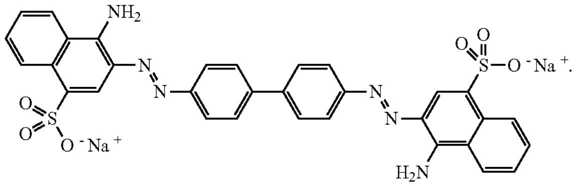

Congo Red O

Accordingly, in an embodiment, formula (I) has a structure of

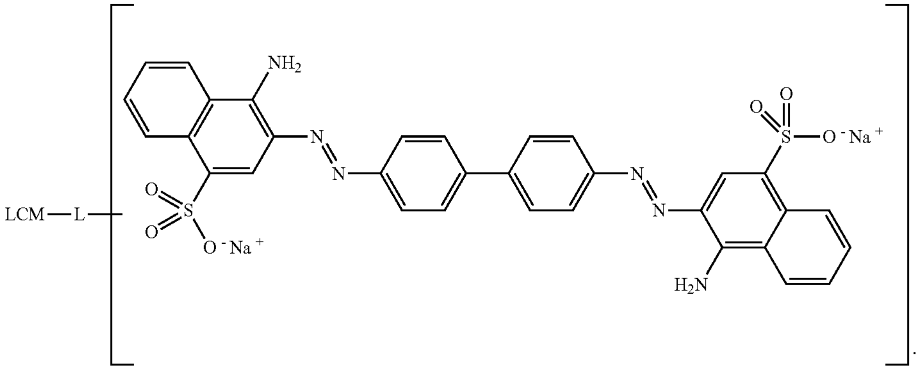

In another particular embodiment, formula (xix) has a structure of:

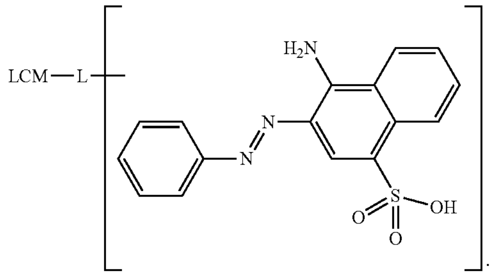

In an alternative embodiment, two or more structures of formula (II) are linked to each other to form a conjugate or hybrid, and such structures are encompassed with the concept of the TM moiety of the compounds according to the present disclosure. In a particular embodiment, the TM moiety of the compound according to the present disclosure is:

In an embodiment, L can covalently bind to any suitable site in formula (II).

In an embodiment, the TM moiety has a structure of formula (VII):

VII

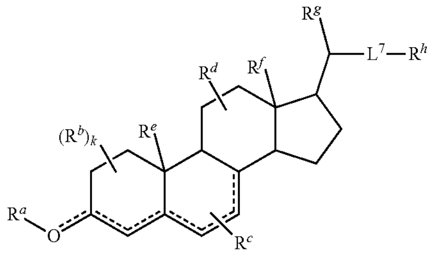

wherein, "⎓" represents single bond or double bond; when "⎓" represents double bond, $R^a$ is absent; when "⎓" represents single bond, $R^a$ is selected from the group consisting of H, OH, —O($C_{1-8}$alkyl), —O($C_{1-8}$silanyl), —C(═O)O($C_{1-26}$alkyl), —C(═O)O($C_{1-26}$alkenyl), wherein the alkenyl comprises 1-8 double bonds;

$R^b$, $R^c$, $R^d$ are each independently selected from the group consisting of H, $C_{1-8}$alkyl, $C_{1-8}$alkenyl, —OH, —O($C_{1-8}$alkyl), —O($C_{1-8}$silanyl);

$R^e$, $R^f$, $R^g$ are each independently selected from the group consisting of H, $C_{1-4}$alkyl, —OH, —O($C_{1-4}$alkyl);

$L^7$ is selected from the group consisting of chemical bond, $C_{1-8}$alkylene;

$R^h$ is selected from the group consisting of H, $C_{1-20}$alkyl, $C_{1-20}$alkenyl, —OH, —O($C_{1-20}$alkyl), —O($C_{1-20}$silanyl), wherein the alkyl or alkenyl is optionally substituted with one or more substituents selected from the group consisting of —OH, $C_{1-8}$alkyl, $C_{1-8}$alkenyl, $C_{1-8}$alkynyl, —O($C_{1-20}$alkyl), —O($C_{1-20}$silanyl);

k is 0, 1 or 2.

In an embodiment, "⎓" represents single bond, $R^a$ is selected from the group consisting of H, OH, —O($C_{1-8}$ alkyl), —C(═O)O($C_{1-22}$alkyl), —C(═O)O($C_{1-22}$alkenyl), wherein the alkenyl comprises 1-8, preferably 2-6, more preferably 3-6 double bonds.

In an embodiment, $R^b$, $R^c$, $R^d$ are H. In another embodiment, $R^e$, $R^f$ are methyl. In another embodiment, $R^g$ is methyl. In another embodiment, $R^h$ is $C_{3-10}$alkyl, preferably $C_{5-8}$alkyl, more preferably $C_{6-7}$alkyl, particularly $C_6$alkyl.

In a particular embodiment, formula (VII) has a structure selected from the group consisting of:

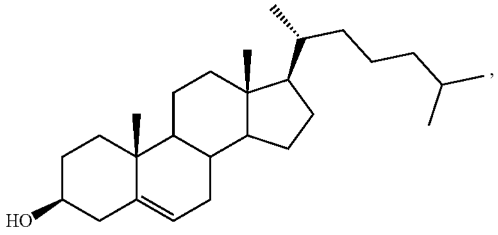

cholesterol

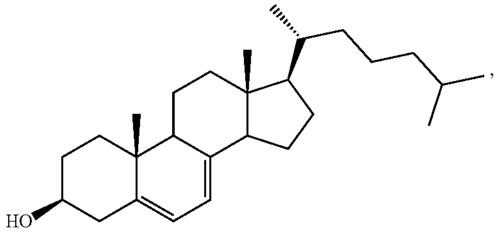

dehydrocholesterol

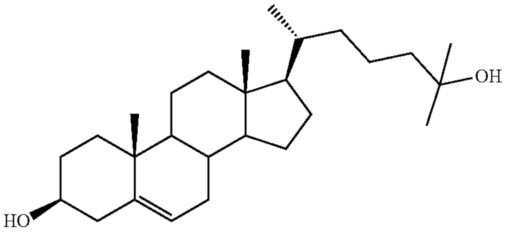

and 25-hydroxycholesterol

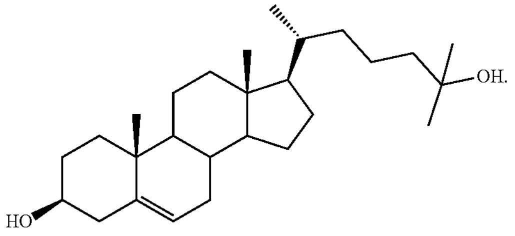

25-hydroxydehydrocholesterol

Accordingly, in an embodiment, formula (I) has a structure of formula (xx), wherein the TM moiety has a structure of above formula (VII) (see above formula (VII) and embodiments thereof) or a pharmaceutically acceptable salt thereof (xx)

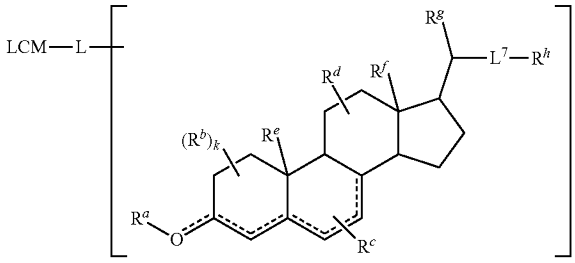

In an embodiment, L can covalently bind to any suitable site in formula (VII).

In a particular embodiment, formula (xx) has a structure selected from the group consisting of:

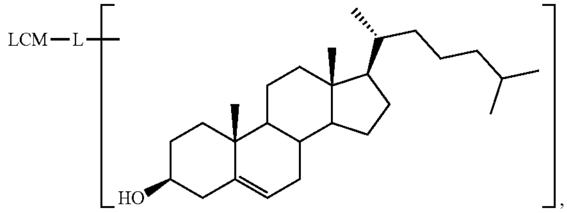

,

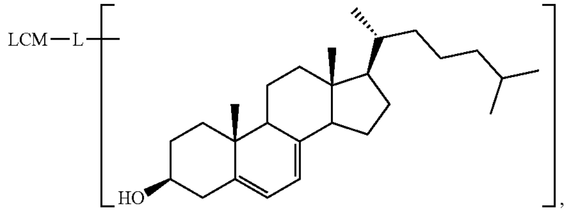

,

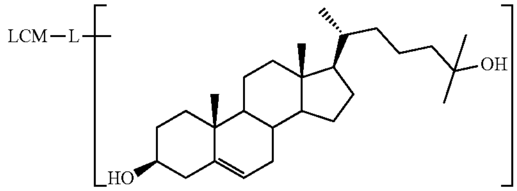

and

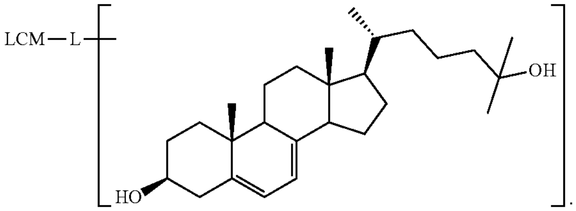

.

In an embodiment, the TM moiety comprises alkynyl or azido. In a particular embodiment, TM moiety is

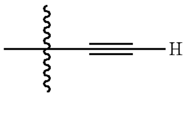

or —$N_3$.

Accordingly, in an embodiment, formula (I) has a structure of formula (xxi) or formula (xxii), wherein the TM moiety is

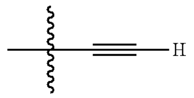

or $—N_3$

LCM—L—≡ (xxi)

LCM—L—$N_3$ (xxii)

Conjugated Compound

Some examples of the conjugated compounds are as described for formula (i)—formula (xxii).

The LCM moiety and L are covalently linked, and the TM moiety and L are covalently linked, where the covalent linking site can be any suitable site. In an embodiment, a carbon atom of the LCM moiety is covalently linked to L. In another embodiment, a heteroatom of the LCM moiety is covalently linked to L. Those skilled in the art can select the appropriate reactions for connection according to the structures of LCM moiety, L, TM moiety, and can also adjust the substituents of LCM moiety, L, TM moiety according to the types of reactions. It should be understood that in the covalent linkages between LCM moiety and L, and between TM moiety and L, the structure of the product (conjugated compound) can be easily determined based on the structures of LCM moiety, L, TM moiety before covalent linkage, and the structures of LCM moiety, L, TM moiety before covalent linkage can be easily determined based on the structure of the product (conjugated compound). In a particular embodiment, both LCM moiety and L comprise hydroxyl groups, and the hydroxyl group of the LCM moiety can form a covalent connection with the hydroxyl group in the L, losing a molecule of water. In another particular embodiment, both TM moiety and L comprise hydroxyl groups, and the hydroxyl group of the TM moiety can form a covalent connection with the hydroxyl group in the L, losing a molecule of water. In another particular embodiment, the L comprises a nucleophilic reaction site, and the LCM moiety comprises an O- or N-containing structure with nucleophilic reactivity, which forms a covalent link with the nucleophilic reaction site in the L. In another particular embodiment, the L comprises a nucleophilic reaction site, and the TM moiety comprises an O- or N-containing structure with nucleophilic reactivity, which forms a covalent link with the nucleophilic reaction site in the L.

In an embodiment, the compound of formula (I) is selected from:

Compound 1A

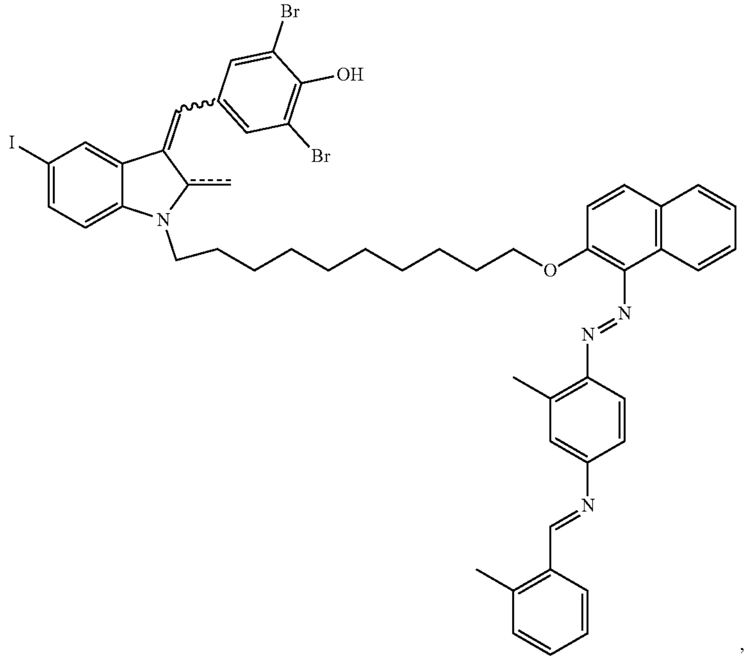

,

-continued
Compound 1B
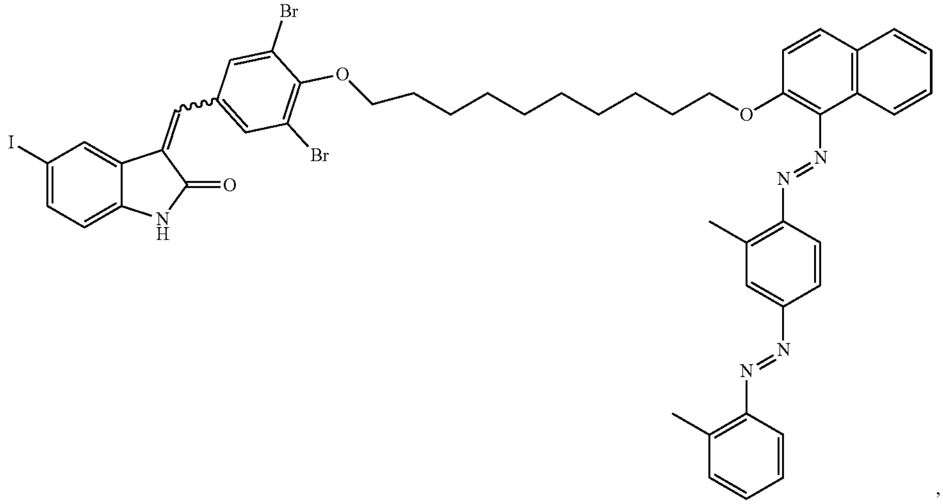
,
Compound 2A
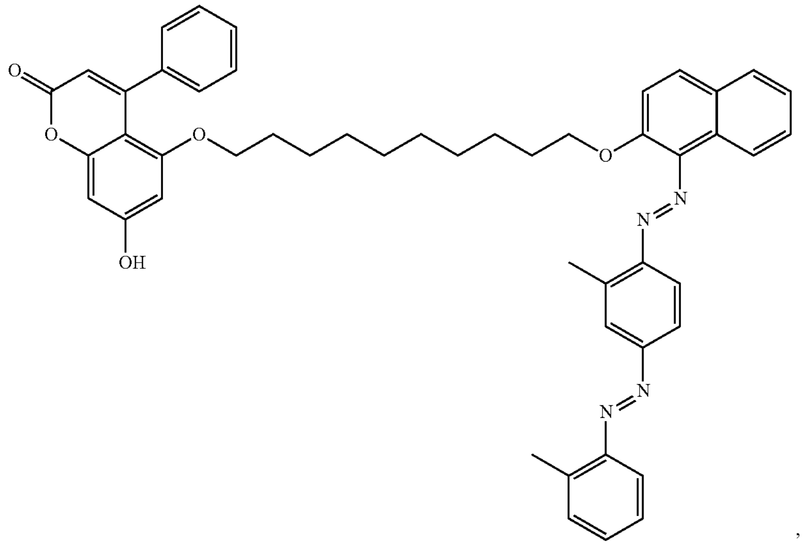
,
Compound 2B
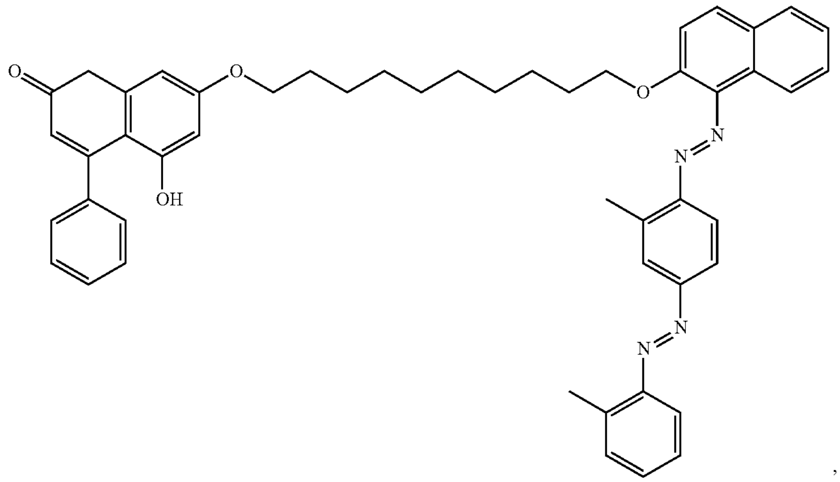
, -continued
Compound 3A
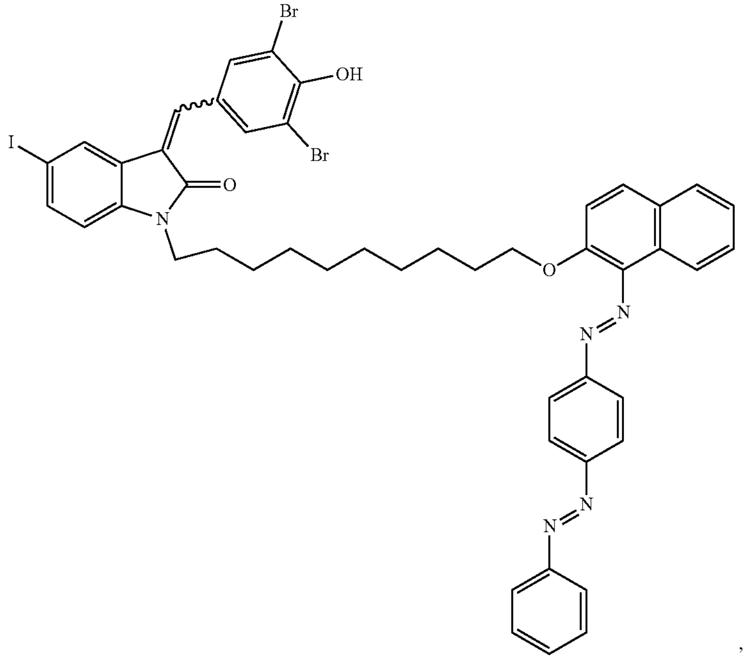
,
Compound 3B
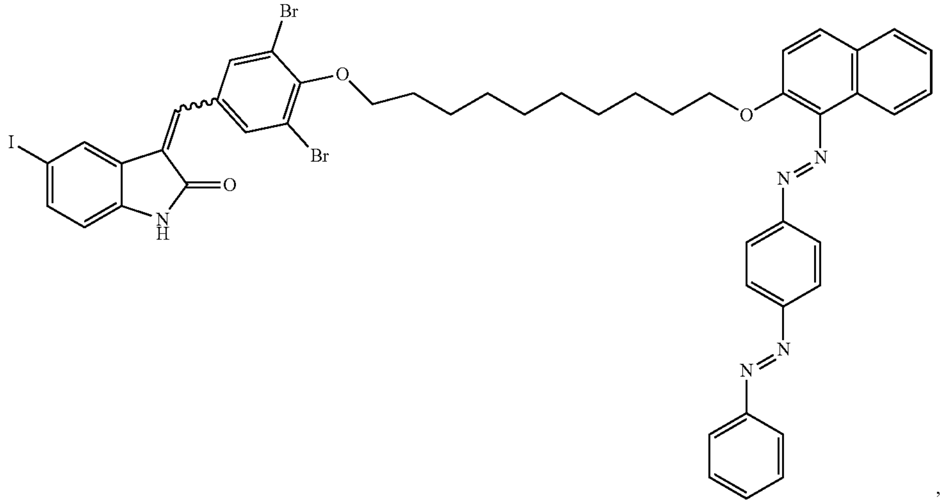
, -continued
Compound 4A
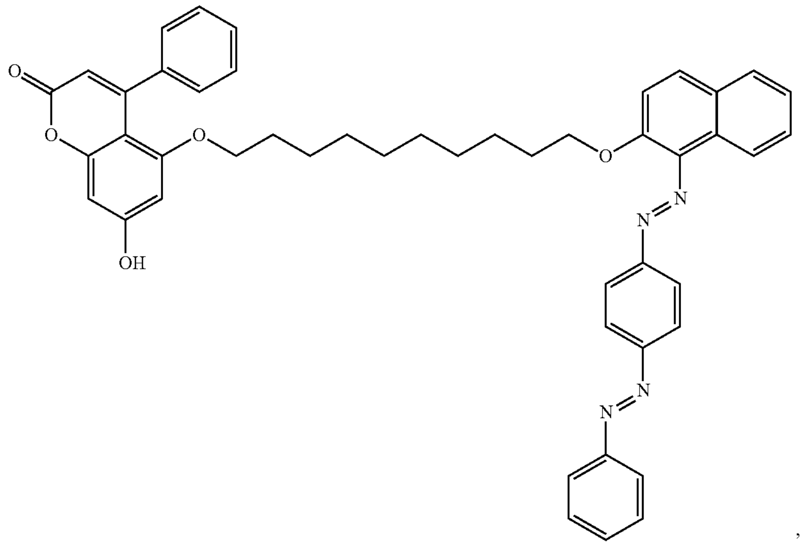
,
Compound 4B
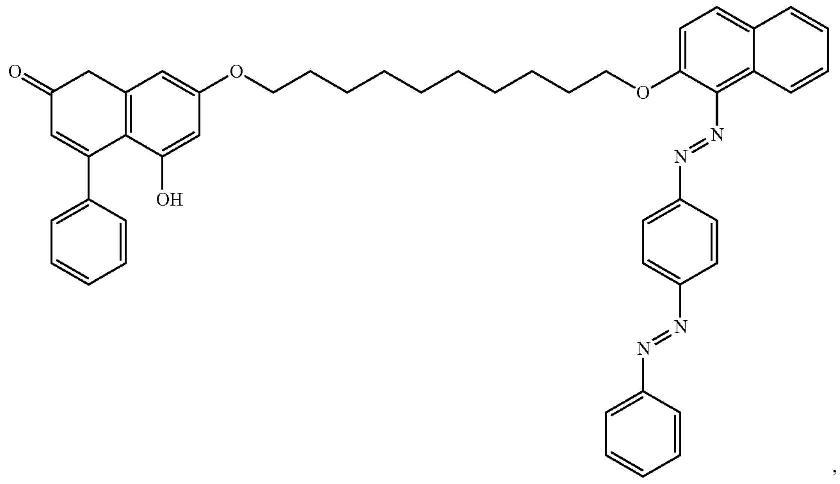
,
Compound 5A
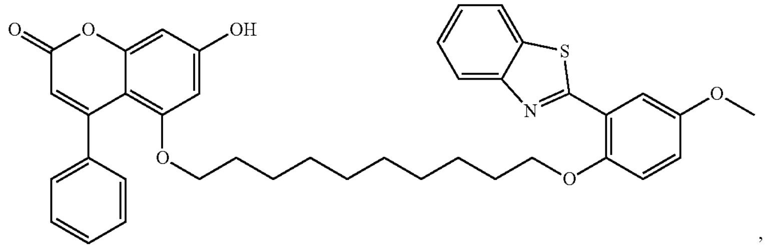
, -continued
Compound 5B
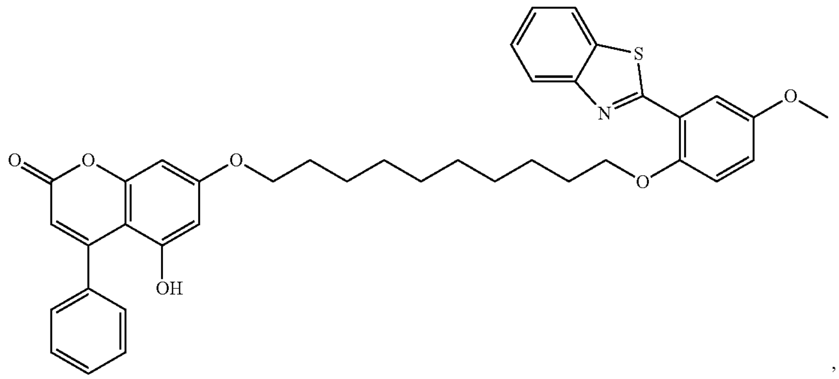
,
Compound 6
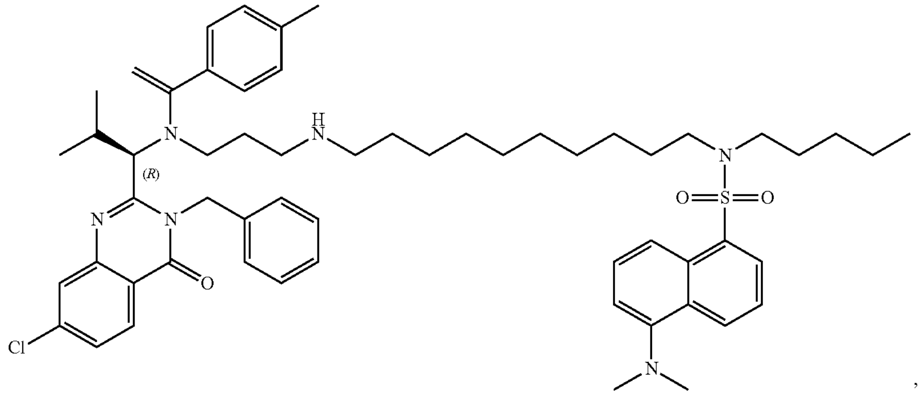
,
Compound 7
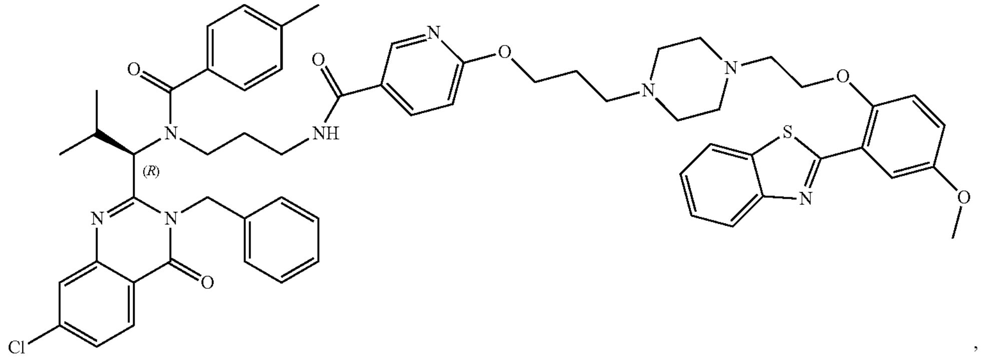
,
Compound 8
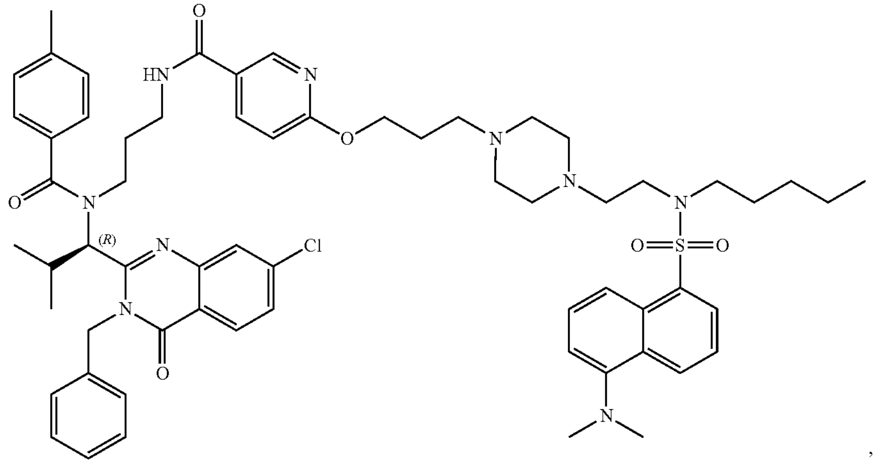
, -continued Compound 9

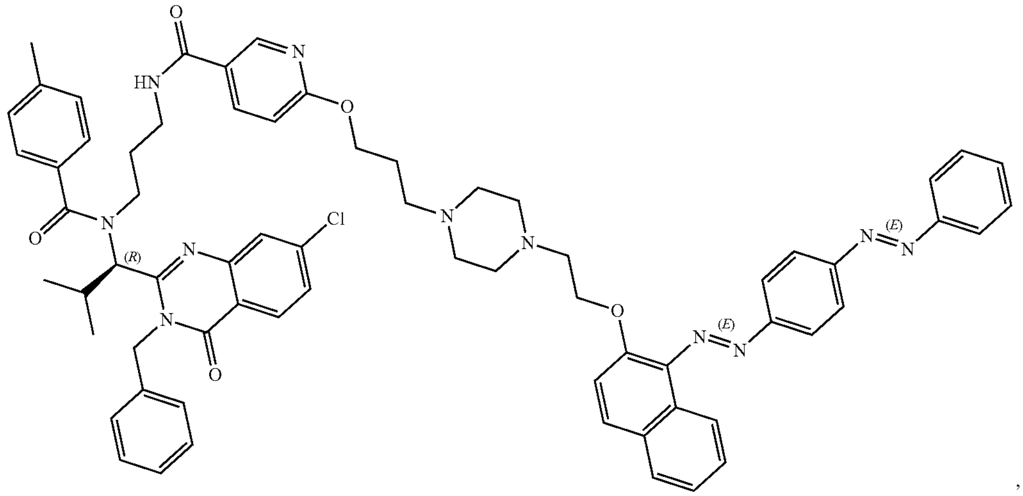

,

Compound 10A

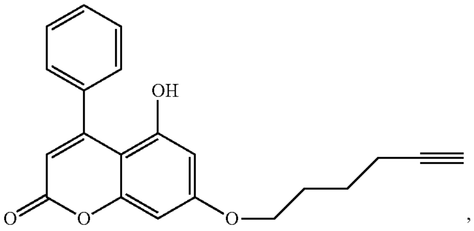

,

Compound 10B

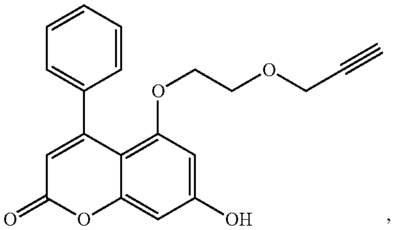

,

Compound 11A

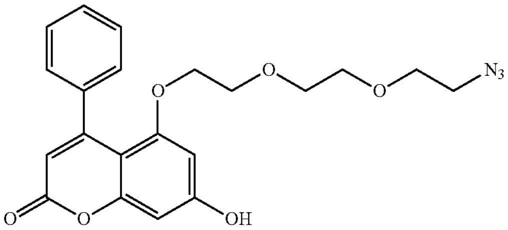

and

Compound 11B

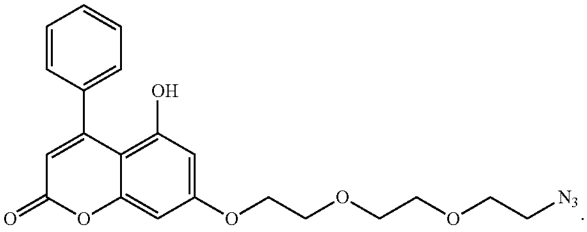

.

In an embodiment, the compound of formula (I) is selected from the group consisting of Compound 1A, 1B, 2A, 2B, 3A, 3B, 4A, 4B, 5A, 6, 7, 8, 9, 10A, 10B and 11A, preferably selected from the group consisting of Compound 1A, 1B, 2A, 2B, 3A, 3B, 4A, 4B, 5A, 6, 7, 8, 9, 10A and 11A. In an embodiment, the compound of formula (I) is selected from the group consisting of Compound 1A, 1B, 2A, 2B, 3A, 3B, 4A, 4B, 5A, 5B, 6, 7, 8 and 9.

Process for Preparing the Compound

In another aspect, provided is a process for preparing the compound according to the present disclosure, comprising: covalently linking a structure moiety capable of binding to LC3 protein and a structure moiety capable of binding to a lipid droplet, to form a "LC3 binding moiety-lipid droplet binding moiety conjugate" ("conjugated compound"). The components of the conjugated compound are as defined above.

In an embodiment, the following method may be used to screen or identify a structure capable of binding to LC3 protein:

(I): contacting a candidate compound with a testing system comprising the LC3 protein or a homologue or a fragment thereof, and (II): selecting a compound that binds to LC3 proteins or a homologue or a fragment thereof.

In an embodiment, the following method may be used to screen or identify a structure capable of binding to lipid droplet:

(I'): contacting a candidate compound with a testing system comprising a target which is a lipid droplet or a lipid droplet marker protein or a neutral lipid known to be present in the target lipid droplet; and (II'): selecting a compound that non-covalently binds to the target in (I').

Pharmaceutical Composition and Pharmaceutical Formulation

Another object of present disclosure is to provide a pharmaceutical composition comprising a prophylactically or therapeutically effective amount of the compound of present disclosure, or a pharmaceutically acceptable salt, stereoisomer, solvate, polymorph, tautomer, isotopic compound, metabolite or prodrug thereof, and one or more pharmaceutically acceptable carriers.

The "pharmaceutically acceptable carrier" refers to a diluent, adjuvant, excipient or vehicle, and within the scope of reasonable medical judgement, it is suitable for contacting human and/or other animal tissues without excessive toxicity, irritation, allergic reaction or other problems or complications corresponding to reasonable benefit/risk ratio.

In one embodiment, the present disclosure provides a capsule containing the compound of the present disclosure without an additional carrier.

The pharmaceutical composition of the present disclosure may be in the form of tablets, chewable tablets, capsules, solutions, parenteral solutions, lozenges, suppositories, and suspensions, etc. The composition can be formulated to contain a daily dose or an appropriate portion of the daily dose in a dosage unit, which can be a single tablet or capsule or a liquid of a suitable volume.

In one embodiment, the solution is prepared from a water-soluble salt, such as hydrochloride. Generally, all compositions are prepared according to known methods in pharmaceutical chemistry. Capsules can be prepared by mixing the compound with a suitable carrier or diluent and filling an appropriate amount of the mixture into the capsule. Commonly used carriers and diluents include, but are not limited to, inert powdered substances, such as a variety of different starches, powdered cellulose, especially crystalline and microcrystalline cellulose, sugars such as fructose, mannitol and sucrose, cereal flour, and similar edible powder.

Tablets can be prepared by direct compression, wet granulation, or dry granulation. The formulation usually adds diluent, binder, lubricant and disintegrant and the compound. Typical diluents include, for example, various types of starch, lactose, mannitol, kaolin, calcium phosphate or calcium sulfate, inorganic salts (such as sodium chloride) and powdered sugar. Powdered cellulose derivatives are also useful. Typical tablet binders are the following substances, such as starch, gelatin, and sugar (such as lactose, fructose, glucose, etc.). Natural and synthetic gums are also suitable, including gum acacia, alginate, methylcellulose, polyvinylpyrrolidone, etc. Polyethylene glycol, ethylcellulose and wax can also act as binders. Polyethylene glycol, ethylcellulose and wax can also act as binders.

Lubricants can be selected from such slippery solids such as talc, magnesium stearate and calcium stearate, stearic acid and hydrogenated vegetable oils. A tablet disintegrant swells when wet to break the tablet and release the compound. They include starch, clay, cellulose, algin and gum. More specifically, for example, corn and potato starch, methylcellulose, agar, bentonite, lignocellulose, powdered natural sponge, anion exchange resin, alginic acid, guar gum, citrus pomace, carboxymethylcellulose and sodium lauryl sulfate can be used. Tablets can be coated with sugar as a flavoring and sealing agent or coated with a film-forming protective agent to optimize the dissolution performance of the tablet. The composition can also be formulated into chewable tablets, for example, by adding some substances to the formulation, such as mannitol.

When it is desired to be administered as a suppository, a typical matrix can be used. Cocoa butter is a traditional suppository matrix, which can be changed by adding wax to slightly increase its melting point. Especially water-miscible suppository matrices including polyethylene glycols of various molecular weights are widely used.

The effect of the compound can be delayed or prolonged by a suitable formulation. For example, slowly dissolving pellets of the compound can be prepared and added to tablets or capsules or used as a sustained release implantable device. The technology also includes preparing several pellets with different dissolution rates and filling the capsule with a mixture of pellets. Tablets or capsules can be coated with a film that resists dissolution for a predictable period. Even parenteral formulations can be prepared as a long-acting formulation by dissolving or suspending the compound in an oily or emulsified vehicle that allows it to be slowly dispersed in the serum.

In one embodiment, the pharmaceutical composition and/or pharmaceutical formulation of present disclosure is provided in form of kit.

Treatment and Use

In one aspect, provided is a method for decreasing lipid droplet in cells including contacting a conjugated compound of present disclosure with a cell or tissue comprising lipid droplet, wherein the lipid droplet is comprised by cells under physiological or pathological conditions, and/or are produced by inducing cells.

Cells or tissues comprising lipid droplet can be, for example, derived from normal cells or tissues, lipid droplet accumulation associated biological models or cells or tissues from clinical patients. In one embodiment, the lipid droplets are those comprised by cells under normal physiological condition. In another embodiment, the lipid droplets are those comprised by cells under pathological condition of lipid metabolism associated disease. In yet another embodiment, the lipid droplets are those generated by cells induced by exogenous substance (for example sodium oleate).

In one aspect, provided is the compound of present disclosure or a pharmaceutically acceptable salt, stereoisomer, solvate, polymorph, tautomer, isotopic compound, metabolite or prodrug thereof, or use of the pharmaceutical composition of present disclosure in the manufacture of a medicament for decreasing lipid droplet in cells.

In yet another aspect, provided is the compound of present disclosure or a pharmaceutically acceptable salt, stereoisomer, solvate, polymorph, tautomer, isotopic compound, metabolite or prodrug thereof, or the pharmaceutical composition, for use in decreasing lipid droplet in cells.

In a further aspect, provided is a method for decreasing lipid droplet in cells, which comprises administering effective amount of the compound of present disclosure or a pharmaceutically acceptable salt, stereoisomer, solvate, polymorph, tautomer, isotopic compound, metabolite or prodrug thereof or the pharmaceutical composition of present disclosure to a subject in need thereof.

In one aspect, provided is use of the compound of present disclosure or a pharmaceutically acceptable salt, stereoisomer, solvate, polymorph, tautomer, isotopic compound, metabolite or prodrug thereof or the pharmaceutical composition of present disclosure in the manufacture of a medicament for the treatment or prevention of lipid metabolism associated disease.

In yet another aspect, provided is the compound of present disclosure or a pharmaceutically acceptable salt, stereoisomer, solvate, polymorph, tautomer, isotopic compound, metabolite or prodrug thereof or the pharmaceutical composition of present disclosure, for use in treating or preventing lipid metabolism associated disease.

In a further aspect, provided is a method for treating or preventing lipid metabolism associated disease comprising administering effective amount of the compound of present disclosure or a pharmaceutically acceptable salt, stereoisomer, solvate, polymorph, tautomer, isotopic compound, metabolite or prodrug thereof or the pharmaceutical composition of present disclosure to a subject in need thereof.

The compound of the present disclosure can be administered to patients orally or parenterally in the form of conventional formulations, the forms of the conventional formulations are, for example, capsules, microcapsules, tablets, granules, powders, lozenges, pills, suppositories, injections, suspensions, syrups, patches, creams, lotions, ointments, gels, sprays, solutions, and emulsions. Suitable formulations can use conventional organic or inorganic additives and are prepared by commonly used methods. The organic or inorganic additives are, for example, excipients (for example, sucrose, starch, mannitol, sorbitol, lactose, glucose, cellulose, talc, calcium phosphate or calcium carbonate), binder (for example, cellulose, methylcellulose, hydroxymethylcellulose, polypropylpyrrolidone, polyvinylpyrrolidone, gelatin, gum acacia, polyethylene glycol, sucrose or starch), disintegrants (for example, starch, carboxymethylcellulose, hydroxypropyl starch, low-substituted hydroxypropylcellulose, sodium bicarbonate, calcium phosphate or calcium citrate), lubricants (for example, magnesium stearate, light anhydrous silicic acid, talc or sodium lauryl sulfate), flavoring agents (for example, citric acid, menthol, glycine or tangerine powder), preservatives (for example, sodium benzoate, sodium bisulfite, methylparaben or propylparaben), stabilizer (for example, citric acid, sodium citrate or acetic acid), suspending agents (for example, methylcellulose, polyvinylpyrrolidone or aluminum stearate), dispersant (for example, hydroxypropyl methylcellulose), diluent (for example, water) and base wax (for example, cocoa butter, white petrolatum or polyethylene glycol).

Dosage regimens can be adjusted to provide the desired optimal response. For example, when the medicine is administered in the form of injection, it can be administered as a single injection, bolus injection and/or continuous infusion, etc. For example, several divided doses may be administered over time, or the dose may be proportionally reduced or increased as indicated by the urgent need of the treatment situation. It should be noted that the dose value may vary with the type and severity of the condition to be alleviated and may include single or multiple doses. Generally, the dose of treatment varies, depending on the considerations, such as the age, gender, and general health of the patient to be treated; the frequency of treatment and the nature of the desired effect; the degree of tissue damage; the duration of symptoms; and other variables that can be adjusted by subject physicians. It should be further understood that for any particular subject, the specific dosing regimen should be adjusted over time according to the needs of the subject and the professional judgment of the person administering the composition or supervising the administration of the composition. The dosage and regimen of the pharmaceutical composition can be easily determined by a person of ordinary skill in the clinical field. For example, the composition or compound of the present disclosure may be administered in divided doses from 4 times a day to once every 3 days, and the dosage may be, for example, 0.01 to 1000 mg/time. The required dose can be administered one or more times to obtain the desired result. The pharmaceutical composition according to the present disclosure can also be provided in unit dosage forms.

Drug Combination

Provided is the compound of present disclosure or a pharmaceutically acceptable salt, stereoisomer, solvate, polymorph, tautomer, isotopic compound, metabolite or prodrug thereof or the pharmaceutical composition of present disclosure or the pharmaceutical formulation, which can be used in combination with other therapeutic agents for treating or preventing lipid metabolism associated disease. In one embodiment, the other therapeutic agent is selected from substance for treating or preventing insulin resistance, substance for decreasing free fatty acid level, and substance for decreasing cholesterol level.

Exemplary embodiments of the present disclosure are also be provided as follows:

<1> A compound or a pharmaceutically acceptable salt, stereoisomer, solvate, polymorph, tautomer, isotopic compound, metabolite, or prodrug thereof, wherein the compound has a structure comprising formula (I)

LCM-L-TM (I)

wherein:

LCM is a LC3 binding moiety;

L is a linker moiety;

TM is a lipid droplet binding moiety.

<2> The compound according to <1> or a pharmaceutically acceptable salt, stereoisomer, solvate, polymorph, tautomer, isotopic compound, metabolite, or prodrug thereof, wherein in formula (I), the LCM moiety is a moiety with affinity to LC3 protein, and the TM moiety is a moiety which can interact non-covalently with the lipid droplet.

<3> The compound according to <1> or <2>, or a pharmaceutically acceptable salt, stereoisomer, solvate, polymorph, tautomer, isotopic compound, metabolite, or prodrug thereof, wherein the formula (1) has a structure of formula (2):

(2)

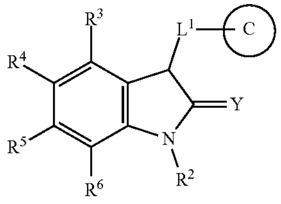

wherein:

Y is O or S;

ring C is selected from the group consisting of $C_{6-10}$ aryl and 5- to 7-membered heteroaryl, the aryl or heteroaryl is optionally substituted with one or more groups each independently selected from the group consisting of $R^{X1}$;

$R^2$ is selected from the group consisting of H, $C_{1-8}$alkyl;

$L^1$ is bond, or is $C_1$-$C_6$ hydrocarbyl chain;

$R^3$, $R^4$, $R^5$, $R^6$ are each independently selected from the group consisting of H and $R^{X2}$;

wherein $R^{X1}$, $R^{X2}$ are as defined in <3>;

$R^{X1}$ and $R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$ alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$ cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$ cyclohydrocarbyl)$_2$, —NH ($C_{1-4}$alkylene-$C_{3-6}$cyclohydrocarbyl), —N($C_{1-4}$alkylene-$C_{3-6}$ cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, ═O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$ aryl-$C_{1-4}$alkyl, wherein the alkyl, alkenyl, alkynyl, cyclohydrocarbyl, heterocyclyl or aryl is optionally substituted with one or more substituents selected from the group consisting of halogen, —$NO_2$, —CN, $C_{1-6}$alkyl, —OH, —O($C_{1-6}$alkyl), —$NH_2$, —NH ($C_{1-6}$alkyl), —N($C_{1-6}$alkyl)$_2$, —COOH, —C(═O)O ($C_{1-6}$alkyl), —C(═O)NH($C_{1-6}$alkyl), —C(═O)N ($C_{1-6}$alkyl)$_2$, —OC(═O)($C_{1-6}$alkyl), —NHC(═O) ($C_{1-6}$alkyl), —C(═O)($C_{1-6}$alkyl);

$R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, —S(═O)$_2OR^{Y1}$, —S(═O)$_2R^{Y1}$, —S(═O)$_2NR^{Y1}R^{Y2}$, —S(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, ═O, ═S, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, ═O and —COOH;

particularly, formula (2) has a structure selected from the group consisting of:

A1

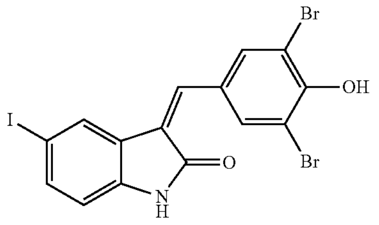

A2

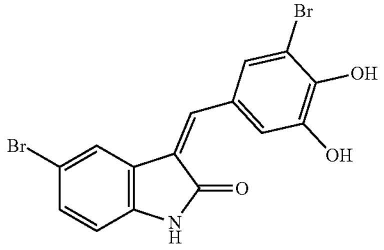

A3

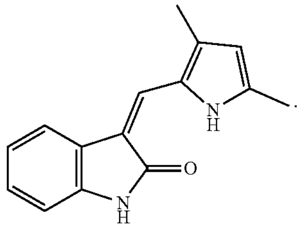

<4> The compound according to <1> or <2>, or a pharmaceutically acceptable salt, stereoisomer, solvate, polymorph, tautomer, isotopic compound, metabolite, or prodrug thereof, wherein the formula (1) has a structure of formula (5):

(5)

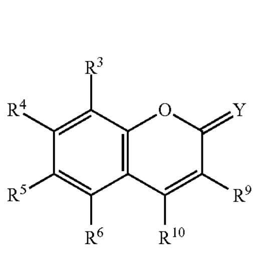

wherein:

Y is O or S;

$R^9$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$; wherein $R^{a1}$, $R^{b1}$, $R^{a2}$, $R^{b2}$ are as defined in <3>;

$R^{10}$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl;

$R^3$ is selected from the group consisting of H, halogen, $C_{1-6}$alkyl, —OH, —$NH_2$, —NH($C_{1-6}$alkyl), —N($C_{1-6}$ alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$;

$R^4$ is selected from the group consisting of H, halogen, —$NO_2$, —CN, $C_{1-6}$alkyl, —$OR^7$, —$SR^7$, —$NR^7R^8$; $R^7$, $R^8$, on each occurrence, are each independently selected from the group consisting of H, $C_{1-6}$alkyl, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —COOH, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), —C(=O)($C_{1-6}$alkyl); wherein $R^7$, $R^8$ are as defined in <3>;

$R^5$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), —C(=O)($C_{1-6}$alkyl), wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), —C(=O)($C_{1-6}$alkyl);

$R^6$ is selected from the group consisting of H, halogen, —$NO_2$, —CN, $C_{1-6}$alkyl, —OH, —O($C_{1-6}$alkyl), —O(benzyl), —SH, —S($C_{1-6}$alkyl), —S(benzyl), —$NH_2$, —NH($C_{1-6}$alkyl), —N($C_{1-6}$alkyl)$_2$, —NH (benzyl), wherein the alkyl or benzyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$;

particularly, formula (5) has a structure of:

A4

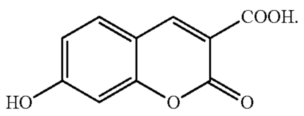

<5> The compound according to <1> or <2>, or a pharmaceutically acceptable salt, stereoisomer, solvate, polymorph, tautomer, isotopic compound, metabolite, or prodrug thereof, wherein the formula (6) has a structure of formula (8):

(8)

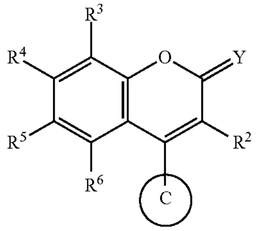

wherein:

Y is O or S;

ring C is

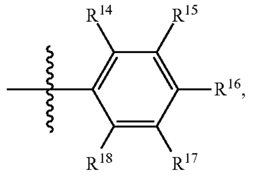

wherein $R^{14}$, $R^{15}$, $R^{16}$, $R^{17}$, $R^{18}$ are each independently selected from the group consisting of H, halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$, —S(=O)$R^7$; wherein $R^{7}$' $R^8$ are as defined in <6>; preferably, $R^{14}$, $R^{15}$, $R^{17}$, $R^{18}$ are each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH(C=O)($C_{1-6}$alkyl), and $R^{16}$ is H or —$OCH_3$;

$R^2$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$; wherein $R^{a2}$, $R^{b2}$ are as defined in <6>; preferably, $R^2$ is selected from the group consisting of H, halogen, $C_{1-6}$alkyl, wherein the alkyl is optionally substituted with one or more substituents selected from the group consisting of halogen, —$NO_2$, —CN, —OH, —$NH_2$ and —COOH;

$R^3$ is selected from the group consisting of H, —OH, $C_{1-6}$alkyl, wherein the alkyl is optionally substituted with one or more substituents selected from the group consisting of halogen, —$NO_2$, —CN, —OH, —SH, —$NH_2$, —NH($C_{1-6}$alkyl), —N($C_{1-6}$alkyl)$_2$, —NH($C_{3-6}$ cyclohydrocarbyl), —N($C_{3-6}$cyclohydrocarbyl)$_2$, —NH($C_{1-4}$alkylene-$C_{3-6}$cyclohydrocarbyl), —N($C_{1-4}$ alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$ and —COOH;

$R^4$ is selected from the group consisting of H, —$OR^7$, —$SR^7$, —$NR^7R^8$; $R^7$, $R^8$, on each occurrence, are each independently selected from the group consisting of H, $C_{1-6}$alkyl, wherein the alkyl is optionally substituted with one or more substituents selected from the group consisting of halogen, $C_{1-6}$alkyl, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$;

$R^5$ is selected from the group consisting of H, $C_{1-6}$alkyl, wherein the alkyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —0(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$ and —COOH; and $R^6$ is selected from the group consisting of H, halogen, $C_{1-6}$alkyl, —OH, —$NH_2$, wherein the alkyl is optionally substituted with one or more substituents selected from the group consisting of halogen, —OH, —$NH_2$;

particularly, formula (8) has a structure selected from the group consisting of:

A5

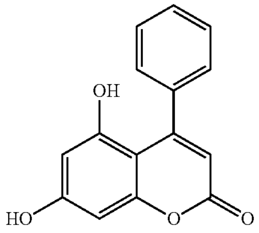

A6

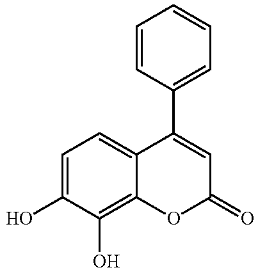

-continued

A7

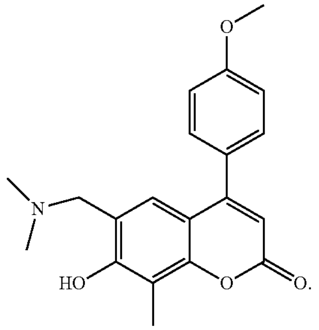

<6> The compound according to <1> or <2>, or a pharmaceutically acceptable salt, stereoisomer, solvate, polymorph, tautomer, isotopic compound, metabolite, or prodrug thereof, wherein the formula (6) has a structure of formula (9):

(9)

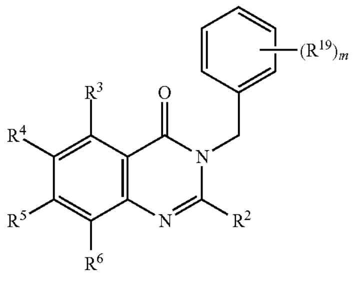

wherein:

$R^2$ is selected from the group consisting of H, halogen, —$NO_2$, —CN, $C_{1-6}$alkyl, $C_{3-6}$ cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$;

$R^{19}$, on each occurrence, is each independently selected from the group consisting of halogen, —$NO_2$, —CN, $C_{1-6}$alkyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —COOH;

m is 0, 1, 2, 3, 4 or 5;

$R^3$, $R^4$, $R^5$, $R^6$ are each independently selected from the group consisting of H and $R^{X2}$;

$R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, ═O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, wherein the alkyl, alkenyl, alkynyl, cyclohydrocarbyl or heterocyclyl is optionally substituted with one or more substituents selected from the group consisting of halogen, —$NO_2$, —CN, $C_{1-6}$alkyl, —OH, —O($C_{1-6}$ alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$ alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl);

$R^{a1}$, $R^{b1}$, $R^{c1}$, $R^{a2}$, $R^{b2}$, $R^{c2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$ cyclohydrocarbyl-$C_{1-4}$alkyl, 3- to 7-membered heterocyclyl, 3- to 7-membered heterocyclyl-$C_{1-4}$alkyl, $C_{6-10}$ aryl, $C_{6-10}$ aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, —S(═O)$_2OR^{Y1}$, —S(═O)$_2R^{Y1}$, —S(═O)$_2NR^{Y1}R^{Y2}$, —S(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, ═O, ═S, —$OR^{Y3}$, —$SR^{Y3}$, —$NR^{Y3}R^{Y4}$, —C(═O)$R^{Y3}$, —C(═O)$OR^{Y3}$ and —C(═O)$NR^{Y3}R^{Y4}$;

$R^{Y1}$, $R^{Y2}$, $R^{Y3}$, $R^{Y4}$ are as defined in <1> or <2>;

particularly, formula (9) has a structure of:

A8

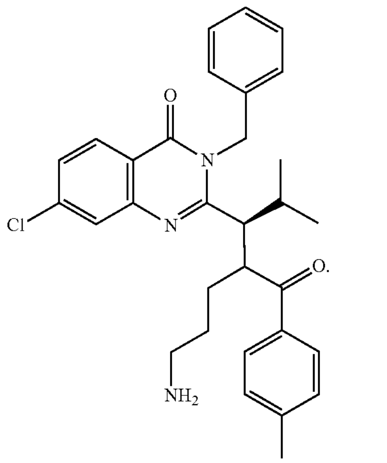

<7> The compound according to <1> or <2>, or a pharmaceutically acceptable salt, stereoisomer, solvate, polymorph, tautomer, isotopic compound, metabolite, or prodrug thereof, wherein the LCM moiety has a structure of formula (10), or a pharmaceutically acceptable salt thereof:

(10)

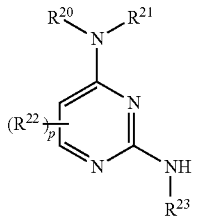

wherein, $R^{20}$ is selected from the group consisting of bicyclic heteroaryl, having 9-10 ring atoms, the ring atoms comprising 1-3 heteroatoms each independently selected from the group consisting of O, S, N, the remaining atoms being C; the heteroaryl is unsubstituted or substituted with at least one group selected from the group consisting of $R^{X3}$;

$R^{21}$ is selected from the group consisting of $C_{1-8}$alkyl;

$R^{22}$ is selected from the group consisting of $R^{X3}$;

$R^{23}$ is phenyl, which is unsubstituted or substituted with at least one group selected from the group consisting of $R^{X3}$;

$R^{X3}$, on each occurrence, is each independently selected from the group consisting of $C_{1-8}$ alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$ alkyl), —C(═O)N($C_{1-8}$alkyl)$_2$, —S(═O)$_2$OH, —S(═O)$_2$(O$C_{1-8}$alkyl), —S(═O)$_2NH_2$, —S(═O)$_2$NH($C_{1-8}$alkyl), —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

p is 0, 1 or 2;

particularly, formula (10) has a structure of:

A9

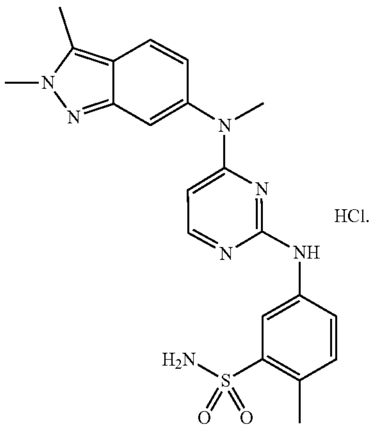

HCl.

<8> The compound according to <1> or <2>, or a pharmaceutically acceptable salt, stereoisomer, solvate, polymorph, tautomer, isotopic compound, metabolite, or prodrug thereof, wherein the LCM moiety has a structure of formula (11), or a pharmaceutically acceptable salt thereof:

(11)

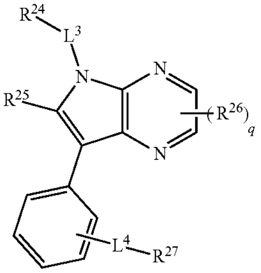

wherein, $R^{24}$ is selected from the group consisting of 3- to 7-membered heterocyclyl; the heterocyclyl is unsubstituted or substituted with at least one group selected from the group consisting of $R^{X3}$;

$L^3$ is selected from a combination consisting of a $C_{1-8}$alkylene and a $C_{3-6}$cycloalkylene;

$R^{25}$ is selected from the group consisting of H, $C_{1-8}$alkyl;

$R^{26}$ is selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$;

$L^4$ is selected from the group consisting of $C_{1-8}$alkylene and $C_{1-8}$alkoxylene;

$R^{27}$ is phenyl, which is unsubstituted or substituted with at least one group selected from the group consisting of $R^{X3}$;

q is 0, 1 or 2;

$R^{X3}$ is as defined in <7>;

particularly, formula (11) has a structure of:

A10

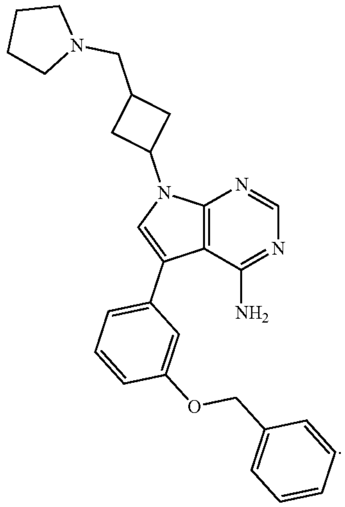

<9> The compound according to <1> or <2>, or a pharmaceutically acceptable salt, stereoisomer, solvate, polymorph, tautomer, isotopic compound, metabolite, or prodrug thereof, wherein the LCM moiety has a structure of formula (12), or a pharmaceutically acceptable salt thereof:

(12)

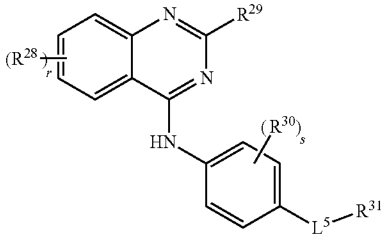

wherein, $R^{28}$ is $C_{1-8}$alkenyl; the alkenyl is substituted with at least one $C_{1-8}$alkyl, the alkyl is optionally substituted with one or more substituents selected from the group consisting of $R^{X4}$;

$R^{29}$ is selected from the group consisting of H, $C_{1-8}$alkyl;

$R^{30}$ is selected from the group consisting of halogen, —$NO_2$, —CN, $C_{1-8}$alkyl, —OH, —O($C_{1-8}$ alkyl), —SH, —S($C_{1-8}$alkyl), —$NH_2$, —NH($C_{1-8}$alkyl), —N($C_{1-8}$alkyl)$_2$;

$L^5$ is selected from the group consisting of —O—, $C_{1-8}$alkylene and $C_{1-8}$alkoxylene;

$R^{31}$ is selected from the group consisting of 6-membered heteroaryl, having 6 ring atoms, the ring atoms comprising 1-2 heteroatoms each independently selected from the group consisting of O, S, N, the remaining atoms being C, the heteroaryl is unsubstituted or substituted with at least one group selected from the group consisting of $R^{X3}$;

r is 0,1,2,3 or 4;

s is 0, 1, 2, 3 or 4;

$R^{X4}$, on each occurrence, is each independently selected from the group consisting of $C_{1-8}$ alkyl, $C_{1-8}$alkenyl, halogen, —CN, —$CF_3$, —$CHF_2$, —$CH_2F$, —$NO_2$, —O($C_{1-8}$alkyl), —S($C_{1-8}$alkyl), —NH($C_{1-8}$alkyl), —N($C_{1-8}$alkyl)$_2$, —OC(═O)($C_{1-8}$alkyl), —NHC(═O)($C_{1-8}$alkyl), —NC(═O)($C_{1-8}$alkyl)$_2$, —OS(═O)$_2$($C_{1-6}$alkyl), —NHS(═O)$_2$($C_{1-8}$alkyl), —N($C_{1-8}$alkyl)S(═O)$_2$($C_{1-8}$alkyl); wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

$R^{X3}$ is as defined in <7>;

particularly, formula (12) has a structure of:

A11

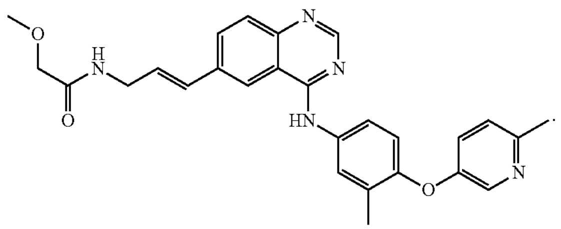

<10> The compound according to <1> or <2>, or a pharmaceutically acceptable salt, stereoisomer, solvate, polymorph, tautomer, isotopic compound, metabolite, or prodrug thereof, wherein the LCM moiety has a structure of formula (13), or a pharmaceutically acceptable salt thereof:

(13)

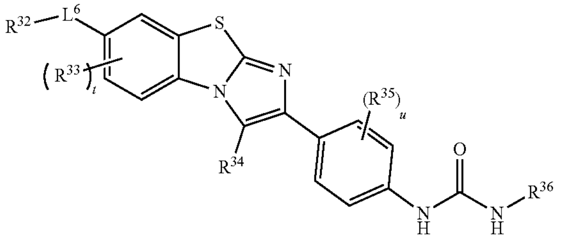

wherein, $R^{32}$ is selected from the group consisting of 3- to 7-membered heterocyclyl; the heterocyclyl is unsubstituted or substituted with at least one group selected from the group consisting of $R^{X3}$;

$L^6$ is selected from the group consisting of —O—, $C_{1-8}$alkylene and $C_{1-8}$alkoxylene;

$R^{33}$, $R^{34}$ are selected from the group consisting of halogen, $C_{1-8}$alkyl;

$R^{35}$ is selected from the group consisting of halogen, —$NO_2$, —CN, $C_{1-8}$alkyl, —OH, —O($C_{1-8}$ alkyl), —SH, —S($C_{1-8}$alkyl), —$NH_2$, —NH($C_{1-8}$alkyl), —N($C_{1-8}$alkyl)$_2$;

$R^{36}$ is selected from the group consisting of 5-membered heteroaryl, having 5 ring atoms, the ring atoms comprising 1-3 heteroatoms each independently selected from the group consisting of O, S, N, the remaining atoms being C, the heteroaryl is unsubstituted or substituted with at least one group selected from the group consisting of $R^{X3}$;

t is 0, 1, 2 or 3;

u is 0, 1, 2, 3 or 4;

$R^{X3}$ is as defined in <7>;

particularly, formula (13) has a structure of:

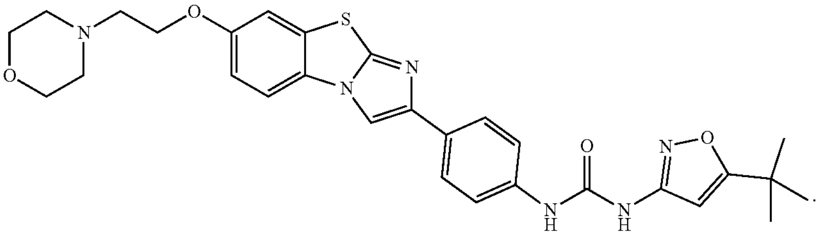 [SMILES: CC(C)(C)c1cc(NC(=O)Nc2ccc(-c3cn4c(n3)sc3cc(OCCN5CCOCC5)ccc34)cc2)no1]

<11> The compound according to <1> or <2>, or a pharmaceutically acceptable salt, stereoisomer, solvate, polymorph, tautomer, isotopic compound, metabolite, or prodrug thereof, wherein the LCM moiety has a structure of formula (14), or a pharmaceutically acceptable salt thereof:

(14)

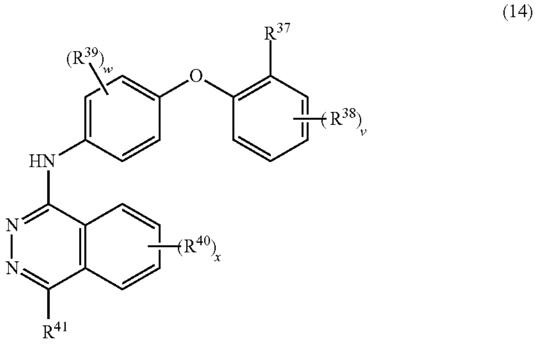

wherein, $R^{37}$ is selected from the group consisting of 6-membered heteroaryl, having 6 ring atoms, the ring atoms comprising 1-2 heteroatoms each independently selected from the group consisting of O, S, N, the remaining atoms being C, the heteroaryl is unsubstituted or substituted with at least one group selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$;

$R^{38}$, $R^{39}$, $R^{40}$ are each independently selected from the group consisting of $R^{X3}$;

$R^{41}$ is selected from the group consisting of 5-membered heteroaryl, having 5 ring atoms, the ring atoms comprising 1-3 heteroatoms each independently selected from the group consisting of O, S, N, the remaining atoms being C, the heteroaryl is unsubstituted or substituted with at least one group selected from the group consisting of $R^{X3}$;

v is 0, 1, 2 or 3;

w is 0, 1, 2, 3 or 4;

x is 0,1,2,3 or 4;

$R^{X3}$ is as defined in <7>;

particularly, formula (14) has a structure of:

A13

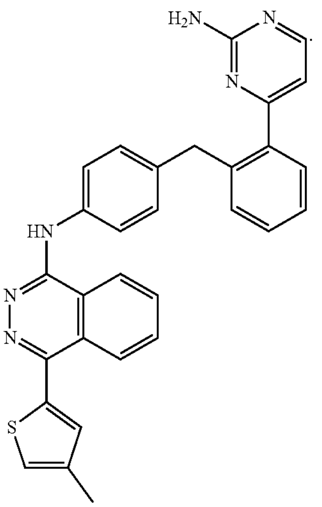

<12> The compound according to any one of <1>-<11>, or a pharmaceutically acceptable salt, stereoisomer, solvate, polymorph, tautomer, isotopic compound, metabolite, or prodrug thereof, wherein in formula (I)

L is chemical bond, or is linear or branched hydrocarbyl comprising 1-60, preferably 1-30, more preferably 2-16 carbon atoms, wherein the carbon atoms are each optionally replaced with one or more heteroatoms, for example 1-3, preferably 1-2, particularly 1; wherein the heteroatoms are selected from the group consisting of O, S, N, P, preferably O, S, or N, more preferably 0, or N, particularly 0; wherein the carbon atoms or heteroatoms are optionally substituted with one or more groups selected from the group consisting of $R^{L1}$, $R^{L2}$, $R^{L3}$, $R^{L4}$ and $R^{L5}$; wherein $R^{L1}$, $R^{L2}$, $R^{L3}$, $R^{L4}$ and $R^{L5}$ are each independently selected from the group consisting of: H, halo, $C_{1-6}$alkyl, —O($C_{1-6}$alkyl), —S($C_{1-6}$alkyl), —NH($C_{1-6}$alkyl), —N($C_{1-6}$alkyl)$_2$, $C_{3-6}$cycloalkyl, $C_{6-10}$ aryl, 5- to 7-membered heteroaryl, 3- to 7-membered heterocyclyl, —O($C_{3-6}$cycloalkyl), —S($C_{3-6}$cycloalkyl), —NH ($C_{3-6}$cycloalkyl), —N($C_{3-6}$cycloalkyl)$_2$, —N($C_{3-6}$cycloalkyl)($C_{1-6}$alkyl), —OH, —$NH_2$, —SH, —S(=O)$_2$ ($C_{1-6}$alkyl), —P(=O)(O$C_{1-6}$alkyl)($C_{1-6}$alkyl), —P(=O)(O$C_{1-6}$alkyl)$_2$, —C≡C—$C_{1-6}$alkyl, —C≡CH, —CH=CH($C_{1-6}$alkyl), —C($C_{1-6}$alkyl)=CH($C_{1-6}$alkyl), —C($C_{1-6}$alkyl)=C($C_{1-6}$alkyl)$_2$, —Si(OH)$_3$, —Si ($C_{1-6}$alkyl)$_3$, —Si(OH)($C_{1-6}$alkyl)$_2$, —C(=O) ($C_{1-6}$alkyl), —COOH, halogen, —CN, —$CF_3$, —$CHF_2$, —$CH_2F$, —$NO_2$, —S(=O)$_2$NH($C_{1-6}$alkyl), —S (=O)$_2$N($C_{1-6}$alkyl)$_2$, —S(=O)NH($C_{1-6}$alkyl), —S(=O)N($C_{1-6}$alkyl)$_2$, —C(=O)NH($C_{1-6}$alkyl), —C(=O)N($C_{1-6}$alkyl)$_2$, —N($C_{1-6}$alkyl)C(=O)NH ($C_{1-6}$alkyl), —N($C_{1-6}$alkyl)C(=O)N($C_{1-6}$alkyl)$_2$, —NHC(=O)NH($C_{1-6}$alkyl), —NHC(=O)N($C_{1-6}$alkyl)$_2$, —NHC(=O)$NH_2$, —N($C_{1-6}$alkyl)S(=O)$_2$NH ($C_{1-6}$alkyl), —N($C_{1-6}$alkyl)S(=O)$_2$N($C_{1-6}$alkyl)$_2$, —NHS(=O)$_2$NH($C_{1-6}$alkyl), —NHS(=O)$_2$N($C_{1-6}$alkyl)$_2$ and NHS(=O)$_2$$NH_2$;

preferably, L is linear group.

<13> The compound according to any one of <1>-<12>, or a pharmaceutically acceptable salt, stereoisomer, solvate, polymorph, tautomer, isotopic compound, metabolite, or prodrug thereof, wherein the TM moiety is selected from the group consisting of a lipid droplet probe, a compound capable of binding to lipid droplet marker protein, and a compound capable of binding to neutral fatty acid in lipid droplet;

preferably, the lipid droplet probe is selected from the group consisting of Sudan I, Sudan II, Sudan III, Oil Red BB, Oil Red O, Sudan Red G, Sudan Black B, Nile Red, BODIPY® 493/503, monodansylpentane, PyrPy 10d, PyrPy 11c, PITE, TPE-AmAl, TPA-BI, LipidGreen, LipidGreen2, LD540, AF8, AF10, AFN, NAP AIEgen dye, LD-BTD1, LipiDye, Phos 2a, Phos 2b, Phos 3a, Phos 3b, SF44, SF58, FAS, DPAS, BTD-Coumarin Hybrid, IND-TPA, photoactivatable AIE probe, LD-TPZn, LQD, photoactivatable AIEgen probe, TPE-AC, TPMN, TTMN, MeTTMN, MeOTTMN, DCMa, DCI, DCFu, NLV-1, StatoMerocynaine dye (SMCy dye);

preferably, the NAP AIEgen dye is selected from the group consisting of NAP-Ph, NAP-Br, NAP-$CF_3$, NAP-Py;

preferably, the BTD-Coumarin Hybrid is BTD-Lip;

preferably, the photoactivatable AIE probe is BZT 3a;

preferably, the photoactivatable AIEgen probe is PhotoAFN 2a-c;

preferably, the SMCy dye is selected from the group consisting of SMCy 3 and SMCy 5.5;

particularly, the TM moiety is selected from the group consisting of Sudan I, Sudan II, Sudan III, Oil Red BB, Oil Red O, Sudan Red G, Sudan Black B; preferably selected from the group consisting of Oil Red 0 and Oil Red BB, particularly Oil Red BB.

<14> The compound according to any one of <1>-<13>, or a pharmaceutically acceptable salt, stereoisomer, solvate, polymorph, tautomer, isotopic compound, metabolite, or prodrug thereof, wherein the TM moiety has a structure of formula (II) or is a conjugate or hybrid formed by connection of two or more of structure of formula (II):

(II)

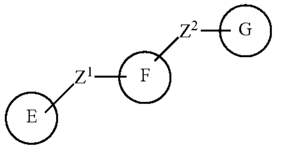

wherein:

ring E and ring F are each independently selected from the group consisting of benzene ring and naphthalene ring; wherein the ring E is optionally substituted with one or more groups selected from the group consisting of $R^E$, the ring F is optionally substituted with one or more groups selected from the group consisting of $R^F$, the ring G is optionally substituted with one or more groups selected from the group consisting of $R^G$;

ring G is absent, or is selected from the group consisting of benzene ring and naphthalene ring;

$Z^1$ is azo group;

$Z^2$ is absent, or is azo group;

$R^E$, $R^F$ and $R^G$, on each occurrence, are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$ cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$ alkyl)—(C═O)($C_{1-6}$alkyl), —NH(C═O)($C_{3-6}$cyclohydrocarbyl), —N($C_{1-6}$alkyl)—(C═O)($C_{3-6}$ cyclohydrocarbyl), —NH(C═O)($C_{1-4}$alkylene-$C_{3-6}$cyclohydrocarbyl), —N($C_{1-6}$alkyl)—(C═O)($C_{1-4}$alkylene-$C_{3-6}$cyclohydrocarbyl), —NH(C═O)(3- to 7-membered heterocyclyl), —N($C_{1-6}$alkyl)—(C═O)(3- to 7-membered heterocyclyl), —COOH, —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$ alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two $R^E$, two $R^F$ or two $R^G$ are bonded each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$.

<15> The compound according to <14>, or a pharmaceutically acceptable salt, stereoisomer, solvate, polymorph, tautomer, isotopic compound, metabolite, or prodrug thereof, wherein the formula (II) has a structure of formula (III):

(III)

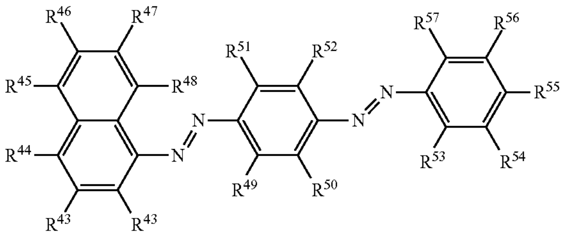

wherein $R^{42}$, $R^{43}$, $R^{44}$, $R^{45}$, $R^{46}R^{47}R^{48}$, $R^{49}$, $R^{50}$, $R^{51}R^{52}R^{53}R^{54}R^{55}R^{56}$ and $R^{57}$ are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$ cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-}$ $_6$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$ alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$ alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$ alkyl)—(C═O)($C_{1-6}$alkyl), —NH(C═O)($C_{3-6}$ cyclohydrocarbyl), —N($C_{1-6}$alkyl)—(C═O)($C_{3-6}$ cyclohydrocarbyl), —NH(C═O)($C_{1-4}$alkylene-$C_{3-6}$ cyclohydrocarbyl), —N($C_{1-6}$alkyl)-(C═O)($C_{1-4}$ alkylene-$C_{3-6}$cyclohydrocarbyl), —NH(C═O)(3- to 7-membered heterocyclyl), —N($C_{1-6}$alkyl)—(C═O)(3- to 7-membered heterocyclyl), —COOH, —C(═O)($C_{1-6}$alkyl), —C(═O)O($C_{1-6}$alkyl), —C(═O)O($C_{3-6}$ cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$ alkyl)$_2$, —COOH, —C(═O)($C_{1-6}$alkyl), —C(═O)$NH_2$, —C(═O)NH($C_{1-6}$alkyl), —C(═O)N($C_{1-6}$ alkyl)$_2$, —S(═O)$_2$OH, —S(═O)$_2$NH($C_{1-6}$alkyl), —S(═O)$_2$N($C_{1-6}$alkyl)$_2$;

preferably, at least one of $R^{42}$, $R^{43}$, $R^{44}$, $R^{45}$, $R^{46}$, $R^{47}$ and $R^{48}$ is —Cl, —Br, —I, —$NO_2$, —CN, ═O, ═S, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl) or —S(═O)N($C_{1-6}$alkyl)$_2$, rest of the groups are each independently selected from the group consisting of H, halogen, —$NO_2$, —CN, ═O, ═S, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)—(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$-S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; or, selected from the group consisting of $R^{42}$, $R^{43}$, $R^{44}$, $R^{45}$, $R^{46}$, $R^{47}$ and $R^{48}$, preferably selected from the group consisting of two adjacent groups of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; and, $R^{49}$, $R^{50}$, $R^{51}$, $R^{52}$, $R^{53}$, $R^{54}$, $R^{55}$, $R^{56}$ and $R^{57}$ are H, or at least one, preferably 1-6, more preferably 1-4, particularly 1, 2 or 4 of $R^{49}$, $R^{50}$, $R^{51}$, $R^{52}$, $R^{53}$, $R^{54}$, $R^{55}$, $R^{56}$ and $R^{5'}$ are $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$;

particularly, formula (III) is selected from the group consisting of:

Oil Red BB

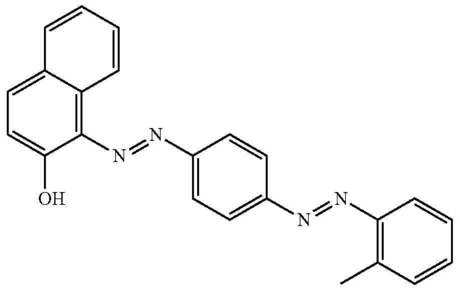

-continued

Oil Red O

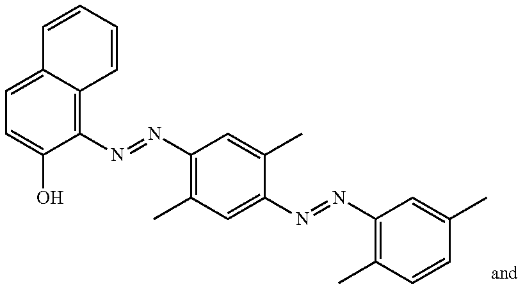

and

Sudan III

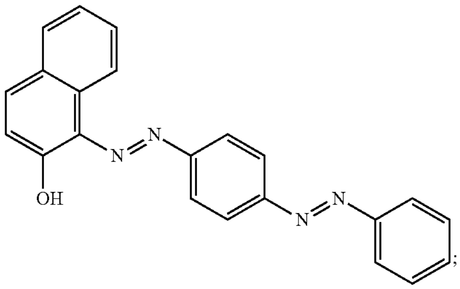

;

particularly, is selected from the group consisting of

Oil Red BB

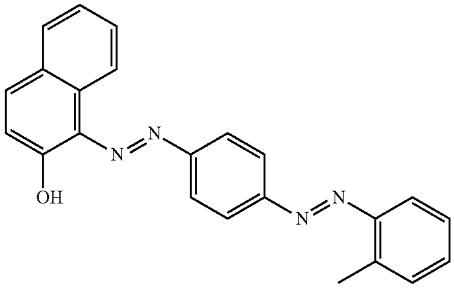

and

Oil Red O

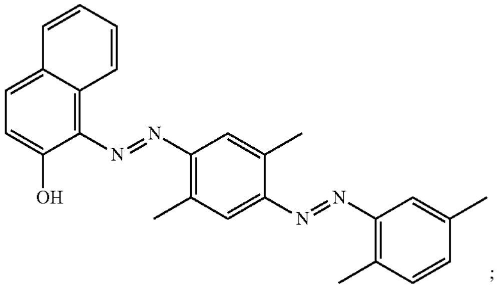

;

particularly

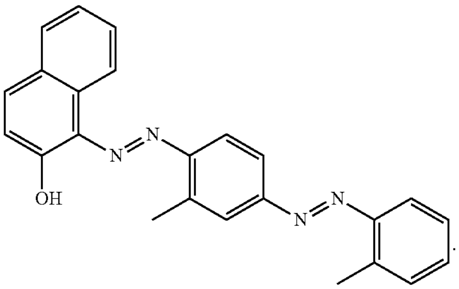

.

Oil Red BB

<16> The compound according to <14>, or a pharmaceutically acceptable salt, stereoisomer, solvate, polymorph, tautomer, isotopic compound, metabolite, or prodrug thereof, wherein the formula (II) has a structure of formula (IV):

(IV)

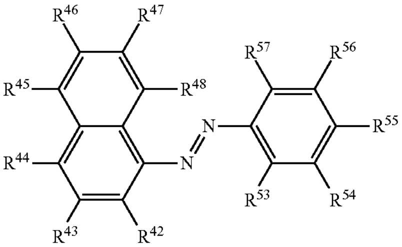

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are as defined in <11>.

particularly, formula (IV) is selected from the group consisting of.

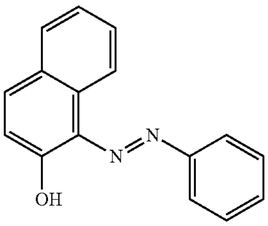

Sudan I

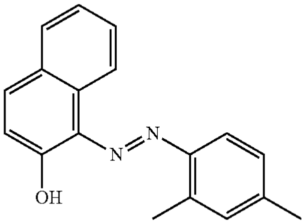

and

Sudan II

-continued

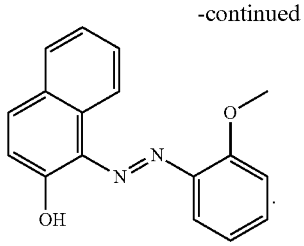

Sudan Red G

<17> The compound according to <14>, or a pharmaceutically acceptable salt, stereoisomer, solvate, polymorph, tautomer, isotopic compound, metabolite, or prodrug thereof, wherein the formula (II) has a structure of formula (V):

(v)

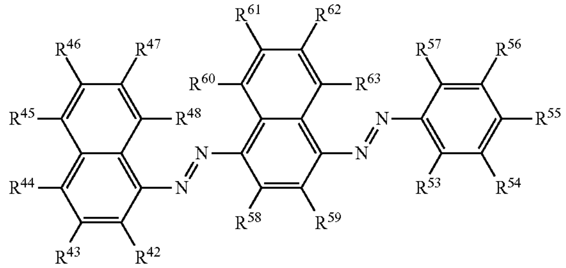

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are as defined in <11>;

wherein $R^{58}$, $R^{59}$, $R^{60}$, $R^{61}$, $R^{62}$ and $R^{63}$ are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$ cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$ alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$ alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$ cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$ cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene-3- to 7-membered heterocyclyl), —N($C_{1-4}$alkylene-3- to 7-membered heterocyclyl)$_2$, —NH(C═O)($C_{1-6}$alkyl), —N($C_{1-6}$alkyl)—(C═O)($C_{1-6}$alkyl), —NH(C═O)($C_{3-6}$cyclohydrocarbyl), —N($C_{1-6}$alkyl)—(C═O)($C_{3-6}$ cyclohydrocarbyl), —NH(C═O)($C_{1-4}$alkylene-$C_{3-6}$ cyclohydrocarbyl), —N($C_{1-6}$alkyl)—(C═O)($C_{1-4}$ alkylene-$C_{3-6}$cyclohydrocarbyl), —NH(C═O)(3- to 7-membered heterocyclyl), —N($C_{1-6}$alkyl)-(C═O)(3- to 7-membered heterocyclyl), —COOH, —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$ cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene-3- to 7-membered heterocyclyl), —C(═O)N($C_{1-4}$alkylene-3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$;

preferably, $R^{58}$, $R^{59}$, $R^{60}$, $R^{61}$, $R^{62}$ and $R^{63}$ are H, or at least one, preferably 1-6, more preferably 1-4, particularly 1, 2 or 4 of $R^{58}$, $R^{59}$, $R^{60}$, $R^{61}$, $R^{62}$ and $R^{63}$ are $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$ cycloalkyl—$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$;

particularly, formula (V) is:

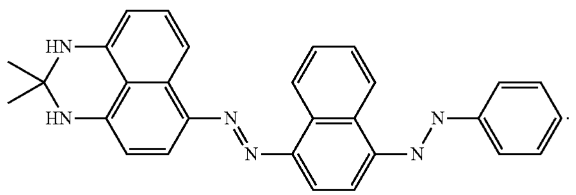

Solvent Black 3

<18> The compound according to <14>, or a pharmaceutically acceptable salt, stereoisomer, solvate, polymorph, tautomer, isotopic compound, metabolite, or prodrug thereof, wherein the TM moiety has the following structure:

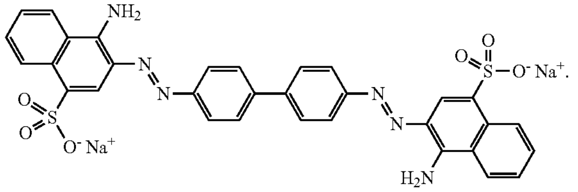

Congo Red O

<19> The compound according to any one of <1>-<13>, or a pharmaceutically acceptable salt, stereoisomer, solvate, polymorph, tautomer, isotopic compound, metabolite, or prodrug thereof, wherein the TM moiety has a structure of formula (VII):

VII

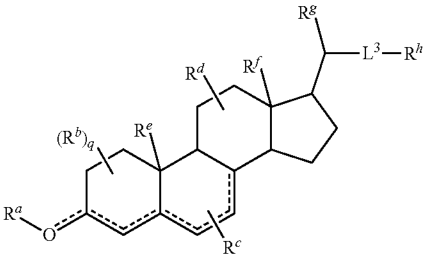

wherein, “ ⎓ ” represents single bond or double bond;

when “ ⎓ ” represents double bond, $R^a$ is absent; when “ ⎓ ” represents single bond, $R^a$ is selected from the group consisting of H, OH, —O($C_{1-8}$alkyl), —O($C_{1-8}$silanyl), —C(═O)O($C_{1-26}$alkyl), —C(═O)O($C_{1-26}$alkenyl), wherein the alkenyl comprises 1-8 double bonds;

$R^b$, $R^c$, $R^d$ are each independently selected from the group consisting of H, $C_{1-8}$alkyl, $C_{1-8}$alkenyl, —OH, —O($C_{1-8}$alkyl), —O($C_{1-8}$silanyl);

$R^b$, $R^c$, $R^d$ are each independently selected from the group consisting of H, $C_{1-4}$alkyl, —OH, —O($C_{1-4}$alkyl);

$L^7$ is selected from the group consisting of chemical bond, $C_{1-8}$alkylene;

$R^h$ is selected from the group consisting of H, $C_{1-20}$alkyl, $C_{1-20}$alkenyl, —OH, —O($C_{1-20}$alkyl), —O($C_{1-20}$silanyl), wherein the alkyl or alkenyl is optionally substituted with one or more substituents selected from the group consisting of —OH, $C_{1-8}$alkyl, $C_{1-8}$alkenyl, $C_{1-8}$alkynyl, —O($C_{1-20}$alkyl), —O($C_{1-20}$silanyl);

q is 0, 1 or 2.

<20> The compound according to <14>, or a pharmaceutically acceptable salt, stereoisomer, solvate, polymorph, tautomer, isotopic compound, metabolite, or prodrug thereof, wherein the TM moiety has a structure selected from the group consisting of:

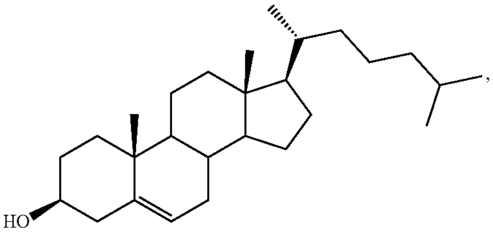, cholesterol

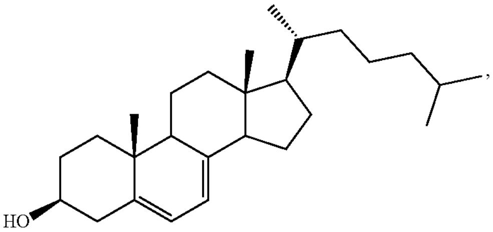, dehydrocholesterol

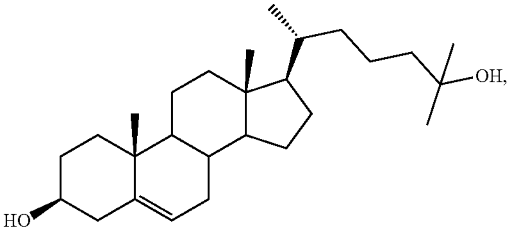, and 25-hydroxycholesterol

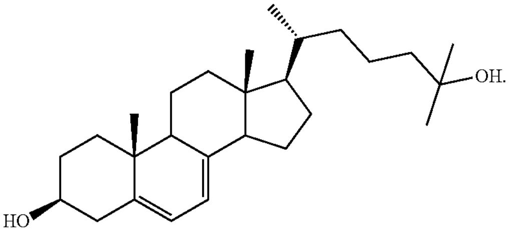.

25-hydroxydehydrocholesterol

<21> The compound according to any one of <1>-<15>, or a pharmaceutically acceptable salt, stereoisomer, solvate, polymorph, tautomer, isotopic compound, metabolite, or prodrug thereof, wherein the compound is selected from Compound 1 and Compound 2

Compound 1

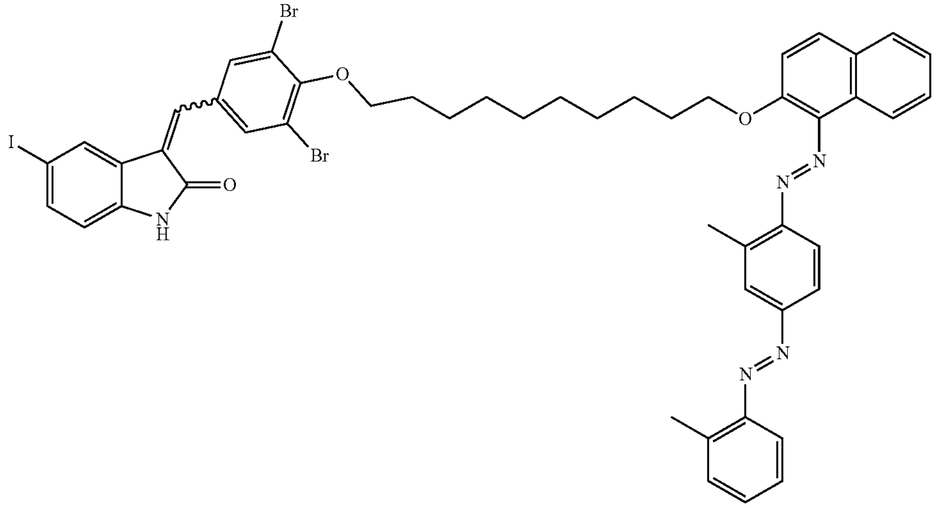

Compound 2

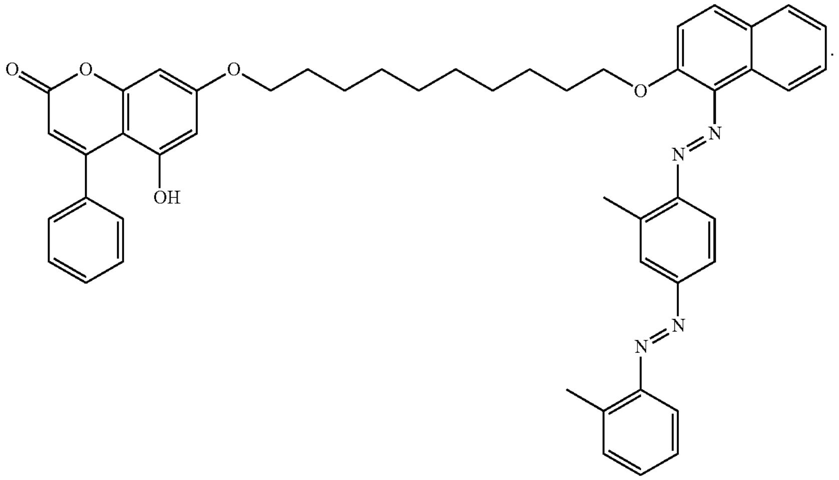

<22> A pharmaceutical composition, comprising the compound according to any one of <1>-<16>, or a pharmaceutically acceptable salt, stereoisomer, solvate, polymorph, tautomer, isotopic compound, metabolite, or prodrug thereof in a prophylactically or therapeutically effective amount, and one or more pharmaceutically acceptable carriers.

<23> Use of the compound according to any one of <1>-<16>, or a pharmaceutically acceptable salt, stereoisomer, solvate, polymorph, tautomer, isotopic compound, metabolite, or prodrug thereof, or the pharmaceutical composition according to <17>, for the manufacture of a medicament for treating a lipid metabolism related disease; preferably, the lipid metabolism related disease is selected from the group consisting of MADD, obesity, NAFLD, type II diabetes, hepatocellular carcinoma, Alzheimer's disease and atherosclerosis.

<24> A method for reducing lipid droplets in a cell, comprising contacting a conjugated compound comprising a LC3 binding moiety and a lipid droplet binding moiety with a cell or tissue comprising the lipid droplets, wherein the lipid droplets are contained by the cell under physiological or pathological conditions and/or produced by the cell under induction.

Beneficial Effects

The compounds according to the present disclosure can selectively reduce the size and number of lipid droplets in the cells by targeting autophagy while have no effect on the autophagy function of the cells. Therefore, the methods according to the present disclosure can effectively reduce the accumulation of lipid droplets and can be useful for prevention and treatment of diseases associated with lipid droplet accumulation.

EXAMPLES

Unless otherwise stated, the instruments and reagents used herein are commercially available.

To ensure to reach an inspection power greater than 0.8, power analysis was conducted for estimated values of each assay by PASS 16 (https://www.ncss.com/software/pass/) before experiments. The said estimated values were based on inventors' previously published results on similar experiments and preliminary experiments. The effect size was also estimated by Cohen's d, two means divided by the standard deviation of the data. The power analysis suggested n≥5 for lipid droplet measurements. In all the experiments herein, we had used a larger n than 5. For animal experiments, we used about 8 mice per group. Unless otherwise stated, bars represent mean and S.E.M.

In all statistical analysis herein,*indicated p<0.05;  indicated p<0.01; * indicated p<0.001, **** indicated p<0.0001, $ indicated p<0.0001. For comparisons between two groups, the statistical analysis was conducted by the two-tailed unpaired t test. For comparisons between three or more groups, in the case of only one variable, the method used was the two-tailed one-way ANOVA. In the case of two variables, the method used was the two-tailed two-way ANOVA.

Abbreviation/Code Name

| | |
|---|---|
| ORBB | Oil Red BB |
| OA | Sodium oleate |
| $ddH_2O$ | double distilled water |

Experimental Materials, Reagents and Methods

Compounds

Compound A1: GW5074, commercially purchased from DC Chemicals, catalog number DC8810;

Compound A2: PubChemID 1759437, commercially purchased from Specs, catalog number AN-655/15003575;

Compound A3: Semaxanib, commercially purchased from Selleck, CAS No. 194413-58-6;

Compound A4: commercially purchased from ChemDiv, CAS No. 779-27-1;

Compound A5: also numbered AN2, PubChem CID 5398649, commercially purchased from ChemDiv, catalog number D715-2435;

Compound A6: commercially purchased from TargetMol, CAS No. 842-01-3;

Compound A7 commercially purchased from ChemDiv;

Compound A8: ispinesib, PubChem CID: 6851740, commercially purchased from Selleck, catalog number S1452;

Compound A9: commercially purchased from Abmole, CAS No. 635702-64-6;

Compound A10: commercially purchased from Targetmol, CAS No. 475489-15-7;

Compound A11: commercially purchased from Sigma, CAS No. 383432-38-0;

Compound A12: commercially purchased from Abmole, CAS No. 950769-58-1;

Compound A13: commercially purchased from Targetmol, CAS No. 945595-80-2;

Sudan IV: Oil Red BB, commercially purchased from sigma, catalog number O0625;

Sudan III: commercially purchased from TCIchemicals, catalog number S0142;

Bafilomycin A1 (bafA): commercially purchased from sigma, catalog number B1793;

10-Bromo-1-decanol: commercially purchased from Sigma, CAS No. 53463-68-6

Propan-2-alkyn-1-yloxy) ethane-1-ol, 2-(2-(2-azidoethoxy) ethoxy) ethane-1-ol, 6-(3-(4-(2-hydroxyethyl) piperazin-1-yl) propyloxy) ethyl nicotinate were provided by Shanghai Medicilon Bio Pharmaceutical Co., Ltd;

Sodium oleate: commercially purchased from Sigma, catalog number O7501;

Lipid droplet probe BODIPY® 493/503 was purchased from Thermo Fisher, catalog number D3922, and DAPI was purchased from Beyotime Biotechnology, article number C1002.

Other reagents could be purchased from for example, Thermo Fisher, Sigma, TCI, etc.

Preparation of Compounds $^1$HNMR displacement (δ) was given in parts per million (ppm). $^1$HNMR was measured with Bruker AVANCE III 400 MHz nuclear magnetic spectrometer, with the internal standard of tetramethylsilane (TMS), and the chemical shift was given in $10^{-6}$ (ppm).

Abbreviations in the nuclear magnetic resonance (NMR) data used in the preparation examples were as shown below:

s: Single peak, d: double peak, t: triple peak, q: quadruple peak, dd: double double peak, qd: quadruple double peak, ddd: double double double peak, ddt: double double triple peak, dddd: double double double double peak, m: multiple peak, br: broad peak, J: coupling constant, Hz: Hertz.

Nuclear magnetic resonance instrument model: Bruker AVANCE III 400 MHz;

Mass spectrometer model: Agilent 1100LC/1946D.

Unless otherwise stated, the reaction temperature was room temperature (15° C.-25° C.).

Unless otherwise stated, the starting materials used in the preparation examples were purchased from the market suppliers and used without further purification.

Cell Lines

Wild-type and Atg5 knockout (Atg5−/−) mouse embryonic fibroblasts (MEFs) were kindly provided by the laboratory of N. Mizushima; the human neuroblastoma cells SH-SY5Y can be purchased from ATCC (cat. no. ATCC® CRL-2266™, RRID: CVCL_0019), human normal liver cell QSG7701 can be purchased from Beyotime Biotechnology Co., Ltd. The wild-type and LC3B homozygous knockout HEK293T cells were purchased from Wuhan ABclonal Technology Inc. (cat. no. RM09015) and validated by western-blots. The adipose cells used to detect endogenous lipid droplet levels were obtained from 3T3-L1 differentiation. Cells were isolated from the subcutaneous white adipose tissue of the mouse peritoneal cavity, cultured in 10% FBS+90% DMEM medium, maintained in a 37° C. incubator with 5% $CO_2$, and passaged at 1:3 every three days.

Western-Blot

Anti-SQSTM1/p62 (Abcam, cat. no. ab56416, RRID: AB_945626), anti-p-tubulin (Abcam, cat. no. ab6046, RRID: AB_2210370), anti-LC3B (Thermo Fisher, cat. no. PA1-16930, RRID: AB_2281384). Peroxidase labeled 2nd antibodies (Abmart, goat anti mouse IgG HRP, cat.no.m21001L, RRID: AB_2713950; goat anti rabbit IgG HRP, cat.no.m21002L, RRID: AB_2713951). The blots were developed with SuperSignal™ West Pico PLUS Chemiluminescent Substrate (Thermo Fisher, cat. no. 34580). The specificity of all antibodies had been validated by previous reports or knock-down or knockout experiments. The signal intensity was quantified by ImageJ.

cDNA plasmids and transfection

The cDNA plasmids mCherry-LC3B (cat. no. 40827) and mRFP-GFP-LC3B (cat. no. 21074) were purchased from Addgene. For transient transfections, the cells were plated at 60~70% confluence. After 12 h, the cDNAs were transfected with Lipofectamine 2000 (Thermo Fisher, cat. no. 11668019) using the forward transfection protocol provided by the manufacturer.

Preparation of the Recombinant Human LC3B (1) A His 8 tag and a TEV protease cleavage site were added to pGEX-6P1 (from GE Healthcare) to prepare a prokaryotic expression vector pGHT. The LC3B gene (GenBank: NM_022818.4) was edited to remove Met and add two Glys at the N-terminus of LC3B, the gene was amplified and cloned into the prepared pGHT.

(2) The expression plasmid pGHT-LC3B was introduced into *Escherichia coli* BL21(DE3)pLsyS for expression. It was purified by HisTrap HP column (GE Healthcare, 17524701). It was then mixed with TEV protease (Sigma, T4455) and dialyzed overnight. Purification was performed with the HisTrap HP column followed by the Superose 6 Increase 10/300 GL size exclusion column (GE Healthcare).

(3) Validation of LC3B: The prepared human LC3B was validated by MALDI-TOF-MS and X-ray diffraction. The method to validate LC3B by X-ray diffraction is site-directed mutation to obtain a mutant LC3BΔG120 protein lacking the G120 lipidation site, and the more stable protein was used for high-resolution X-ray diffraction. The known LC3 protein crystal structure (PDB ID: 1UGM) was used as the search model for molecular replacement, the structure of the published LC3BΔG120 (PDB ID: 6J04, 1.90 Å) was resolved by molecular replacement for structural alignment.

Induction of Lipid Droplets (1) Preparation of 10 mM OA-BSA stock solution: 3 ml of 20 mM Sodium oleate (OA) solution+3 ml of 20% BSA solution.

(2) Preparation of 10% BSA solution: 3 ml $ddH_2O$+3 ml 20% BSA solution.

(3) The solutions prepared in (1) and (2) was filtered through the 0.22 μM filter membrane.

(4) The multi-well plates laid with sterile coverslips were used, washed with 1×PBS, and cells were plated with 2 ml per well, $5\times10^4$ cells.

(5) OA-BSA stock solution was prepared into OA-BSA working solution (50× final concentration, 200 μM), and 40 μl of OA-BSA working solution was added to each well to induce lipid droplets. For the non-OA induction group, 40 μl of 10% BSA solution was added to the control well, and the amount of BSA was the same as that of the experimental group.

(6) Incubated in a 37° C. incubator with 5% $CO_2$, when cells grew to 60-70% confluence, the cells were treated with compounds, or the mCherry-LC3B plasmids were transfected and treated the cells with compounds.

General Test Methods for Compound Treatment in Cells

Compounds were formulated into DMSO stock solutions. Stock compounds were diluted with DMSO into the indicated concentrations of working solutions prior to use in the treatment of cells. After induction of the lipid droplets with OA for the indicated time, the test compounds were added to the cells respectively. Control wells were replaced with the equal volume of DMSO. Unless otherwise stated, the compounds were diluted into 10× solutions using the culture medium and added to the culture medium for 24 hours of incubation. Cells were treated with compounds in a 37° C. incubator with 5% $CO_2$.

BODIPY Staining of Lipid Droplets (1) Preparation of 2 μM BODIPY solution: 1 μl of 20 mM BODIPY® 493/503 was diluted with 9 μl of 1×PBS, and then 6 μl of the diluted solution was added into 6 ml of 1×PBS.

(2) Preparation of 1:1000 DAPI solution: 6 μl of 5 mg/ml DAPI was added into 6 ml of 1×PBS.

(3) The original medium in the multi-well plates was removed, washed and the cells was fixed, 1 ml of the BODIPY solution prepared in (1) was added to each well, and stained for 15 minutes. The staining solution was aspirated and washed with 1×PBS.

(4) 1 ml of the DAPI solution prepared in (2) was added to each well, and stained for 10 min. The staining solution was aspirated and washed with 1×PBS.

(5) The coverslips laid in the multi-well plates were removed, and imaged with the Zeiss 880 confocal microscope after mounted, and analyzed the size and number of lipid droplets with ImageJ.

BODIPY staining of tissues

Livers were removed and weighed, dissected into parts, and then immediately fixed with 4% PFA for 48 hours at 4° C. The tissues were incubated in 15% sucrose for about 24 hours at 4° C. and then in 30% sucrose for about 48 hours. The liver was then frozen with OCT cryo-embedding agent (Thermo Fisher, NEG50™ cat. no. 6502). 15 μm thick liver cryosections were prepared and mounted on glass slides and left to stand at room temperature for 10 minutes. The cryosections were then rapidly immersed in ice-cold 4% PFA in 1×PBS solution for 1 hour for fixation. Immediately after fixation, the cryosections were washed with 1×PBS. The cryosections were incubated with BODIPY® 493/503 (1:5000 from the 1 mg/mL stock solution in DMSO; Thermo Fisher, cat. no. D3922) for 30 min and 1:1000 DAPI for 10 min at room temperature. The cryosections were washed with 1×PBS and mounted.

Imaging Detection of Autophagosomes (1) In MEF cells, mCherry-LC3B was expressed by cDNA plasmid transfection.

(2) The medium was replaced with fresh medium 10% FBS+90% DMEM 12 hours after transfection.

(3) OA was added to the culture medium 30 hours after transfection to induce lipid droplets.

(4) Compounds were added to treat cells 6 hours after induction.

(5) 24 hours after compounds addition, cells were fixed and BODIPY stained.

(6) The coverslips laid in the multi-well plates were removed and imaged with the Zeiss 880 confocal microscope after mounted to observe the number and size of LC3B puncta.

Imaging of mCherry-LC3B or mRFP-GFP-LC3B Transfected Cells

Method <A> or <B> was used:

<A> DAPI Staining

Cells were fixed, permeabilized and stained with the above 1:1000 DAPI solution.

<B> Immunofluorescence

Cells were blocked in 4% BSA+0.1% Triton X-100 in 1×PBS for 30 min and incubated overnight at 4° C. with primary antibody goat polyclonal Lamin B1 (1:200, Santa Cruz Biotechnology, cat. no. sc-6216, RRID: AB_648156), washed with blocking buffer, and incubated with secondary antibody (1:500, Alexa Flour488 donkey anti-goat, Jackson immunoResearch Lab, cat.no. 705-547-003, RRID: AB_2340431) at room temperature for 1 hour. The samples were washed three times and stained with DAPI for 10 min at room temperature.

Imaging Detection of Autophagosomes-Lipid Droplets Colocalization (1) In MEF cells, mCherry-LC3B was expressed by cDNA plasmid transfection.

(2) OA was added to the culture medium 30 hours after transfection to induce lipid droplets.

(3) Compounds were added to treat cells 6 hours after induction.

(4) 3 hours after compounds addition, cells were fixed and BODIPY stained.

(5) The coverslips laid in the multi-well plates were removed, and imaged with the Zeiss 880 confocal microscope after mounted to observe the aggregation of LC3 puncta around the lipid droplets.

Cellular Staining Using LysoTracker, MitoTracker or CellMask

LysoTracker staining: the medium was removed from the dish and the prewarmed (37° C.) probe-containing culture medium (500 nM, LysoTracker™ Green DND-26, Thermo Fisher., cat. no. L7526) was added, the cells were incubated for 3 hours, and then Hoechst 33342 (Thermo Fisher., cat. no. H3570) was added. The staining solution was removed after 5 minutes and the coverslips were rinsed three times with Live Cell Imaging solution (Thermo Fisher, cat. no. A14291DJ). The coverslips were mounted and them were imaged immediately using the Zeiss 880 confocal microscope.

MitoTracker staining and CellMask staining were performed the same as LysoTracker staining, except using MitoTracker™ Green FM (500 nM, Thermo Fisher, cat. no. M7514) staining for 3 hours to detect total mitochondria; MitoTracker™ Red CMXRos. (500 nM, Thermo Fisher, cat. no. M7512) staining for 3 hours to detect healthy mitochondria; and CellMask™ (2000×, CellMask™ Plasma Membrane Stains, Thermo Fisher, cat. no. C10046) staining for 5 minutes at 37° C.

Picro-Sirius Red Staining 15-micrometer cryosections were obtained from the liver (see "BODIPY staining of tissues" and processed for visualization of fibrosis by picro-sirius red staining as described in the literature (Sookoian S et al., Fatty Liver Disease Progresses into Severe NASH when Physiological Mechanisms of Tissue Homeostasis Collapse. Ann Hepatol 2018; 17:182-186.). The liver cryosections were washed with 1×PBS and then incubated at room temperature for 1 hour with the solution containing 0.1% vol/vol Direct Red 80 Direct Red 80 (for staining collagen in red as an indicator for liver fibrosis) and 0.04% Fast Green (Sigma-Aldrich, cat. no. F7258, for general protein staining as a background) in saturated aqueous solution of picric acid (Sigma., cat. no. P6744-1GA). The samples were imaged by using an Olympus inverted fluorescence microscope IX73, and the histological fibrosis images were analyzed by the imageJ software.

Compound-Protein Interaction Measurements by MST

The recombinant GST-LC3B proteins were prepared and purified, dialyzed into 1×PBS, and then labelled with the red fluorophore with the protein labeling kit RED-NHS (Nanotemper, cat. no. L001).

The tested stock compounds (25 mM) were serially diluted into the same buffer (20 mM HEPES pH=7.5, 150 mM NaCl) with the same final DMSO concentration (2.5%) for the MicroScale Thermophoresis (MST) assay. The MST experiments were performed using the Monolith NT.115 instrument (NanoTemper Technologies). The reaction buffer contains 20 mM HEPES, pH 7.4, 150 mM NaCl, and the protein concentration was 500 nM. The MST data were collected under 40% infrared laser power and 20% light-emitting diode power. The data were analyzed by Nanotemper software.

db/db Mouse and NASH Mouse Models

Mice were group-housed (up to 5 adult mice per cage) in individually vented cages with a 12 h light/dark cycle.

<1> db/db Mouse

Experimental animals: nineteen-week-old db/db male mice (C57BL/6J-$Lepr^{db}$/$Lepr^{db}$) were obtained from Shanghai Model Organisms Co., Ltd., and acclimatized for at least 1 week before experiments. The mice had ad libitum access to standard chow and water.

Normal control: The C57BL/6 male mice fed on standard irradiated chow diet (Shuyishuer Inc. cat. no. D12450J) from Changzhou Shuyishuer Biotechnology Co., Ltd. (Shuyishuer Inc.) were used as the normal control.

<2> NASH Mouse Models

Experimental animals: ten-week-old C57BL/6 male mice were obtained from Hangzhou Ziyuan Inc. The mice had ad libitum access to water and a choline-deficient, L-amino acid-defined, high-fat diet (CDAHFD) containing 60% kcal fat obtained from Changzhou Shuyishuer Inc. for twelve weeks (including the two-week compound-injection period) to generate the non-alcoholic steatohepatitis (NASH) models.

Absolute Quantitative Lipidomics

The experiments and data analysis were supported by Shanghai Applied Protein Technology Co., Ltd.

Chemical reagents: MS-grade methanol, MS-grade acetonitrile, HPLC-grade isopropanol were purchased from Thermo Fisher. HPLC-grade formic acid and HPLC-grade ammonium formate were purchased from Sigma-Aldrich.

Sample preparation and lipid extraction: lipids were extracted according to MTBE method: the appropriate amount of internal lipid standards was added to the samples and then the samples were homogenized with 200 μL of water and 240 μL of methanol. Then 800 μL of MTBE was added, and the samples were sonicated for 20 minutes at 4° C. followed by standing at room temperature for 30 min. The solution was centrifuged at 14,000 g for 15 min at 10° C. and the upper layer was obtained and dried under nitrogen.

LC-MS/MS method for lipid analysis: the liquid phase separation was performed on the CSH C18 reverse phase chromatography column (1.7 μm, 2.1 mm×100 mm, Waters). The resulting lipid extracts were re-dissolved in 200 μL 90% isopropanol/acetonitrile, centrifuged at 14,000 g for 15 min, and 3 μL of sample was injected. Solvent A (acetonitrile: water (6:4, vol/vol) with 0.1% formic acid and 0.1 mM ammonium formate and solvent B (acetonitrile: isopropanol (1:9, vol/vol) with 0.1% formic acid and 0.1 mM ammonium formate were used for elution. The initial mobile phase was 30% solvent B at a flow rate of 300 μL/min. It was held for 2 min, and then linearly increased to 100% solvent B in 23 min, followed by equilibrating with 5% solvent B for 10 min. The mass spectrometry was in positive and negative modes, respectively. ESI (Electron Spray Ionization) parameters were optimized and preset for all measurements as follows: Ion source temperature, 300° C.; Capillary temperature, 350° C., ion spray voltage 3000V, S-Lens RF Level 50%, and scan range of the instruments m/z 200-1800.

Identification of lipids was performed by LipidSearch™ software (Thermo Fisher), a search engine for the identification of lipid species based on MS/MS math. The LipidSearch™ database contains more than 30 lipid classes and more than 1,500,000 fragment ions. Both mass tolerance for precursor and fragment were set to 5 ppm.

Preparing Example 1 Compound 1A: 3-(3,5-dibromo-4-hydroxylbenzylidene)-5-iodo-1-(10-((1-((E)-(4-((E)-phenyldiazenyl)phenyl)diazenyl)naphthalen-2-yl)oxy)decyl)indol-2-one
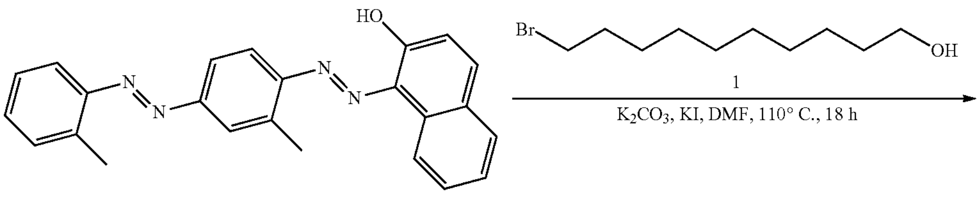
C1
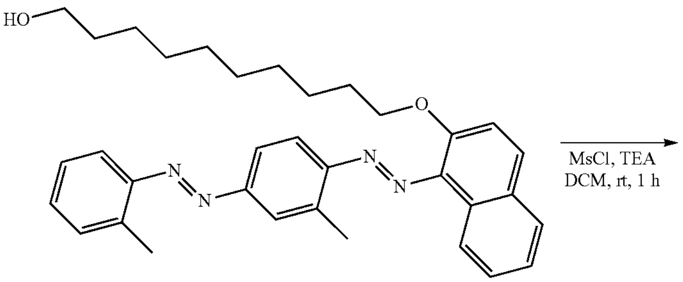
2
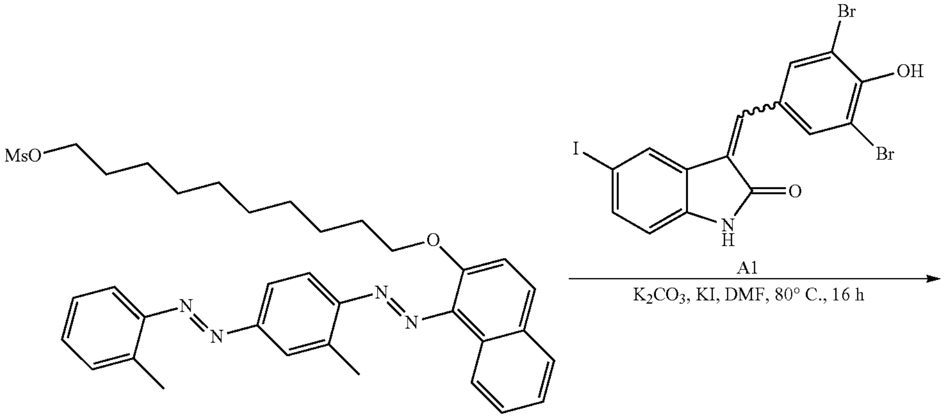
3

-continued

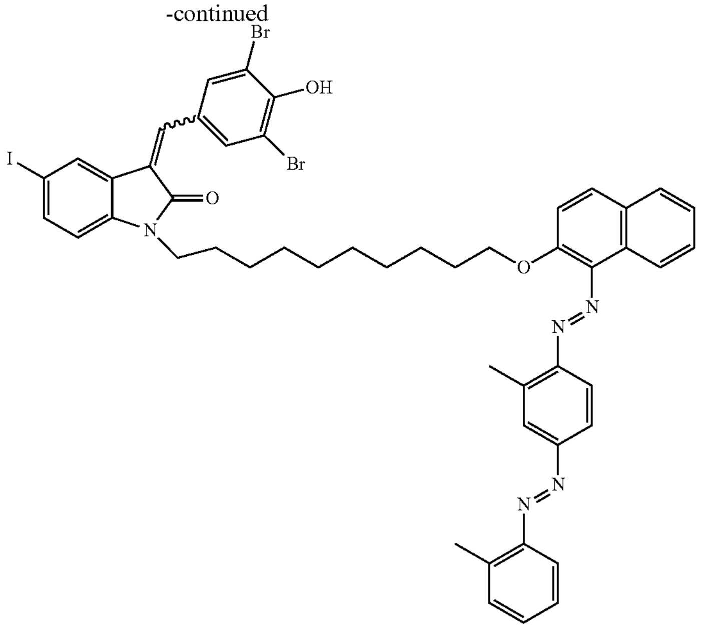

Compound 1A

Step 1: intermediate 2: 10-((1-((E)-(2-methyl-4-((E)-o-methylphenyldiazenyl)phenyl)diazenyl)naphthalen-2-yl)oxy)decyl-1-ol Sudan IV (i.e., Oil Red BB, 2 g, 5.26 mmol), 10-bromo-1-decanol (1.36 g, 5.78 mmol), potassium carbonate (4.36 g, 31.8 mmol) and potassium iodide (88 mg, 0.053 mmol) were added to 100 mL DMF (30 mL) in the flask and stirred at 110° C. for 18 hours. The reaction was cooled to room temperature, water (200 mL) was added, and extracted with ethyl acetate (2×100 mL). The organic layers were combined, and the solvents were removed. The obtained residue was purified by column chromatography (petroleum ether/ethyl acetate=5/1) to obtain intermediate 2 as red oil (620 mg, yield: 22%).

MS m/z (ESI): 537.1 $[M+H]^+$

Step 2: intermediate 3: 10-((1-((E)-(2-methyl-4-((E)-o-methylphenyldiazenyl)phenyl)diazenyl)naphthalen-2-yl)oxy)decylmethanesulfonate Intermediate 2 (300 mg, 0.56 mmol) and triethylamine (113 mg, 1.12 mmol) were dissolved in methylene chloride (5 mL), and methanesulfonyl chloride (76.6 mg, 0.67 mmol) was added dropwise. The mixture was stirred at room temperature for 1 hour. 50 mL of water was added to the reaction solution and extracted with dichloromethane (2×50 mL). The organic layers were combined, and the solvents were removed. The obtained residue was purified by column chromatography (petroleum ether/ethyl acetate=5/1) to obtain intermediate 3 as red oil (320 mg, yield: 93%).

MS m/z (ESI): 615.1 $[M+H]^+$

Step 3: Compound 1A

Compound A1 (520 mg, 1.0 mmol), intermediate 3 (921 mg, 1.5 mmol), potassium carbonate (690 mg, 5.0 mmol) and potassium iodide (16.6 mg, 0.1 mmol) were dissolved in DMF (10 mL) and reacted at 80° C. for 16 hours. The reaction was cooled to room temperature, quenched with water (20 mL), extracted with ethyl acetate (80 mL×2). The organic phases were combined and washed with water (20 mL×3) and saturated sodium chloride solution (50 mL×1), dried over anhydrous sodium sulfate, filtered, and the solvents were removed under reduced pressure. The obtained residue was prepared by column chromatography (petroleum ether: ethyl acetate=3:1) and reversed phase silica gel column (100% acetonitrile) to obtain Compound 1A as red solid (23 mg, 2.3%).

MS m/z (ESI): 1040.1 $[M+H]^+$ $^1H$ NMR (500 MHz, $CDCl_3$): δ 8.61-8.59 (m, 2H), 7.94-7.72 (m, 7H), 7.66 (dd, J=8.0 Hz, 3.0 Hz, 1H), 7.61-7.19 (m, 9H), 6.57-6.53 (m, 1H), 4.22-4.19 (m, 2H), 3.69-3.65 (m, 2H), 2.86-2.85 (m, 3H), 2.76-2.75 (m, 3H), 1.84-1.81 (m, 2H), 1.62-1.57 (m, 2H), 1.50-1.43 (m, 2H), 1.28-1.24 (m, 10H).

Wherein, Compound A1 (3-(3,5-dibromo-4-hydroxylbenzylidene)-5-iodoindolin-2-one) is Compound GW5074 reported by Li et. al., in 2019 as mentioned above, which can bind to LC3 with affinity. Compound A1 is commercially available or can be prepared according to the following procedures.

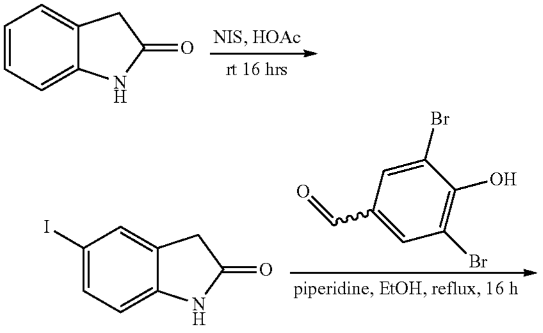

4

-continued

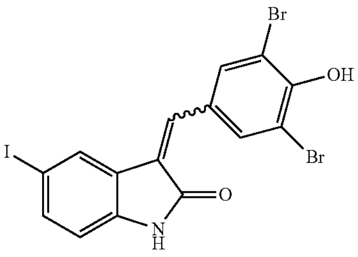

A1

Step 1: intermediate 4: 5-iodoindolin-2-one

Indoline-2-one (3.0 g, 22.5 mmol) and NIS (6.1 g, 27.0 mmol) were dissolved in acetic acid (30 mL). The mixture was stirred at room temperature for 16 hours, and then the reaction solution was concentrated using a rotary evaporator to remove most of the solvents. The obtained residue was further slurred with ethyl acetate, filtered, and the filter cake was rinsed with a small amount of ethyl acetate and dried to obtain the product as red solid intermediate 4 (4.6 g, yield: 79.3%).

MS m/z (ESI): 259.9 $[M+H]^+$

Step 2: Compound A1 (3-(3,5-dibromo-4-hydroxylbenzylidene)-5-iodoindolin-2-one)

Intermediate 4 (2.0 g, 7.72 mmol) was dissolved in ethanol (20 mL), to which were added 3,5-dibromo-4-hydroxybenzaldehyde (2.16 g, 7.72 mmol) and piperidine (131 mg, 1.54 mmol).

The mixture was reacted at 80° C. for 16 hours. The reaction solution was cooled to room temperature, filtered, and the filter cake was rinsed with diethyl ether and petroleum ether, and dried to obtain Compound A1 as yellow solid (1.8 g, 45.0%).

MS m/z (ESI): 521.7 $[M+H]^+$

NMR spectrum was shown in FIG. 1.

Preparing Example 2 Compound 2A: 7-hydroxy-5-((10-((1-((E)-(2-methyl-4-((E)-o-methylphenyldiazenyl)phenyl)diazenyl)naphthalen-2-yl)oxy)decyl)oxy)-4-phenyl-2H-chromen-2-one

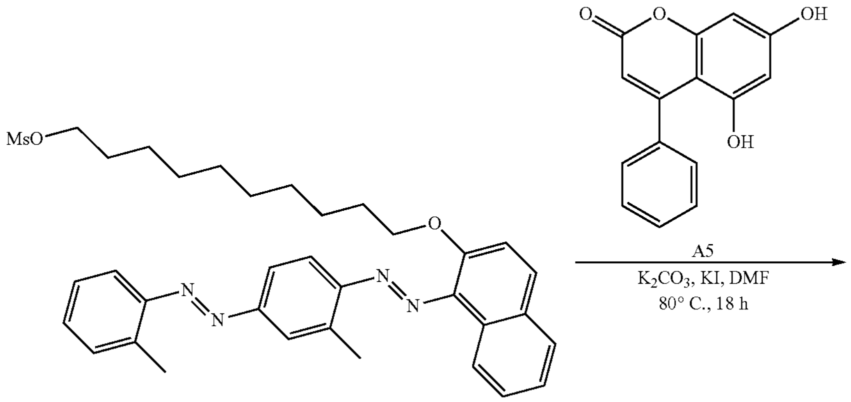

3

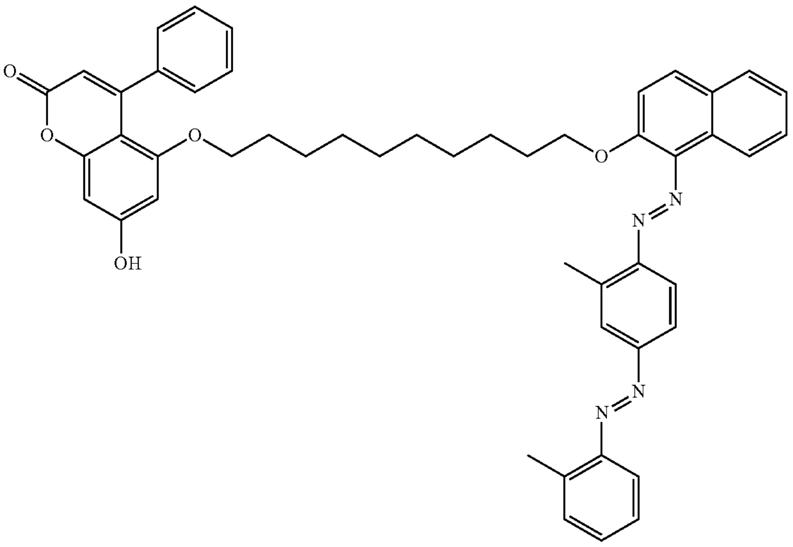

Compound 2A

Intermediate 3 (242 mg, 0.39 mmol), Compound A5 (100 mg, 0.39 mmoL), potassium carbonate (272 mg, 1.97 mmol) and potassium iodide (7 mg, 0.04 mmol) were added to a 100 mL flask with DMF (3 mL), and the mixture stirred at 80° C. for 18 hours. The reaction was cooled to room temperature, water (50 mL) was added, and the mixture was extracted with ethyl acetate (2×30 mL). The organic layers were combined, and the solvents were removed. The obtained residue was purified by reverse phase chromatography to obtain Compound 2A as red solid (15.3 mg, yield: 5%).

MS m/z (ESI): 773.0 $[M+H]^+$ $^1H$ NMR (400 MHz, $CDCl_3$) δ 8.61 (d, J=8.5 Hz, 1H), 7.98-7.79 (m, 5H), 7.66 (d, J=7.8 Hz, 1H), 7.61-7.53 (m, 1H), 7.49-7.34 (m, 4H), 7.30 (d, J=3.2 Hz, 5H), 7.21 (d, J=4.0 Hz, 2H), 6.59 (s, 1H), 6.12 (s, 1H), 5.93 (s, 1H), 4.23 (t, J=6.3 Hz, 2H), 3.54 (t, J=6.1 Hz, 2H), 2.86 (s, 3H), 2.76 (s, 3H), 1.92-1.78 (m, 2H), 1.47 (s, 2H), 1.31 (s, 2H), 1.20 (s, 2H), 1.10 (s, 2H), 1.00 (d, J=6.6 Hz, 4H), 0.76 (d, J=6.9 Hz, 2H).

Wherein, Compound A5 (5,7-dihydroxy-4-phenyl-2H-coumarin) is Compound AN2 reported by Li et. al., in 2019 (Li, Z., Wang, C., Wang, Z. et al. Allele-selective lowering of mutant HTT protein by HTT-LC3 linker compounds. *Nature* 575, 203-209 (2019)), which can bind to LC3 with affinity. Compound A5 is commercially available or can be prepared according to the following procedures.

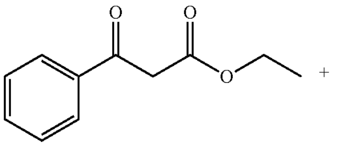

-continued

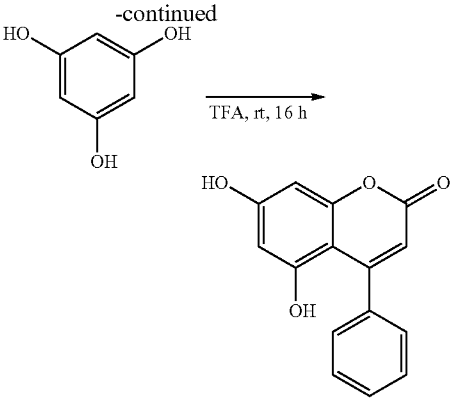

A5

Ethyl 3-oxo-3-phenylpropionate (0.20 g, 1.0 mmol) and 1,3,5-trihydroxybenzene (0.12 g, 1.0 mmol) were added to the reaction flask, 1 mL of trifluoro acetic acid was added, and the mixture was stirred at room temperature for 16 hours. After the reaction was completed, water (5 mL) was added, the product was filtered. The obtained solid was purified by reverse phase chromatography to obtain Compound A5 as yellow solid (100 mg, yield: 39.3%).

MS m/z (ESI): 255.1 $[M+H]^+$

Figure 2:
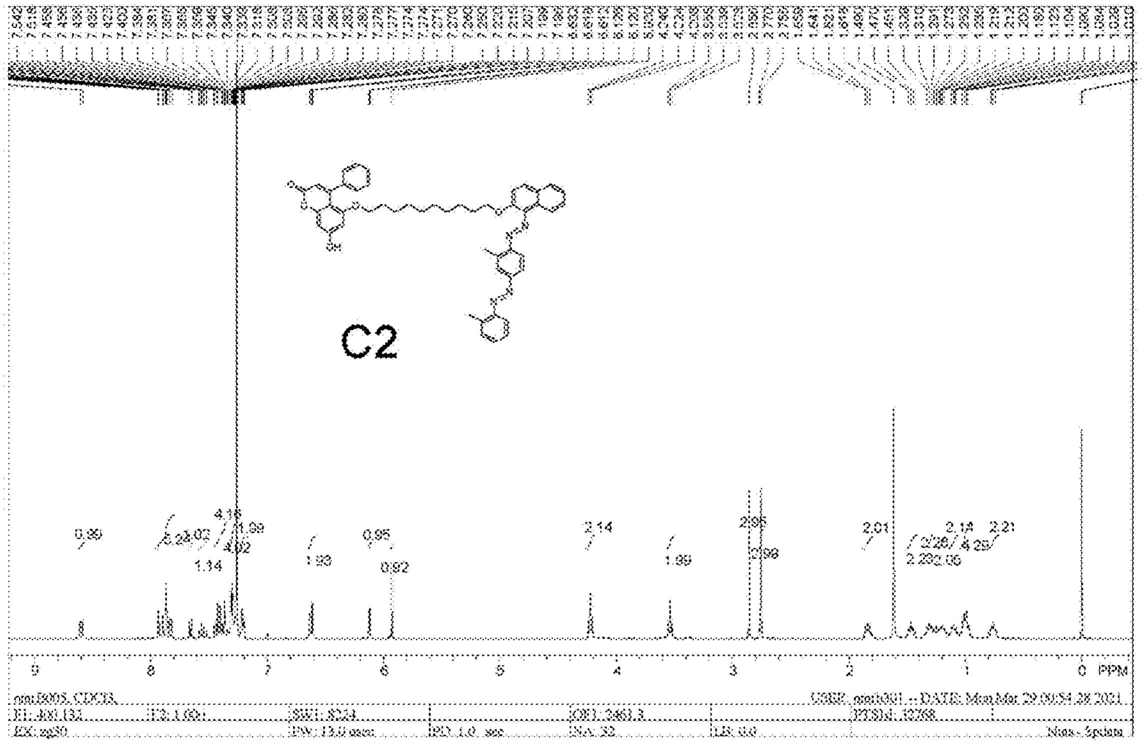
FIG. 2: $^1$H NMR and $^1$H-$^1$H NOESY spectrums of Compound 2A. Among them, two auxiliary lines intersecting at right angle and the auxiliary circle at the intersection in the $^1$H-$^1$H NOESY spectrum show the signals associated with Ha and Hb in the figure.
Figure 2:
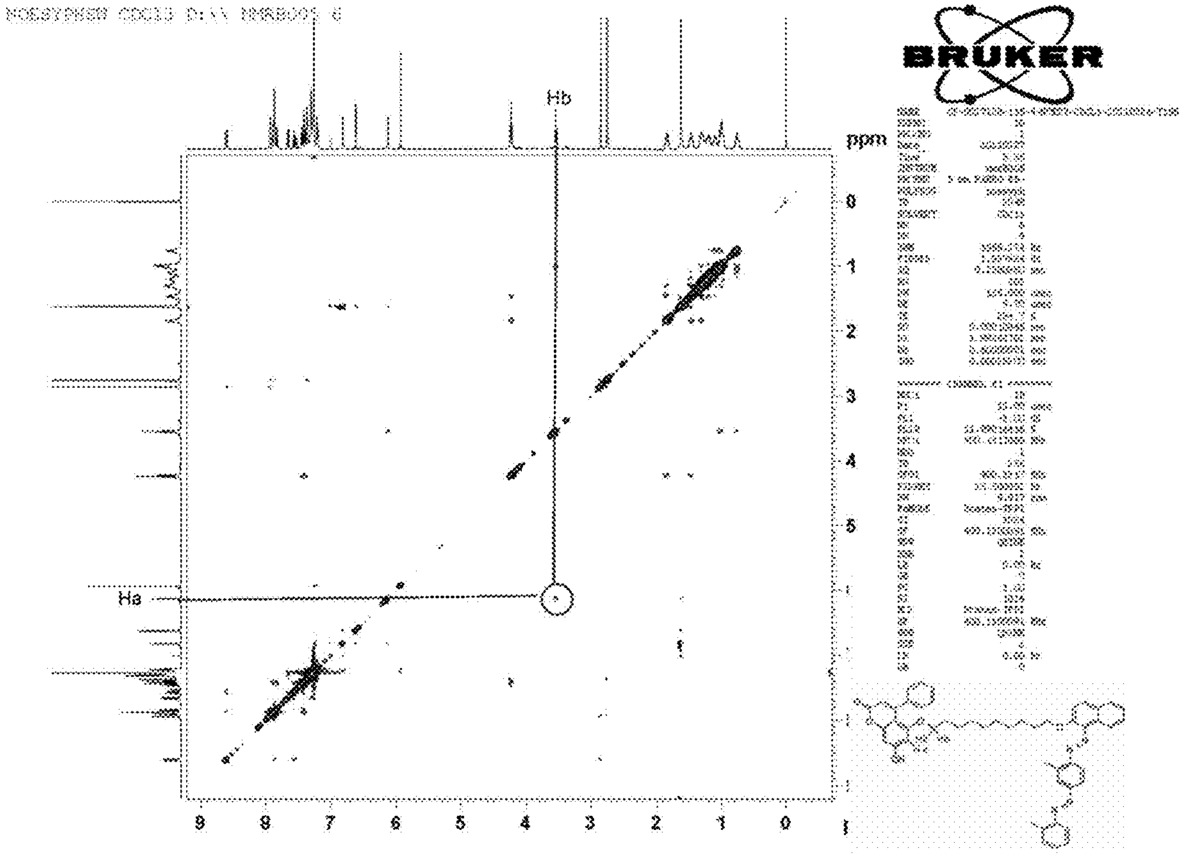

NMR spectrum was shown in FIG. 2.

Preparing Example 3 Compound 3A: 3-(3,5-dibromo-4-hydroxylbenzylidene)-5-iodo-1-(10-((1-((E)-(4-((E)-phenyldiazenyl)phenyl)diazenyl)naphthalen-2-yl)oxy)decyl)indol-2-one

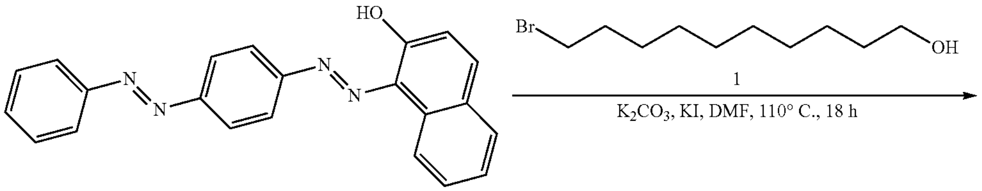

Sudan III

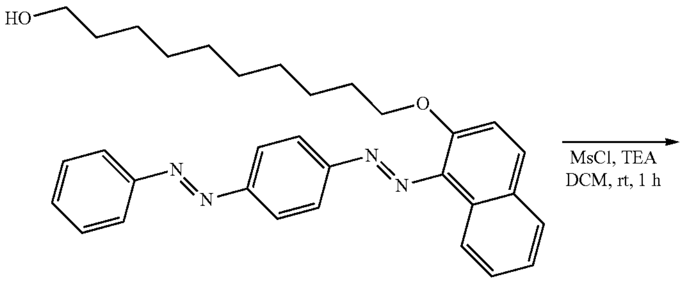

5

-continued

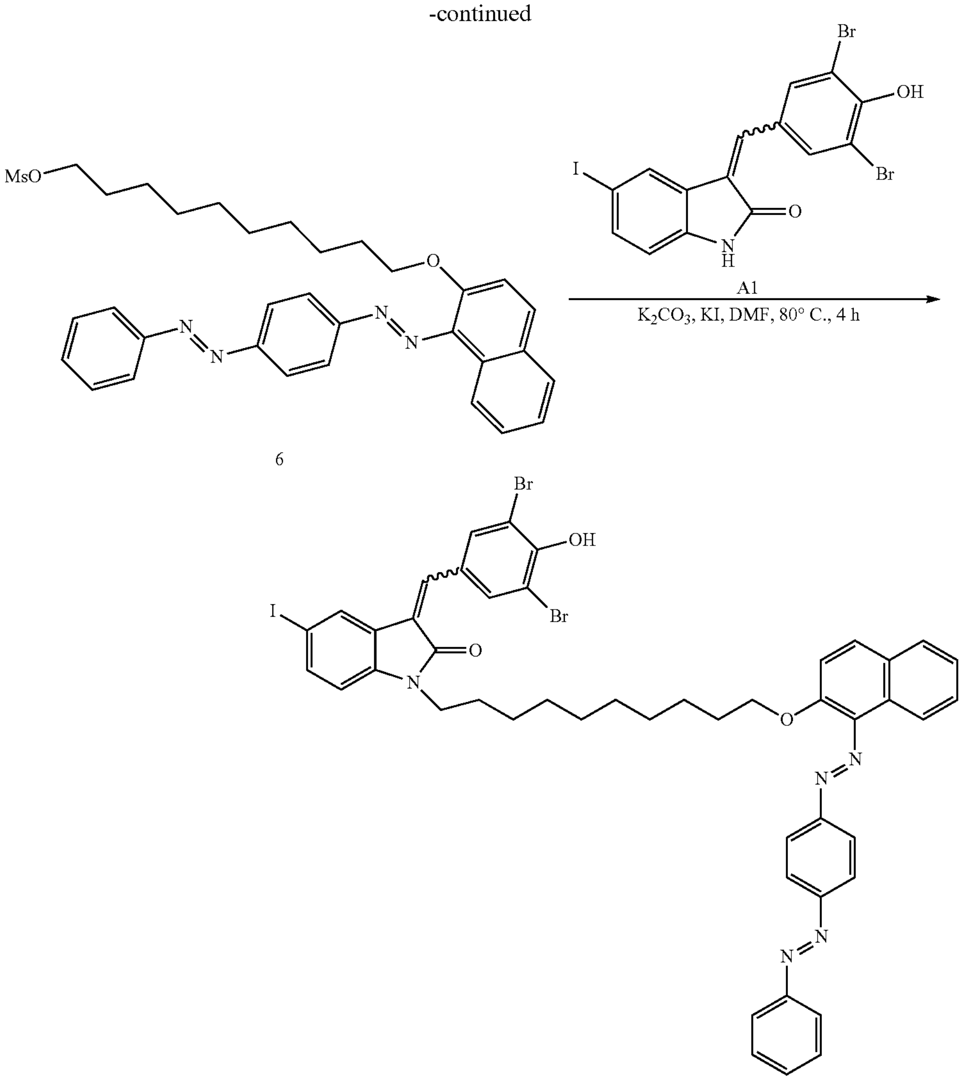

6

Compound 3A

Step 1: intermediate 5: 10-((1-((E)-(4-((E)-phenyldiazenyl)phenyl)diazenyl)naphthalen-2-yl)oxy)decan-1-ol Sudan III (1.056 g, 3 mmol), 10-bromo-1-decanol (1.062 g, 4.5 mmol), potassium carbonate (2.07 g, 15 mmol) and potassium iodide (166 mg, 1 mmol) were added to a 100 mL flask with DMF (15 mL), and the mixture was stirred at 110° C. for 16 hours. The reaction was cooled to room temperature, what (200 mL) was added, and extracted with ethyl acetate (2×80 mL). The organic layers were combined, and the solvents were removed. The obtained residue was purified by column chromatography (petroleum ether/ethyl acetate=5/1) to obtain intermediate 5 as red oil (1.3 g, yield: 85%).

MS m/z (ESI): 509.0 $[M+H]^+$

Step 2: intermediate 6: 10-((1-((E)-(4-((E)-phenyldiazenyl)phenyl)diazenyl)naphthalen-2-yl)oxy) decylmethanesulfonate Intermediate 5 (3 g, 5.9 mmol), and triethylamine (1.2 g, 11.8 mmol), were dissolved in methylene chloride (20 mL), and methanesulfonyl chloride (808 mg, 7.08 mmol) was added dropwise. The mixture was stirred at room temperature for 1 hour. 50 mL of water was added to the reaction solution and extracted with dichloromethane (2×50 mL). The organic layers were combined, and the solvents were removed. The obtained residue was purified by column chromatography (petroleum ether/ethyl acetate=3/1) to obtain intermediate 6 as red oil(1.8 g, MS m/z (ESI): 587.0 $[M+H]^+$ Step 3: Compound 3

Compound A1 (520 mg, 1.0 mmol), intermediate 6 (587 mg, 1.0 mmol), cesium carbonate (3.26 g, 10.0 mmol) and potassium iodide (166 mg, 1 mmol) were dissolved in DMF (20 mL) and reacted at 50° C. for 3 hours. The reaction was cooled to room temperature, quenched with water (20 mL), and the mixture was extracted with ethyl acetate (80 mL×2). The organic phases were combined and washed with water (20 mL×3) and saturated brine (50 mL×1), dried over anhydrous sodium sulfate, filtered, and the solvents were removed under reduced pressure. The obtained residue was purified by column chromatography (petroleum ether: ethyl acetate=3:1) to obtain Compound 3A as red solid (300 mg, 30%).

MS m/z (ESI): 1010.0 $[M+H]^+$ $^1H$ NMR (500 MHz, $CDCl_3$): δ 8.53 (s, 1H), 8.51 (d, J=8.0 Hz, 1H), 8.08-8.15 (m, 4H), 7.82-7.72-7.97 (m, 5H), 7.74 (s, 1H), 7.19-7.60 (m, 8H), 6.55 (t, J=8.4 Hz, 1H), 4.17-4.21 (m, 2H), 3.65-3.69 (m, 4H), 1.43-1.80 (m, 6H), 1.23-1.29 (m, 10H).

Figure 3:
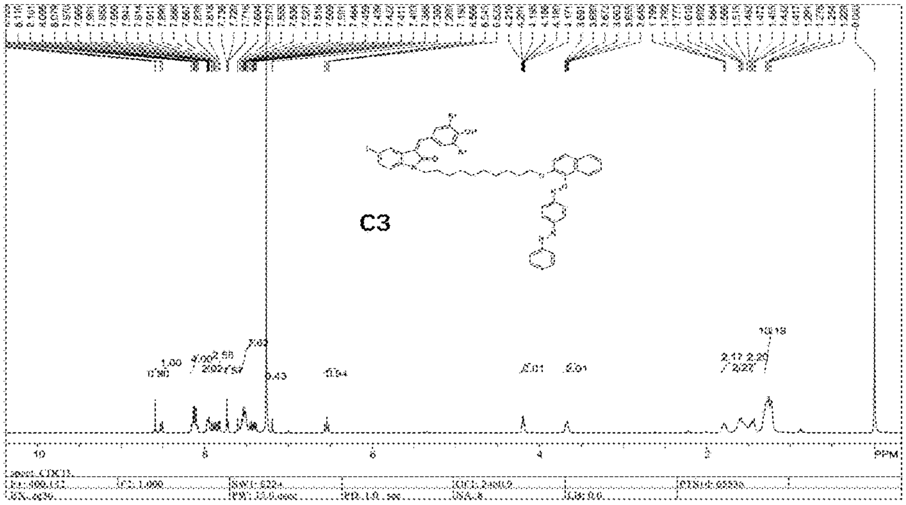
FIGS. 3-12: NMR spectrums of Compounds 3A, 4A, 5A, 6, 7, 8, 9, 10A, 10B and 11A, respectively.

NMR spectrum was shown in FIG. 3.

Preparing Example 4 Compound 4A: 7-hydroxy-4-phenyl-5-((10-((1-((E)-(4-((E)-phenyldiazenyl)phenyl)diazenyl)naphthalen-2-yl)oxy)decyl)oxy)-2H-chromen-2-one

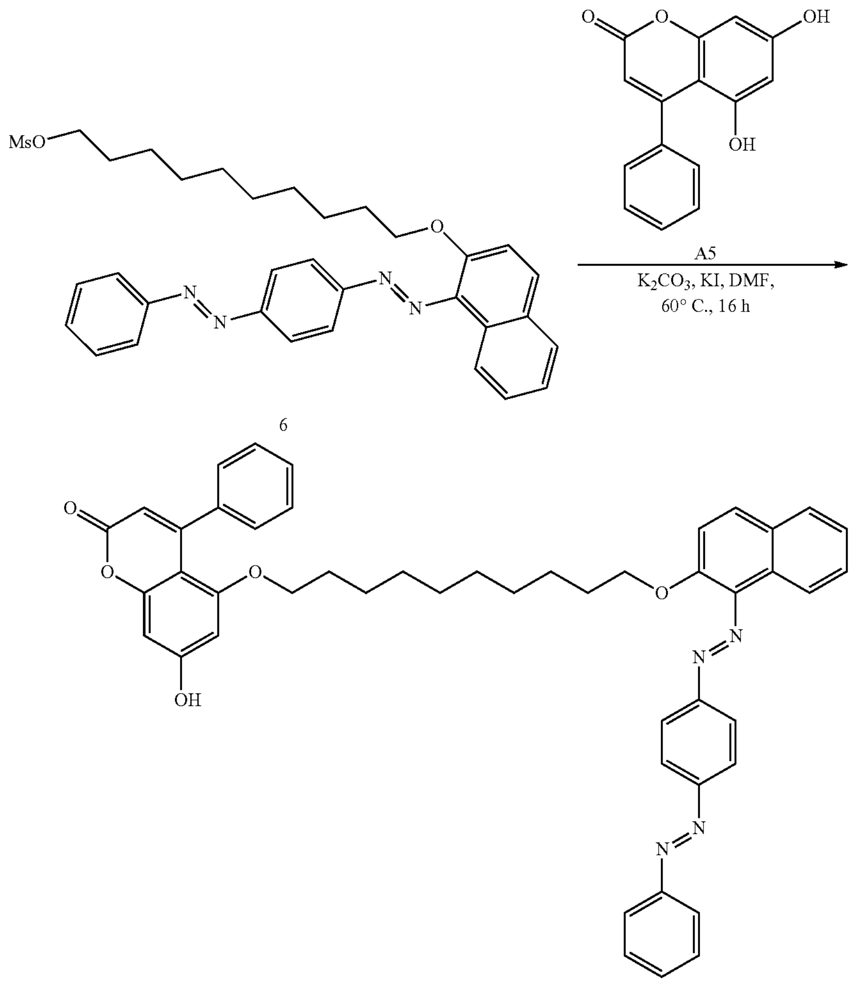

6

Compound 4A

Intermediate 6 (1.172 g, 2 mmol), Compound A5 (1.016 g, 4 mmol) and potassium carbonate (1.656 g, 12 mmol) were added to a 100 mL flask with DMF (10 mL), and the mixture stirred at 60° C. for 18 hours. The reaction was cooled to room temperature, water (50 mL) was added, and the mixture was extracted with ethyl acetate (2×30 mL). The organic layers were combined, and the solvents were removed. The obtained residue was purified by column chromatography (petroleum ether: ethyl acetate=2:1-1:1) to obtain Compound 4A as red solid (201 mg, yield: 13%).

MS m/z (ESI): 745.0 $[M+H]^+$ $^1H$ NMR (400 MHz, $CDCl_3$) δ 8.52 (d, J=8.8 Hz, 1H), 8.09-8.16 (m, 4H), 7.82-7.97 (m, 4H), 7.39-7.56 (m, 6H), 7.19-7.31 (m, 5H), 6.73 (bs, 1H), 6.61 (d, J=2.4 Hz, 1H), 6.12 (d, J=2.4 Hz, 1H), 5.93 (s, 1H), 4.21 (t, J=6.4 Hz, 2H), 3.52 (t, J=6.4 Hz, 2H), 1.79-1.83 (m, 2H), 0.77-1.48 (m, 14H).

Figure 4:
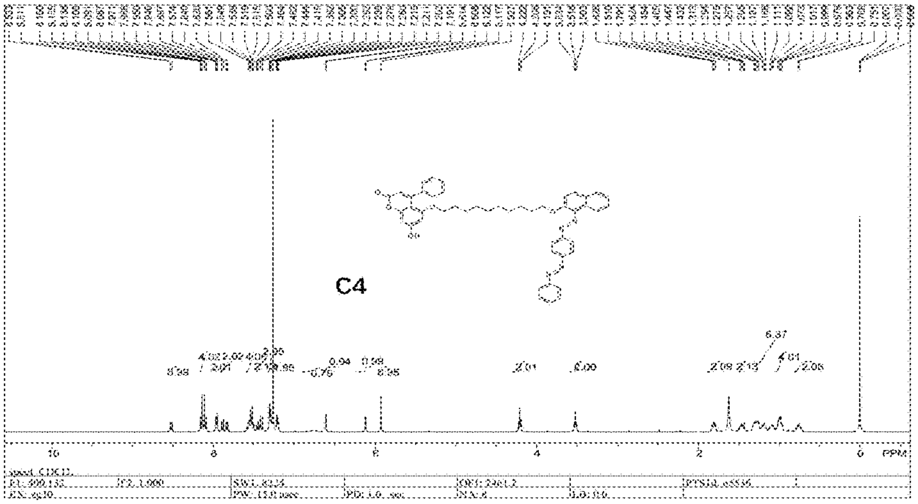

NMR spectrum was shown in FIG. 4.

Preparing Example 5 Compound 5A: 5-((10-(2-(benzo[d]thiazol-2-yl)-4-methoxyphenyloxy)decyl)oxy)-7-hydroxy-4-phenyl-2H-chromen-2-one

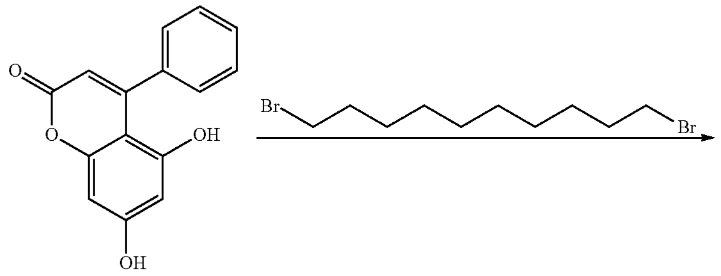

A5

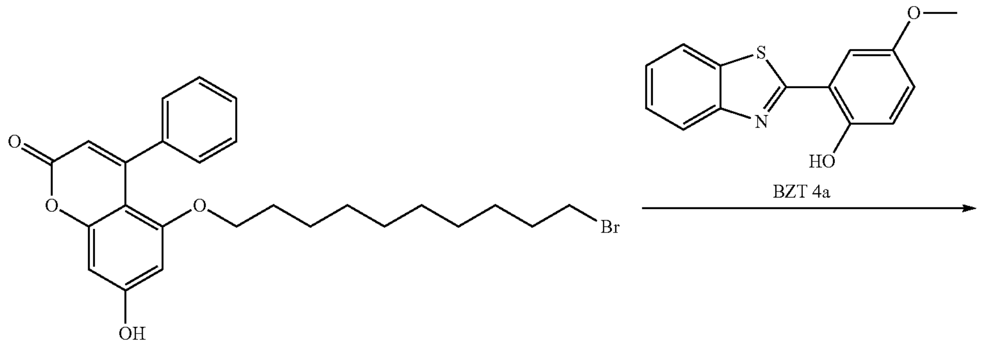

Intermediate 7

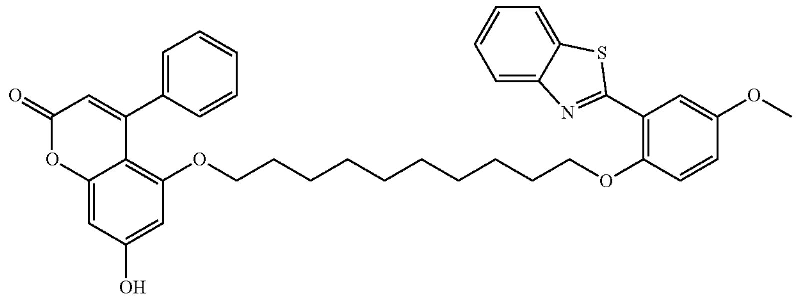

Compound 5A

Step 1: intermediate 7: 5-((10-bromodecyl)oxy)-7-hydroxy-4-phenyl-2H-chromen-2-one Compound A5 (100 mg, 0.39 mmol), 1,10-dibromodecane (117.0 mg, 0.39 mmol) and $K_2CO_3$ (165 mg, 1.2 mmol) were dissolved in DMF (5 mL). The mixture was stirred under room temperature for 8 hours. The reaction was monitored with TLC for completion. Water (50 mL) was added to the reaction liquid, which was extracted with dichloromethane (50 mL×2). The solvents were rotated off. The obtained residue was purified by column chromatography (petroleum ether: ethyl acetate=3:1) to obtain product as red solid (100 mg, 54.32%).

Step 2: Preparation of Compound 5A

Intermediate 7(100 mg, 0.21 mmol), Compound BZT 4a (53.9 mg, 0.21 mmol) and $K_2CO_3$ (83 mg, 0.63 mmol) were added to a 100 mL flask and were reacted at normal temperature for 8 hours. The reaction was monitored with TLC for completion. Water (20 mL) was added to the reaction liquid, which was extracted with ethyl acetate three times. The organic phase was concentrated, and the concentrated crude was purified by column chromatography to obtain Compound 5A (31 mg, 22.7%).

$^1$H NMR (400 MHz, DMSO) δ 10.62 (s, 1H), 8.17-8.04 (m, 2H), 7.96 (d, J=3.1 Hz, 1H), 7.51 (d, J=7.1 Hz, 1H), 7.42 (d, J=7.2 Hz, 1H), 7.33 (s, 3H), 7.24 (s, 2H), 7.13 (d, J=12.1 Hz, 1H), 6.39 (s, 1H), 6.24 (s, 1H), 5.75 (s, 1H), 4.24 (s, 2H), 3.83 (s, 3H), 3.61 (s, 2H), 2.07-1.86 (m, 4H), 1.55 (s, 2H), 1.38 (s, 3H), 1.14 (s, 2H), 0.99 (s, 4H), 0.85 (s, 1H), 0.72 (s, 2H).

Figure 5:
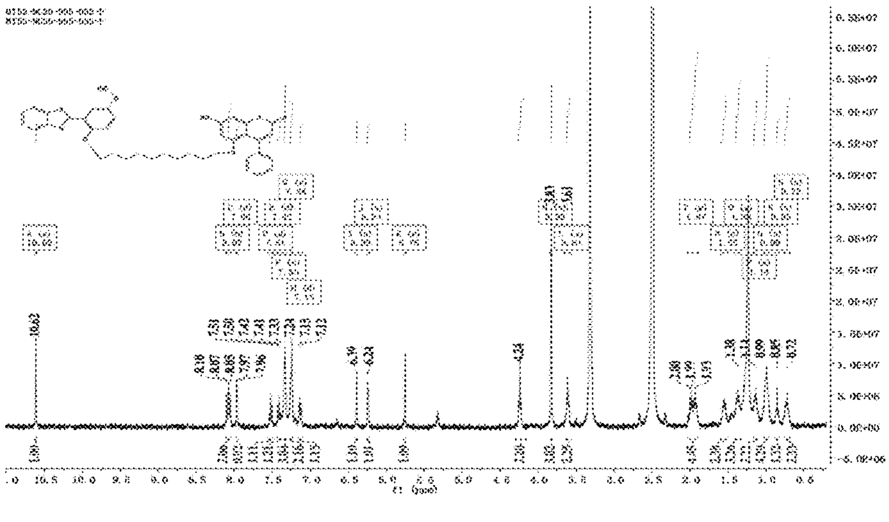

NMR spectrum was shown in FIG. 5.

Preparing Example 6 Compound 6: (R)—N-(1-(3benzyl-7-chloro-4-oxo-3,4-dihydroquinazolin-2-yl)-2-methylpropyl)-N-(3-((10-((5-(dimethylamino)-N-pentylnaphthyl)-1-sulfonamide)decyl)amino)propyl)-4-methylbenzamide

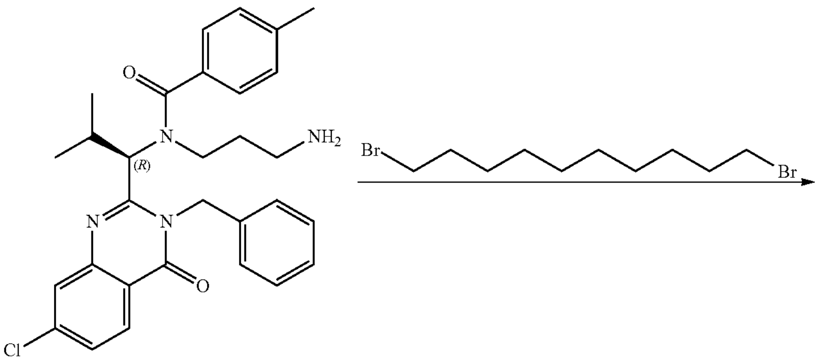

A8

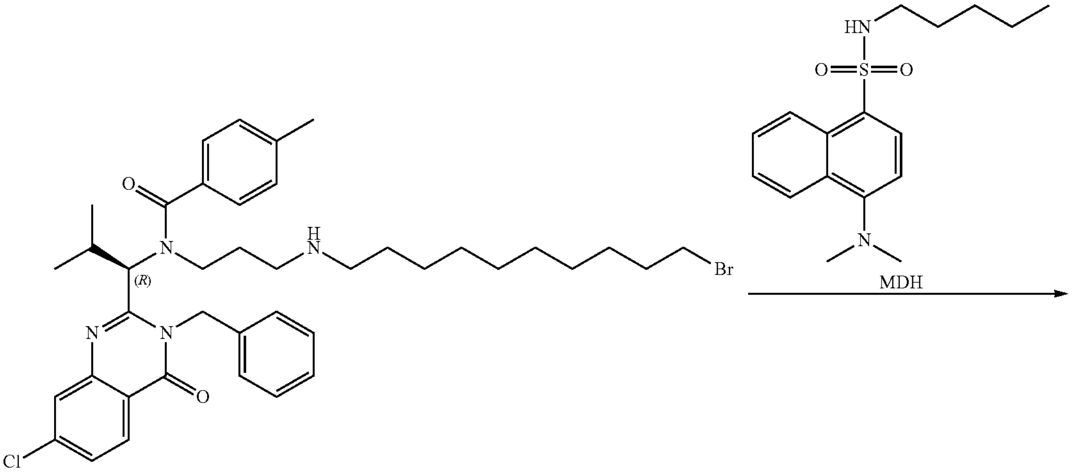

intermediate 8

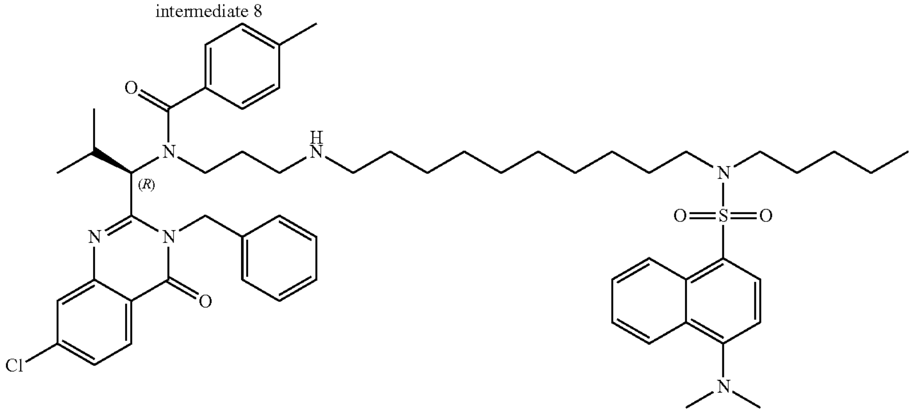

Compound 6

Step 1: intermediate 8: (R)—N-(1-(3-benzyl-7-chloro-4-oxo-3,4-dihydroquinazolin-2-yl)-2-methylpropyl)-N-(3-((10-bromodecyl)amino)propyl)-4-methyl benzamide Compound A8 (1 g, 1.9 mmol), 1,10-dibromodecane (566.2 mg, 1.9 mmol) were added to a 50 mL flask with DMF (10 mL). The mixture was stirred at 60° C. for 16 hours. The reaction was cooled to room temperature, the solvents were removed, and water (30 ml) was added. The mixture was extracted with ethyl acetate (80 mL×2). The organic layers were combined, and the solvents were removed. The obtained residue was purified by column chromatography (petroleum ether/ethyl acetate=5/1) to obtain product as white solid (560 mg, yield: 40.15%).

Step 2: Preparation of Compound 6

Intermediate 8 (100 mg, 0.14 mmol), 1,10-dibromodecane (45 mg, 0.14 mmol) and $K_2CO_3$ (30 mg, 0.21 mmol) were dissolved in DMF (5 mL). The mixture was stirred under room temperature for 8 hours. The reaction was monitored with TLC for completion. Water (50 mL) was added to the reaction liquid, which was extracted with dichloromethane (50 mL×2). The organic layers were combined, and the solvents were removed. The obtained residue was purified by column chromatography to obtain product as white solid (20.4 mg, yield: 14.96%).

$^1H$ NMR (400 MHz, DMSO) δ 8.47 (d, J=8.7 Hz, 1H), 8.22 (d, J=2.1 Hz, 1H), 8.15 (d, J=8.7 Hz, 1H), 8.09 (d, J=6.6 Hz, 1H), 7.80 (s, 1H), 7.62 (ddd, J=18.7, 9.9, 5.2 Hz, 3H), 7.36 (d, J=7.3 Hz, 2H), 7.30 (s, 1H), 7.25 (t, J=8.8 Hz, 7H), 5.91 (d, J=16.3 Hz, 1H), 5.53 (d, J=10.3 Hz, 1H), 5.08 (d, J=15.7 Hz, 1H), 3.28-3.26 (m, 1H), 3.19 (d, J=6.9 Hz, 4H), 2.81 (s, 6H), 2.32 (s, 4H), 1.98 (s, 4H), 1.39 (s, 4H), 1.23 (s, 4H), 1.05 (s, 20H), 0.89 (d, J=6.7 Hz, 3H), 0.70 (t, J=7.1 Hz, 4H), 0.46 (d, J=6.3 Hz, 3H).

Figure 6:
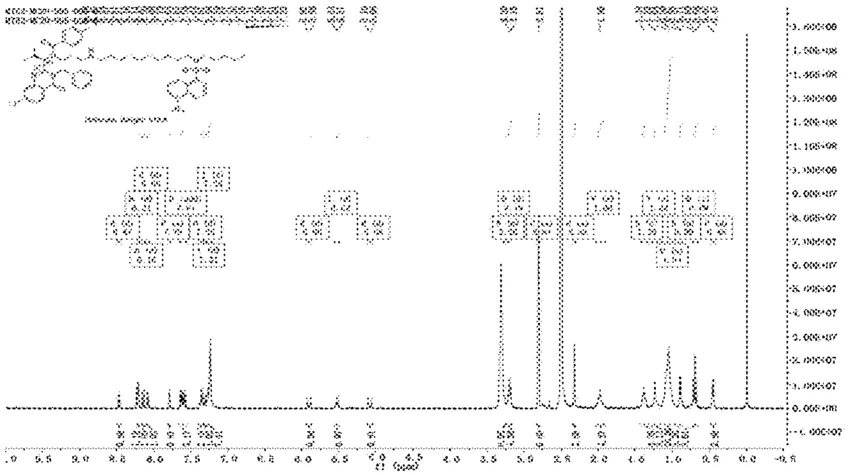

NMR spectrum was shown in FIG. 6.

Preparing Example 7 Compound 7: (R)-6-(3-(4-(2-(2-(benzo[d]thiazol-2-yl)-4-methoxyphenyloxy)ethyl)piperazin-1-yl)propyloxy)-N-(3-(N-(1-(3-phenyl-7-chloro-4-oxo-3,4-dihydroquinazolin-2-yl)-2-methylpropyl)-4-methylbenzamide)propyl)nicotinamide

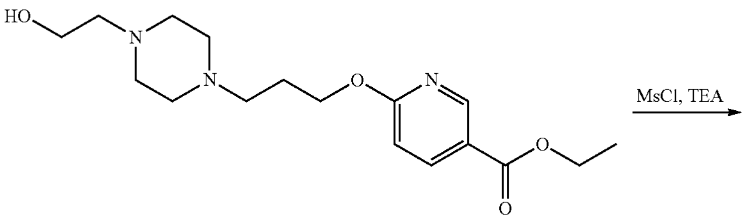

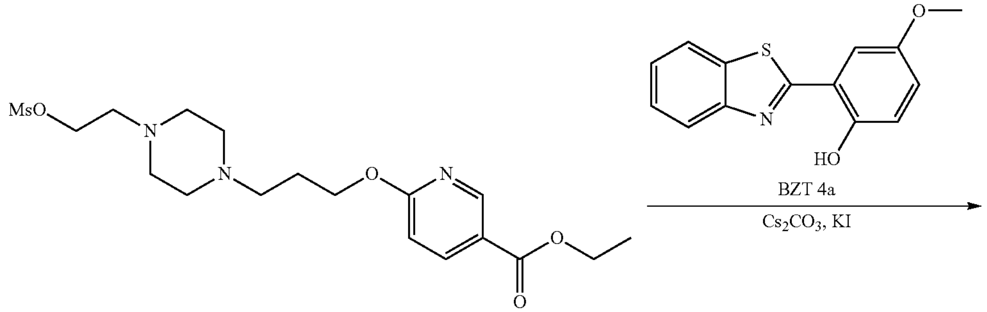

Intermediate 9

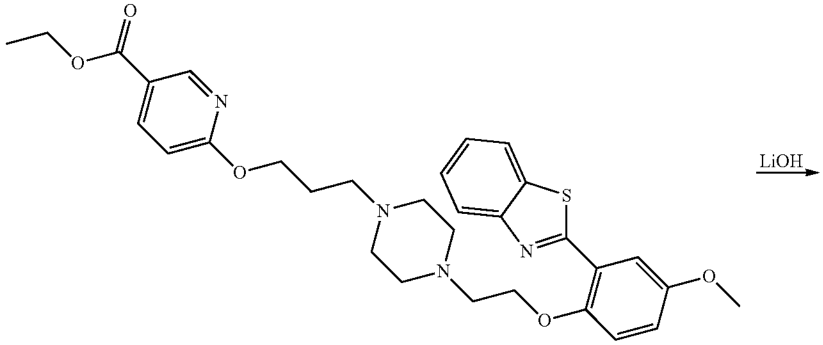

Intermediate 10

-continued

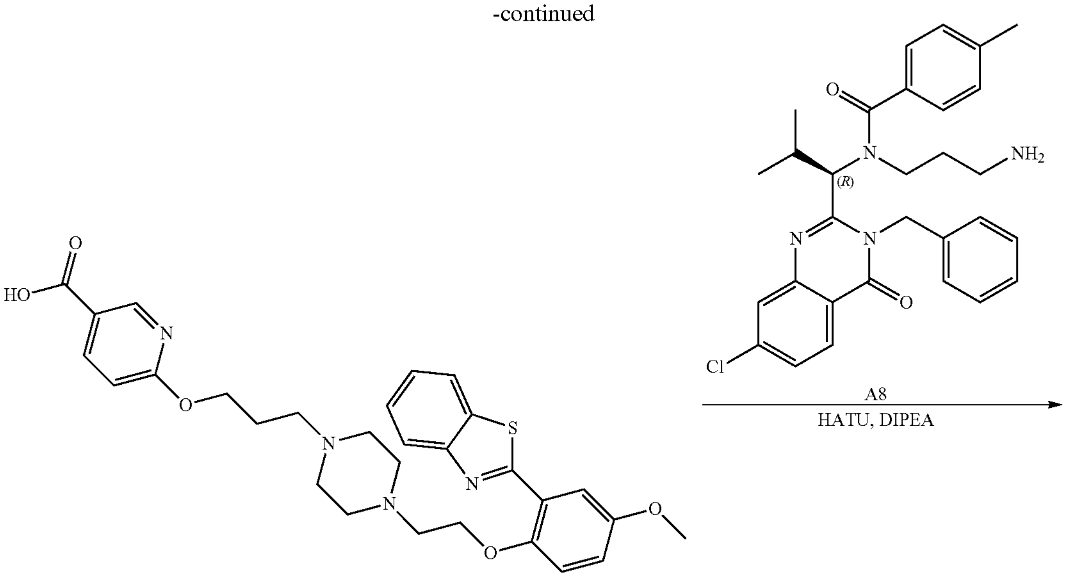

Intermediate 11

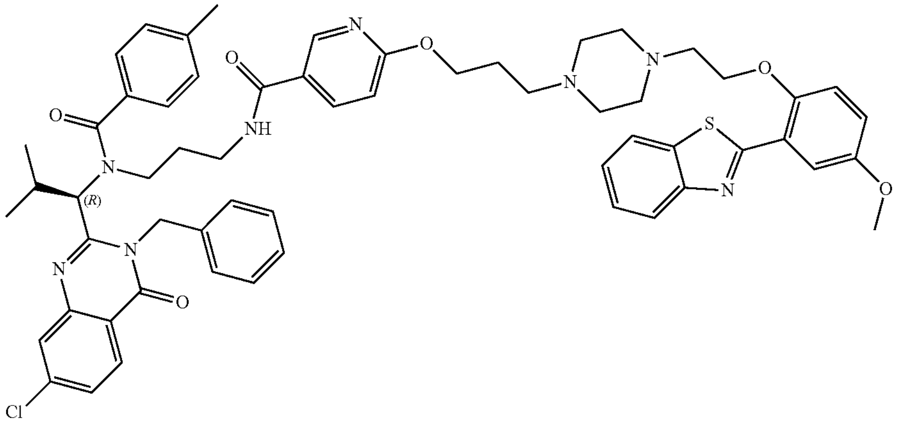

Compound 7

Step 1: intermediate 9: ethyl 6-(3-(4-(2-((methylsulfonyl)oxy)ethyl)piperazin-1-yl)propyloxy)nicotinate Ethyl 6-(3-(4-(2-hydroxylethyl)piperazin-1-yl) propyl oxy)nicotinate (850 mg, 2.52 mmol) was added to a 100 mL flask, to which were added DCM (15 mL), triethylamine (764 mg, 7.57 mmol). MsCl (345 mg, 3.03 mmol) was added dropwise under the protection of nitrogen. The mixture was stirred at 25° C. for 0.5 hour and water (200 mL) was added. The mixture was extracted with ethyl acetate (80 mL×2). The organic layers were combined, and the solvents were removed to obtain product (800 mg, yield: 76%).

Step 2: intermediate 10: ethyl 6-(3-(4-(2-(2-(benzo [d]thiazol-2-yl)-4-methoxyphenyloxy)ethyl)piperazin-1-yl)propyloxy)nicotinate Intermediate 9 (800 mg, 1.93 mmol), BZT 4a (495 mg, 1.93 mmol) and cesium carbonate (1.9 g, 5.78 mmol) were dissolved in DMF (10 mL). The mixture was stirred at 60° C. for 5 hours. Water (50 mL) was added to the reaction liquid, which was extracted with ethyl acetate (50 mL×2). The organic layers were combined, and the solvents were removed. The obtained residue was purified by column chromatography (petroleum ether/ethyl acetate=1/1) to obtain product (1 g, yield: 90%).

MS m/z (ESI): 577.0 $[M+H]^+$

Step 3: intermediate 11: 6-(3-(4-(2-(2-(benzo [d]thiazol-2-yl)-4-methoxyphenyloxy)ethyl)piperazin-1-yl) propyl oxy)nicotinic acid Intermediate 10 (200 mg, 0.350 mmol) and lithium hydroxide (29 mg, 0.698 mmol) were dissolved in methanol (10 mL). The mixture was stirred at 40° C. for 1 hour. The reaction liquid was rotated to dryness. Water (50 mL) was added, and the reaction mixture was extracted with ethyl acetate (50 mL×2). The organic layers were combined, and the solvents were removed to obtain product (120 mg, yield: 63%).

Step 3: Preparation of Compound 7

Intermediate 11 (60 mg, 0.109 mmol) was dissolved in DMF(10 mL), to which were added Compound A8 (56 mg, 0.109 mmol), HATU(83 mg, 0.219 mmol) and DIEA(42 mg, 0.328 mmol). The mixture was stirred at 25° C. overnight and subjected to acid method to obtain product (32.6 mg, yield: 29%).

MS m/z (ESI): 1047.0 $[M+H]^+$.

$^1H$ NMR (400 MHz, DMSO) δ 8.28 (s, 1H), 8.19 (d, J=9.1 Hz, 1H), 8.09 (dd, J=15.3, 7.7 Hz, 3H), 7.96 (d, J=3.1 Hz, 1H), 7.82 (t, J=3.9 Hz, 1H), 7.60 (d, J=6.1 Hz, 3H), 7.53 (t, J=7.8 Hz, 1H), 7.42 (t, J=8.0 Hz, 1H), 7.35 (t, J=7.6 Hz, 2H), 7.31-7.26 (m, 2H), 7.21 (dd, J=16.5, 6.8 Hz, 4H), 7.13 (d, J=8.5 Hz, 2H), 6.35 (d, J=9.5 Hz, 1H), 5.87 (d, J=15.5 Hz, 1H), 5.51 (d, J=11.1 Hz, 1H), 5.02 (d, J=15.6 Hz, 1H), 4.31 (t, J=6.0 Hz, 2H), 3.93 (d, J=20.0 Hz, 2H), 3.82 (s, 3H), 3.25

(s, 4H), 2.88 (t, J=5.3 Hz, 2H), 2.69 (d, J=10.5 Hz, 3H), 2.26 (d, J=52.9 Hz, 10H), 1.83-1.71 (m, 2H), 1.41 (s, 1H), 0.87 (d, J=7.0 Hz, 3H), 0.44 (d, J=6.1 Hz, 3H).

Figure 7:
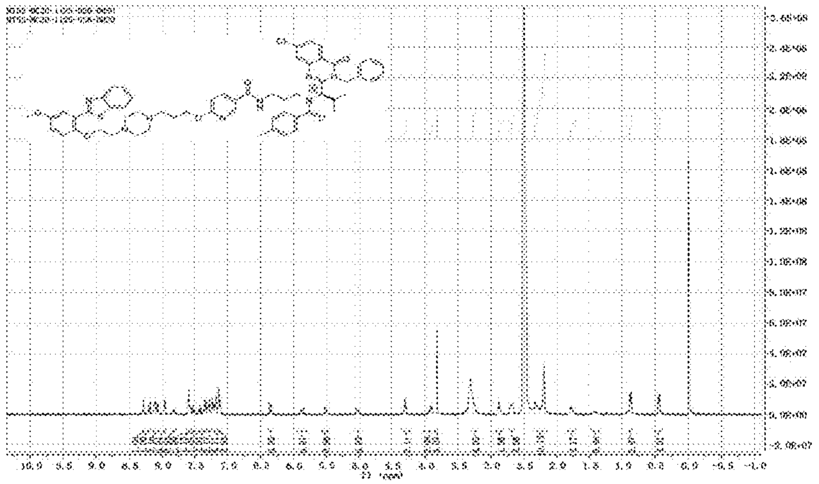

NMR spectrum was shown in FIG. 7.

Preparing Example 8 Compound 8: (R)—N-(3-(N-(1-(3-phenyl-7-chloro-4-oxo-3,4-dihydroquinazolin-2-yl)-2-methylpropyl)-4-methylbenzamide)propyl)-6-(3-(4-(2-((5-(dimethylamino)-N-pentylnaphthyl)-1-sulfonamide)ethyl)piperazin-1-yl)propyloxy) nicotinamide

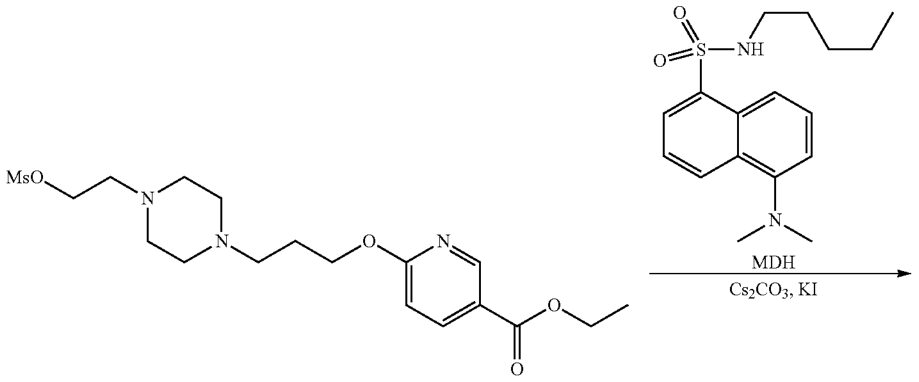

Intermediate 9

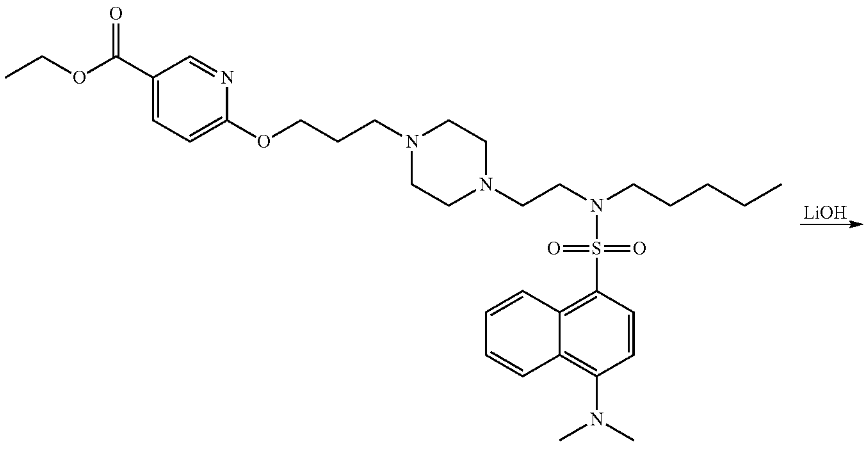

Intermediate 12

Figure 8:
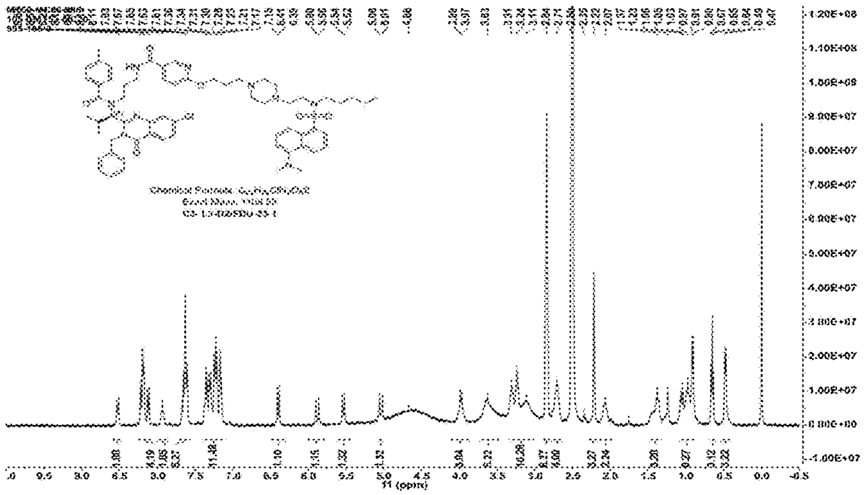

-continued
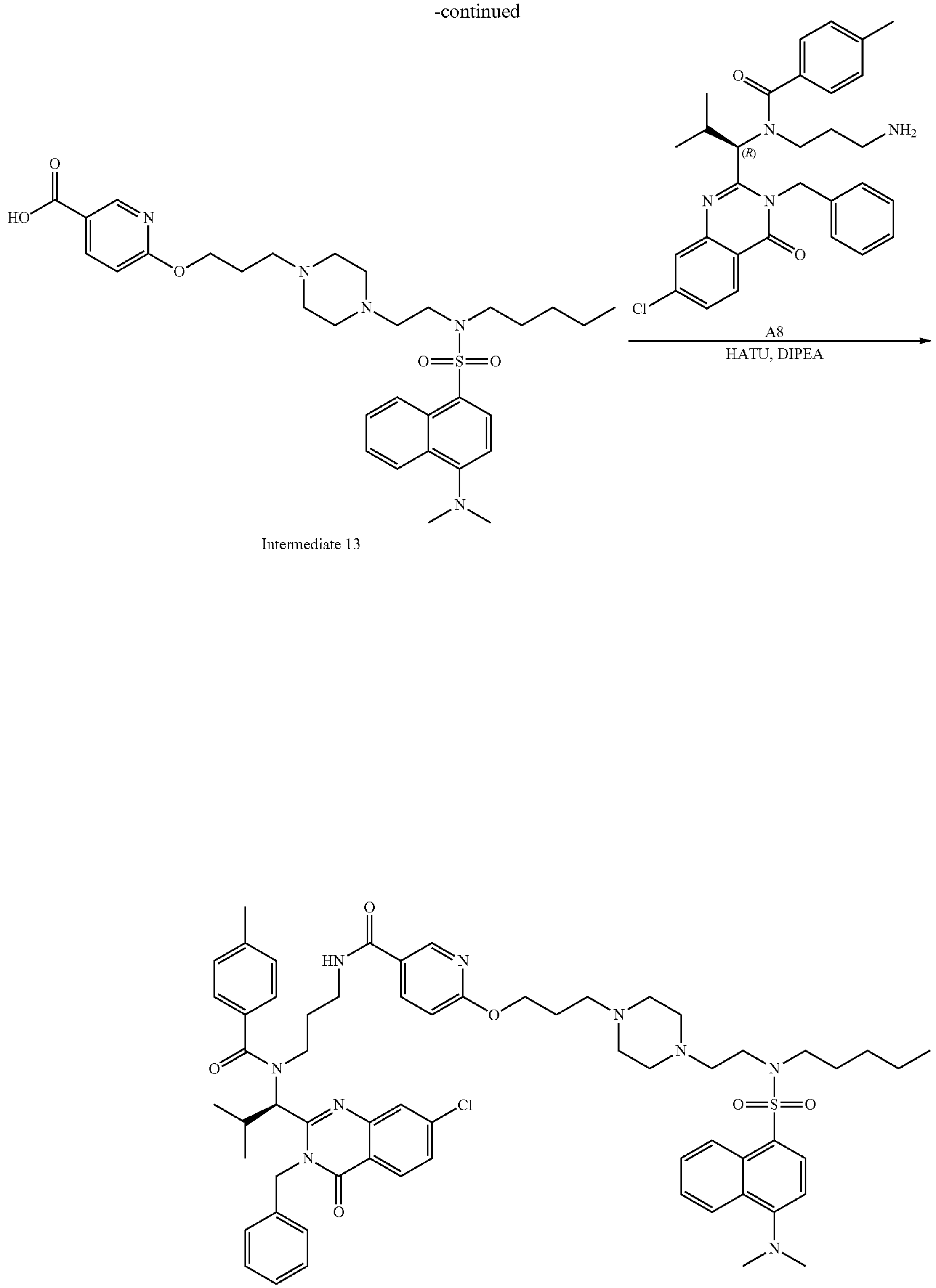
Intermediate 13
Compound 8
Similar procedures in Preparing Example 7, where MDH was used instead of BZT 4a, were followed to obtain Compound 8,
MS m/z (ESI): 1110.6 $[M+H]^+$.
NMR spectrum was shown in FIG. 8.

Preparing Example 9 compound 9: N-3(N—((R)-1-(3-phenyl-7-chloro-4-oxo-3,4-dihydroquinazolin-2-yl)-2-methylpropyl)-4-methylbenzamide)propyl)-6-(3-(4-(2-((1-((E)-(4-((E)-phenyldiazenyl)phenyl)diazenyl)naphthalen-2-yl)oxo)ethyl)piperazin-1-yl)propyloxy)nicotinamide
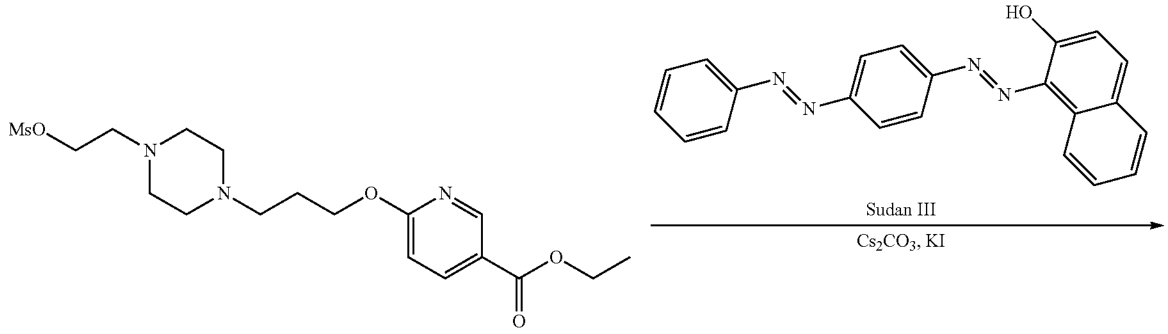
Intermediate 9
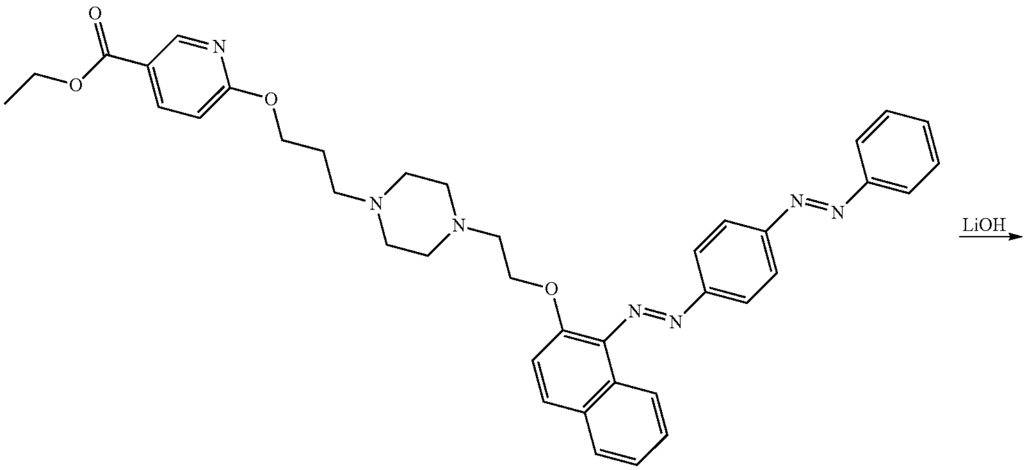
Intermediate 14
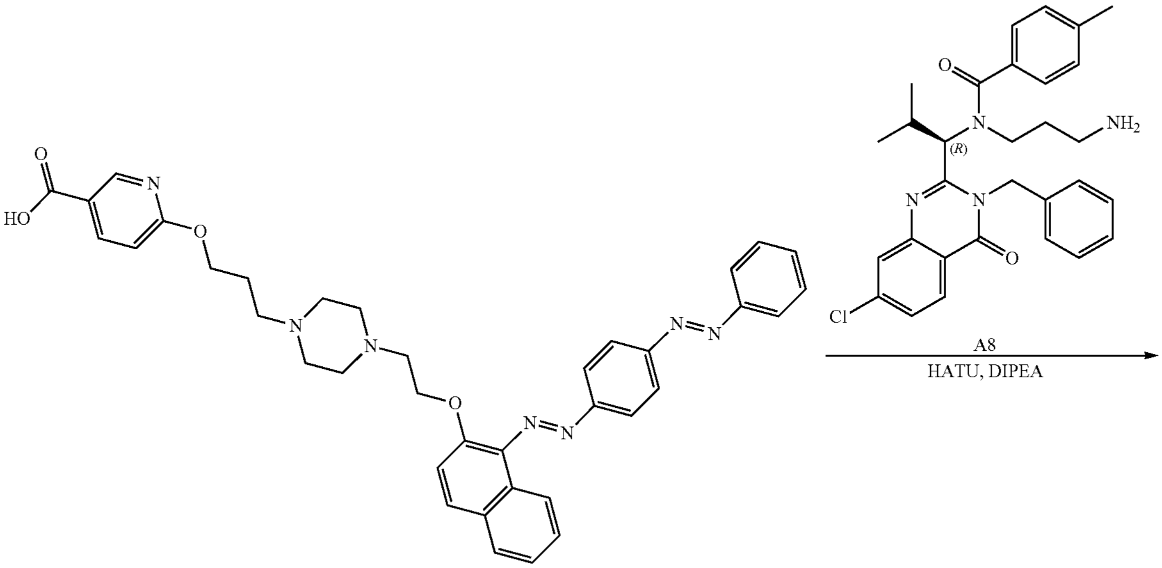
Intermediate 15

-continued

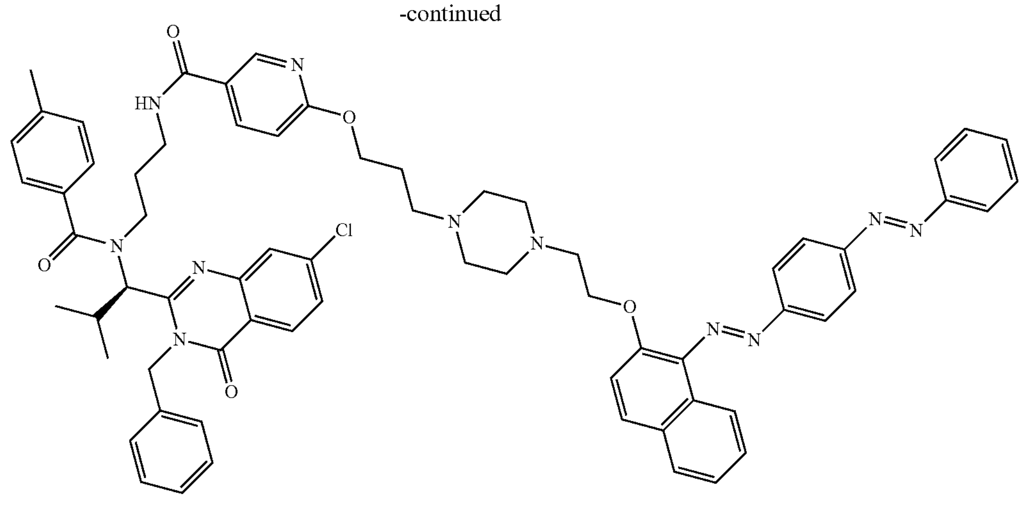

Compound 9

Similar procedures in Preparing Example 7, where Sudan III was used instead of BZT 4a, were followed to obtain Compound 9.

MS m/z (ESI): 1142.0 $[M+H]^+$.

$^1$H NMR (400 MHz, DMSO) δ 8.44 (d, J=7.9 Hz, 1H), 8.22-8.05 (m, 7H), 8.03-7.90 (m, 3H), 7.82 (s, 1H), 7.71-7.43 (m, 9H), 7.32 (dd, J=17.2, 6.8 Hz, 3H), 7.19 (dd, J=27.8, 12.8 Hz, 6H), 6.35 (s, 1H), 5.86 (d, J=16.0 Hz, 1H), 5.51 (d, J=10.6 Hz, 1H), 5.02 (d, J=15.9 Hz, 1H), 4.35 (s, 1H), 3.89 (s, 2H), 2.68 (s, 5H), 2.26 (d, J=58.8 Hz, 9H), 1.74 (s, 1H), 1.48-1.30 (m, 1H), 0.87 (d, J=6.2 Hz, 4H), 0.43 (s, 3H),-0.00 (s, 6H).

Figure 9:
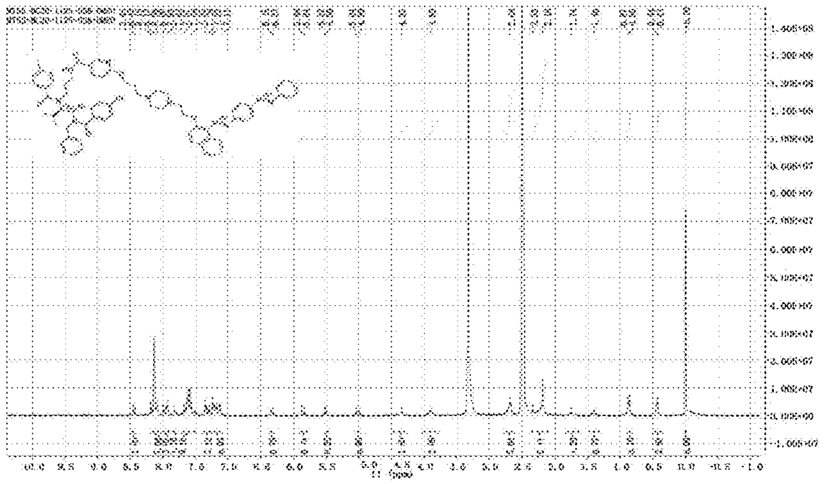

NMR spectrum was shown in FIG. 9.

Preparing Example 10 Compound 10A: 5-hydroxy-4-phenyl-7-(2-(prop-2-ynyl-1-yloxy)ethoxy)-2H-chromen-2-one; Compound 10B: 7-hydroxy-4-phenyl-5-(2-(prop-2-ynyl-1-yloxy)ethoxy)-2H-chromen-2-one

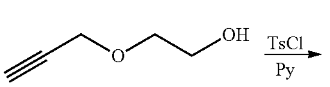

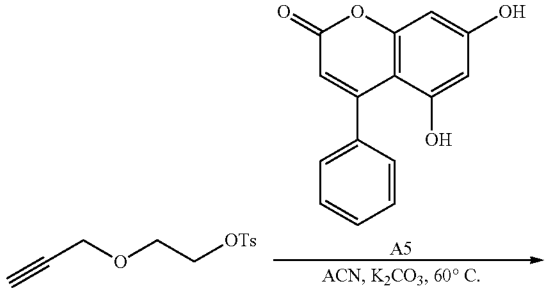

Intermediate 16

-continued

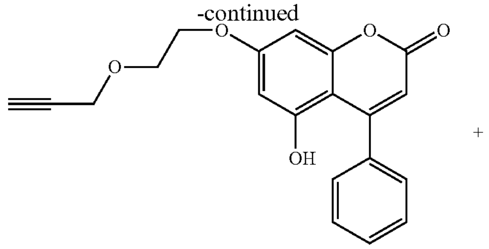

Compound 10A

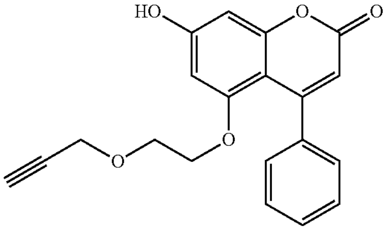

Compound 10B

Step 1: intermediate 16: 4-methyl benzenesulfonic acid 2-(prop-2-ynyl-1-yloxy)ethyl ester To a solution of 2-(prop-2-ynyl-1-yloxy)ethanol (3 g) in pyridine was added TsCl (8.5 g) and the resulting reaction liquid was stirred under room temperature for 16 hours. Water (200 mL) was added to the reaction liquid, which was extracted with ethyl acetate (80 mL×2). The organic layers were combined, and the solvents were removed. The obtained residue was purified by column chromatography (petroleum ether/ethyl acetate=5/1) to obtain product as white oil (1 g, yield: 13%).

$^1$H NMR (400 MHz, DMSO) δ 7.79 (d, J=8.0 Hz, 2H), 7.48 (d, J=8.0 Hz, 2H), 4.16-4.14 (m, 2H), 4.10 (s, 2H), 3.63-3.61 (m, 2H), 3.44 (s, 1H), 2.42 (s, 3H).

Step 2: Preparation of Compound 10A and Compound 10B

Intermediate 2 (230 mg), Compound 5A (230 mg) and $K_2CO_3$ (188 mg) were dissolved in ACN. The mixture was stirred at 60° C. for 1 hour. Water (50 mL) was added to the reaction liquid, which was extracted with dichloromethane (50 mL×2). The organic layers were combined, and the solvents were removed. The obtained residue was purified by column chromatography to obtain Compound 10B (14.57 mg, yield 4.6%) and Compound 10A (6.02 mg, yield 2%) as white solid.

Figure 10:
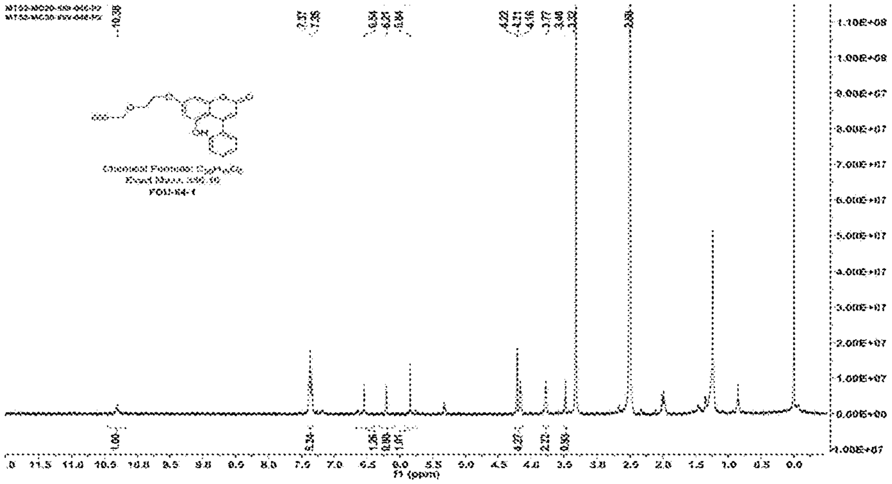

Compound 10A, NMR spectrum was shown in FIG. 10.

Figure 11:
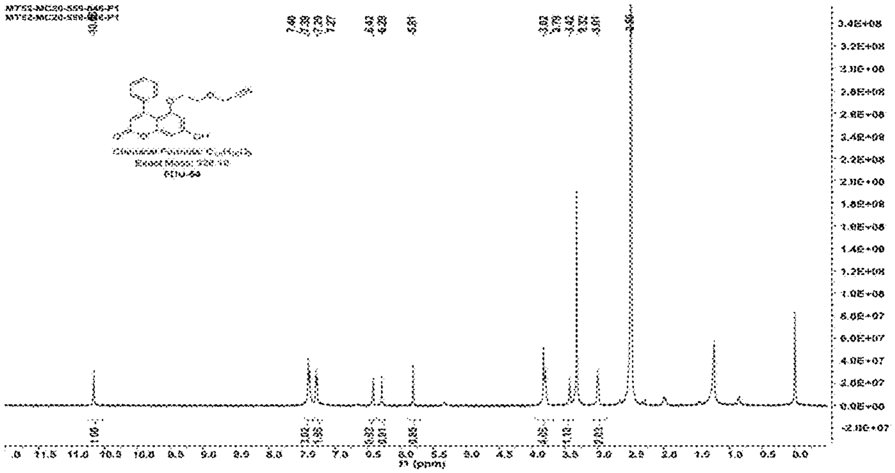

Compound 10B, NMR spectrum was shown in FIG. 11.

Preparing Example 11 Compound 11A: 5-(2-(2-(2-azidoethoxy)ethoxy)ethoxy)-7-hydroxy-4-phenyl-2H-chromen-2-one

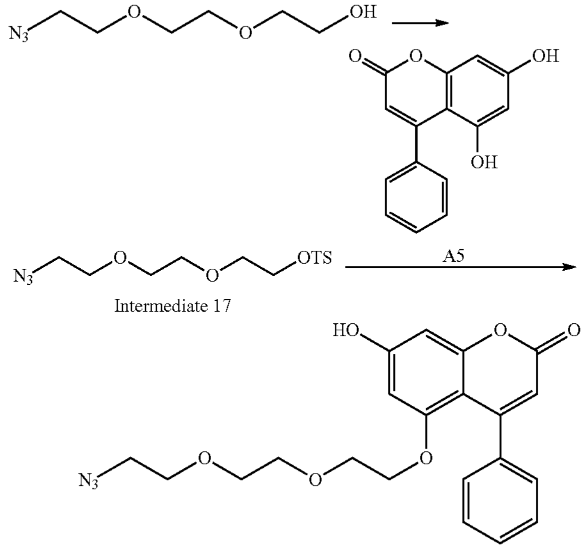

Intermediate 17

Compound 11A

Step 1: intermediate 17: 4-methyl benzenesulfonic acid 2-(2-(2-azidoethoxy)ethoxy)ethyl ester 2-(2-(2-azido ethoxy)ethoxy)ethanol (100 mg, 0.57 mmol), TsCl (162 mg, 0.85 mmol) were added to a 10 mL flask with DCM (5 mL), which was stirred at 60° C. for 16 hours. The reaction was cooled to room temperature, the solvents were removed, and water (10 ml) was added. The mixture was extracted with ethyl acetate (80 mL×2). The organic layers were combined, and the solvents were removed. The obtained residue was purified by column chromatography (petroleum ether/ethyl acetate=5/1) to obtain product as white solid (150 mg, yield: 80%).

Step 2: Preparation of Compound 11A

Intermediate 17(50 mg, 0.15 mmol), Compound 5A (38.1 mg, 0.15 mmol) and $K_2CO_3$(41 mg, 0.3 mmol) were dissolved in DMF (5 mL). The mixture was stirred under room temperature for 8 hours. The reaction was monitored with TLC for completion. Water (50 mL) was added to the reaction liquid, which was extracted with dichloromethane (50 mL×2). The organic layers were combined, and the solvents were removed. The obtained residue was purified by column chromatography to obtain product as white solid (13 mg, yield: 21.09%).

$^1$H NMR (400 MHz, DMSO) δ 10.68 (s, 1H), 7.39 (dd, J=5.1, 1.9 Hz, 3H), 7.29 (dd, J=6.4, 3.1 Hz, 2H), 6.41 (d, J=2.1 Hz, 1H), 6.28 (d, J=2.1 Hz, 1H), 5.80 (s, 1H), 3.79-3.75 (m, 2H), 3.57-3.53 (m, 2H), 3.46-3.42 (m, 2H), 3.39-3.35 (m, 2H), 3.23-3.19 (m, 2H), 3.01-2.96 (m, 2H).

Figure 12:
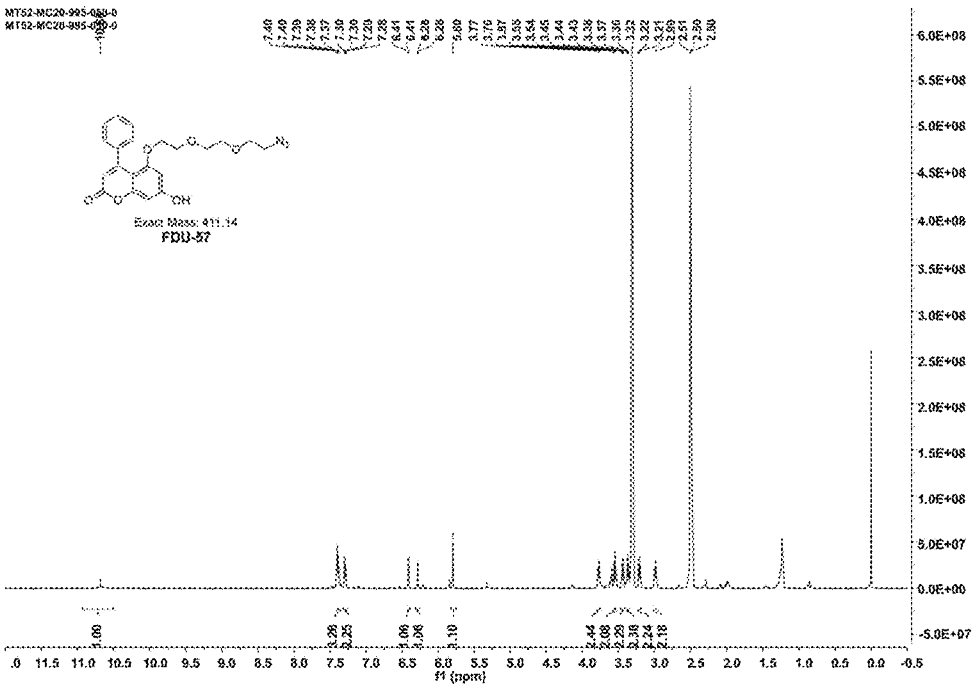

NMR spectrum was shown in FIG. 12.

Figure 13:
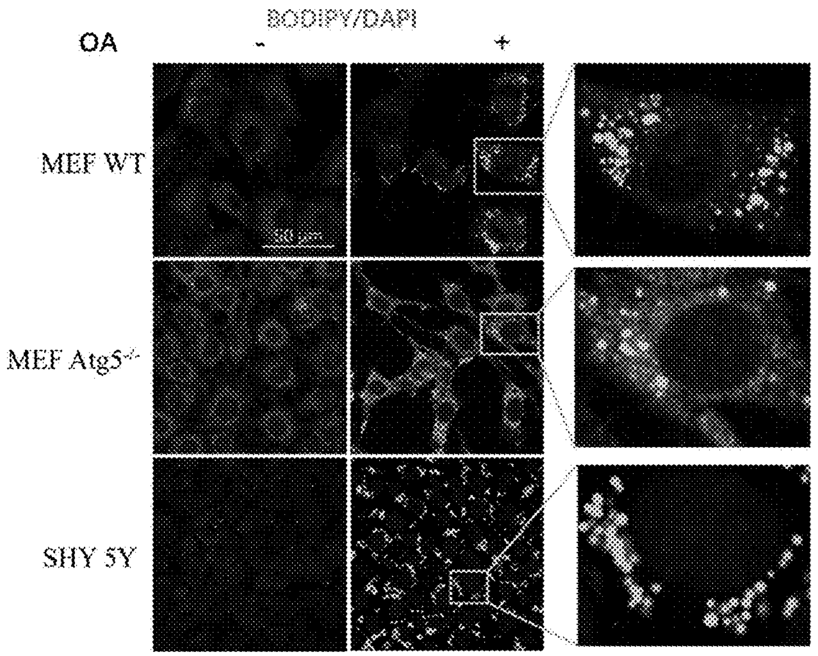
FIG. 13: Representative images of induced lipid droplets (green: lipid droplets; blue: nuclei) in wild-type and Atg5 knockout MEF cells and SH-SY5Y cells. Compound concentrations are as indicated, treatment time is 24h, lipid droplets are stained with BODIPY® 493/503, Scale bar=50 μm.

Example 1 Induction and Detection of Lipid Droplets in MEF Cells and SH-SU5Y Cells 1.1 Induction and Detection of Lipid Droplet Wild type MEF cells or SH-SY5Y cells were cultured in a DMEM culture medium containing 10% FBS. Cells were plated according to the method as described above (12 well plate was plated with aseptic treated slides). When cells grew to a confluence of 60-70%, lipid droplets were induced with OA for 30 h according to the method as described above, and then conduct batches of biological replicates as shown in the figures. No OA was added to act as a control. After induction, the lipid droplets were stained (BODIPY® 493/503 staining) according to the method as described above. The result was shown in FIG. 13. The average amount and average size of lipid droplets were calculated according to the method as described above. The results showed high overall identity between each biological replicates. It can be observed that the green signals without addition OA induction had a low amount and size, and they were all in cytoplasma, and thus the observation method was specific.

Figure 14:
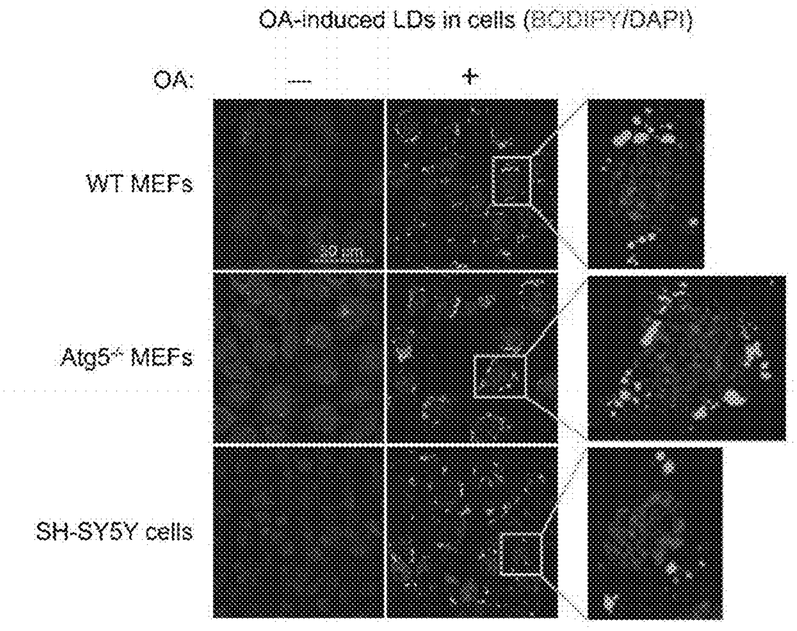
FIG. 14: Induction of lipid droplets by extracellular oleic acid (OA) treatment. Images of BODIPY 493/503 staining shows the staining results of cells with or without OA induction (6 hours after adding OA versus the control).

In addition, it was observed that the induced lipid droplets were formed rapidly within 0.5 h, and they reached the plateau at about 5 h after treatment, and remained stable within 24 h after induction (FIG. 14). Therefore, at 6 hours after the induction, and when the lipid droplets reached the plateau, cells in the examples herein were treated with the compounds.

Figure 15:
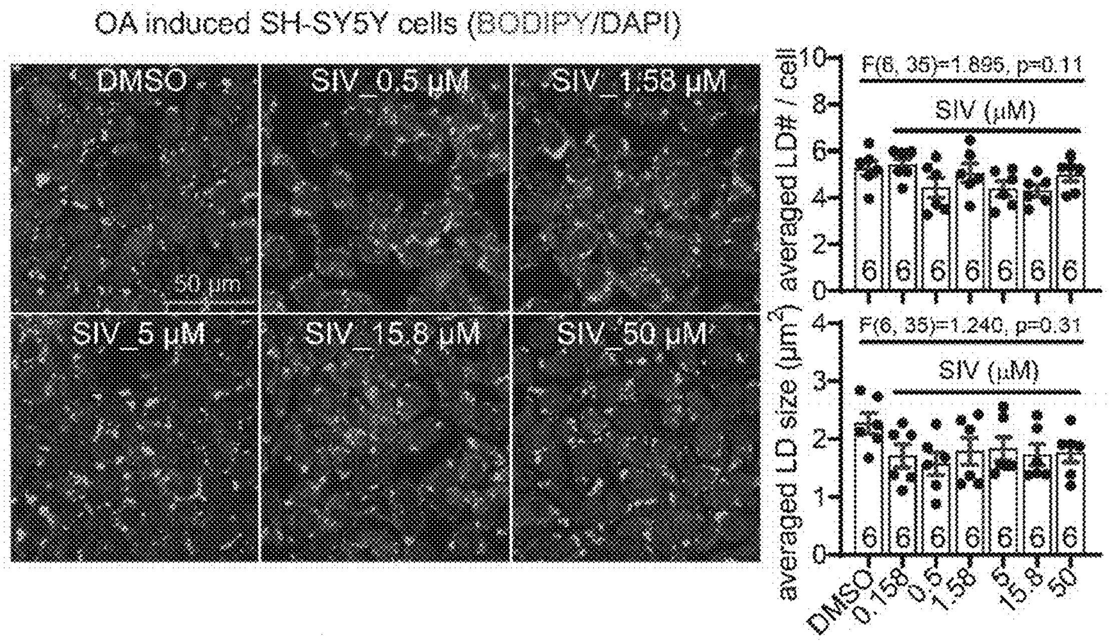
FIG. 15: Unconjugated LC3 binding compounds or lipid droplet binding compounds do not influence BODIPY signals. (B) OA-induced lipid droplets in SH-SY5Y cells are stained with BODIPY in the presence of 50 μM Sudan IV, and no decrease in lipid droplet signals is observed. (C-D) BODIPY493/503 staining results of OA-induced lipid droplets in the cells treated with unconjugated LC3-binding compounds or lipid droplet-binding compounds.

1.2 Test Method of Verifying Lipid Droplet Under Presence of High Concentration of Compounds Compounds of present disclosure did not compete with BODIPY for lipid droplet detection, and it was proved by the following experiment:

Under the presence of 50 μM of Sudan IV, the lipid droplet in MEF or SH-SY5Y cells which are induced by OA was stained according to method as described above. Compared with DMSO control group, it was observed that the lipid droplet had no signal change (FIG. 15).

It suggested that even under the highest compound concentration in the examples herein, the interaction between lipid droplets and compounds did not affect lipid droplet detection.

Example 2 Reduction of Lipid Droplets in MEF Cells by Compound 1A and Compound 2A Wild type MEF cells were cultured in a DMEM culture medium containing 10% FBS. Cells were plated according to the method as described above (12 well plate was plated with aseptic treated slides). When cells grew to a confluence of 60-70%, lipid droplets were induced with OA for 30 h according to the method as described above.

Figure 16A:
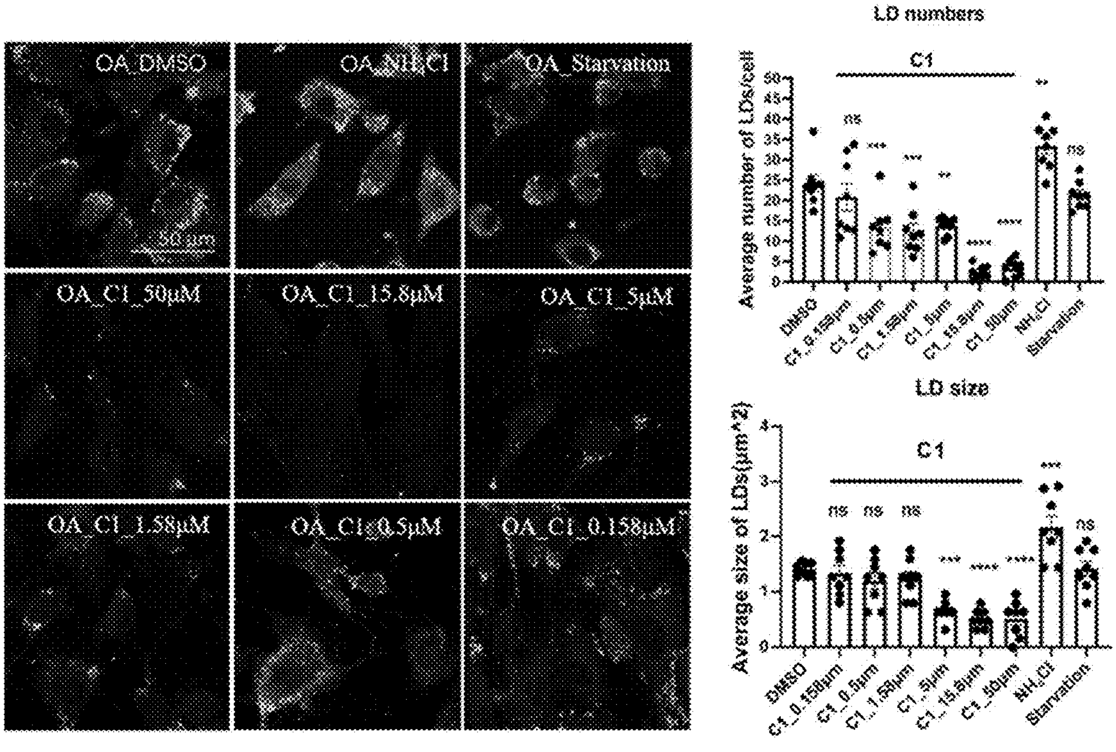
FIG. 16A: Left: representative images of Compound 1A reducing the induced lipid droplets (green: lipid droplets; blue: nuclei) in wild-type MEF cells. Compound concentrations are as indicated, treatment time is 24h, lipid droplets are stained with BODIPY® 493/503, Scale bar=50 μm. Right: the statistics of the change of the lipid droplets number and size are shown in the right figure (n=8 for each concentration). Statistical analysis is performed using one-way ANOVA and Dunnett's post-hoc analysis (compared to the DMSO group).
Figure 16B:
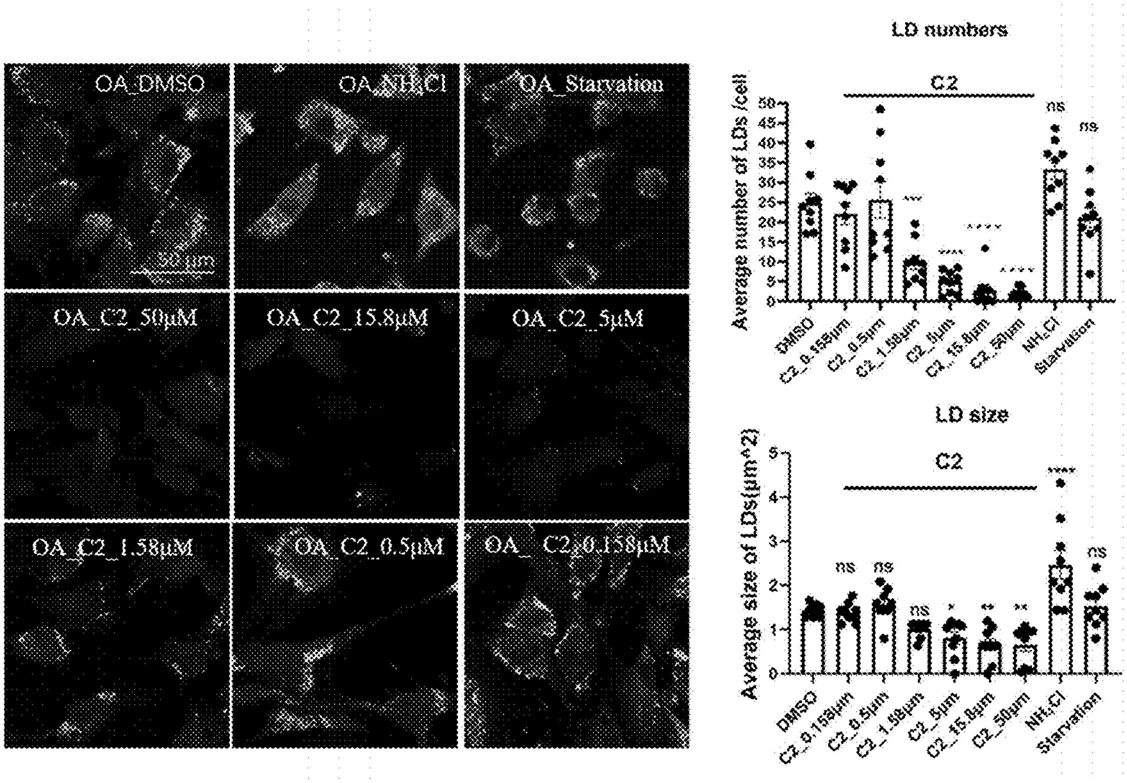
FIG. 16B: Left: representative images of Compound 2A reducing the induced lipid droplets (green: lipid droplets; blue: nuclei) in wild-type MEF cells, compound concentrations are as indicated, treatment is time 24h, lipid droplets are stained with BODIPY® 493/503, Scale bar=50 μm. Right: the statistics of the change of the lipid droplets number and size are shown in the right figure (n=9 for each concentration). Statistical analysis is performed using one-way ANOVA and Dunnett's post-hoc analysis (compared to the DMSO group).

At the time point of 6th hour after initiation of induction, the cells were treated (treated for 24 hours) with Compound 1A or Compound 2A (compound concentrations were 50 μM, 15.8 μM, 5 μM, 1.58 μM, 0.5 μM, 0.158 μM) according to the method as described above. The lipid droplet was stained according to the method as described above, and the result was as shown in FIG. 16. Under the concentration range of 0.5 μM-50 μM, Compound 1A significantly reduced the amount of lipid droplets, and under concentration range of 5 μM-50 μM, Compound 1A significantly reduced the size of lipid droplets. Under the concentration range of 1.58 μM-50 μM, Compound 2A significantly reduced the amount and size of lipid droplets. When the compound had a concentration of about 5-15 μM, most lipid droplets were removed. Autophagy blocker $NH_4Cl$ slightly increased the amount or size of lipid droplets (the amount was not significant, size of lipid droplet was significant increased), and activation of autophagy by starvation did not significantly change the amount or size of lipid droplets. This suggested that selectively targeting lipid droplets to autophagy could reduce lipid droplets more efficiently than enhancing global autophagy.

Figure 17:
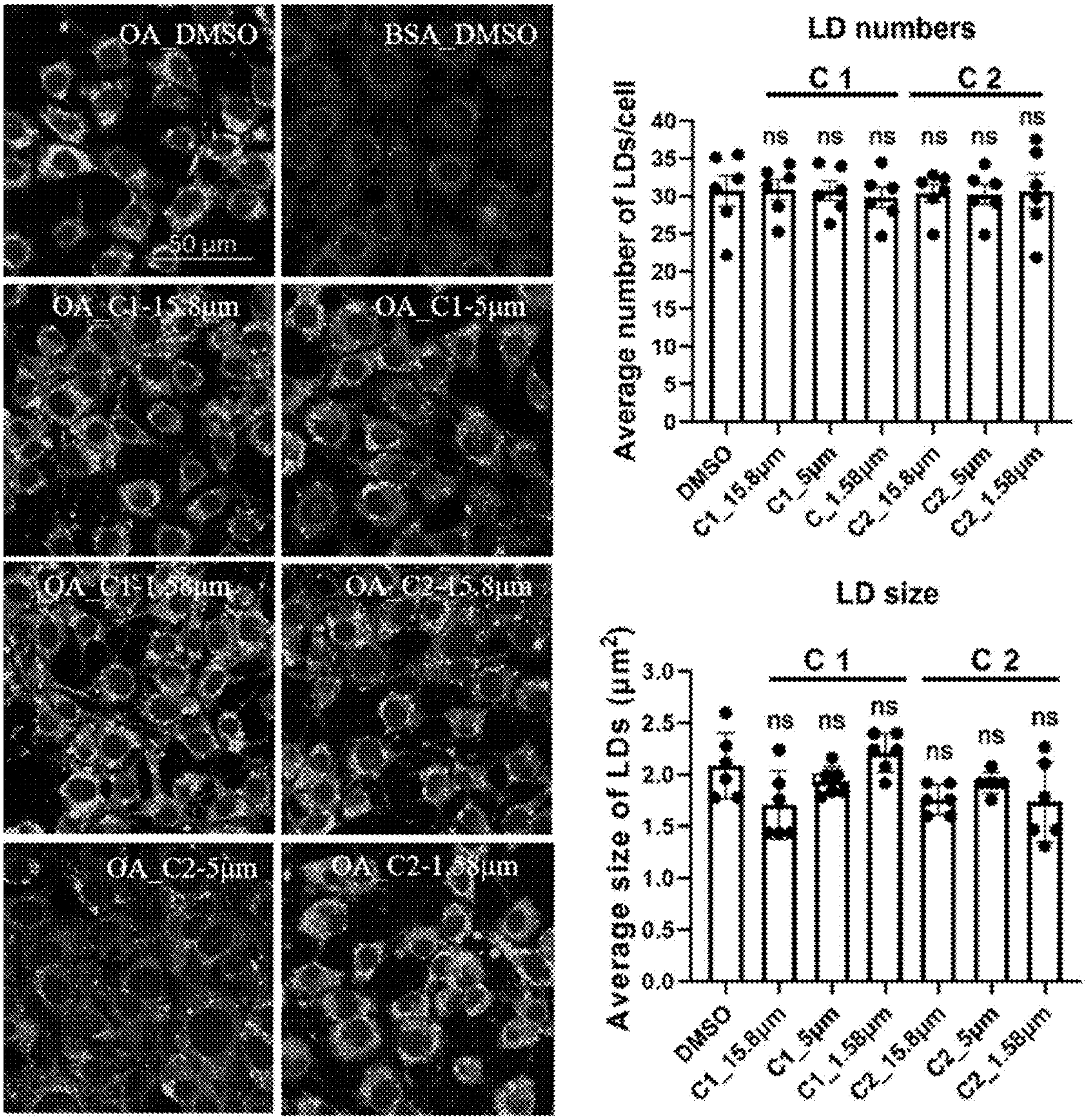
FIG. 17: Left: representative images of Compound 1A and Compound 2A not reducing lipid droplets (green: lipid droplets; blue: nuclei) in autophagy-deficient MEF cells. After adding Compound 1A or Compound 2A as shown in the figure (the concentrations are as indicated), Compound 1A or Compound 2A treatment does not change the level of lipid droplets in autophagy-deficient MEF (Atg5−/−) cells, compound treatment time is 24h, lipid droplets are stained with BODIPY® 493/503, Scale bar=50 μm. Right: the statistics of the change of the lipid droplets number and size are shown in the right figure (n=6 for each concentration). Statistical analysis is performed using one-way ANOVA and Dunnett's post-hoc analysis (compared to the DMSO group).

Example 3 Compound 1A and Compound 2A Did not Reduce Lipid Droplets in Autophagy-Deficient MEF Cells Wild type MEF cells and autophagy-deficient MEF cells (Atg5−/−) were cultured in a DMEM culture medium containing 10% FBS. Cells were plated according to the method as described above (12 well plate was plated with aseptic treated slides). When cells grew to a confluence of 60-70%, lipid droplets were induced with OA for 30 h according to the method as described above. At the time point of 6th hour after initiation of induction, OA induced lipid droplets for 30 h, and the cells were treated (treated for 24 hours) with Compound 1A or Compound 2A according to the method as described above. Wherein, the compound for use in treating wild type MEF cells had a concentration of 5 μM, 1.58 μM, 0.5 μM, and the compound for use in treating MEF Atg5−/− cells had a concentration of 5 μM. The control wells were replaced with DMSO (treated with DMSO). The lipid droplet was stained according to the method as described above, and the result was as shown in FIG. 17. The addition of Compound 1A or Compound 2A at a concentration of 1.5 μM or 5 μM to wild type MEF cells significantly reduced lipid droplets; in autophagy-deficient MEF cells (Atg5−/−), Compound 1A or Compound 2A at a concentration of 5 μM was ineffective. In addition, after 6 hours of OA induction for lipid droplets, DMSO treated cells were treated with 5 mM $NH_4Cl$ to inhibit autophagy, and lipid droplets were continued to be induced for 24 hours, and a slight increase on lipid droplets was observed relative to cells that were not treated with $NH_4Cl$. After 26 hours of OA induction for lipid droplets, the culture medium of DMSO treated cells was replaced with EBSS, and starved for 4 hours to induce autophagy, and a slight reduction on lipid droplets was observed relative to cells without starvation treatment. Therefore, lipid droplets can be degraded via cell autophagy. The compound of present disclosure could promote the degradation of lipid droplets via cell autophagy.

Figure 18A:
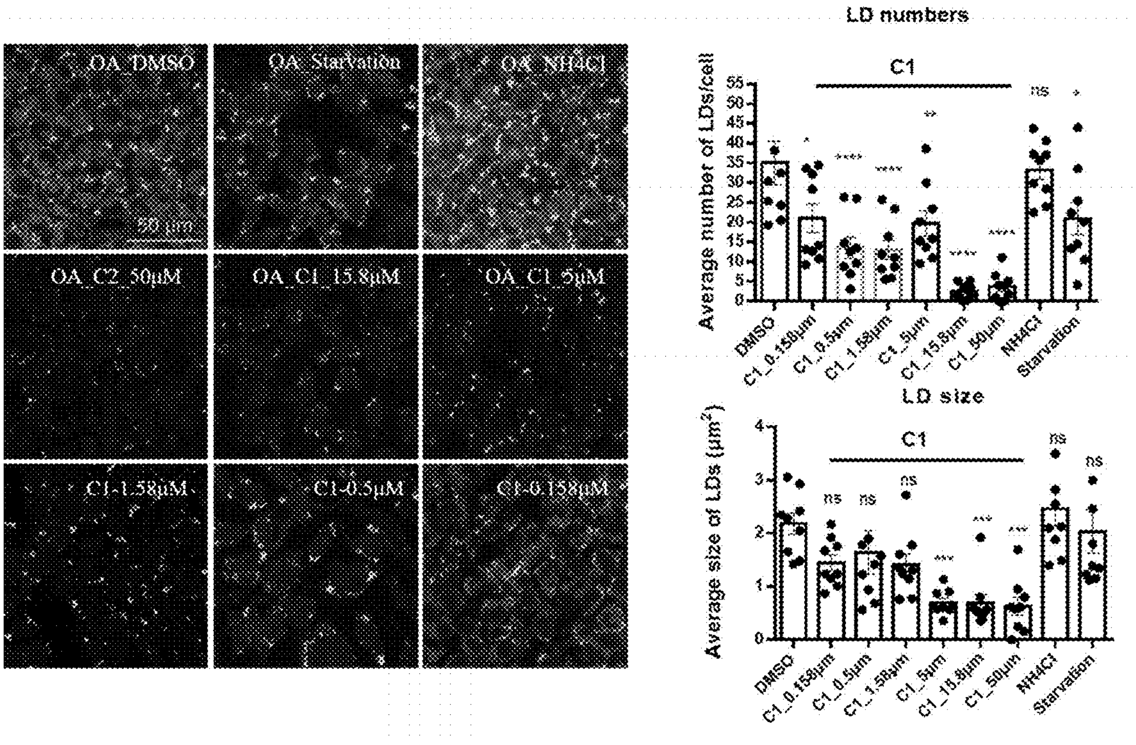
FIG. 18: Representative images (left) and quantifications (right) of Compound 1A (FIG. 18A) and Compound 2A (FIG. 18B) reducing lipid droplets (green: lipid droplets; blue: nuclei) in SH-SY5Y cells. Starvation for 4 hours by replacing medium with EBSS to induce autophagy (EBSS) or treatment with 5 mM $NH_4Cl$ to inhibit autophagy, significantly reduces or slightly increases lipid droplets, respectively. Compound 1A or Compound 2A treatment significantly reduces lipid droplet levels in SH-SY5Y cells after the addition of Compound 1A or Compound 2A as shown in the figure (the concentrations were as indicated). Compound treatment time is 24h, lipid droplets are stained with BODIPY® 493/503, Scale bar=50 μm. Right: the statistics of the change of the lipid droplets number and size are shown in the right figure (n=9 for each concentration). Statistical analysis is performed using one-way ANOVA and Dunnett's post-hoc analysis (compared to the DMSO group).
Figure 18B:
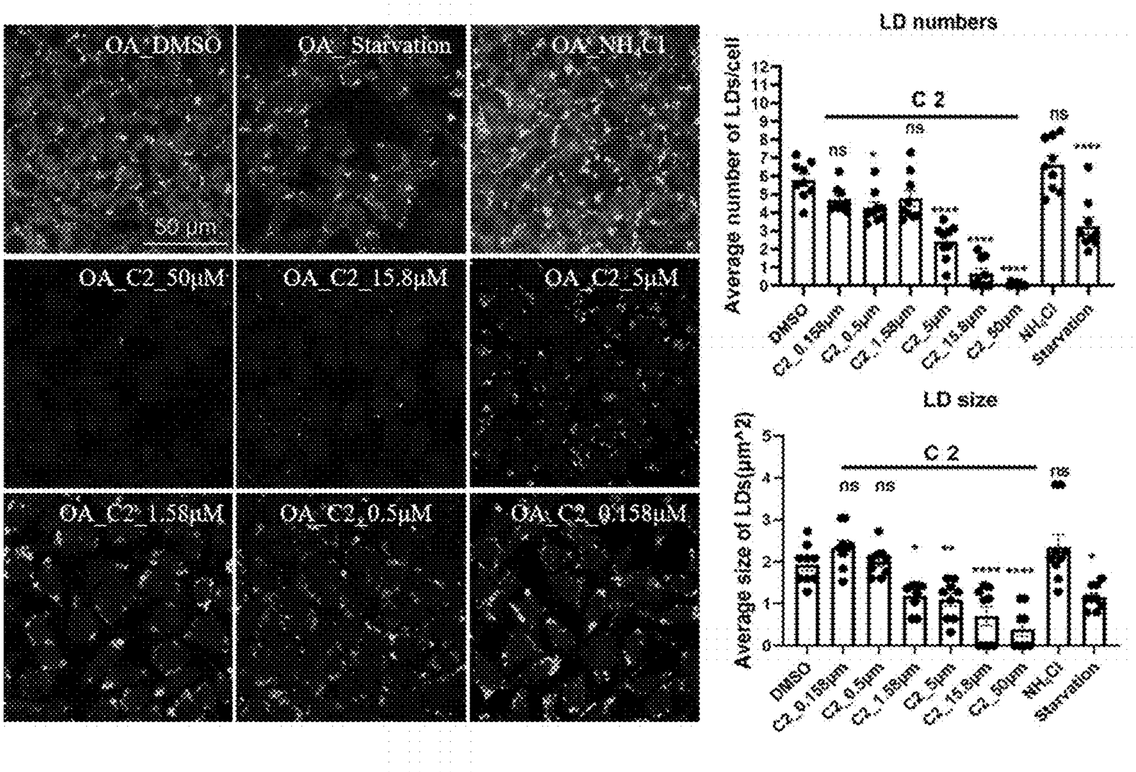

Example 4 Effect of Compound 1A and Compound 2A on Lipid Droplet Reduction in SH-SY5Y Cells The reduction of lipid droplets in SH-SY5Y cells by Compound 1A and Compound 2A was detected by a method that was similar to Example 2, and the result was shown in FIG. 18. Within the concentration range of 1.58 μM-50 μM, Compound 1A of Compound 2A could significantly reduce the amount of lipid droplet, and within the concentration range of 5 μM-50 μM, Compound 1A of Compound 2A could significantly reduce the size of lipid droplet.

Figure 19:
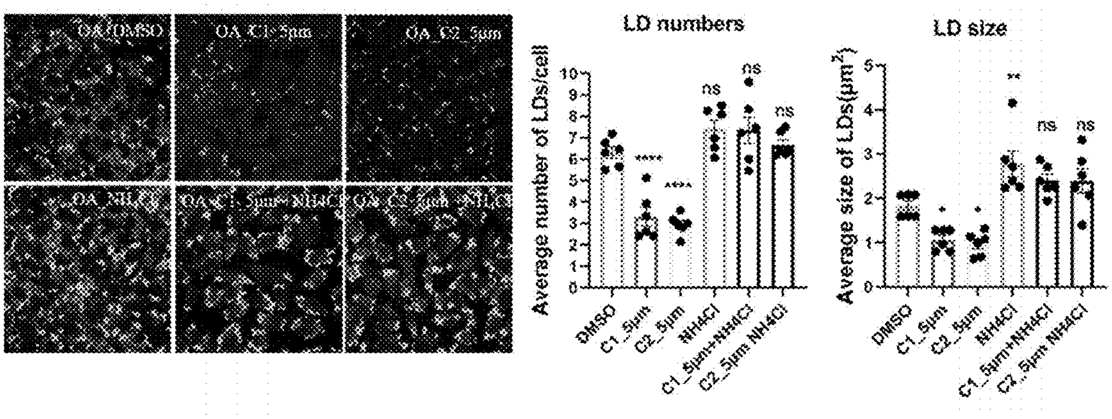
FIG. 19: Left: Representative images of Compound 1A and Compound 2A not reducing lipid droplets (green: lipid droplets; blue: nuclei) in SH-SY5Y cells in the presence of the autophagy blocker $NH_4Cl$ (5 mM). After adding Compound 1A or Compound 2A as shown in the figure (the concentrations were as indicated) and adding $NH_4Cl$ (5 mM) at the same time, Compound 1A or Compound 2A treatment does not change the lipid droplet levels in SH-SY5Y cells, compound treatment time is 24h, lipid droplets are stained with BODIPY® 493/503, Scale bar=50 μm. Right: the statistics of the change of the lipid droplets number and size are shown in the right figure (n=6 for each concentration). Statistical analysis is performed using one-way ANOVA and Dunnett's post-hoc analysis (compared to the DMSO group).

Example 5 Compound 1A and Compound 2A Did not Reduce Lipid Droplets in SH-SY5Y Cells Under the Presence of Autophagy Inhibitor By a method similar to Example 4, but after 6 hours from OA induction of lipid droplets, while the test compound was added into cells, autophagy inhibitor ammonium chloride ($NH_4Cl$, final concentration of 5 mM) was added simultaneously. After continuous treatment for 24 hours, the lipid droplets were stained. The result was shown in FIG. 19. Under the presence of autophagy inhibitor, Compound 1A and Compound 2A did not reduce lipid droplets in SH-SY5Y cells. Therefore, the compound of present disclosure reduced lipid droplets by targeting autophagy of cells.

Example 6 Unconjugated LC3 Binding Compound or Lipid Droplet Probe Did not Reduce Lipid Droplets in MEF Cells or SH-SY5Y Cells The effects of unconjugated LC3 binding Compound A1, A5 and unconjugated lipid droplet probe ORBB (Sudan IV) respectively on lipid droplets in SH-SY5Y cells (FIG. 20A) and MEF cells (FIG. 20B) were detected by a method similar to Example 2.

Figure 20A:
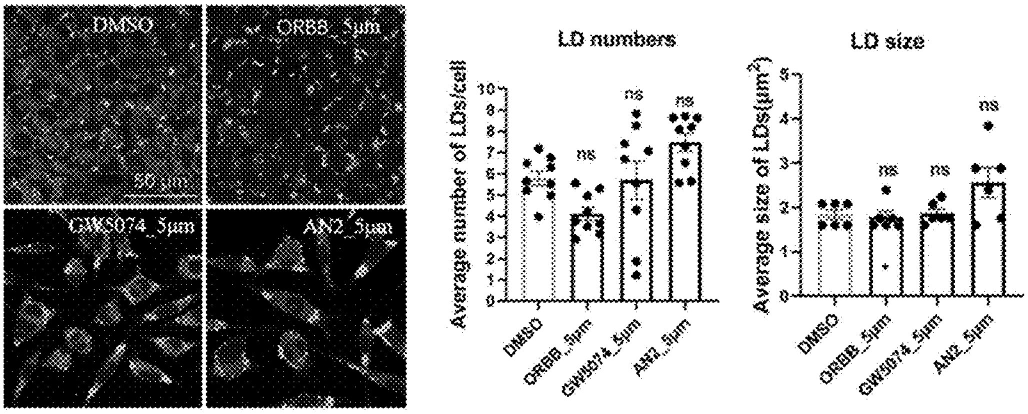
FIG. 20: Representative images (left) and quantifications (right) of compounds effects on OA-induced lipid droplets (green: lipid droplets; blue: nuclei) in SH-SY5Y cells (FIG. 20A) and wild-type MEF cells (FIG. 20B). Compound concentrations are as indicated, treatment time is 24h, lipid droplets are stained with BODIPY® 493/503, Scale bar=50 μm. Right: the statistics of the change of the lipid droplets number and size are shown in the right figure (n=9 for each concentration in figure A, n=6 for each concentration in figure B). Statistical analysis is performed using one-way ANOVA and Dunnett's post-hoc analysis (compared to the DMSO group). Unconjugated LC3-binding compounds or lipid droplet probes does not reduce the number and size of lipid droplets in SH-SY5Y cells or MEF cells.
Figure 20B:
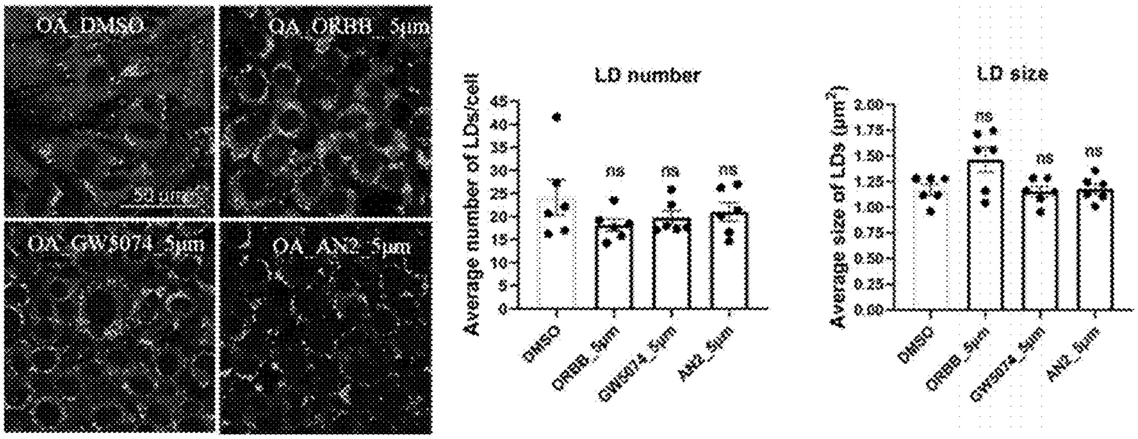

After the SH-SY5Y cells were treated with Compound A1, A5 or Sudan IV at a concentration of 5 μM, lipid droplets did not significantly decrease or become smaller (FIG. 20A). After the MEF cells were treated with Compound A1, A5 or Sudan IV at a concentration of 5 μM, lipid droplets did not significantly decrease or become smaller (FIG. 20B). Therefore, when compounds that could only bind to LC3 or compounds that could only bind to lipid droplet were present alone (i.e., in unconjugated form), they did not have the effect of reducing lipid droplets. In compounds of present disclosure, LC3 binding moiety was covalently linked with lipid droplet binding moiety, and thus could achieve the effect of reducing lipid droplet.

Example 7 Reducing Effect of Compound on Lipid Drops in 3T3-L1 Fat Precursor Cell Differentiated Fat Cells 7.1 Preparation of 3T3-L1 Fat Precursor Cell Differentiated Fat Cells 3T3-L1 cells were plated, medium was renewed. Then induction culture medium was used to initiate inducing differentiation, and then cultured for 45-48 h; medium was renewed, and mature culture medium was used and cultured for 2 days; medium was renewed, and mature culture medium was used and cultured for another 2 days; medium was renewed, and normal culture medium was used and cultured for 2 days (more and larger lipid droplets may be observed at this point). Wherein, normal culture medium: 10% FBS+90% DMEM+1% P/S, mature culture medium: 10% FBS+90% DMEM, 50 μg/mL Insulin (Sigma). Induction culture medium: 10% FBS+90% DMEM+5 μg/mL Insulin (Sigma)+0.5 mM IBMX (Isobutymethyxanthine)+1 μM Dexmethasone.

Figure 21:
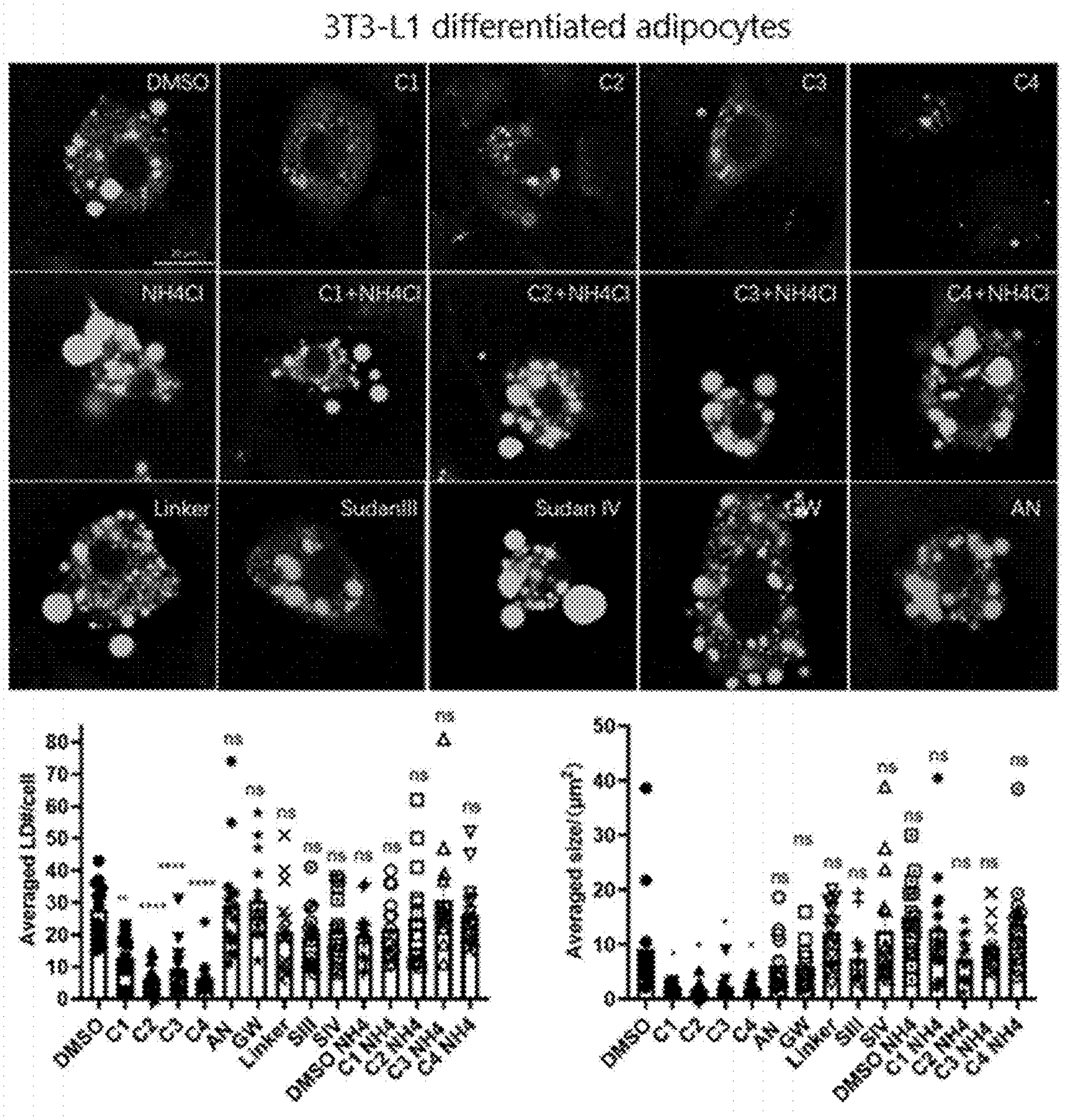
FIG. 21: Top: Representative images of 3T3-L1 preadipocytes-differentiated adipose cells (green: lipid droplets; blue: nuclei) in the absence of induction. Compounds significantly reduce lipid droplets in WAC, and in the case of treatment with 5 mM $NH_4Cl$ to inhibit autophagy, lipid droplets are slightly increased, while other control compounds do not influence lipid droplets. Compound treatment time is 24h, lipid droplets are stained with BODIPY® 493/503, Scale bar=50 μm. Right: The statistics of the change of the lipid droplets number and size are shown as follows (n=15). Statistical analysis is performed using one-way ANOVA and Dunnett's post-hoc analysis (compared to the DMSO group).

7.2 Effects of Compound on Lipid Droplets in 3T3-L1 Fat Precursor Cell Differentiated Fat Cells Conjugated compounds (Compound 1A and Compound 2A, Compound 3A, Compound 4A, Linker (10-bromo-1-decanol), LC3 binding Compound A1, A5 and lipid droplet probe Sudan IV, Sudan III) were added for treatment, and DMSO acted as a control. Compound 1A+$NH_4Cl$ group, Compound 2A+$NH_4Cl$ group, Compound 3A+$NH_4Cl$ group and Compound 4A+$NH_4Cl$ group were set at the same time, and the time for treatment were all 24 hours, wherein conjugated compound/A1/A5/Sudan III/Sudan IV were all 5 μM, and $NH_4Cl$ was 5 mM. The experiment results were shown in FIG. 21, wherein conjugated compound could reduce the amount of lipid droplets and could change the size of lipid droplets. Under the treatment of $NH_4Cl$, the effect of the compound on lipid droplets was blocked, and it could as well be observed that LC3 binding Compound A1, A5, Linker, lipid droplet probe Sudan IV, Sudan III showed no significant effect on the amount/size of lipid droplets. In the compounds of present disclosure, LC3 binding moiety was covalently linked with lipid droplet binding moiety, and thus could achieve the effect of reducing human fat cell endogenous lipid droplet.

Example 8 Affinity Activity of the Compounds for LC3

8.1 OI-RD Detection of Affinity Activity with LC3B

According to method of prior art (Zhu et al., Sensors (Basel) 2016, 16(3), 378; Fei et al., J Biomed Opt 2010, 15(1), 016018), contact microarray dot printer (SmartArrayer 136, CapitalBio Corporation) was used to prepare compound chips. Each compound was dot printed 3 copies. The compounds that not fixed on surface of the chips were washed, and the chips were sealed and cleaned. OI-RD microscope was used to scan the images. LC3B (SEQ ID NO: 3) was used as target protein. The compound chips and target protein (with a concentration of 238 nM) were incubated together for 2 hours. The chips were washed and scanned. OI-RD images before, during and after incubation with target protein were obtained. The signal change in real-time dynamic change image was analyzed, and the signal was collected once per 10 millisecond. The affinity reaction parameters between the compound and LC3B were calculated, and the result was shown in Table 1.

TABLE 1

Equilibrium dissociation constants of affinity reaction between the compound and LC3B detected by OI-RD

| | Compound A1 | Compound A5 | Compound A8 |
|---|---|---|---|
| $K_d$ (nM) | 467.7 | 540.1 | 238.2 |

8.2 MST Detection of Affinity Activity with LC3B

Figure 22:
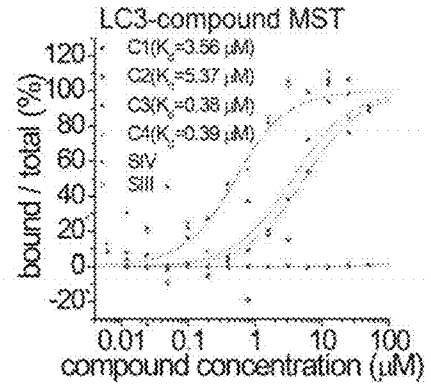
FIG. 22: Measurements of conjugated compounds, Sudan III, Sudan IV and LC3B binding affinity by MST. In the range of submicromolar to micromolar, Kd values of conjugated compounds are observed and the lipid droplet probes have no affinity to LC3B.

According to the method as described above, microscale thermophoresis was used to verify the affinity activity between the compound and LC3B, and the result was shown in Table 2 and Table 3. The results showed that there was an interaction between the conjugated compound and LC3B (FIG. 22). No interaction between lipid droplet binding compound (Sudan III or Sudan IV) and LC3B was observed.

TABLE 2

Equilibrium dissociation constants of affinity reaction between the conjugated compound and LC3B

| Compound | $K_d$ (μM) | Compound | $K_d$ (μM) |
|---|---|---|---|
| Compound 1A | 3.56 | Compound 2A | 5.37 |
| Compound 3A | 0.38 | Compound 4A | 0.39 |

TABLE 3

Equilibrium dissociation constants of affinity reaction between the LC3 binding compound and LC3B

| Compound | $K_d$ | Compound | $K_d$ |
|---|---|---|---|
| Compound A1 | 4.76 μM | Compound A2 | 2.35 μM |
| Compound A3 | 34.5 nM | Compound A4 | 3 μM |
| Compound A5 | 3.95 μM | Compound A7 | 671.6 nM |
| Compound A8 | 0.462 ± 0.11 μM | Compound A9 | 2.58 ± 0.245 μM |
| Compound A10 | 3.98 ± 0.537 μM | Compound A11 | 2.78 ± 0.577 μM |
| Compound A12 | 21.3 ± 1.69 μM | Compound A13 | 5.19 ± 0.282 μM |

Example 9 Detection of TAG-Conjugated Compound-LC3B Complex

TAG is one of the main lipid components in lipid droplets, and it interacted with Sudan III or Sudan IV. Sudan III or Sudan IV may be recruited for use to stain lipid droplets. The inventor detected the TAG-conjugated compound-LC3 ternary complex in vitro by the following modified ELISA method.

Mouse triglyceride ELISA kit (Mybiosource, cat. no. MBS2516318) was used for detection. Some adjustment was made on the detection relative to the scheme from the manufacturer.

Recombinant purified LC3-GST was added to all samples, such that GST antibody can be used for final detection. The well containing only recombination purification acted as a blank control.

The mouse TAG that could specifically bind to antibody was used to precoat the assay plates. The washing buffer from the kit was added to each well to incubate for 5 minutes, and then the solution was aspirated. Each of the wells was added with 100 μL of TAG containing solution (30 μL 3 μg/mL of TAG that pre-dissolved in standard solution+70 μL $ddH_2O$) immediately. The plate was covered, and slight vortex was performed for mixing, and then incubated at 37° C. for 1 hour. The solution was aspirated and each of the wells was added with 250 μL of washing buffer. Soaked for 1 to 2 minutes, and the solution was aspirated or poured out from each well. Such washing step was repeated for 3 times. 100 μL of test compound (5 μM of Compound 1A, Compound 2A, Compound 3A or Compound 4A, DMSO acted as a control) diluted in the working solution was immediately added, and incubated for 1 hour at 37° C. Washed for 3 times, and 250 μL of washing buffer for each time, and then 100 μL of HRP labeled anti-GST antibody (1:2000 in working solution, ProteinTech, cat. no. HRP-66001) was added to each well. The plate was covered, and then incubated at 37° C. for 30 minutes. The solution was aspirated or poured out from each well. Washed for 5 times, and 250 μL of washing buffer for each time. 90 μL of substrate reagent was added to each well, and the plate was covered, and incubated at 37° C. for no more than 10 minutes. The reaction time could be shortened until the actual color changed. 50 μL of reaction terminated liquid was added to each well in the same order as the addition of substrate solution to ensure the same reaction time. The optical density (OD value) of each well was determined by BioTek Synergy 2 plate reader, wherein the wavelength was set as 450 nm.

Figure 23:
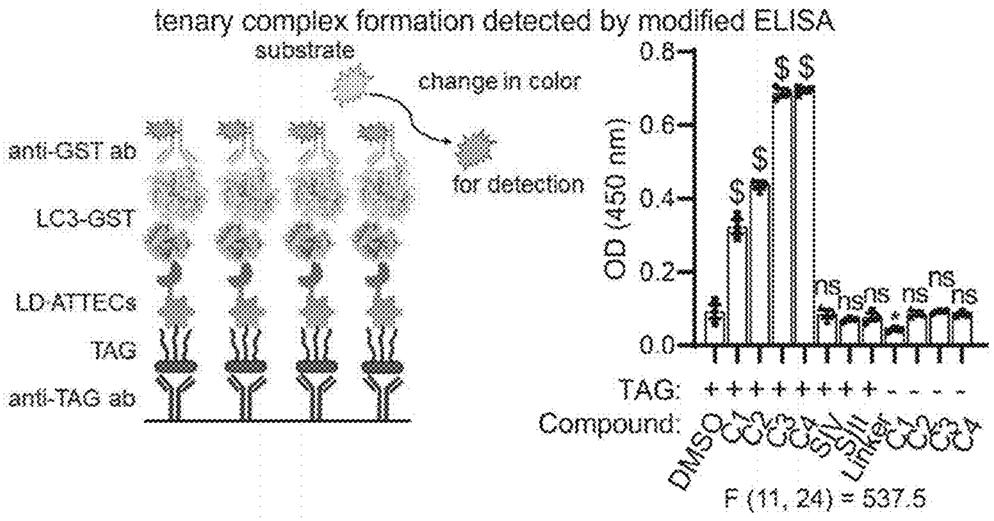
FIG. 23: Left: Schematic illustration of measurements of the ternary complex formation using modified ELISA assays; Right: the blank corrected ELISA signals of the samples (n=3).

The assay result proved that TAG-conjugated compound-LC3 ternary complex was formed in vitro (FIG. 23), suggesting that lipid droplet binding compounds (e.g., Sudan III or Sudan IV) were sufficient to target lipid droplets to autophagosome in cells, and the conjugated compounds of present disclosure could target TAG or TAG-containing lipids to cell autophagy.

Figure 24:
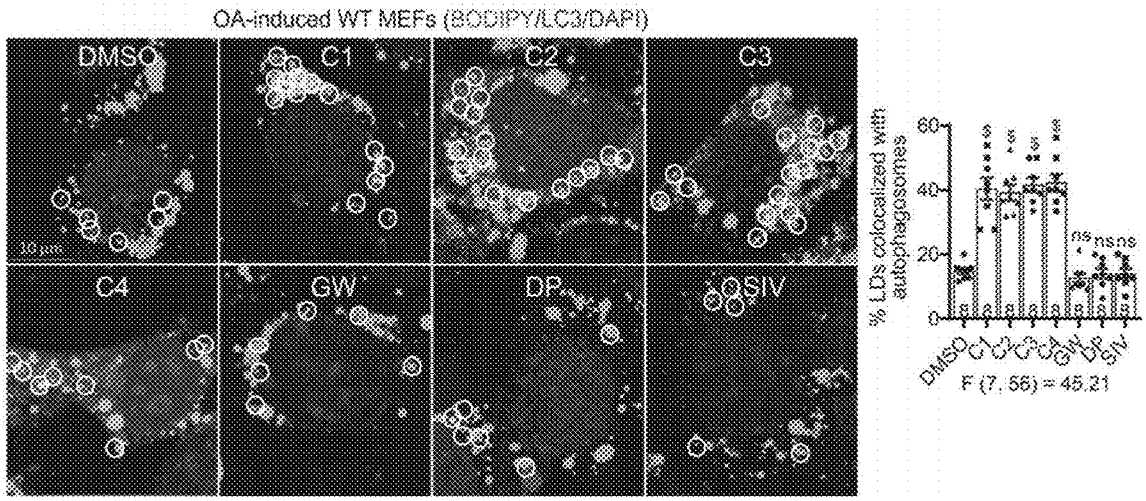
FIG. 24: Left: Aggregation points (red) of the autophagosome marker protein LC3B indicated by mCherry show autophagosomes, BODIPY® 493/503 staining indicates lipid droplets (green) and DAPI indicates nuclei (blue). The average size of lipid droplets is larger than that of autophagosomes. The ratio of red overlapping green or closely surrounding green indicates the colocalization of autophagosomes with lipid droplets. Right: The percentage of lipid droplets partially colocalized with autophagosomes in the samples. Experimental results are from 2 independent transfection batches. Analysis is performed using one-way ANOVA and Dunnett's post-hoc analysis (compared to the DMSO group).

Example 10 Colocalization of Autophagosome and Lipid Droplets in Cell Under the Influence of the Compound In MEF cells, mCherry-LC3B was expressed by cDNA plasmid transfection. At 30th hour of overexpression, OA was added into cells for lipid droplet induction. 6 hours later, the compound was added for 3 hours' treatment, and then cells were subjected to immunostaining. Due to short time of treatment, the lipid droplets were still not significantly reduced by the compound. Lipid droplets (green) were stained with BODIPY stain, and nucleus were indicated with DAPI stain. The aggregation point of autophagosome labeled protein LC3B indicated by mCherry showed the autophagosome. The lipid droplets had a larger average size than that of autophagosome, and the ratio of red overlapping with green or the ratio of red clinging to green indicated the colocalization of autophagosome with lipid droplets. In FIG. 24, the colocalized autophagosome-lipid droplet was marked with circles. After the MEF cells were treated with 5 μM of Compound 1A or Compound 2A or Compound 3A or Compound 4A, compared to DMSO control, the ratio of colocalization of red and green aggregation point was significantly increased (FIG. 24). T Therefore, the compound of present disclosure could increase the identification of lipid droplets by autophagosome. No such effect was observed in cells treated with control Compound A1, A5 or lipid droplet probe Sudan IV.

Figure 25:
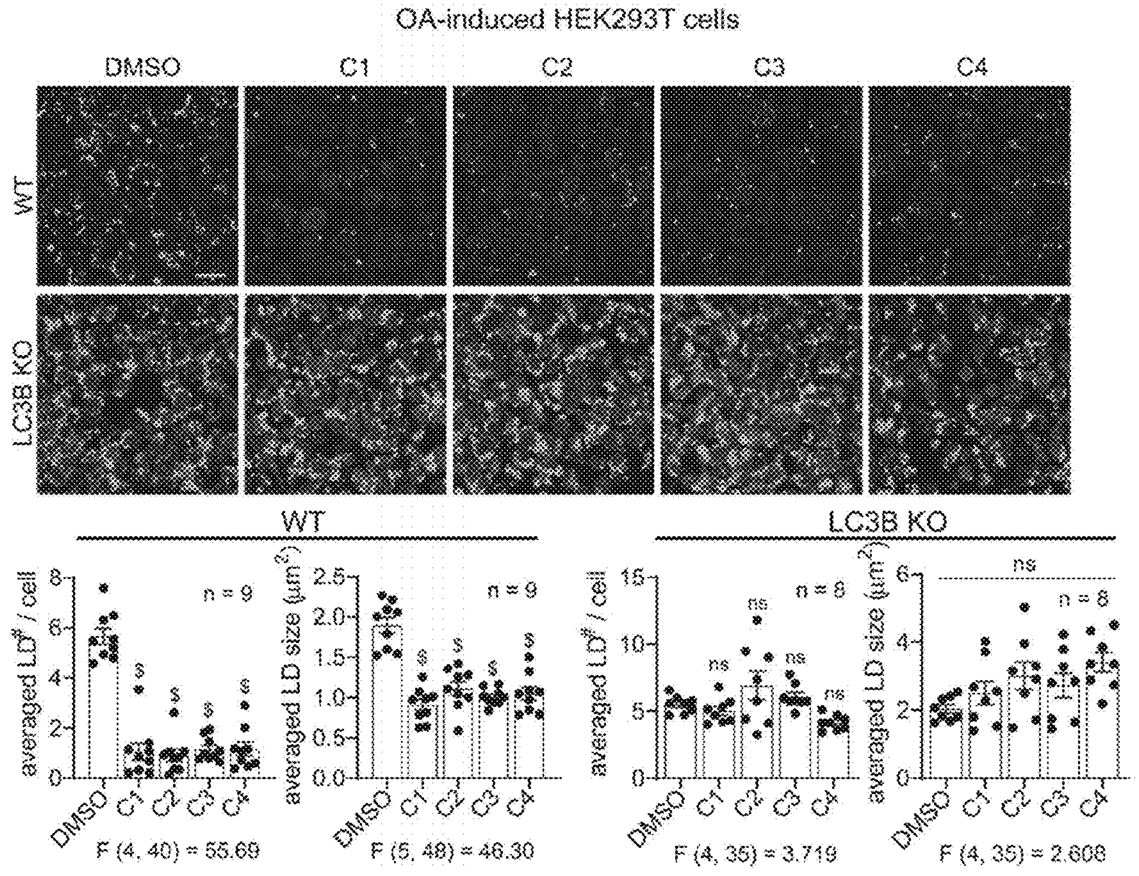
FIG. 25: The lipid droplets in wild-type and LC3B knockout HEK293T cells are treated with compounds. BODIPY493/503 staining. Scale bar: 20 μm.

Example 11 Compound Did not Reduce Lipid Droplets in LC3B Knockout HEK293T Cells The effect of conjugated compounds (Compound 1A, Compound 2A, Compound 3A or Compound 4A at a concentration of 5 μM) on lipid droplets in LC3B knockout HEK293T cells was tested by a method similar to Example 2. The knockout of LC3B gene largely blocked reduction of lipid droplets that induced by conjugated compounds (Compound 1A, Compound 2A, Compound 3A or Compound 4A) (FIG. 25).

Example 12 the Compound Did not Affect the Level of Autophagy Function, the Amount of Autophagosomes, Lysosomes and the Level of Autophagy Substrate Indicator Did not Change 12.1 Autophagosome Imaging Wild type MEF cells were plated according to the method as described above (12 well plate was plated with aseptic treated slides). When cells grew to a confluence of 60-70%, mCherry-LC3B plasmid was transfected, and after 12 hours' transfection, the medium was replaced as a fresh culture medium (i.e., MEF cells normal culture medium). After 36 hours, compound (Compound 1A, Compound 2A, Compound 3A or Compound 4A, at a concentration of 5 μM) was added for 24 hours' treatment, and then the cells were stained with BODIPY according to the method as described above (FIG. 26A).

12.2 Lysosome Imaging

By a method similar to Example 2, the wild type MEF cell were treated with the compound, and then the cells were stained with Lysotracker according to the method as described above to observe lysosome (FIG. 26B).

12.3 Cell Imaging of Transfected mRFP-GFP-LC3B

By a method similar to 12.1, the cells were transfected with mRFP-GFP-LC3B plasmid. The cells that transfect mRFP-GFP-LC3B were imaged according to the method as described above, and dual fluorescent autophagic flux was observed (FIG. 26C).

12.4 Effect of Compound on Cells Treated with Bafilomycin A1

Wild type MEF cells were plated according to the method as described above. When cells grew to a confluence of 80-90%, the compound was added for 24 hours' treatment. At the time point of 18th hour of the compound treatment, 500 nM of BFA (Bafilomycin A1, also referred as bafA) was added. Western blot experiment was conducted. The result indicated that the increased expression of LC3-II and SQSTM1/P62 induced by Bafilomycin A1 was not affected by conjugated compounds (FIG. 26D).

Figure 26:
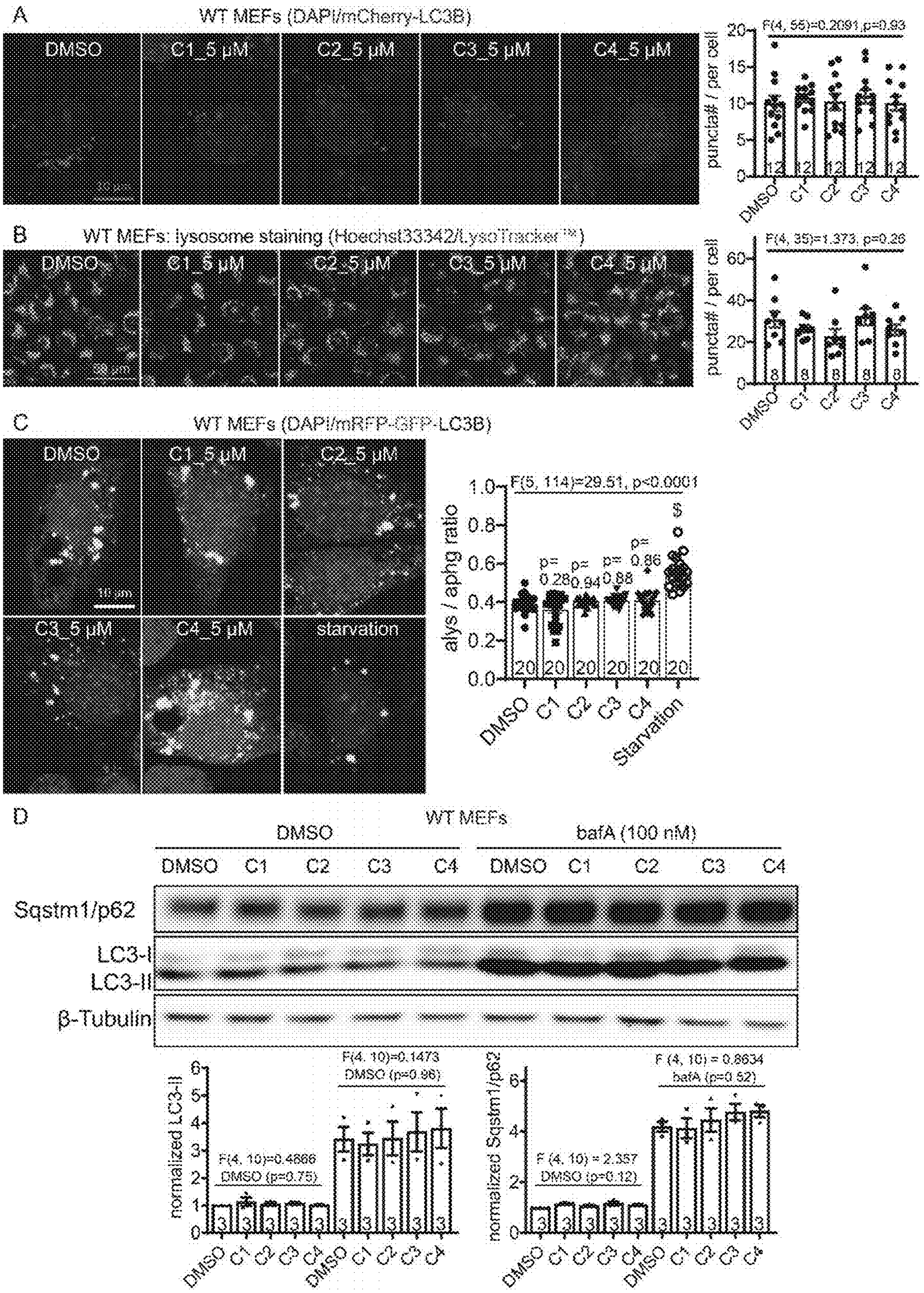
FIG. 26: Compounds do not influence the levels of autophagy function. (A) Compound-treated mCherry-LC3B transfected MEF cells do not change the LC3B puncta number. (B) Lysotracker staining shows no change in lysosome number. (C) mRFP-GFP-LC3B transfected MEF cells are treated with compounds or starvation (medium replacement with EBSS for 4 hours). Red only puncta indicate autolysosomes and yellow puncta indicate autophagosomes. No change in the ratio of autolysosomes (ALYS; red+, green−)/autophagosomes (APHG; red+, green+) is observed, suggesting that compounds have no influence on autophagy flux. (D) western-blots show no changes in LC3B and SQSTM1/p62 in MEF cells treated with compounds, LC3-II indicates autophagosomes, and the internal control is Tubulin. The statistical results are shown as follows. Statistical analysis is performed using one-way ANOVA and Dunnett's post-hoc analysis (compared to the DMSO group).

The result showed that there was no significant change on the amount of autophagosome or lysosome (FIG. 26A-B), autophagosome-lysosome fusion (FIG. 26C) and levels of autophagy markers (LC3-II and SQSTM1/p62) (FIG. 26D). Above all, it proved that there was no change on autophagic flux.

Example 13 Compound 1 or Compound 2 Did not Affect the Integrity of Cell Membrane of Nuclear Membrane, and Did not Impair Mitochondrion Function Wild type MEF cells were treated with conjugated compound (Compound 1A, Compound 2A, Compound 3A or Compound 4A at a concentration of 5 μM) according to a method similar to Example 2. After treatment for 24 hours, according to the method as described above, immunostaining was conducted with Lamin B1 (FIG. 27A), CellMask™ (FIG. 27B), MitoTracker™ Red and MitoTracker™ Green (FIG. 27C), and nuclear membrane, cell membrane, healthy mitochondrion as well as total mitochondrion were observed.

Figure 27:
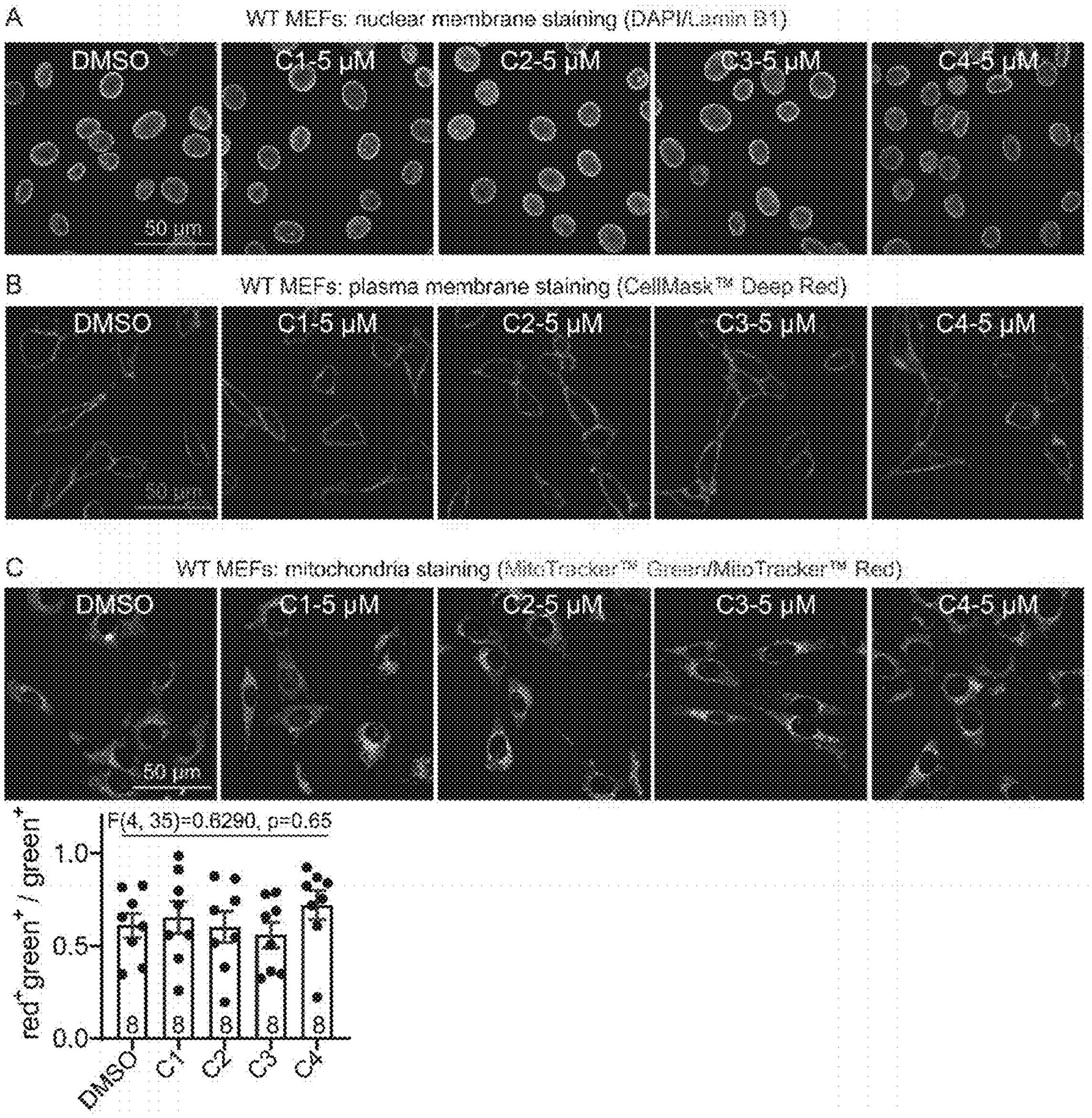
FIG. 27: (A-B) Representative staining images (from >3 replicates) showing compounds do not impair nuclear membranes (A, Lamin B1 immunostaining) or cell membranes (B, CellMask™ staining). (C) Red indicates healthy mitochondria (MitoTracker™ Red): green indicates total mitochondria (MitoTracker™ Green). The ratio of total red+ green+ area/green+area each well indicates the ratio of healthy mitochondria, representing the integrity of mitochondria membranes.

The result showed that the conjugated compound did not impair the nuclear membrane (FIG. 27A) or cell membrane (FIG. 27B), mitochondrion membrane (FIG. 27C). It indicated that the conjugated compound of present disclosure reduced the lipid droplets mainly composed of neutral lipids, meanwhile it did not affect the integrity of cell membrane or nuclear membrane mainly composed of polar lipids and did not impair mitochondrion function.

Example 14 Reducing Effect of Compound 1A and Compound 2A on Lipid Droplets in Human Normal Liver Cell Line QSG7701

10% FBS+90% RPMI 1640 culture medium was used for cultivation, cell incubator culture condition of 37° C. and 5% $CO_2$ was used. Cells were plated as 50 thousands/well (12 well plate was plated with aseptic treated slides). When cells grew to a confluence of 80-90%, the compound (Compound 1A or Compound 2A, at a concentration of 5 μM) was added for treatment, and LC3 binding Compound A1, A5, lipid droplet probe Sudan IV as well as DMSO acted as a control. Time for treatment was 24 hours, and Compound 1A/Compound 2A/A1/A5/Sudan IV were all 5 μM, and $NH_4Cl$ was 5 mM. The test result was shown in FIG. 28. Although human normal liver cell has relatively less amount of endogenous lipid droplets, Compound 1A and Compound 2A could reduce the amount of lipid droplets, but LC3 binding Compound A1, A5, lipid droplet probe Sudan IV had no significant effect on lipid droplets. In the compounds of present disclosure, LC3 binding moiety was covalently linked with lipid droplet binding moiety, and thus could achieve the effect of reducing liver cell endogenous lipid droplet.

Example 15 Effect of Compound 5A, 6, 7, 8, 9, 10A, 10B and 11A on MEF Cells 15.1 the Reducing Effect of the Compound on Lipid Droplets in MEF Cells The reducing effect of Compound 5A, 6, 7, 8, 9, 10A, 10B and 11A on lipid droplets in wild type MEF cells was detected according to a method similar to Example 2.

15.2 TAG Detection of MEF Cells

Wild type MEF cells of OA induced lipid droplets were treated with conjugated compound (Compound 1A, Compound 2A, Compound 3A or Compound 4A, at a concentration of 5 μM) according to a method similar to Example 2. After treatment for 24 hours, cells were collected, split, fractured, and supernatant was taken to determine the protein concentration. The TG assay kit A110-1-1 of Nanjing Jiancheng Biological Company was used for the determination to calculate TAG level per unit protein concentration.

Figure 29:
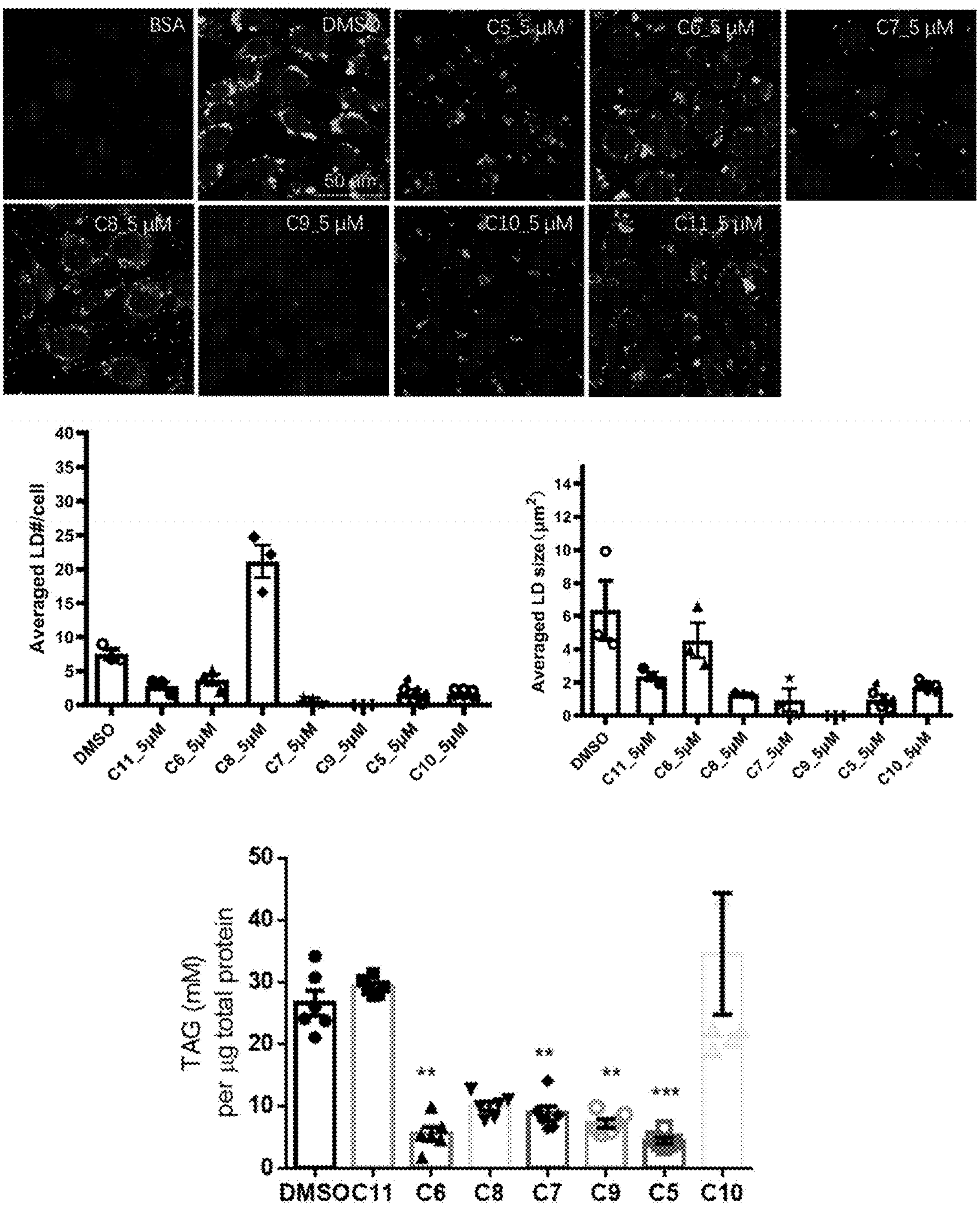
FIG. 29: Top: Compounds reduce the induced lipid droplets in wild-type MEF cells. Compound concentrations are 5 μm, treatment time is 24h, lipid droplets are stained with BODIPY® 493/503, Scale bar=50 μm. Middle left, middle right, bottom: the statistics of the change of the lipid droplets number and size and results of measurement of cellular TAG levels. Statistical analysis is performed using one-way ANOVA and Dunnett's post-hoc analysis (compared to the DMSO group).

The result was shown in FIG. 29. Under the concentration range of 5 μM, all tested compounds showed a significant reducing effect on the amount of lipid droplets.

Example 16 Determination of Compound In Vivo of Intraperitoneal Injection Mouse

Experiments were conducted by SIM-Servier joint laboratory.

(1) Male mice were injected intraperitoneally (ip) with Compound 3A (30 mg/kg, administration volume of 150 μL) or DMSO for a control.

(2) Anesthetized with chloral hydrate (200 μL/kg of 10% stored solution) at indicated time point, and cardiac blood was collected with a vacuum blood collection tube. The cardiac blood samples were centrifuged at 10,000 r.p.m for 5 minutes to obtain cardiac plasma. According to a similar method, mice portal vein plasma samples were prepared. After collection of cardiac blood, 1×PBS was used to perfuse the mice to remove blood. The mice were Euthanized, and livers were removed to obtain liver samples. 5 times of volume of methanol: acetonitrile (50:50, vol/vol) was added to each liver sample, and then homogenized. After ultrasonication for 15 minutes, the homogenate was centrifuged for 5 minutes, and 20 μL of supernatant was mixed with 20 μL of water for 30 seconds, and then subjected into LC-MS/MS.

(3) LC-MS/MS analysis: the Acquity ultra-high performance liquid chromatography (UPLC) system (Waters Corporation) that connected to a Xevo TQ-S mass spectrometer (Waters Corporation) was used. Column: Acquity UPLC BEH C18 (1.7 μm 2.1×50 mm). Flow rate: flow rate of 0.5 mL/min with addition of water. Gradient elution was conducted by using solvent A (water with 0.1% formic acid and 5 mM $NH_4Ac$) and solvent B (acetonitrile: methanol=9/1, vol/vol, 0.1% formic acid).

Figure 31:
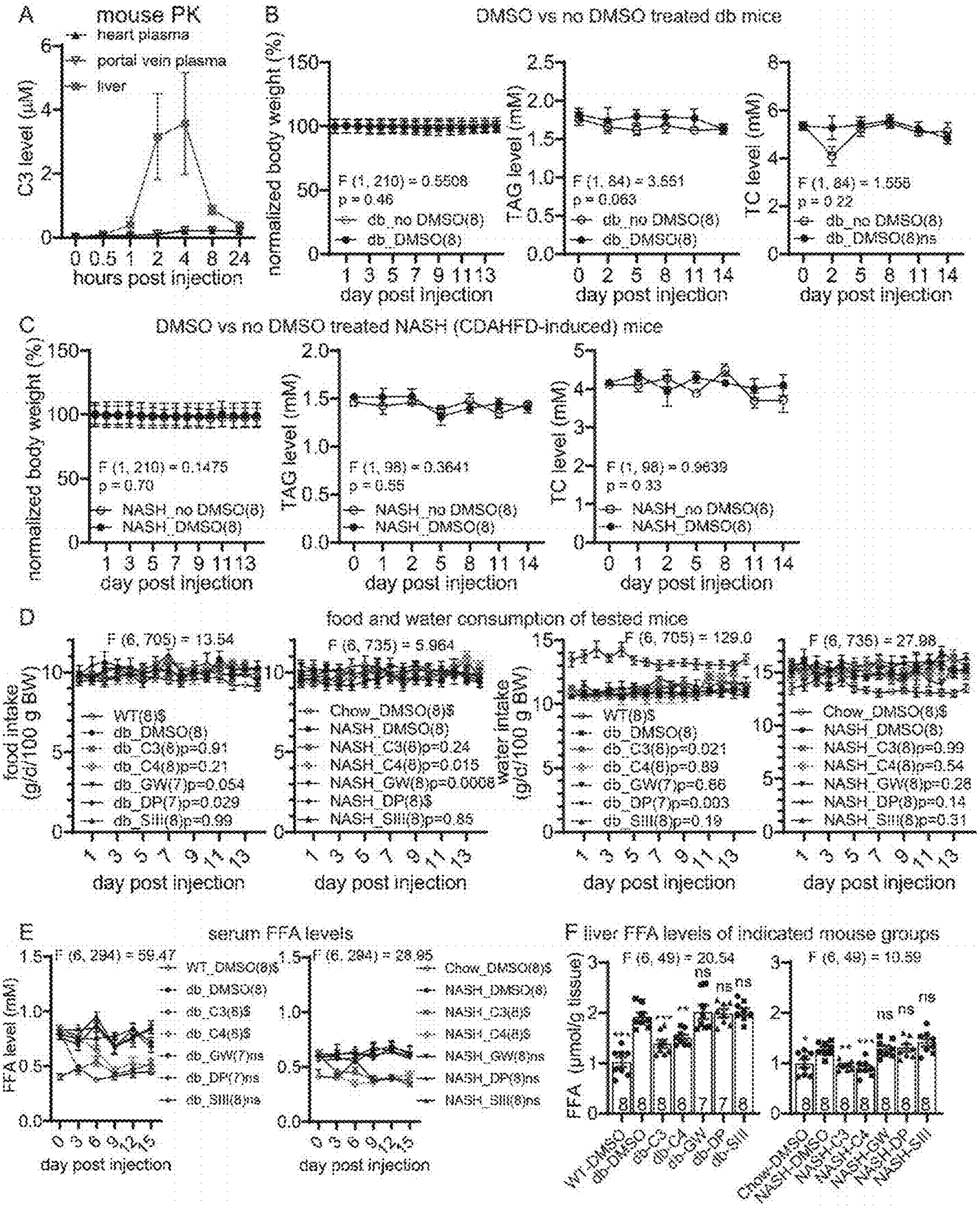
FIG. 31: (A) Measurement of Compound 3A concentration in liver and plasma samples collected at the indicated time points after intraperitoneal injection of Compound 3A (30 mg/kg). (B) Body weight, serum TC and TAG levels of DMSO-containing vehicle injected versus non DMSO-containing vehicle injected db/db mice. It is shown that DMSO does not lower these indicators but caused an insignificant increase of the serum TAG instead. The DMSO group presented here is the same group used in FIG. 25. (C) Experiments similar to (B) are performed in NASH mice. The DMSO group presented here is the same group used in FIG. 33. (D) Body weight normalized food and water intake, which are the same groups presented in FIG. 25, FIG. 30. The WT_DMSO group is the same as the Chow_DMSO group. Noted that in db mice, Compound 4A and Compound 3A lead to a marginally significant increase rather than decrease in body weight-normalized food and water intake, respectively. (E-F) Serum (E) and endpoint liver (F) free fatty acid (FFA) levels for the indicated groups, which are the same groups presented in FIG. 25, FIG. 30. For measurements at multiple time points, statistical analysis is performed using two-way ANOVA and Dunnett's post-hoc analysis (compared to the DMSO group). For endpoint measurements for multiple groups, one-way ANOVA and Dunnett's post-hoc analysis comparison (compared to the DMSO group) are performed.

By determining the in vivo compound, it was determined that 30 mg/kg was an appropriate injection dose, and the compound concentration after intraperitoneal injection could reach about micromolar range (FIG. 31A).

Example 17 Effect of the Compound on db/db Mouse and NASH Mouse

Mouse experiments were performed according to ARRIVE (Animal Research: Report of in vivo experiments) guidelines, which complied with all relevant ethical regulations. The animal experiment protocol was approved by the Animal Care and Use Committee of Shanghai Medical College of Fudan University (Approval No. 202004001S).

db/db mice and mouse NASH models were prepared according to the method as described above. C57BL/6 male mice fed with standard irradiated feed (Shuyishuer Inc. cat. no. D12450J, comprising 10 kcal % fat) from Changzhou SYSE Bio-tech Co., LTD were used as normal controls.

17.1 Experimental Method:

Compound 3A and Compound 4A with lower molecular weight and higher affinity for LC3B were intraperitoneally injected to determine the effect of the compound on experimental animals. Specifically:

(1) Administration

Mice were randomly divided into 7 groups, wherein 8 mice in each group, and the mice in each group were subjected to intraperitoneal injection to administer: (1) only vehicle (no DMSO) group: 0% DMSO+39% PEG300 (Selleck, cat. no. S6704)+5% Tween-80 (Selleck, cat. no. S6702)+56% distilled water, (2) DMSO group: 1% DMSO+39% PEG300+5% Tween-80+55% $H_2O$ (DMSO vehicle), (3) $C_3$ group: Compound 3A was in DMSO vehicle, (4) $C_4$ group: Compound 4A in DMSO vehicle, (5) SIII group: Sudan III DMSO vehicle, (6) GW5074 group: Compound A1 in DMSO vehicle, (7) DP group: Compound A5 in DMSO vehicle. For groups (3)-(7), the compound (30 mg/kg, administration volume 150 μL) was administered through intraperitoneally injection for consecutive 2 weeks, and once a day. The food and water intake were measured with an analytical electronic balance.

(2) Sample Collection

Bodyweight was weighed every day.

If time permitted, tail vein blood (30-50 μL) was collected every 1-3 days.

24 hours after the time point of the last injection, end point maxillary surface blood sampling was performed on each mouse. All mice were Euthanized by cervical dislocation, and then tissue sample (e.g., liver samples) were obtained and stored in Eppendorf tubes at −80° C. for assay.

(3) Measurement of Lean Body Weight Vs. Body Fat Based on Nuclear Magnetic Resonance (NMR)

12 days after initiation of administration, each mouse was scanned by a minispec nuclear magnetic resonance (NMR) instrument (Bruker LF50 II "Minispec" body composition analyzer, Bruker Optics) that was designed for experimental animals, and based on the measurement of solid and liquid parts of the samples, the body fat and lean body weight were determined by this device.

(4) Measurement of TAG, TC and FFA Levels in Serum and Liver Samples

Serum: Tail vein blood samples (30-50 μL) were left to coagulate in EDTA.K2 blood collection tubes (Jiangsu Kangjian Medical Products Co., Ltd., model KJ002) at room temperature without interference, and then centrifuged at 2,000×g for 10 minutes at 4° C. to remove the clot. Supernatant was collected to obtain the serum.

Liver: Liver samples were obtained as described in (2). 100 mg of liver tissue was homogenized in 0.9 mL of absolute alcohol under ice-cold conditions, and then centrifuged (2,500 r.p.m/min, 10 min). Supernatant was collected, and then stored at −80° C.

The kits were used according to the instruction from manufacturer (TAG: TG kit, cat. no. A110-1-1; TC: T-CHO kit, cat. no. A111-1. FFA: NEFA kit, cat. No. A042-2-1; they were all from Nanjing Jiancheng Bioengineering Institute). TAG, TC and FFA levels in serum and liver samples were determined.

(5) Absolute Quantitative Lipidomics

According to the lipidomic method as described above, the contents of liver total lipid, glycerolipid, sterol lipid, neutral sphingolipid and polar lipid were analyzed. The log 2-fold change ($log_2$ FC) and statistical significance (p-value) relative to the DMSO group were calculated.

17.2 db/db Mouse

Figure 30:
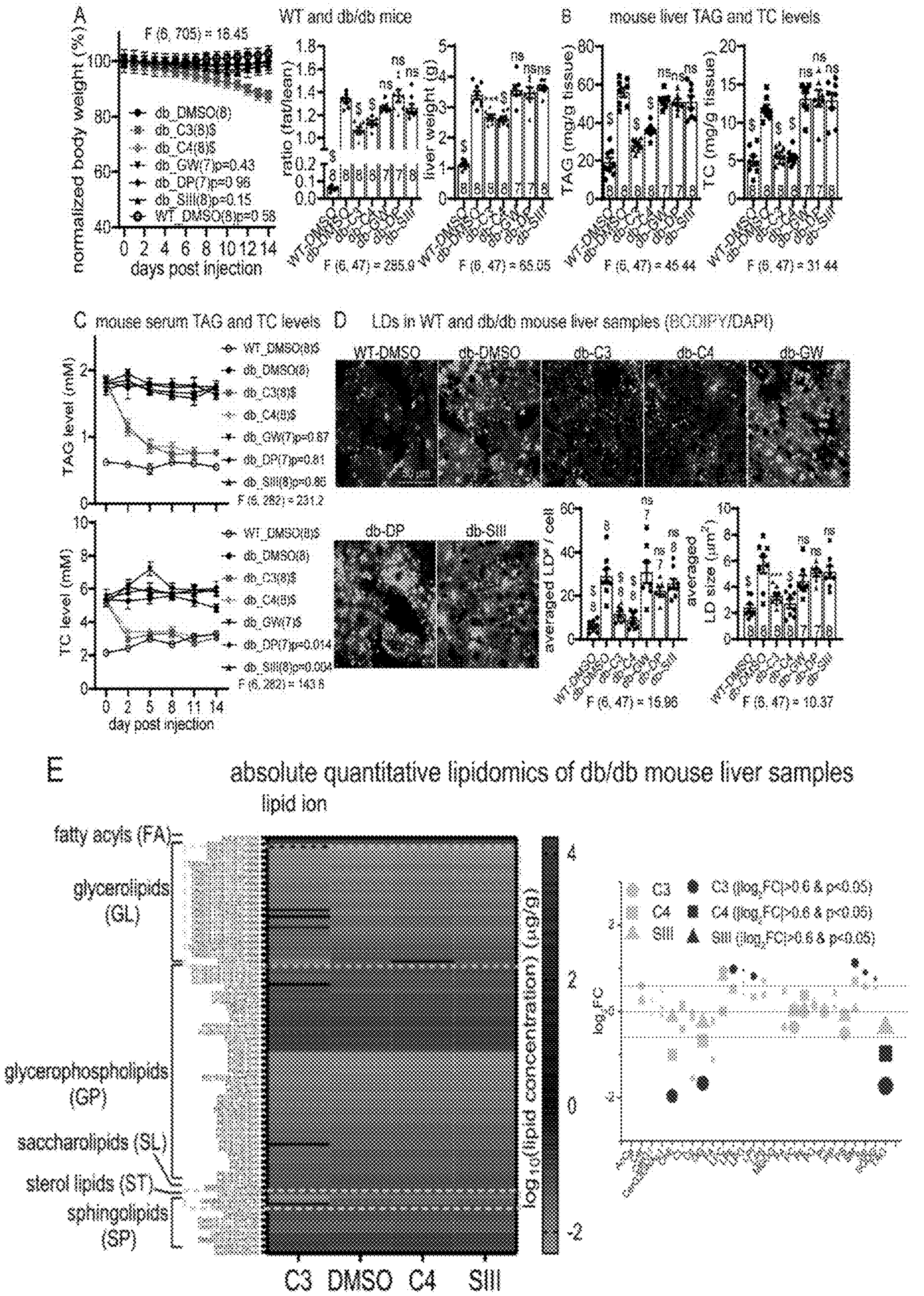
FIG. 30: (A) Left: body weight (measured each day and normalized to the averaged weight of day 0), middle figure: body fat/lean body weight ratio (after injection for 12 days) and liver weight (endpoint measurement after injection for 14 days). (B) The endpoint measurements (after injection for 14 days) of the triacylglycerol (TAG) and total cholesterol (TC) levels of liver. (C) Serum triacylglycerol (TAG) and total cholesterol (TC) levels in db/db mice at different time points after injection. (D) The BODIPY493/503 staining of the endogenous lipid droplets in the liver slice samples from the mice injected for 14 days. For statistics, images of each mouse (from at least 3 slices) are averaged. (E) Absolute quantitative lipidomics of liver in db/db mice (4 per group). Left: the lipid concentrations in the samples, shown as log 10. Darker red or brighter green indicates lower concentrations. The several major regions are shown by the dashed cyan boxes. The DMSO data is placed in the middle for easier comparison. Right: $\log_2$ FC compared to DMSO for different lipid class (X axis). A few lipid classes with extremely low abundance (total concentration<1 μg/g) are neglected. The area of each symbol represents the abundance of the lipid class in the DMSO group. The red color indicates significant change ($|\log_2 FC|>0.6$, $p<0.05$, by the two-tailed unpaired t test). For measurements at multiple time points, statistical analysis is performed using two-way ANOVA and Dunnett's post-hoc analysis (compared to the DMSO group). For endpoint measurements for multiple groups, one-way ANOVA and Dunnett's post-hoc analysis comparison (compared to the DMSO group) are performed.

The effect of Compound 3A and Compound 4A on db/db mouse was shown in FIG. 30.

No significant difference was observed between mice injected with DMSO vehicle and mice without DMSO vehicle, and thus the possible effect from DMSO could be excluded (FIG. 31B-C).

One mouse in group A1 and one mouse in group DP died in the experiment, and thus were excluded.

Compared with DMSO group, the following effect were observed in db/db mice administered with Compound 3A or Compound 4A:

(1) Total body weight was gradually reduced with a weight loss of about 15% within 2 weeks (FIG. 30A). This effect was not observed in any of the control groups (FIG. 30A).

(2) The ratio of body fat/lean body weight and liver weight were also significantly reduced (FIG. 30A).

(3) TAG and TC levels in liver and serum were significantly reduced and reached levels comparable to WT controls (FIG. 30B-C).

(4) There was no significant reduction in body weight-normalized food and water intake (FIG. 31D), and thus the above effects were unlikely due to the changes in food and water intake.

(5) FFA levels in serum and liver were significantly reduced (FIG. 31E-F).

(6) The liver lipid droplets were stained by BODIPY493/503, and it was observed that the amount and size of lipid droplets were significantly reduced (FIG. 30D). This result was consistent with that in biochemical assays.

(7) Absolute quantitative lipidomics analysis showed that the effects of administration of Compound 3A or Compound 4A on lipid levels in db/db mice were:

Liver total lipid concentration: administration of Compound 3A reduced liver lipid level by 62.0±23.2%, and administration of Compound 4A reduced liver lipid level by 41.5±13.9%.

The levels of different lipid species and the calculated $log_2$ FC and p-values compared to DMSO group are shown in FIG. 30E:

<1> Most glycerolipids, sterol lipids and neutral sphingolipids: reduced (FIG. 30E, left figure, see dashed cyan frame: darker red or brighter green indicated lower levels). This observation results were consistent with the predicted mechanism that the conjugated compound of present disclosure targeted neutral lipids or lipid droplets to cell autophagy for degradation via LC3 binding moiety and lipid droplet binding moiety.

Figure 28:
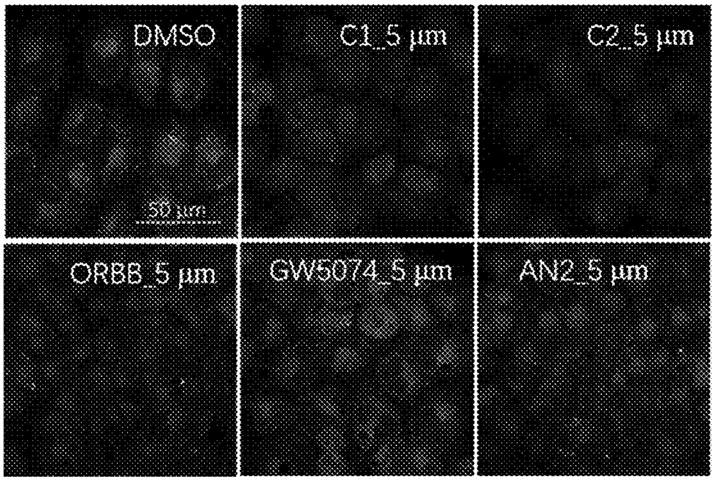
FIG. 28: Representative images of endogenous lipid droplets (green: lipid droplets; blue: nuclei) in the human normal liver cell line QSG7701 in the absence of induction (n=6). Compound 1A and Compound 2A significantly reduce lipid droplets in WAC and in the case of treatment with 5 mM $NH_4Cl$ to inhibit autophagy, lipid droplets are slightly increased, while other control compounds do not influence lipid droplets. Compound treatment time is 24h, lipid droplets are stained with BODIPY® 493/503, Scale bar=50 μm. Because the endogenous lipid droplets of this liver cell line are too few and too small to be accurately counted, there is no statistical result.

<2> Polar lipids, e.g., glycerophospholipids: did not reduce (FIG. 30E, left figure), it indicated that the conjugated compound of present disclosure did not impair integrity of intracellular membranes or cell membrane (also see FIG. 28).

<3> TAG: significantly reduced in mice administered with Compound 3A or Compound 4A, but not reduced in mice administered with Sudan III (FIG. 30E, right figure).

<4> Other major neutral lipids, e.g., cholesteryl ester (ChE) and diglyceride (DG): significantly reduced in mice administered with Compound 3A, and slightly reduced in mice administered with Compound 4A, and not reduced in mice administered with Sudan III (FIG. 30E, right figure).

<5> Other lipid levels were unchanged or in very low abundance (indicated by smaller symbols).

Figure 32:
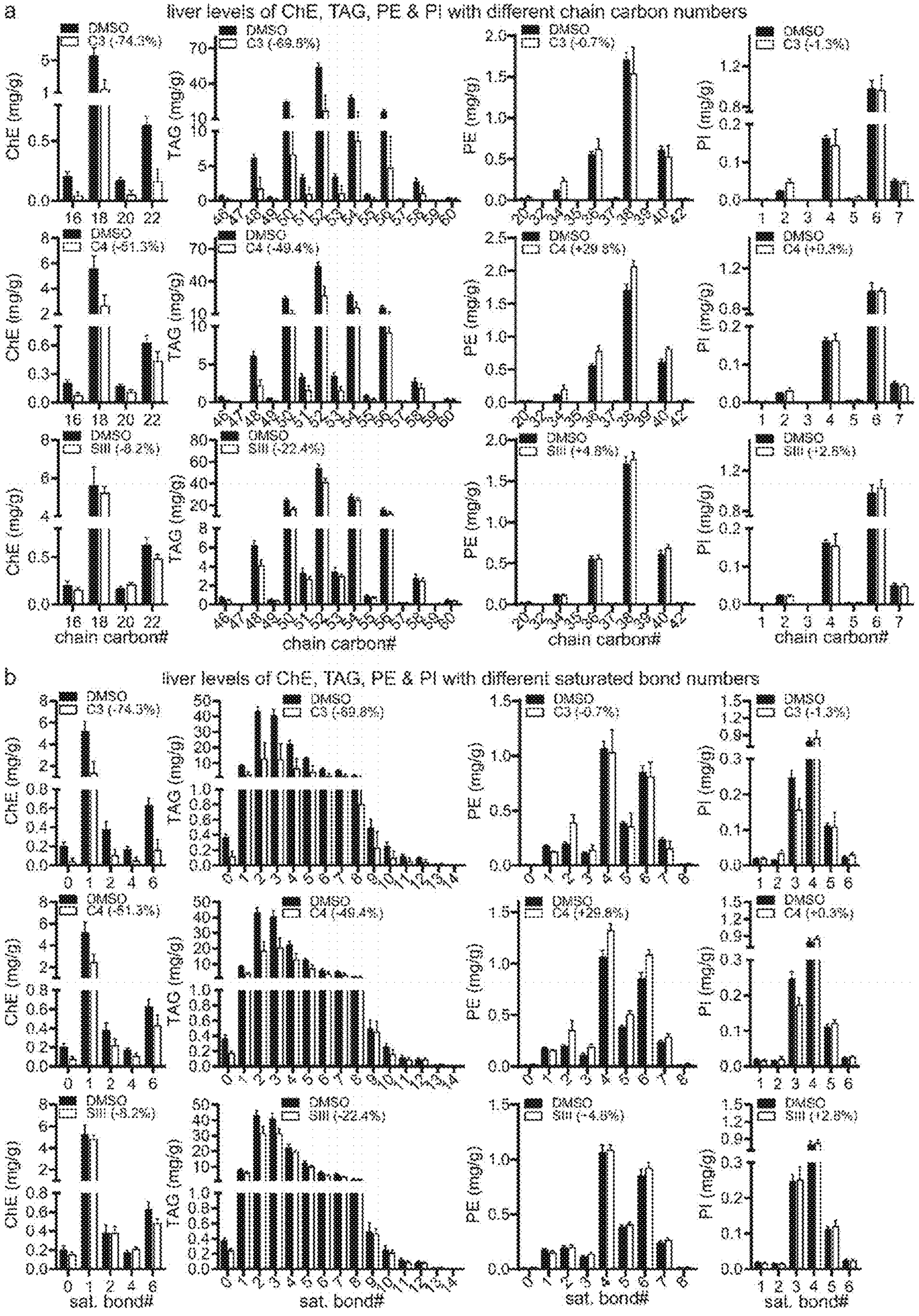
FIG. 32: Analysis of exemplar lipids of liver based on the lipidomics data. (A) Levels of ChE, TAG, PE or PI with different fatty acid chain carbon numbers (chain carbon #). The numbers in the brackets indicate the overall change of the liver samples from the mice treated with compounds compared to the DMSO control.

<6> Different lipids, especially analysis of some key typical lipids, including neutral lipids TAG and ChE, and polar lipids phosphatidylethanolamine (PE) and phosphatidylinositol (PI) were analyzed. It was observed that TAG and ChE with different chain carbon numbers or saturated bond numbers were all reduced in mice administered with Compound 3A or Compound 4A, while PE and PI were unaffected (FIG. 32A-B).

17.3 NASH Mouse

Figure 33:
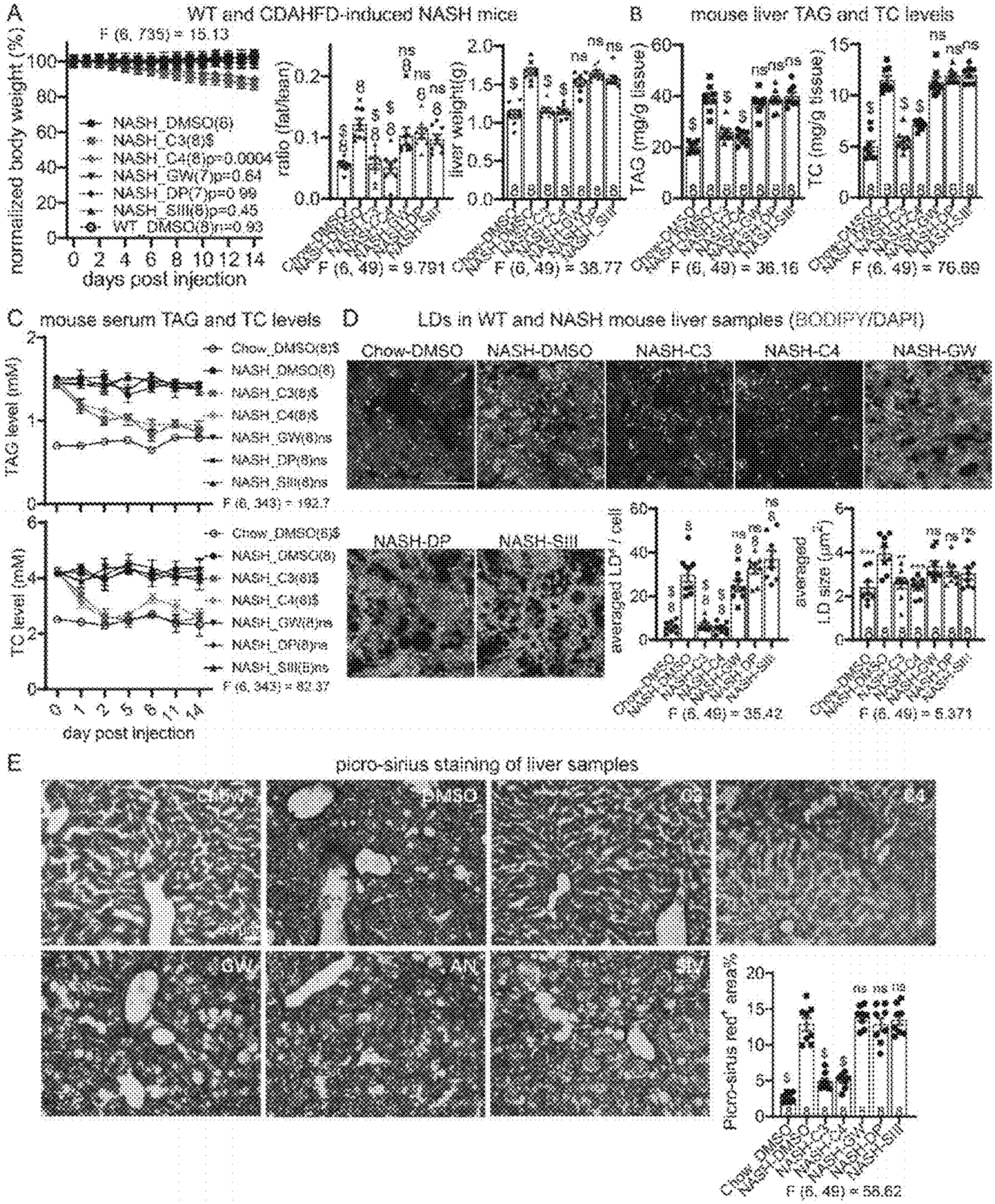
FIG. 33: (A) Left: body weight (measured each day and normalized to the averaged weight of day 0), middle figure: body fat/lean body weight ratio (after injection for 12 days) and liver weight (endpoint measurement after injection for 14 days). (B) The endpoint measurements (after injection for 14 days) of the triacylglycerol (TAG) and total cholesterol (TC) levels of liver. (C) Serum triacylglycerol (TAG) and total cholesterol (TC) levels in NASH mice at different time points after injection. (D) The BODIPY493/503 staining of the endogenous lipid droplets in the liver slice samples from the mice injected for 14 days, Scale bar=50 μm. (E) Picrosirius staining to evaluate the interstitial fibrosis in the liver samples from the mice injected for 14 days. The red+ area is normalized relative to green+ area to evaluate the degree of liver fibrosis. For measurements at multiple time points, statistical analysis is performed using two-way ANOVA and Dunnett's post-hoc analysis (compared to the DMSO group). For endpoint measurements for multiple groups, one-way ANOVA and Dunnett's post-hoc analysis comparison (compared to the DMSO group) are performed.

The effect of Compound 3A and Compound 4A on mouse NASH model was shown in FIG. 33.

Similar to the results obtained in db/db mice as described in 16.2 above, it was observed in the NASH mice administered with Compound 3A or Compound 4A:

(1) Body weight was significantly reduced (FIG. 33A).

(2) Ratio of body fat/lean body weight and liver weight were significantly reduced to close to the normal control groups fed with standard feed (FIG. 33A, wherein, the normal control group was the same as the WT group in FIG. 30).

(3) Serum and liver TAG and TC levels were reduced at both molecular and cellular levels (FIG. 33B-C).

(4) The liver lipid droplets were significantly reduced (FIG. 33D).

(5) Liver fibrosis were developed in NASH mice. It was observed through the picro-sirius staining method as described above that compared with control compound, in NASH mice administered with Compound 3A or Compound 4A, degree of interstitial fibrosis in liver tissue was significantly reduced (FIG. 33E), suggesting that the conjugated compound of present disclosure had potential therapeutic effects.

SEQUENCE LISTING

[SEQ ID NO: 1] LC3A Isoform 1:
MPSDRPFKQRRSFADRCKEVQQIRDQHPSKIPVIIERYKGEKQLPVLD
KTKFLVPDHVNMSELVKIIRRRLQLNPTQAFFLLVNQHSMVSVSTPIA
DIYEQEKDEDGFLYMVYASQETFGF

[SEQ ID NO: 2] LC3A Isoform 2:
MKMRFFSSPCGKAAVDPADRCKEVQQIRDQHPSKIPVIIERYKGEKQL
PVLDKTKFLVPDHVNMSELVKIIRRRLQLNPTQAFFLLVNQHSMVSVS
TPIADIYEQEKDEDGFLYMVYASQETFGF

[SEQ ID NO: 3] LC3B:
MPSEKTFKQRRTFEQRVEDVRLIREQHPTKIPVIIERYKGEKQLPVLD
KTKFLVPDHVNMSELIKIIRRRLQLNANQAFFLLVNGHSMVSVSTPIS
EVYESEKDEDGFLYMVYASQETFGMKLSV

[SEQ ID NO: 4] LC3C:
MPPPQKIPSVRPFKQRKSLAIRQEEVAGIRAKFPNKIPVVVERYPRET
FLPPLDKTKFLVPQELTMTQFLSIIRSRMVLRATEAFYLLVNNKSLVS
MSATMAEIYRDYKDEDGFVYMTYASQETFGCLESAAPRDGSSLEDRPC
NPL

The invention claimed is:

1. A compound or a pharmaceutically acceptable salt, stereoisomer, solvate, polymorph, tautomer, isotopic compound, metabolite, or prodrug thereof, wherein the compound has a structure comprising formula (I)

LCM-L-TM (I)

wherein:

LCM is a LC3 binding moiety, which is a moiety with affinity to LC3 protein;

L is a linker moiety;

TM is a lipid droplet binding moiety, which interacts non-covalently with the lipid droplet;

wherein the formula (I) has a structure of formula (xv):

(xv)

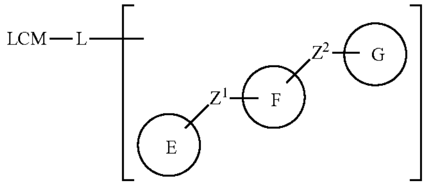

wherein:

L has a structure of formula (a), or a pharmaceutically acceptable salt thereof:

-Dy- (a)

wherein y is an integer greater than 1; and y is an integer less than or equal to 30, preferably less than or equal to 20, more preferably less than or equal to 16, further preferably less than or equal to 12;

each D is independently selected from the group consisting of: bond, —$CR^{L1}R^{L2}$—, —O—, —S—, —S(═O)—, S(═O)$_2$—, —$NR^{L3}$—, —S(═O)$_2$ $NR^{L3}$—, —S(═O)$NR^{L3}$—, —C(═O)$NR^{L3}$—, —$NR^{L3}$C(═O)$NR^{L4}$—, —$NR^{L3}$S(═O)$_2$$NR^{L4}$—, —C(═O)—, —$CR^{L1}$═$CR^{L2}$—, —C≡C—, —$SiR^{L1}R^{L2}$—, —P(═O)$R^{L1}$—, —P(═O)$OR^{L1}$—, $C_{3-6}$cycloalkyl optionally substituted with 0-6 $R^{L1}$ and/or $R^{L2}$ groups, 3- to 7-membered heterocyclyl optionally substituted with 0-6 $R^{L1}$ and/or $R^{L2}$ groups, aryl optionally substituted with 0-6 $R^{L1}$ and/or $R^{L2}$ groups, and heteroaryl optionally substituted with 0-6 $R^{L1}$ and/or $R^{L2}$ groups; wherein $R^{L1}$, $R^{L2}$, $R^{L3}$, $R^{L4}$ and $R^{L5}$ are each independently selected from the group consisting of: H, halo, $C_{1-6}$alkyl, —O($C_{1-6}$alkyl), —S($C_{1-6}$alkyl), —NH($C_{1-6}$alkyl), —N($C_{1-6}$alkyl)$_2$, $C_{3-6}$cycloalkyl, $C_{6-10}$aryl, 5- to 7-membered heteroaryl, 3- to 7-membered heterocyclyl, —O($C_{3-6}$cycloalkyl), —S($C_{3-6}$cycloalkyl), —NH ($C_{3-6}$cycloalkyl), —N($C_{3-6}$cycloalkyl)$_2$, —N($C_{3-6}$cycloalkyl)($C_{1-6}$alkyl), —OH, —NH$_2$, —SH, —S(═O)$_2$ ($C_{1-6}$alkyl), —P(═O)(O$C_{1-6}$alkyl)($C_{1-6}$alkyl), —P(═O)(O$C_{1-6}$alkyl)$_2$, —C≡C—$C_{1-6}$alkyl, —C≡CH, —CH═CH($C_{1-6}$alkyl), —C($C_{1-6}$alkyl)═CH($C_{1-6}$alkyl), —C($C_{1-6}$alkyl)═C($C_{1-6}$alkyl)$_2$, —Si(OH)$_3$, —Si ($C_{1-6}$alkyl)$_3$, —Si(OH)($C_{1-6}$alkyl)$_2$, —C(═O) ($C_{1-6}$alkyl), —COOH, halogen, —CN, —$CF_3$, —$CHF_2$, —$CH_2F$, —$NO_2$, —S(═O)$_2$NH($C_{1-6}$alkyl), —S(═O)$_2$ N($C_{1-6}$alkyl)$_2$, —S(═O)NH($C_{1-6}$alkyl), —S(═O)N ($C_{1-6}$alkyl)$_2$, —C(═O)NH($C_{1-6}$alkyl), —C(═O)N ($C_{1-6}$alkyl)$_2$, —N($C_{1-6}$alkyl)C(═O)NH($C_{1-6}$alkyl), —N($C_{1-6}$alkyl)C(═O)N($C_{1-6}$alkyl)$_2$, —NHC(═O) NH($C_{1-6}$alkyl), —NHC(═O)N($C_{1-6}$alkyl)$_2$, —NHC (═O)NH$_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —NHS(═O)$_2$ NH($C_{1-6}$alkyl), —NHS(═O)$_2$N($C_{1-6}$alkyl)$_2$ and NHS (═O)$_2$NH$_2$;

$R^{L1}$ or $R^{L2}$ is each independently linked to another D group to form cycloalkyl and/or heterocyclyl moiety which is optionally substituted with 0-4 $R^{L5}$ groups;

ring E and ring F are each independently selected from the group consisting of benzene ring and naphthalene ring; wherein the ring E is optionally substituted with one or more $R^E$, the ring F is optionally substituted with one or more;

ring G is absent, or is selected from the group consisting of benzene ring and naphthalene ring, and the ring G is optionally substituted with one or more $R^G$;

$Z^1$ is azo group;

$Z^2$ is absent, or is azo group;

$R^E$, $R^F$ and $R^G$, on each occurrence, are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$ alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O) ($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —NH$_2$, —NH($C_{1-6}$alkyl), —N($C_{1-6}$alkyl)$_2$, —NH ($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, —NH(C═O)($C_{1-6}$alkyl), —N($C_{1-6}$alkyl)-(C═O)($C_{1-6}$alkyl), —NH(C═O)($C_{3-6}$cyclohydrocarbyl), —N($C_{1-6}$alkyl)-(C═O)($C_{3-6}$cyclohydrocarbyl), —NH(C═O)($C_{1-4}$alkylene-$C_{3-6}$cyclohydrocarbyl), —N($C_{1-6}$alkyl)-(C═O)($C_{1-4}$alkylene-$C_{3-6}$cyclohydrocarbyl), —NH(C═O)(3- to 7-membered heterocyclyl), —N($C_{1-6}$alkyl)-(C═O)(3- to 7-membered heterocyclyl), —COOH, —C(═O) ($C_{1-6}$alkyl), —C(═O)O($C_{1-6}$alkyl), —C(═O)O ($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)NH$_2$, —C(═O) NH($C_{1-6}$alkyl), —C(═O)N($C_{1-6}$alkyl)$_2$, —C(═O)NH ($C_{1-4}$alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene- 3- to 7-membered heterocyclyl), —C(═O)N($C_{1-4}$alkylene- 3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —NH$_2$, —NH($C_{1-6}$alkyl), —N($C_{1-6}$alkyl)$_2$, —COOH, —C(═O)($C_{1-6}$alkyl), —C(═O)NH$_2$, —C(═O)NH($C_{1-6}$alkyl), —C(═O)N ($C_{1-6}$alkyl)$_2$, —S(═O)$_2$OH, —S(═O)$_2$NH($C_{1-6}$alkyl), and —S(═O)$_2$N($C_{1-6}$alkyl)$_2$; or two $R^E$, two $R^F$ or two $R^G$ are bonded each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —NH$_2$, —NH($C_{1-6}$alkyl), —N($C_{1-6}$alkyl)$_2$, —COOH, —C(═O)($C_{1-6}$alkyl), —C(═O)NH$_2$, —C(═O)NH ($C_{1-6}$alkyl), —C(═O)N($C_{1-6}$alkyl)$_2$, —S(═O)$_2$OH, —S(═O)$_2$NH($C_{1-6}$alkyl), and —S(═O)$_2$N($C_{1-6}$ alkyl)$_2$;

wherein the LCM moiety has a structure of formula (2):

(2)

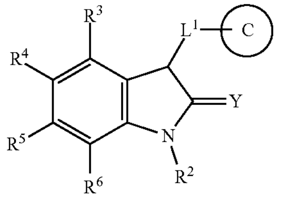

wherein:

Y is O or S;

ring C is selected from the group consisting of $C_{6-10}$aryl and 5- to 7-membered heteroaryl, the aryl or heteroaryl is optionally substituted with one or more $R^{X1}$;

$R^2$ is selected from the group consisting of H and $C_{1-8}$alkyl;

$L^1$ is bond, or is $C_1$-$C_6$ hydrocarbyl chain;

$R^3$, $R^4$, $R^5$, $R^6$ are each independently selected from the group consisting of H and $R^{X2}$;

$R^{X1}$ and $R^{X2}$, on each occurrence, are each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(═O)$OR^7$, —C(═O)$NR^7R^8$, —OC(═O)$R^7$, —NC(═O)$R^7R^8$, —C(═O)$R^7$, —S(═O)$_2OR^7$, —S(═O)$_2R^7$, —S(═O)$_2NR^7R^8$, —OS(═O)$_2R^7$, —NS(═O)$_2R^7R^8$, —S(═O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$ alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, ═O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, and $C_{6-10}$aryl-$C_{1-4}$alkyl, wherein the alkyl, alkenyl, alkynyl, cyclohydrocarbyl, heterocyclyl or aryl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), —C(═O)($C_{1-6}$alkyl);

or wherein the LCM moiety has a structure of formula (5):

(5)

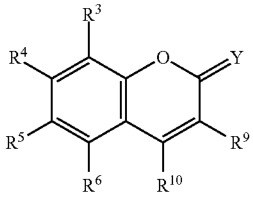

Y is O or S;

$R^9$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(═O)$OR^{a1}$, —C(═O)$NR^{a1}R^{b1}$, —C(═O)$R^{a1}$, —S(═O)$_2OR^{a1}$, —S(═O)$_2R^{a1}$, —S(═O)$_2NR^{a1}R^{b1}$, —S(═O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(═O)$OR^{a2}$, —C(═O)$NR^{a2}R^{b2}$, —C(═O)$R^{a2}$, —S(═O)$_2OR^{a2}$, —S(═O)$_2R^{a2}$, —S(═O)$_2NR^{a2}R^{b2}$ and —S(═O)$R^{a2}$;

$R^{10}$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, and 3- to 7-membered heterocyclyl-$C_{1-4}$alkyl;

$R^3$ is selected from the group consisting of H, halogen, $C_{1-6}$alkyl, —OH, —$NH_2$, —NH($C_{1-6}$alkyl), and —N($C_{1-6}$alkyl)$_2$, wherein the alkyl is optionally substituted with one or more substituents selected from the group consisting of halogen, —OH, —O($C_{1-6}$alkyl), —$NH_2$, —NH($C_{1-6}$alkyl), and —N($C_{1-6}$alkyl)$_2$:

$R^4$ is selected from the group consisting of H, halogen, —$NO_2$, —CN, $C_{1-6}$alkyl, —$OR^7$, —$SR^7$, —$NR^7R^8$;

$R^7$, $R^8$, on each occurrence, are each independently selected from the group consisting of H and $C_{1-6}$alkyl, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, —COOH, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), and —C(═O)($C_{1-6}$alkyl);

$R^5$ is selected from the group consisting of H, halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), and —C(═O)($C_{1-6}$alkyl), wherein the alkyl is optionally substituted with one or more substituents selected from the group consisting of halogen, —OH, —O($C_{1-6}$alkyl), —$NH_2$, —NH($C_{1-6}$alkyl), —N($C_{1-6}$alkyl)$_2$, —C(═O)O($C_{1-6}$alkyl), —C(═O)NH($C_{1-6}$alkyl), —C(═O)N($C_{1-6}$alkyl)$_2$, —OC(═O)($C_{1-6}$alkyl), —NHC(═O)($C_{1-6}$alkyl), and —C(═O)($C_{1-6}$alkyl);

$R^6$ is selected from the group consisting of H, halogen, —$NO_2$, —CN, $C_{1-6}$alkyl, —OH, —O($C_{1-6}$alkyl), —O(benzyl), —SH, —S($C_{1-6}$alkyl), —S(benzyl), —$NH_2$, —NH($C_{1-6}$alkyl), —N($C_{1-6}$alkyl)$_2$, and —NH(benzyl), wherein the alkyl or benzyl is optionally substituted with one or more substituents selected from the group consisting of halogen, —OH, —O($C_{1-6}$alkyl), —$NH_2$, —NH($C_{1-6}$alkyl), and —N($C_{1-6}$alkyl)$_2$;

$R^{a1}$, $R^{b1}$, $R^{a2}$, $R^{b2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$aryl, $C_{6-10}$aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(═O)$OR^{Y1}$, —C(═O)$NR^{Y1}R^{Y2}$, —C(═O)$R^{Y1}$, —S(═O)$_2OR^{Y1}$, —S(═O)$_2R^{Y1}$, —S(═O)$_2NR^{Y1}R^{Y2}$, and —S(═O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, ═O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$aryl, $C_{6-10}$aryl-$C_{1-4}$alkyl, 5- to 10-membered heteroaryl, and 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, =O and —COOH;

or wherein the LCM moiety has a structure of formula (8):

(8)

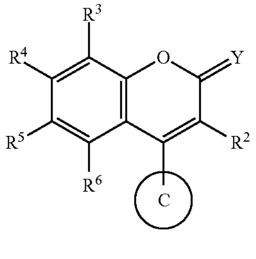

wherein:

Y is O or S;

ring C is

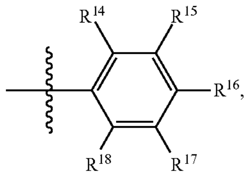

wherein $R^{14}$, $R^{15}$, $R^{16}$, $R^{17}$, $R^{18}$ are each independently selected from the group consisting of H, halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$, and —S(=O)$R^7$; wherein $R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, and $C_{6-10}$aryl-$C_{1-4}$alkyl, wherein the alkyl, alkenyl, alkynyl, cyclohydrocarbyl, heterocyclyl or aryl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), and —C(=O)($C_{1-6}$alkyl); preferably, $R^{14}$, $R^{15}$, $R^{17}$, $R^{18}$ are each independently selected from the group consisting of H, halogen, —$NO_2$, —CN, $C_{1-6}$alkyl, —OH, —$NH_2$, —NH($C_{1-6}$alkyl), —N($C_{1-6}$alkyl)$_2$, —NH(C=O)($C_{1-6}$alkyl), and $R^{16}$ is H or —$OCH_3$ $R^2$ is selected from the group consisting of H, halogen, $C_{1-6}$alkyl, $C_{3-6}$cyclohydrocarbyl, $C_{3-6}$cyclohydrocarbyl-$C_{1-4}$alkyl, 3- to 7-membered heterocyclyl, and 3- to 7-membered heterocyclyl-$C_{1-4}$alkyl, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$; wherein $R^{a2}$, $R^{b2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$aryl, $C_{6-10}$aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$ and —S(=O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$; preferably, $R^2$ is selected from the group consisting of H, halogen, $C_{1-6}$alkyl, wherein the alkyl is optionally substituted with one or more substituents selected from the group consisting of halogen, —$NO_2$, —CN, —OH, —$NH_2$ and —COOH;

$R^3$ is selected from the group consisting of H, —OH, and $C_{1-6}$alkyl, wherein the alkyl is optionally substituted with one or more substituents selected from the group consisting of halogen, —$NO_2$, —CN, —OH, —SH, —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene-3- to 7-membered heterocyclyl)$_2$ and —COOH;

$R^4$ is selected from the group consisting of H, —$OR^7$, —$SR^7$, and —$NR^7R^8$; $R^7$, $R^8$, on each occurrence, are each independently selected from the group consisting of H and $C_{1-6}$alkyl, wherein the alkyl is optionally substituted with one or more substituents selected from the group consisting of halogen, $C_{1-6}$alkyl, —OH, —O($C_{1-6}$alkyl), —$NH_2$, —NH($C_{1-6}$alkyl), —N($C_{1-6}$alkyl)$_2$, —COOH, —C(=O)O($C_{1-6}$alkyl), —C(=O)NH($C_{1-6}$alkyl), and —C(=O)N($C_{1-6}$alkyl)$_2$;

$R^5$ is selected from the group consisting of H and $C_{1-6}$alkyl, wherein the alkyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$ and —COOH; and $R^6$ is selected from the group consisting of H, halogen, $C_{1-6}$alkyl, —OH, and —$NH_2$, wherein the alkyl is optionally substituted with one or more substituents selected from the group consisting of halogen, —OH, and —$NH_2$;

or wherein the LCM moiety has a structure of formula (9):

(9)

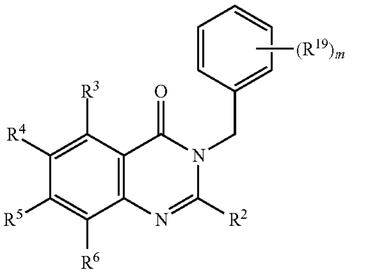

wherein:

$R^2$ is selected from the group consisting of H, halogen, —$NO_2$, —CN, $C_{1-6}$alkyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2$$OR^{a1}$, —S(=O)$_2$$R^{a1}$, —S(=O)$_2$$NR^{a1}R^{b1}$, and —S(=O)$R^{a1}$, wherein the alkyl, cyclohydrocarbyl or heterocyclyl is optionally substituted with one or more substituents selected from the group consisting of halogen, —$NO_2$, —CN, $C_{1-6}$alkyl, —$OR^{a2}$, —$SR^{a2}$, —$NR^{a2}R^{b2}$, —C(=O)$OR^{a2}$, —C(=O)$NR^{a2}R^{b2}$, and —C(=O)$R^{a2}$;

$R^{19}$, on each occurrence, is each independently selected from the group consisting of halogen, —$NO_2$, —CN, $C_{1-6}$alkyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2$$OR^7$, —S(=O)$_2$$R^7$, —S(=O)$_2$$NR^7R^8$, —OS(=O)$_2$$R^7$, —NS(=O)$_2$$R^7R^8$, and —S(=O)$R^7$, wherein the alkyl is optionally substituted with one or more substituents selected from the group consisting of halogen, —$NO_2$, —CN, —OH, —O($C_{1-6}$alkyl), —$NH_2$, —NH($C_{1-6}$alkyl), —N($C_{1-6}$alkyl)$_2$, and —COOH;

m is 0, 1, 2, 3, 4 or 5;

$R^3$, $R^4$, $R^5$, $R^6$ are each independently selected from the group consisting of H and $R^{X2}$;

$R^{X2}$, on each occurrence, is each independently selected from the group consisting of halogen, —$NO_2$, —CN, $C_{1-6}$alkyl, $C_{2-6}$alkenyl, $C_{2-6}$alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2$$OR^7$, —S(=O)$_2$$R^7$, —S(=O)$_2$$NR^7R^8$, —OS(=O)$_2$$R^7$, —NS(=O)$_2$$R^7R^8$, and —S(=O)$R^7$, wherein the alkyl, alkenyl or alkynyl is optionally substituted with one or more substituents selected from the group consisting of halogen, —$NO_2$, —CN, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, =O, —COOH and $C_{1-6}$alkyl;

$R^7$, $R^8$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, and 3- to 7-membered heterocyclyl-$C_{1-4}$alkyl, wherein the alkyl, alkenyl, alkynyl, cyclohydrocarbyl or heterocyclyl is optionally substituted with one or more substituents selected from the group consisting of halogen, —$NO_2$, —CN, $C_{1-6}$alkyl, —OH, —O($C_{1-6}$alkyl), —$NH_2$, —NH($C_{1-6}$alkyl), —N($C_{1-6}$alkyl)$_2$, —COOH, —C(=O)O($C_{1-6}$alkyl), —C(=O)NH($C_{1-6}$alkyl), —C(=O)N($C_{1-6}$alkyl)$_2$, —OC(=O)($C_{1-6}$alkyl), —NHC(=O)($C_{1-6}$alkyl), and —C(=O)($C_{1-6}$alkyl);

$R^{a1}$, $R^{b1}$, $R^{a2}$, $R^{b2}$, on each occurrence, are each independently selected from the group consisting of H, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, $C_{6-10}$aryl, $C_{6-10}$aryl-$C_{1-4}$alkyl, 5- to 10-membered heteroaryl, 5- to 10-membered heteroaryl-$C_{1-4}$alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2$$OR^{Y1}$, —S(=O)$_2$$R^{Y1}$, —S(=O)$_2$$NR^{Y1}R^{Y2}$, and —S(=O)$R^{Y1}$, wherein the alkyl, alkenyl, alkynyl, cyclohydrocarbyl, heterocyclyl, aryl or heteroaryl is optionally substituted with one or more substituents selected from the group consisting of halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

$R^{Y1}$, $R^{Y2}$, $R^{Y3}$, $R^{Y4}$, on each occurrence, are each independently selected from the group consisting of H, $C_{1-8}$alkyl, $C_{3-10}$cyclohydrocarbyl, $C_{3-10}$cyclohydrocarbyl-$C_{1-4}$alkyl, 3- to 10-membered heterocyclyl, 3- to 10-membered heterocyclyl-$C_{1-4}$alkyl, $C_{6-10}$aryl, $C_{6-10}$aryl-$C_{1-4}$alkyl, 5- to 10-membered heteroaryl, and 5- to 10-membered heteroaryl-$C_{1-4}$alkyl, wherein the alkyl, alkenyl, alkynyl, cyclohydrocarbyl, heterocyclyl, aryl or heteroaryl is optionally substituted with one or more substituents selected from the group consisting of halogen, —$NO_2$, —CN, $C_{1-8}$alkyl, $C_{2-8}$alkenyl, $C_{2-8}$alkynyl, —OH, —SH, —$NH_2$, =O and —COOH;

or wherein the LCM moiety has a structure of formula (10):

(10)

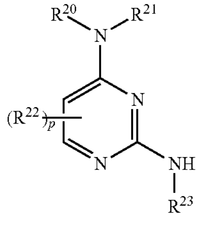

wherein, $R^{20}$ is bicyclic heteroaryl, having 9-10 ring atoms, the ring atoms comprising 1-3 heteroatoms each independently selected from the group consisting of O, S, and N, the remaining atoms being C: the heteroaryl is unsubstituted or substituted with at least one $R^{X3}$;

$R^{21}$ is $C_{1-8}$alkyl;

$R^{22}$ is $R^{X3}$;

$R^{23}$ is phenyl, which is unsubstituted or substituted with at least one $R^{X3}$;

$R^{X3}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$alkyl), —C(═O)N($C_{1-8}$alkyl)$_2$, —S(═O)$_2$OH, —S(═O)$_2$(O$C_{1-8}$alkyl), —S(═O)$_2$NH$_2$, —S(═O)$_2$NH($C_{1-8}$alkyl), and —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH:

p is 0, 1 or 2;

or wherein LCM moiety has a structure of formula (11):

(11)

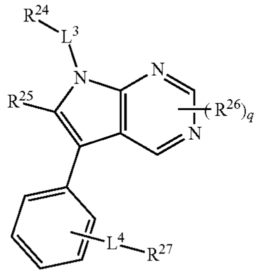

wherein, $R^{24}$ is 3- to 7-membered heterocyclyl; the heterocyclyl is unsubstituted or substituted with at least one $R^{X3}$;

$L^3$ is selected from the group consisting of a $C_{1-8}$alkylene and a $C_{3-6}$cycloalkylene;

$R^{25}$ is selected from the group consisting of H and $C_{1-8}$alkyl;

$R^{26}$ is selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), and —N($C_{1-8}$alkyl)$_2$;

$L^4$ is selected from the group consisting of $C_{1-8}$alkylene and $C_{1-8}$alkoxylene;

$R^{27}$ is phenyl, which is unsubstituted or substituted with at least one $R^{X3}$;

q is 0, 1 or 2;

$R^{X3}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$alkyl), —C(═O)N($C_{1-8}$alkyl)$_2$, —S(═O)$_2$OH, —S(═O)$_2$(O$C_{1-8}$alkyl), —S(═O)$_2$NH$_2$, —S(═O)$_2$NH($C_{1-8}$alkyl), and —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

or wherein the LCM moiety has a structure of formula (12):

(12)

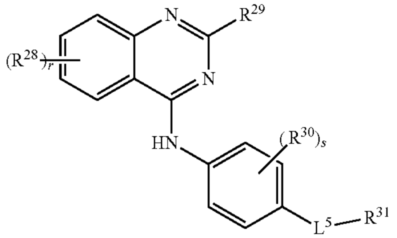

wherein, $R^{28}$ is $C_{1-8}$alkenyl; the alkenyl is substituted with at least one $C_{1-8}$alkyl, the alkyl is optionally substituted with one or more $R^{X4}$:

$R^{29}$ is selected from the group consisting of H and $C_{1-8}$alkyl;

$R^{30}$ is selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), and —N($C_{1-8}$alkyl)$_2$:

$L^5$ is selected from the group consisting of —O—, $C_{1-8}$alkylene and $C_{1-8}$alkoxylene:

$R^{31}$ is 6-membered heteroaryl, having 6 ring atoms, the ring atoms comprising 1-2 heteroatoms each independently selected from the group consisting of O, S, and N, the remaining atoms being C, the heteroaryl is unsubstituted or substituted with at least one $R^{X3}$;

r is 0, 1, 2, 3 or 4:

s is 0, 1, 2, 3 or 4:

$R^{X4}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —O($C_{1-8}$alkyl), —S($C_{1-8}$alkyl), —NH($C_{1-8}$alkyl), —N($C_{1-8}$alkyl)$_2$, —OC(═O)($C_{1-8}$alkyl), —NHC(═O)($C_{1-8}$alkyl), —NC(═O)($C_{1-8}$alkyl)$_2$, —OS(═O)$_2$($C_{1-6}$alkyl), —NHS(═O)$_2$($C_{1-8}$alkyl), and —N($C_{1-8}$alkyl)S(═O)$_2$($C_{1-8}$alkyl); wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

$R^{X3}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$alkyl), —C(═O)N($C_{1-8}$alkyl)$_2$, —S(═O)$_2$OH, —S(═O)$_2$(O$C_{1-8}$alkyl), —S(═O)$_2$NH$_2$, —S(═O)$_2$NH($C_{1-8}$alkyl), and —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

or wherein the LCM moiety has a structure of formula (13):

(13)

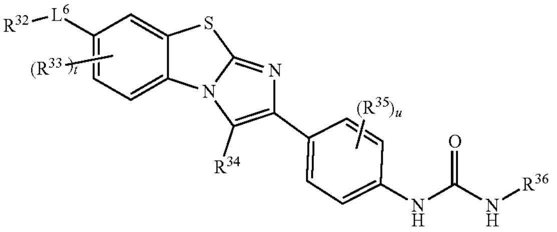

wherein, $R^{32}$ is 3- to 7-membered heterocyclyl; the heterocyclyl is unsubstituted or substituted with at least one $R^{X3}$;

$L^6$ is selected from the group consisting of —O—, $C_{1-8}$alkylene and $C_{1-8}$alkoxylene;

$R^{33}$, $R^{34}$ are selected from the group consisting of halogen and $C_{1-8}$alkyl;

$R^{35}$ is selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), and —N($C_{1-8}$alkyl)$_2$;

$R^{36}$ is 5-membered heteroaryl, having 5 ring atoms, the ring atoms comprising 1-3 heteroatoms each independently selected from the group consisting of O, S, and N, the remaining atoms being C, the heteroaryl is unsubstituted or substituted with at least one $R^{X3}$;

t is 0, 1, 2 or 3;

u is 0, 1, 2, 3 or 4;

$R^{X3}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$alkyl), —C(═O)N($C_{1-8}$alkyl)$_2$, —S(═O)$_2$OH, —S(═O)$_2$(O$C_{1-8}$alkyl), —S(═O)$_2NH_2$, —S(═O)$_2$NH($C_{1-8}$alkyl), and —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH;

or wherein the LCM moiety has a structure of formula (14):

(14)

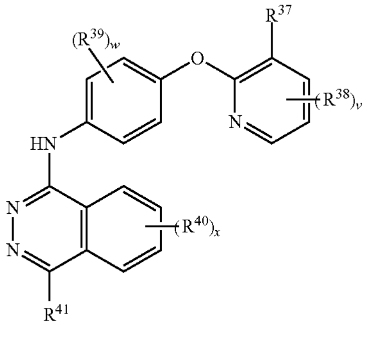

wherein, $R^{37}$ is 6-membered heteroaryl, having 6 ring atoms, the ring atoms comprising 1-2 heteroatoms each independently selected from the group consisting of O, S, and N, the remaining atoms being C, the heteroaryl is unsubstituted or substituted with at least one group selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), and —N($C_{1-8}$alkyl)$_2$;

$R^{38}$, $R^{39}$, $R^{40}$ are each independently $R^{X3}$;

$R^{41}$ is 5-membered heteroaryl, having 5 ring atoms, the ring atoms comprising 1-3 heteroatoms each independently selected from the group consisting of O, S, and N, the remaining atoms being C, the heteroaryl is unsubstituted or substituted with at least one $R^{X3}$;

v is 0, 1, 2 or 3;

w is 0, 1, 2, 3 or 4;

x is 0, 1, 2, 3 or 4;

$R^{X3}$, on each occurrence, is each independently selected from the group consisting of $C_{1-8}$alkyl, $C_{1-8}$alkenyl, halogen, —CN, —$CF_3$, —$CHF_2$, —$CH_2F$, —$NO_2$, —OH, —O($C_{1-8}$alkyl), —SH, —S($C_{1-8}$alkyl), —$NH_2$, —NH($C_{1-8}$alkyl), —N($C_{1-8}$alkyl)$_2$, —COOH, —C(═O)O($C_{1-8}$alkyl), —C(═O)NH($C_{1-8}$alkyl), —C(═O)N($C_{1-8}$alkyl)$_2$, —S(═O)$_2$OH, —S(═O)$_2$(O$C_{1-8}$alkyl), —S(═O)$_2NH_2$, —S(═O)$_2$NH($C_{1-8}$alkyl), and —S(═O)$_2$N($C_{1-8}$alkyl)$_2$; wherein the alkyl is optionally substituted with one or more substituents selected from the group consisting of halogen, —$NO_2$, —CN, $C_{1-8}$alkyl, —OH, —O($C_{1-8}$alkyl), —SH, —S($C_{1-8}$alkyl), —$NH_2$, —NH($C_{1-8}$alkyl), —N($C_{1-8}$alkyl)$_2$, ═O and —COOH.

2. The compound according to claim 1, or a pharmaceutically acceptable salt, stereoisomer, solvate, polymorph, tautomer, isotopic compound, metabolite, or prodrug thereof, wherein:

D is each independently selected from the group consisting of —$CR^{L1}R^{L2}$—, —O— and —$NR^{L3}$—; preferably, $R^{L1}$, $R^{L2}$ and $R^{L3}$ are H; preferably, L has a structure selected from the group consisting of

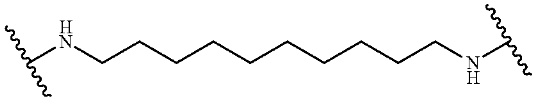
,

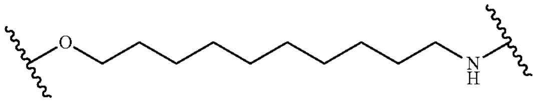
,

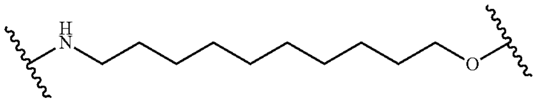
,

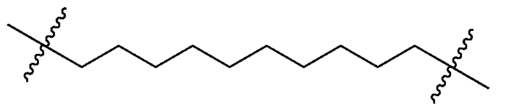
and

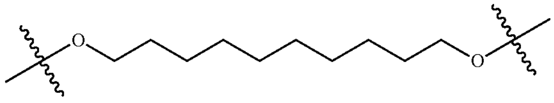
.

3. The compound according to claim 1, or a pharmaceutically acceptable salt, stereoisomer, solvate, polymorph, tautomer, isotopic compound, metabolite, or prodrug thereof, wherein:

D is each independently selected from the group consisting of —C(═O)—, heteroaryl optionally substituted with 0-6 $R^{L1}$ and/or $R^{L2}$ group, —O—, —$CR^{L1}R^{L2}$—, and 3- to 7-membered heterocyclyl optionally substituted with 0-6 $R^{L1}$ and/or $R^{L2}$ groups, and —$NR^{L3}$; preferably, each of $R^{L1}$, $R^{L2}$ and $R^{L3}$ are H; preferably, L has a structure of

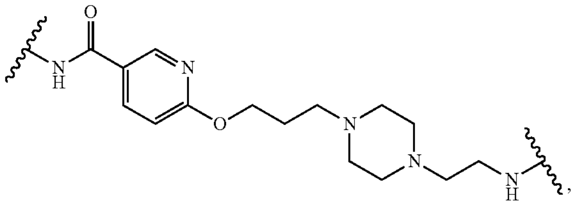

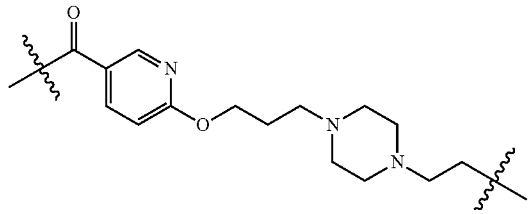

or

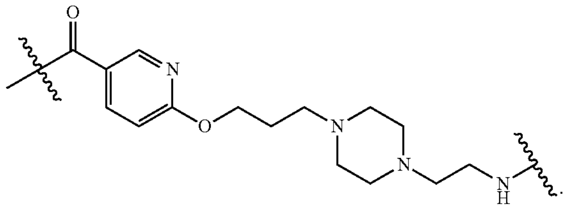

4. The compound according to claim 1, or a pharmaceutically acceptable salt, stereoisomer, solvate, polymorph, tautomer, isotopic compound, metabolite, or prodrug thereof, wherein the formula (I) has a structure selected from the group consisting of:

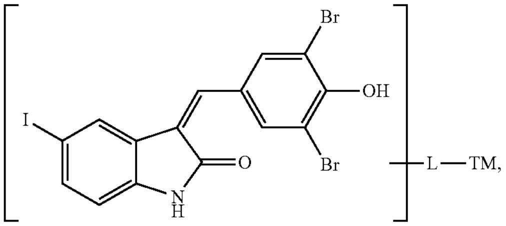

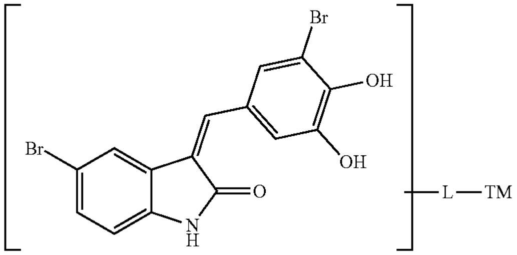

and

-continued

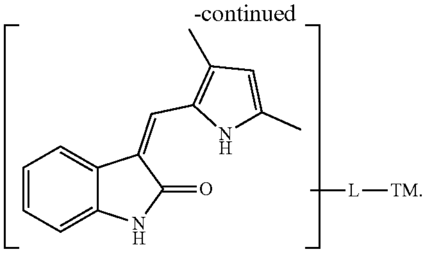

5. The compound according to claim 1, or a pharmaceutically acceptable salt, stereoisomer, solvate, polymorph, tautomer, isotopic compound, metabolite, or prodrug thereof, wherein the formula (I) has a structure of:

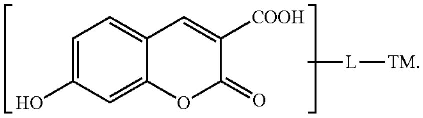

6. The compound according to claim 1, or a pharmaceutically acceptable salt, stereoisomer, solvate, polymorph, tautomer, isotopic compound, metabolite, or prodrug thereof, wherein the formula (I) has a structure selected from the group consisting of:

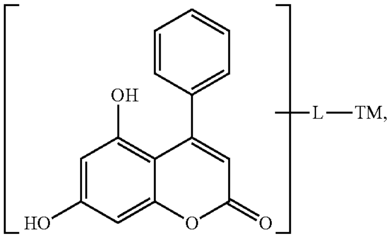

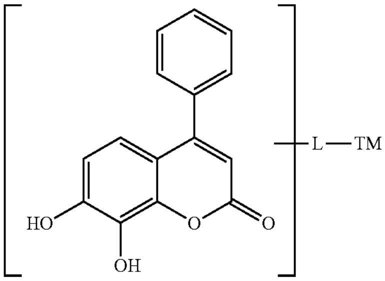

and

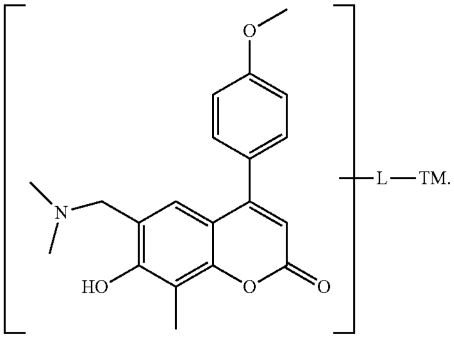

7. The compound according to claim 1, or a pharmaceutically acceptable salt, stereoisomer, solvate, polymorph, tautomer, isotopic compound, metabolite, or prodrug thereof, wherein the formula (I) has a structure of:

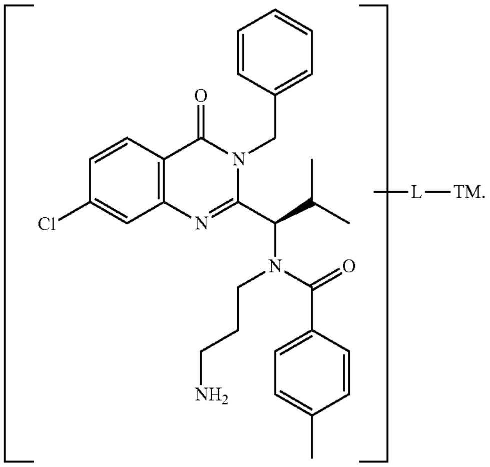

8. The compound according to claim 1, or a pharmaceutically acceptable salt, stereoisomer, solvate, polymorph, tautomer, isotopic compound, metabolite, or prodrug thereof, wherein the formula (I) has a structure of:

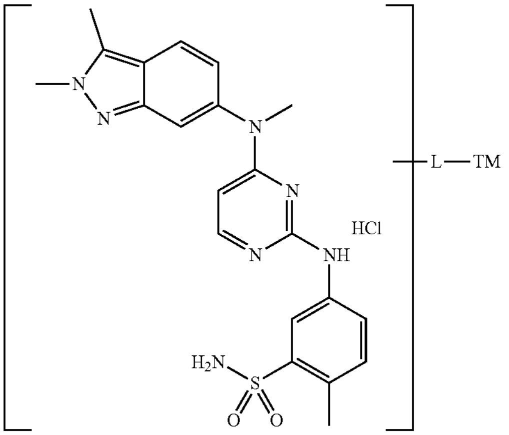

or

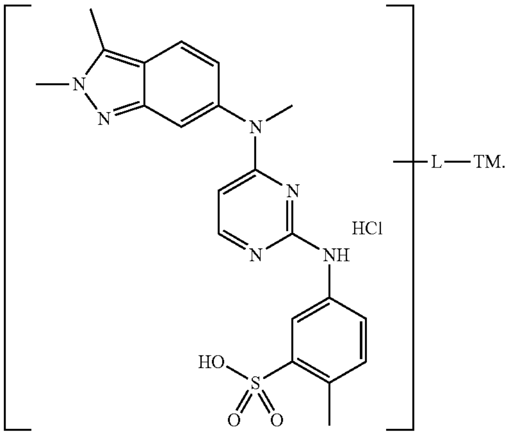

9. The compound according to claim 1, or a pharmaceutically acceptable salt, stereoisomer, solvate, polymorph, tautomer, isotopic compound, metabolite, or prodrug thereof, wherein the formula (I) has a structure of:

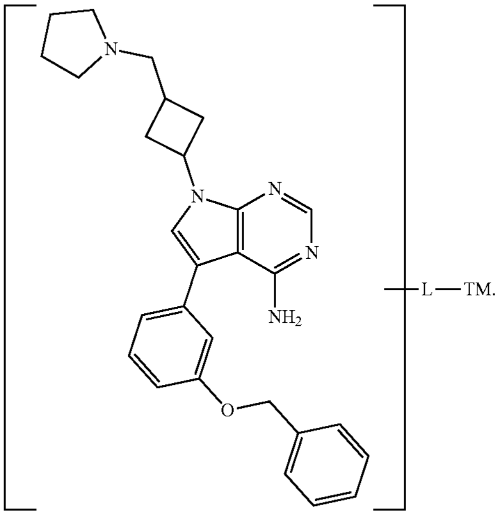

10. The compound according to claim 1, or a pharmaceutically acceptable salt, stereoisomer, solvate, polymorph, tautomer, isotopic compound, metabolite, or prodrug thereof, wherein the formula (I) has a structure of:

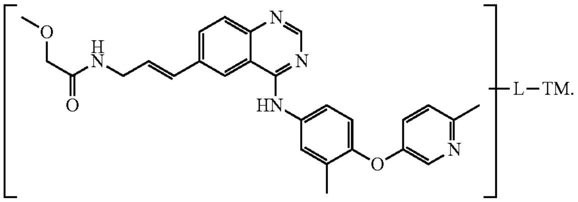

11. The compound according to claim 1, or a pharmaceutically acceptable salt, stereoisomer, solvate, polymorph, tautomer, isotopic compound, metabolite, or prodrug thereof, wherein the formula (I) has a structure of:

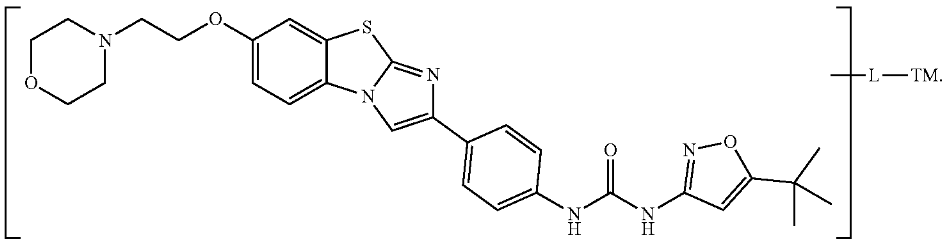

12. The compound according to claim 1, or a pharmaceutically acceptable salt, stereoisomer, solvate, polymorph, tautomer, isotopic compound, metabolite, or prodrug thereof, wherein the formula (I) has a structure of:

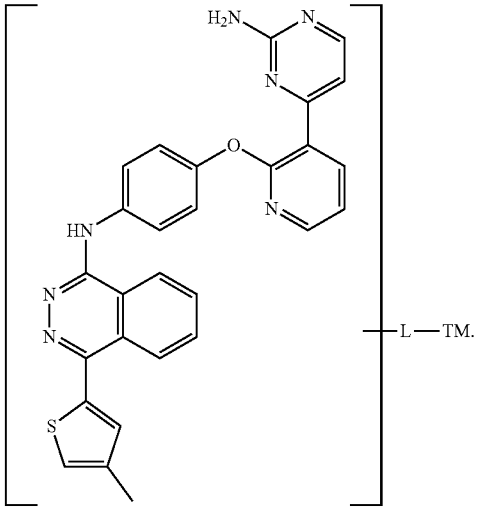

13. The compound according to claim 1, or a pharmaceutically acceptable salt, stereoisomer, solvate, polymorph, tautomer, isotopic compound, metabolite, or prodrug thereof, wherein the TM moiety is selected from the group consisting of Sudan III, Sudan IV, particularly Sudan III.

14. The compound according to claim 1, or a pharmaceutically acceptable salt, stereoisomer, solvate, polymorph, tautomer, isotopic compound, metabolite, or prodrug thereof, wherein the formula (I) has a structure of formula (xvi):

(xvi)

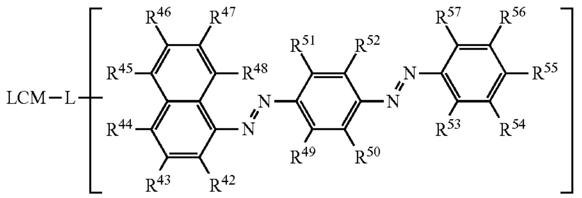

wherein $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are each independently selected from the group consisting of H, halogen, —$NO_2$, —CN, ═O, ═S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C═O)($C_{1-6}$alkyl), —O(C═O)($C_{3-6}$cyclohydrocarbyl), —O(C═O)($C_{1-4}$alkylene-$C_{3-6}$cyclohydrocarbyl), —O(C═O)(3- to 7-membered heterocyclyl), —O(C═O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$ alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, —NH(C═O)($C_{1-6}$alkyl), —N($C_{1-6}$alkyl)-(C═O)($C_{1-6}$alkyl), —NH(C═O)($C_{3-6}$cyclohydrocarbyl), —N($C_{1-6}$alkyl)-(C═O)($C_{3-6}$cyclohydrocarbyl), —NH(C═O)($C_{1-4}$alkylene-$C_{3-6}$cyclo hydrocarbyl), —N($C_{1-6}$alkyl)-(C═O)($C_{1-4}$alkylene-$C_{3-6}$cyclohydrocarbyl), —NH(C═O)(3- to 7-membered heterocyclyl), —N($C_{1-6}$alkyl)-(C═O)(3- to 7-membered heterocyclyl), —COOH, —C(═O)($C_{1-6}$alkyl), —C(═O)O($C_{1-6}$alkyl), —C(═O)O($C_{3-6}$cyclohydrocarbyl), —C(═O)O($C_{1-4}$alkylene-$C_{3-6}$cyclohydrocarbyl), —C(═O)O(3- to 7-membered heterocyclyl), —C(═O)O($C_{1-4}$alkylene)-(3- to 7-membered heterocyclyl), —C(═O)$NH_2$, —C(═O)NH($C_{1-6}$alkyl), —C(═O)N($C_{1-6}$alkyl)$_2$, —C(═O)NH($C_{1-4}$alkylene-$C_{3-6}$cyclohydrocarbyl), —C(═O)N($C_{1-4}$alkylene-$C_{3-6}$cyclohydrocarbyl)$_2$, —C(═O)NH(3- to 7-membered heterocyclyl), —C(═O)N(3- to 7-membered heterocyclyl)$_2$, —C(═O)NH($C_{1-4}$alkylene- 3- to 7-membered heterocyclyl), —C(═O)N($C_{1-4}$alkylene- 3- to 7-membered heterocyclyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), and —S(═O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), and —S(═O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), and —S(═O)$_2$N($C_{1-6}$alkyl)$_2$ preferably, at least one of $R^{42}$, $R^{43}$, $R^{44}$, $R^{45}$, $R^{46}$, $R^{47}$ and $R^{48}$ is —Cl, —Br, —I, —$NO_2$, —CN, ═O, ═S, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)-(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$, —S(═O)$_2$OH, —S(═O)$_2$NH($C_{1-6}$alkyl), —S(═O)$_2$N($C_{1-6}$alkyl)$_2$, —S(═O)NH($C_{1-6}$alkyl) or —S(═O)N($C_{1-6}$alkyl)$_2$, rest of the groups are each independently selected from the group consisting of H, halogen, —$NO_2$, —CN, ═O, ═S, $C_{1-6}$alkyl, —OH, —O($C_{1-6}$alkyl), —SH, —S($C_{1-6}$alkyl), —$NH_2$, —NH($C_{1-6}$alkyl), —N($C_{1-6}$alkyl)$_2$, —NH(C═O)($C_{1-6}$alkyl), —N($C_{1-6}$alkyl)-(C═O)($C_{1-6}$alkyl), —COOH, —C(═O)($C_{1-6}$alkyl), —C(═O)$NH_2$, —C(═O)NH($C_{1-6}$alkyl), —C(═O)N($C_{1-6}$alkyl)$_2$-S(═O)$_2$OH, —S(═O)$_2$NH($C_{1-6}$alkyl), —S(═O)$_2$N($C_{1-6}$alkyl)$_2$, —S(═O)NH($C_{1-6}$alkyl), —S(═O)N($C_{1-6}$alkyl)$_2$, wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; or, selected from the group consisting of $R^{42}$, $R^{43}$, $R^{44}$, $R^{45}$, $R^{46}$, $R^{47}$ and $R^{48}$, preferably selected from the group consisting of two adjacent groups of $R^{44}$ and $R^{45}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —S(═O)$_2$OH; and, $R^{49}$, $R^{50}$, $R^{51}$, $R^{52}$, $R^{53}$, $R^{54}$, $R^{55}$, $R^{56}$ and $R^{57}$ are H, or at least one, preferably 1-6, more preferably 1-4, particularly 1, 2 or 4 of $R^{49}$, $R^{50}$, $R^{51}$, $R^{52}$, $R^{53}$, $R^{54}$, $R^{55}$, $R^{56}$ and $R^{57}$ are $C_{1-6}$alkyl or —O($C_{1-6}$alkyl), preferably $C_{1-3}$alkyl or —O($C_{1-3}$alkyl), wherein the $C_{1-3}$alkyl is particularly preferably methyl, the —O($C_{1-3}$alkyl) is particularly preferably methoxy, rest of the groups are each independently selected from the group consisting of H, halogen, $C_{1-6}$alkyl, $C_{3-6}$cycloalkyl, $C_{3-6}$cycloalkyl —$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, —O($C_{1-6}$alkyl), —SH, —S($C_{1-6}$alkyl), —$NH_2$, —NH($C_{1-6}$alkyl), —N($C_{1-6}$alkyl)$_2$;

particularly, formula (xvi) has a structure of:

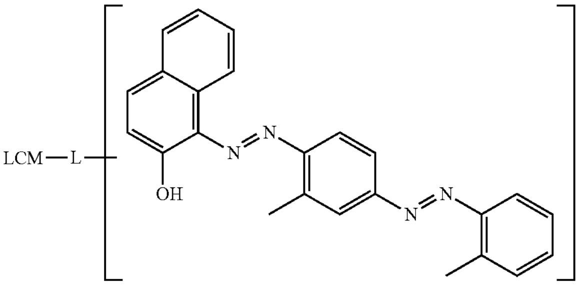

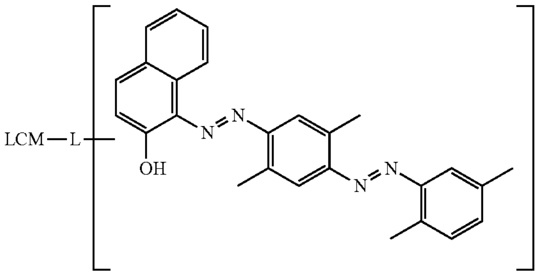

and

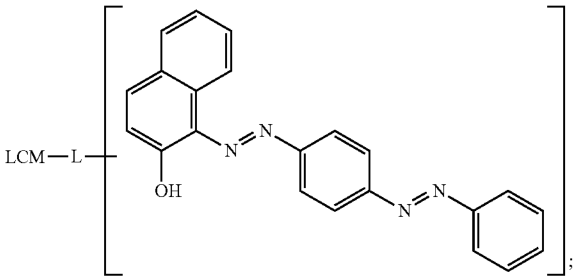

;

particularly, is selected from the group consisting of

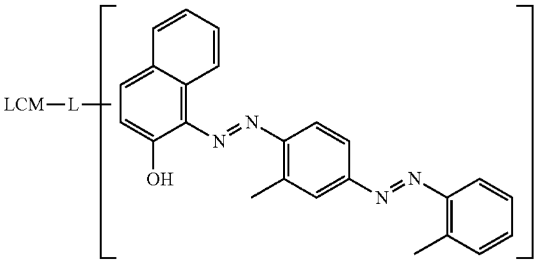

and

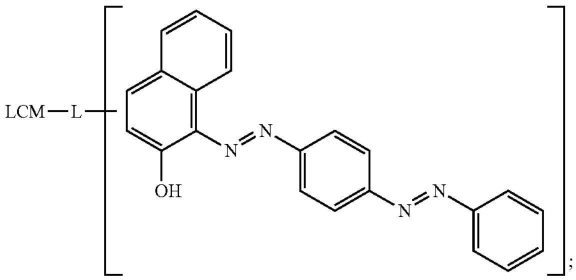

;

particularly,

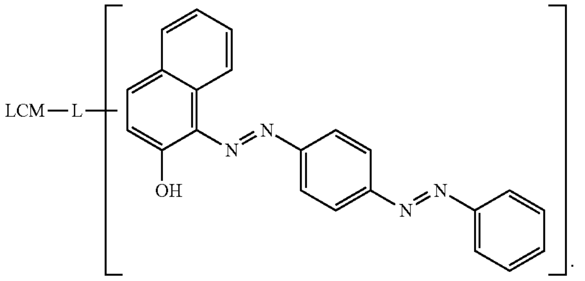

15. The compound according to claim 1, or a pharmaceutically acceptable salt, stereoisomer, solvate, polymorph, tautomer, isotopic compound, metabolite, or prodrug thereof, wherein the formula(I) has a structure of formula (xvii):

(xvii)

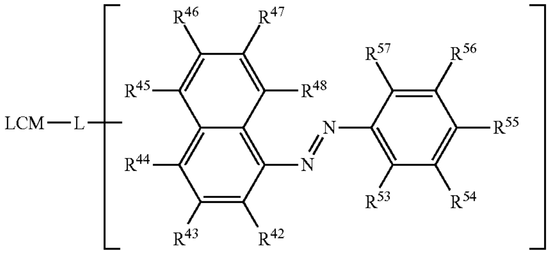

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are each independently selected from the group consisting of H, halogen, —$NO_2$, —CN, =O, =S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C=O)($C_{1-6}$alkyl), —O(C=O)($C_{3-6}$cyclohydrocarbyl), —O(C=O)($C_{1-4}$alkylene-$C_{3-6}$cyclohydrocarbyl), —O(C=O)(3- to 7-membered heterocyclyl), —O(C=O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, —NH(C=O)($C_{1-6}$alkyl), —N($C_{1-6}$alkyl)-(C=O)($C_{1-6}$alkyl), —NH(C=O)($C_{3-6}$cyclohydrocarbyl), —N($C_{1-6}$alkyl)-(C=O)($C_{3-6}$cyclohydrocarbyl), —NH(C=O)($C_{1-4}$alkylene-$C_{3-6}$cyclohydrocarbyl), —N($C_{1-6}$alkyl)-(C=O)($C_{1-4}$alkylene-$C_{3-6}$cyclohydrocarbyl), —NH(C=O)(3- to 7-membered heterocyclyl), —N($C_{1-6}$alkyl)-(C=O)(3- to 7-membered heterocyclyl), —COOH, —C(=O)($C_{1-6}$alkyl), —C(=O)O($C_{1-6}$alkyl), —C(=O)O($C_{3-6}$cyclohydrocarbyl), —C(=O)O($C_{1-4}$alkylene-$C_{3-6}$cyclohydrocarbyl), —C(=O)O(3- to 7-membered heterocyclyl), —C(=O)O($C_{1-4}$alkylene)-(3- to 7-membered heterocyclyl), —C(=O)$NH_2$, —C(=O)NH($C_{1-6}$alkyl), —C(=O)N($C_{1-6}$alkyl)$_2$, —C(=O)NH($C_{1-4}$alkylene-$C_{3-6}$cyclohydrocarbyl), —C(=O)N($C_{1-4}$alkylene-$C_{3-6}$cyclohydrocarbyl)$_2$, —C(=O)NH(3- to 7-membered heterocyclyl), —C(=O)N(3- to 7-membered heterocyclyl)$_2$, —C(=O)NH($C_{1-4}$alkylene- 3- to 7-membered heterocyclyl), —C(=O)N($C_{1-4}$alkylene- 3- to 7-membered heterocyclyl)$_2$, —S(=O)$_2$OH, —S(=O)$_2$NH($C_{1-6}$alkyl), —S(=O)$_2$N($C_{1-6}$alkyl)$_2$, —S(=O)NH($C_{1-6}$alkyl), and —S(=O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), —C(=O)N($C_{1-6}$alkyl)$_2$, —S(=O)$_2$OH, —S(=O)$_2$NH($C_{1-6}$alkyl), and —S(=O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), —C(=O)N($C_{1-6}$alkyl)$_2$, —S(=O)$_2$OH, —S(=O)$_2$NH($C_{1-6}$alkyl), and —S(=O)$_2$N($C_{1-6}$alkyl)$_2$ particularly, formula (xvii) is selected from the group consisting of:

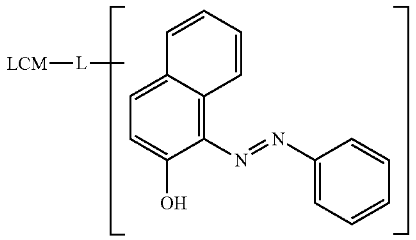

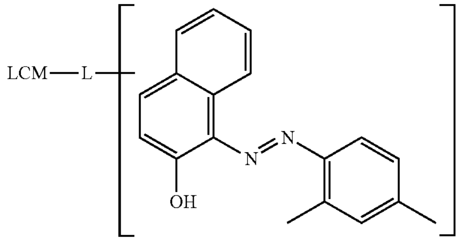

and

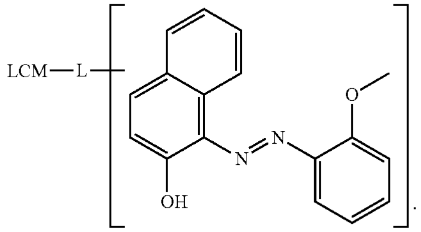

16. The compound according to claim 1, or a pharmaceutically acceptable salt, stereoisomer, solvate, polymorph, tautomer, isotopic compound, metabolite, or prodrug thereof, wherein the formula (I) has a structure of formula (xviii):

(xviii)

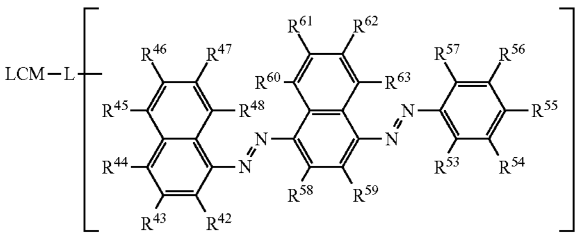

wherein $R^{42}$, $R^{43}$, $R^{44}$, $R^{45}$, $R^{46}$, $R^{47}$, $R^{48}$, $R^{53}$, $R^{54}$, $R^{55}$, $R^{56}$ and $R^{57}$ are each independently selected from the group consisting of H, halogen, —$NO_2$, —CN, =O, =S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C=O)($C_{1-6}$alkyl), —O(C=O)($C_{3-6}$cyclohydrocarbyl), —O(C=O)($C_{1-4}$alkylene-$C_{3-6}$cyclohydrocarbyl), —O(C=O)(3- to 7-membered heterocyclyl), —O(C=O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, —NH(C=O)($C_{1-6}$alkyl), —N($C_{1-6}$alkyl)-(C=O)($C_{1-6}$alkyl), —NH(C=O)($C_{3-6}$cyclohydrocarbyl), —N($C_{1-6}$alkyl)-(C=O)($C_{3-6}$cyclohydrocarbyl), —NH(C=O)($C_{1-4}$alkylene-$C_{3-6}$cyclohydrocarbyl), —N($C_{1-6}$alkyl)-(C=O)($C_{1-4}$alkylene-$C_{3-6}$cyclohydrocarbyl), —NH(C=O)(3- to 7-membered heterocyclyl), —N($C_{1-6}$alkyl)-(C=O)(3- to 7-membered heterocyclyl), —COOH, —C(=O)($C_{1-6}$alkyl), —C(=O)O($C_{1-6}$alkyl), —C(=O)O($C_{3-6}$cyclohydrocarbyl), —C(=O)O($C_{1-4}$alkylene-$C_{3-6}$cyclohydrocarbyl), —C(=O)O(3- to 7-membered heterocyclyl), —C(=O)O($C_{1-4}$alkylene)-(3- to 7-membered heterocyclyl), —C(=O)$NH_2$, —C(=O)NH($C_{1-6}$alkyl), —C(=O)N($C_{1-6}$alkyl)$_2$, —C(=O)NH($C_{1-4}$alkylene-$C_{3-6}$cyclohydrocarbyl), —C(=O)N($C_{1-4}$alkylene-$C_{3-6}$cyclohydrocarbyl)$_2$, —C(=O)NH(3- to 7-membered heterocyclyl), —C(=O)N(3- to 7-membered heterocyclyl)$_2$, —C(=O)NH($C_{1-4}$alkylene- 3- to 7-membered heterocyclyl), —C(=O)N($C_{1-4}$alkylene- 3- to 7-membered heterocyclyl)$_2$, —S(=O)$_2$OH, —S(=O)$_2$NH($C_{1-6}$alkyl), —S(=O)$_2$N($C_{1-6}$alkyl)$_2$, —S(=O)NH($C_{1-6}$alkyl), and —S(=O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), —C(=O)N($C_{1-6}$alkyl)$_2$, —S(=O)$_2$OH, —S(=O)$_2$NH($C_{1-6}$alkyl), and —S(=O)$_2$N($C_{1-6}$alkyl)$_2$; or two adjacent groups selected from the group consisting of $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ are bonded to each other, together with the atom(s) attached thereto to form $C_{3-10}$hydrocarbyl ring or 3- to 7-membered heterocyclic ring, wherein the hydrocarbyl ring or heterocyclic ring is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), —C(=O)N($C_{1-6}$alkyl)$_2$, —S(=O)$_2$OH, —S(=O)$_2$NH($C_{1-6}$alkyl), and —S(=O)$_2$N($C_{1-6}$alkyl)$_2$;

wherein $R^{58}$, $R^{59}$, $R^{60}$, $R^{61}$, $R^{62}$ and $R^{63}$ are each independently selected from the group consisting of H, halogen, —$NO_2$, —CN, =O, =S, $C_{1-6}$alkyl, $C_{2-6}$alkenyl, $C_{2-6}$alkynyl, $C_{3-6}$cyclohydrocarbyl, $C_{3-6}$cyclohydrocarbyl-$C_{1-4}$alkyl, 3- to 7-membered heterocyclyl, 3- to 7-membered heterocyclyl-$C_{1-4}$alkyl, —OH, —O($C_{1-6}$alkyl), —O($C_{3-6}$cyclohydrocarbyl), —O($C_{1-4}$alkylene-$C_{3-6}$cyclohydrocarbyl), —O(3- to 7-membered heterocyclyl), —O($C_{1-4}$alkylene)-(3- to 7-membered heterocyclyl), —O(C=O)($C_{1-6}$alkyl), —O(C=O)($C_{3-6}$cyclohydrocarbyl), —O(C=O)($C_{1-4}$alkylene-$C_{3-6}$cyclohydrocarbyl), —O(C=O)(3- to 7-membered heterocyclyl), —O(C=O)($C_{1-4}$alkylene)-(3- to 7-membered heterocyclyl), —SH, —S($C_{1-6}$alkyl), —S($C_{3-6}$cyclohydrocarbyl), —S($C_{1-4}$alkylene-$C_{3-6}$cyclohydrocarbyl), —S(3- to 7-membered heterocyclyl), —S($C_{1-4}$alkylene)-(3- to 7-membered heterocyclyl), —$NH_2$, —NH($C_{1-6}$alkyl), —N($C_{1-6}$alkyl)$_2$, —NH($C_{3-6}$cyclohydrocarbyl), —N($C_{3-6}$cyclohydrocarbyl)$_2$, —NH($C_{1-4}$alkylene-$C_{3-6}$cyclohydrocarbyl), —N($C_{1-4}$alkylene-$C_{3-6}$cyclohydrocarbyl)$_2$, —NH(3- to 7-membered heterocyclyl), —N(3- to 7-membered heterocyclyl)$_2$, —NH($C_{1-4}$alkylene- 3- to 7-membered heterocyclyl), —N($C_{1-4}$alkylene- 3- to 7-membered heterocyclyl)$_2$, —NH(C=O)($C_{1-6}$alkyl), —N($C_{1-6}$alkyl)-(C=O)($C_{1-6}$alkyl), —NH(C=O)($C_{3-6}$cyclohydrocarbyl), —N($C_{1-6}$alkyl)-(C=O)($C_{3-6}$cyclohydrocarbyl), —NH(C=O)($C_{1-4}$alkylene-$C_{3-6}$cyclohydrocarbyl), —N($C_{1-6}$alkyl)-(C=O)($C_{1-4}$alkylene-$C_{3-6}$cyclohydrocarbyl), —NH(C=O)(3- to 7-membered heterocyclyl), —N($C_{1-6}$alkyl)-(C=O)(3- to 7-membered heterocyclyl), —COOH, —C(=O)($C_{1-6}$alkyl), —C(=O)O($C_{1-6}$alkyl), —C(=O)O($C_{3-6}$cyclohydrocarbyl), —C(=O)O($C_{1-4}$alkylene-$C_{3-6}$cyclohydrocarbyl), —C(=O)O(3- to 7-membered heterocyclyl), —C(=O)O($C_{1-4}$alkylene)-(3- to 7-membered heterocyclyl), —C(=O)$NH_2$, —C(=O)NH($C_{1-6}$alkyl), —C(=O)N($C_{1-6}$alkyl)$_2$, —C(=O)NH($C_{1-4}$alkylene-$C_{3-6}$cyclohydrocarbyl), —C(=O)N($C_{1-4}$alkylene-$C_{3-6}$cyclohydrocarbyl)$_2$, —C(=O)NH(3- to 7-membered heterocyclyl), —C(=O)N(3- to 7-membered heterocyclyl)$_2$, —C(=O)NH($C_{1-4}$alkylene- 3- to 7-membered heterocyclyl), —C(=O)N($C_{1-4}$alkylene- 3- to 7-membered heterocyclyl)$_2$, —S(=O)$_2$OH, —S(=O)$_2$NH($C_{1-6}$alkyl), —S(=O)$_2$N($C_{1-6}$alkyl)$_2$, —S(=O)NH($C_{1-6}$alkyl), and —S(=O)N($C_{1-6}$alkyl)$_2$, wherein the alkyl, alkylene, alkenyl, alkynyl, cyclohydrocarbyl or heterocyclyl is optionally substituted with one or more substituents selected from the group consisting of halogen, nitro, cyano, —OH, —O($C_{1-6}$alkyl), —SH, —S($C_{1-6}$alkyl), —$NH_2$, —NH($C_{1-6}$alkyl), —N($C_{1-6}$alkyl)$_2$, —COOH, —C(=O)($C_{1-6}$alkyl), —C(=O)$NH_2$, —C(=O)NH($C_{1-6}$alkyl), $—C(=O)N(C_{1-6}alkyl)_2$, $—S(=O)_2OH$, $—S(=O)_2NH(C_{1-6}alkyl)$, and $—S(=O)_2N(C_{1-6}alkyl)_2$;

preferably, $R^{58}$, $R^{59}$, $R^{60}$, $R^{61}$, $R^{62}$ and $R^{63}$ are H, or at least one, preferably 1-6, more preferably 1-4, particularly 1, 2 or 4 of $R^{58}$, $R^{59}$, $R^{60}$, $R^{61}$, $R^{62}$ and $R^{63}$ are $C_{1-6}$alkyl or $—O(C_{1-6}alkyl)$, preferably $C_{1-3}$alkyl or $—O(C_{1-3}alkyl)$, wherein the $C_{1-3}$alkyl is particularly preferably methyl, the $—O(C_{1-3}alkyl)$ is particularly preferably methoxy, rest of the groups are each independently selected from the group consisting of H, halogen, $C_{1-6}$alkyl, $C_{3-6}$cycloalkyl, $C_{3-6}$cycloalkyl-$C_{1-4}$alkyl, 3- to 7-membered heterocyclyl, 3- to 7-membered heterocyclyl-$C_{1-4}$alkyl, preferably selected from the group consisting of H and halogen, particularly preferably H; wherein the alkyl is optionally substituted with one or more substituents selected from the group consisting of halogen, —OH, $—O(C_{1-6}alkyl)$, —SH, $—S(C_{1-6}alkyl)$, $—NH_2$, $—NH(C_{1-6}alkyl)$, $—N(C_{1-6}alkyl)_2$;

particularly, formula (xviii) is:

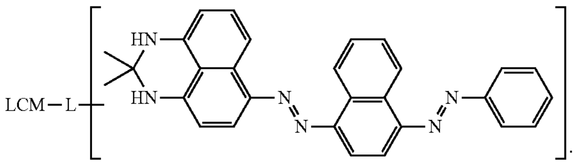

17. The compound according to claim 1, or a pharmaceutically acceptable salt, stereoisomer, solvate, polymorph, tautomer, isotopic compound, metabolite, or prodrug thereof, wherein the formula (I) has the following structure:

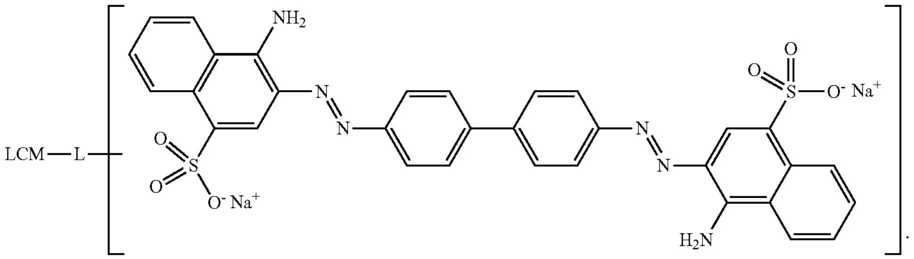

18. The compound according to claim 1, or a pharmaceutically acceptable salt, stereoisomer, solvate, polymorph, tautomer, isotopic compound, metabolite, or prodrug thereof wherein the compound is selected from the group consisting of Compound 1A

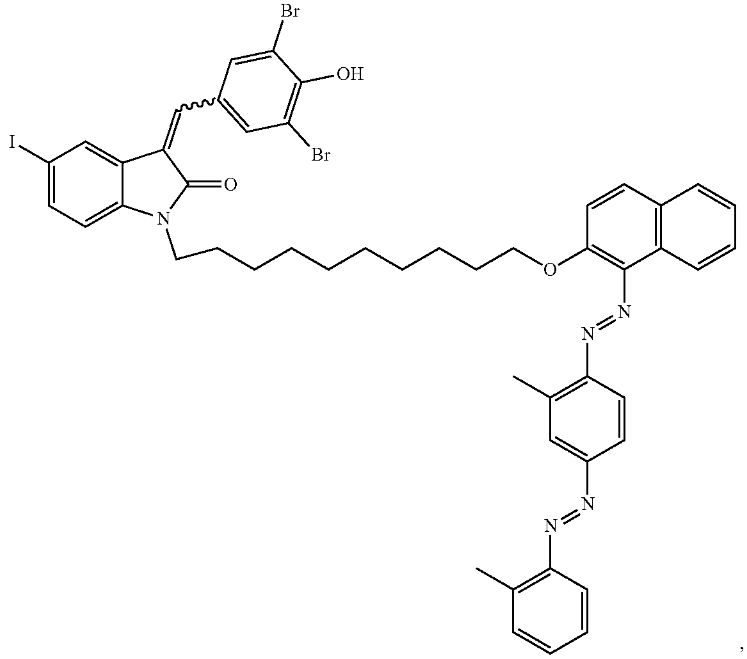

,

-continued
Compound 1B
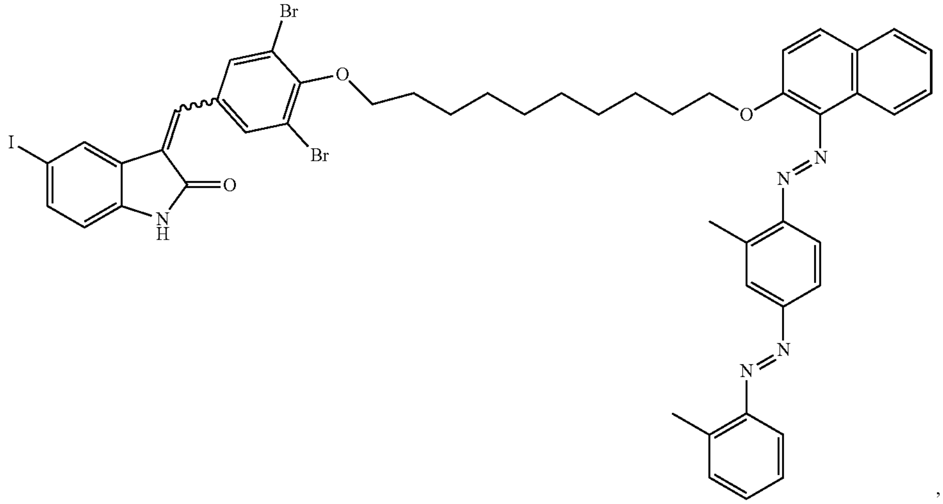
,
Compound 2A
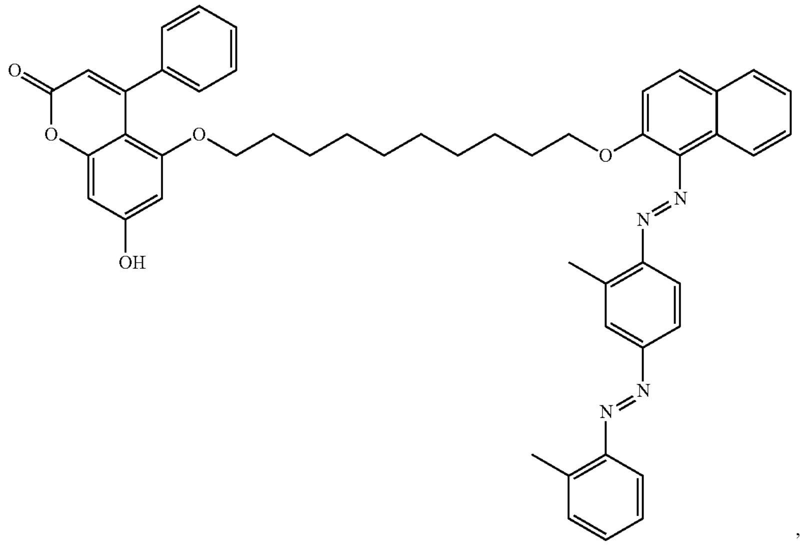
,
Compound 2B
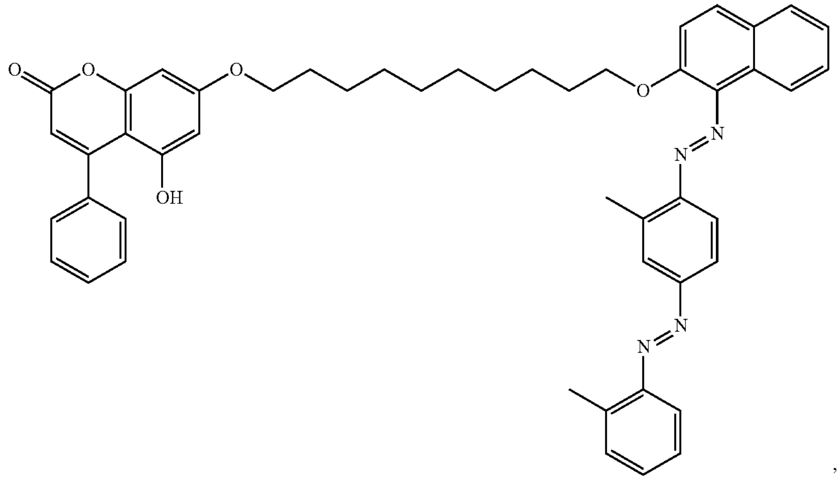
, -continued
Compound 3A
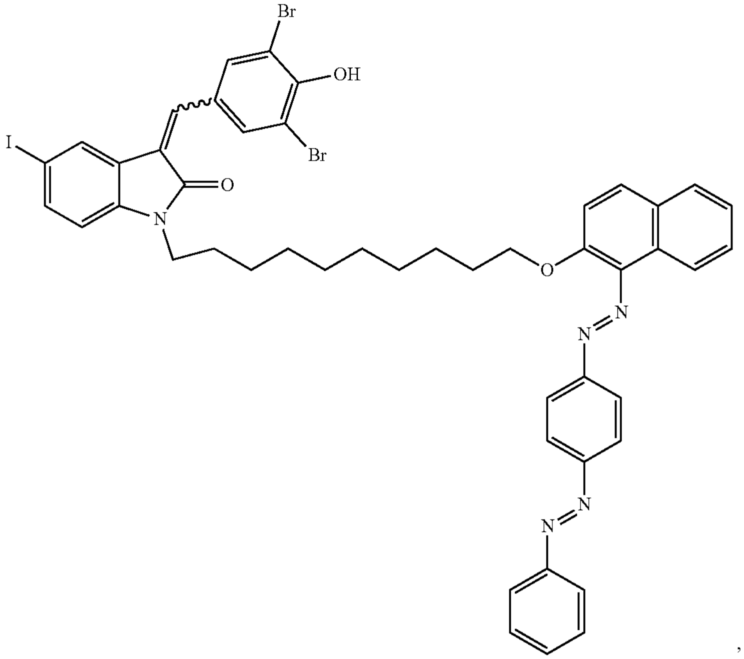
,
Compound 3B
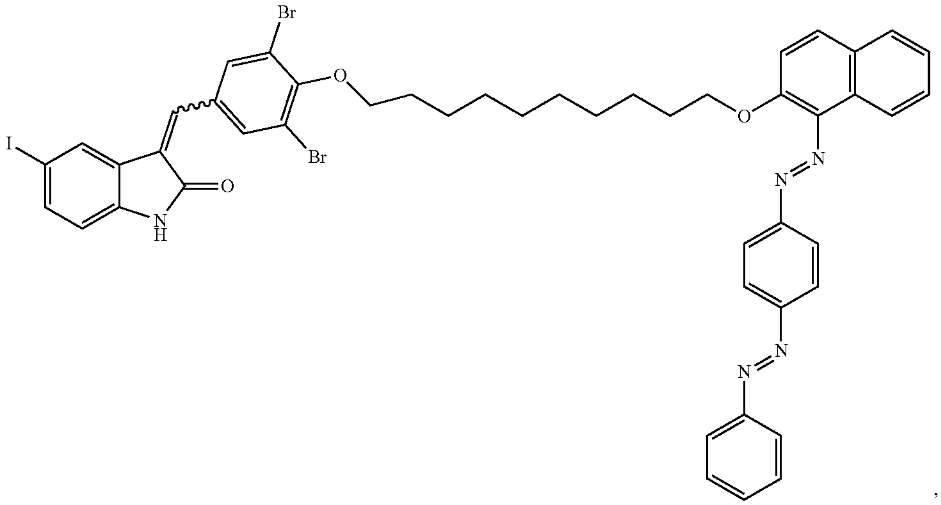
, -continued Compound 4A

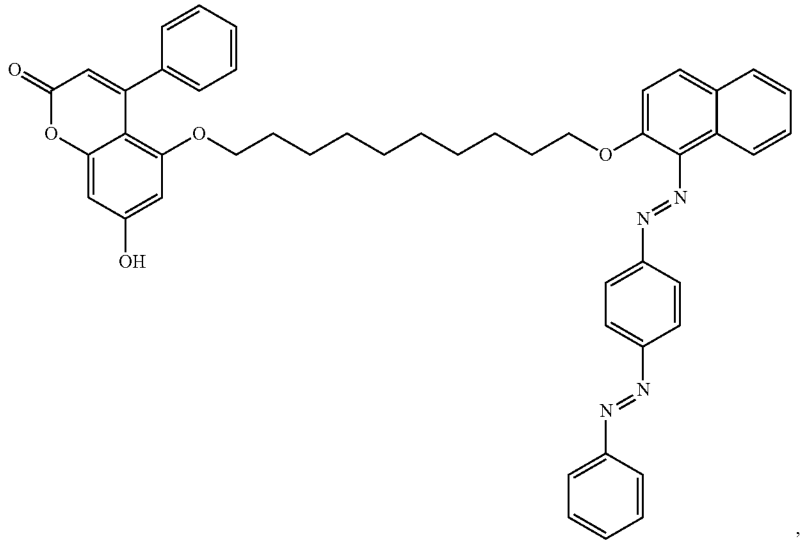

, and

Compound 4B

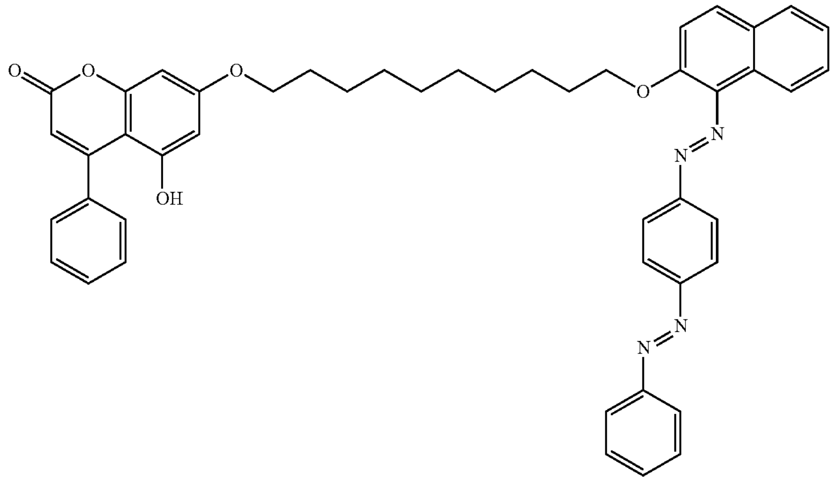

and

Compound 9

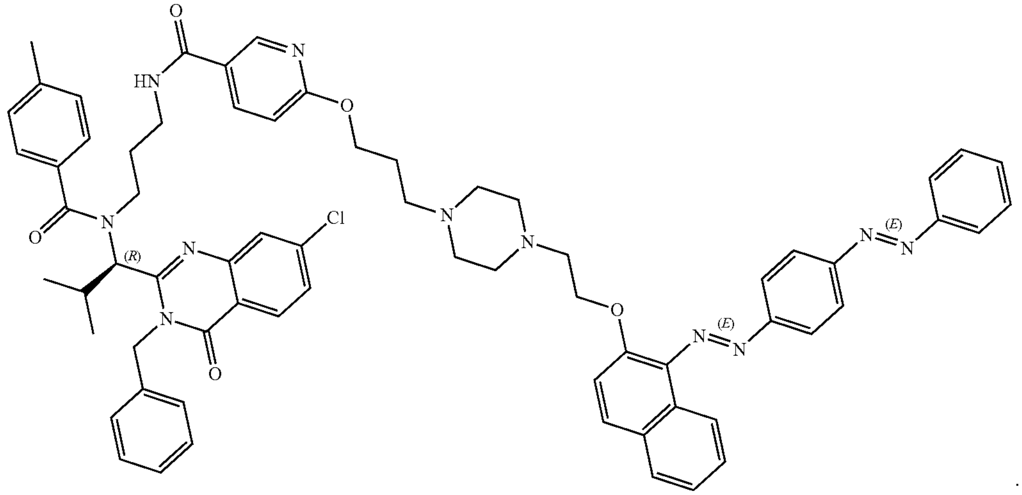

.

19. A pharmaceutical composition, comprising the compound according to claim 1, or a pharmaceutically acceptable salt, stereoisomer, solvate, polymorph, tautomer, isotopic compound, metabolite, or prodrug thereof in a prophylactically or therapeutically effective amount, and one or more pharmaceutically acceptable carriers.

20. A method for treating a lipid metabolism related disease, comprising administering to a subject in need thereof a therapeutically effective amount of the compound according to claim 1, or a pharmaceutically acceptable salt, stereoisomer, solvate, polymorph, tautomer, isotopic compound, metabolite, or prodrug thereof;

preferably, the lipid metabolism related disease is selected from the group consisting of MADD, obesity, NAFLD, type II diabetes, hepatocellular carcinoma, Alzheimer's disease and atherosclerosis.

21. A method for reducing lipid droplets in a cell, comprising contacting a conjugated compound comprising a LC3 binding moiety and a lipid droplet binding moiety with a cell or tissue comprising the lipid droplets, wherein the lipid droplets are contained by the cell under physiological or pathological conditions and/or produced by the cell under induction;

wherein the conjugated compound is the compound according to claim 1, or a pharmaceutically acceptable salt, stereoisomer, solvate, polymorph, tautomer, isotopic compound, metabolite, or prodrug thereof.

22. A method for treating a lipid metabolism related disease, comprising administering to a subject in need thereof the pharmaceutical composition according to claim 19, wherein the lipid metabolism related disease is selected from the group consisting of MADD, obesity, NAFLD, type II diabetes, hepatocellular carcinoma, Alzheimer's disease and atherosclerosis.

* * * * *

SEQUENCE LISTING

```
<160> NUMBER OF SEQ ID NOS: 4

<210> SEQ ID NO 1
<211> LENGTH: 121
<212> TYPE: PRT
<213> ORGANISM: Homo sapiens

<400> SEQUENCE: 1

Met Pro Ser Asp Arg Pro Phe Lys Gln Arg Arg Ser Phe Ala Asp Arg
1               5                   10                  15

Cys Lys Glu Val Gln Gln Ile Arg Asp Gln His Pro Ser Lys Ile Pro
            20                  25                  30

Val Ile Ile Glu Arg Tyr Lys Gly Glu Lys Gln Leu Pro Val Leu Asp
        35                  40                  45

Lys Thr Lys Phe Leu Val Pro Asp His Val Asn Met Ser Glu Leu Val
    50                  55                  60

Lys Ile Ile Arg Arg Arg Leu Gln Leu Asn Pro Thr Gln Ala Phe Phe
65                  70                  75                  80

Leu Leu Val Asn Gln His Ser Met Val Ser Val Ser Thr Pro Ile Ala
                85                  90                  95

Asp Ile Tyr Glu Gln Glu Lys Asp Glu Asp Gly Phe Leu Tyr Met Val
            100                 105                 110

Tyr Ala Ser Gln Glu Thr Phe Gly Phe
        115                 120


<210> SEQ ID NO 2
<211> LENGTH: 125
<212> TYPE: PRT
<213> ORGANISM: Homo sapiens

<400> SEQUENCE: 2

Met Lys Met Arg Phe Phe Ser Ser Pro Cys Gly Lys Ala Ala Val Asp
1               5                   10                  15

Pro Ala Asp Arg Cys Lys Glu Val Gln Gln Ile Arg Asp Gln His Pro
            20                  25                  30

Ser Lys Ile Pro Val Ile Ile Glu Arg Tyr Lys Gly Glu Lys Gln Leu
        35                  40                  45

Pro Val Leu Asp Lys Thr Lys Phe Leu Val Pro Asp His Val Asn Met
    50                  55                  60

Ser Glu Leu Val Lys Ile Ile Arg Arg Arg Leu Gln Leu Asn Pro Thr
65                  70                  75                  80

Gln Ala Phe Phe Leu Leu Val Asn Gln His Ser Met Val Ser Val Ser
                85                  90                  95

Thr Pro Ile Ala Asp Ile Tyr Glu Gln Glu Lys Asp Glu Asp Gly Phe
            100                 105                 110

Leu Tyr Met Val Tyr Ala Ser Gln Glu Thr Phe Gly Phe
        115                 120                 125


<210> SEQ ID NO 3
<211> LENGTH: 125
<212> TYPE: PRT
<213> ORGANISM: Homo sapiens

<400> SEQUENCE: 3

Met Pro Ser Glu Lys Thr Phe Lys Gln Arg Arg Thr Phe Glu Gln Arg
1               5                   10                  15

Val Glu Asp Val Arg Leu Ile Arg Glu Gln His Pro Thr Lys Ile Pro
            20                  25                  30
```

-continued

```
Val Ile Ile Glu Arg Tyr Lys Gly Glu Lys Gln Leu Pro Val Leu Asp
        35                  40                  45

Lys Thr Lys Phe Leu Val Pro Asp His Val Asn Met Ser Glu Leu Ile
    50                  55                  60

Lys Ile Ile Arg Arg Arg Leu Gln Leu Asn Ala Asn Gln Ala Phe Phe
65                  70                  75                  80

Leu Leu Val Asn Gly His Ser Met Val Ser Val Ser Thr Pro Ile Ser
                85                  90                  95

Glu Val Tyr Glu Ser Glu Lys Asp Glu Asp Gly Phe Leu Tyr Met Val
            100                 105                 110

Tyr Ala Ser Gln Glu Thr Phe Gly Met Lys Leu Ser Val
        115                 120                 125


<210> SEQ ID NO 4
<211> LENGTH: 147
<212> TYPE: PRT
<213> ORGANISM: Homo sapiens

<400> SEQUENCE: 4

Met Pro Pro Pro Gln Lys Ile Pro Ser Val Arg Pro Phe Lys Gln Arg
1               5                   10                  15

Lys Ser Leu Ala Ile Arg Gln Glu Glu Val Ala Gly Ile Arg Ala Lys
            20                  25                  30

Phe Pro Asn Lys Ile Pro Val Val Val Glu Arg Tyr Pro Arg Glu Thr
        35                  40                  45

Phe Leu Pro Pro Leu Asp Lys Thr Lys Phe Leu Val Pro Gln Glu Leu
    50                  55                  60

Thr Met Thr Gln Phe Leu Ser Ile Ile Arg Ser Arg Met Val Leu Arg
65                  70                  75                  80

Ala Thr Glu Ala Phe Tyr Leu Leu Val Asn Asn Lys Ser Leu Val Ser
                85                  90                  95

Met Ser Ala Thr Met Ala Glu Ile Tyr Arg Asp Tyr Lys Asp Glu Asp
            100                 105                 110

Gly Phe Val Tyr Met Thr Tyr Ala Ser Gln Glu Thr Phe Gly Cys Leu
        115                 120                 125

Glu Ser Ala Ala Pro Arg Asp Gly Ser Ser Leu Glu Asp Arg Pro Cys
    130                 135                 140

Asn Pro Leu
145
```